US012613245B2

(12) United States Patent
Lyden et al.

(10) Patent No.: US 12,613,245 B2
(45) Date of Patent: Apr. 28, 2026

(54) METHODS FOR DETECTING AND INHIBITING BRAIN METASTASIS

(71) Applicant: CORNELL UNIVERSITY, Ithaca, NY (US)

(72) Inventors: David C. Lyden, New York, NY (US); Goncalo Rodrigues, New York, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 494 days.

(21) Appl. No.: 17/769,245

(22) PCT Filed: Oct. 15, 2020

(86) PCT No.: PCT/US2020/055849
§ 371 (c)(1),
(2) Date: Apr. 14, 2022

(87) PCT Pub. No.: WO2021/076808
PCT Pub. Date: Apr. 22, 2021

(65) Prior Publication Data
US 2024/0319195 A1 Sep. 26, 2024

Related U.S. Application Data

(60) Provisional application No. 62/915,391, filed on Oct. 15, 2019.

(51) Int. Cl.
*G01N 33/574* (2006.01)
*A61P 35/04* (2006.01)
*C07K 16/18* (2006.01)
*C12Q 1/6886* (2018.01)
*A61K 39/00* (2006.01)

(52) U.S. Cl.
CPC ........ *G01N 33/57484* (2013.01); *A61P 35/04* (2018.01); *C07K 16/18* (2013.01); *C12Q 1/6886* (2013.01); *A61K 2039/505* (2013.01); *C07K 2317/76* (2013.01); *C07K 2317/92* (2013.01); *C12Q 2600/118* (2013.01); *C12Q 2600/158* (2013.01)

(58) Field of Classification Search
CPC ................................................. G01N 33/57484
USPC ......................................................... 424/133.1
See application file for complete search history.

(56) References Cited

U.S. PATENT DOCUMENTS

| | | | |
|---|---|---|---|
| 2014/0148348 A1 | 5/2014 | Kuslich et al. | |
| 2014/0155280 A1 | 6/2014 | Lapointe et al. | |
| 2016/0117443 A1 | 4/2016 | Van Ooijen et al. | |
| 2016/0319361 A1 | 11/2016 | Spetzler et al. | |
| 2017/0108503 A1 | 4/2017 | Klass et al. | |
| 2019/0049435 A1 | 2/2019 | Lyden et al. | |
| 2019/0202892 A1 | 7/2019 | Lewis et al. | |
| 2020/0071765 A1 | 3/2020 | Zheng | |

FOREIGN PATENT DOCUMENTS

| | | |
|---|---|---|
| CA | 2875418 | 6/2015 |
| WO | 2011127219 | 10/2011 |
| WO | 2013033609 | 3/2013 |
| WO | 2013033629 | 3/2013 |
| WO | 2013159099 | 10/2013 |
| WO | 2018223094 | 12/2018 |
| WO | 2020205299 | 8/2020 |

OTHER PUBLICATIONS

Xu et al (Int J Clin Exp Pathol, 2015, 8(3): 2909-2918).*
Hurwitz et al (The Oncologist, 2013, 18: 1004-1012).*
Aprile et al (J Cancer Res Clin Oncol, 2009, 135: 451-457).*
Zhang et al (Int J Cancer, 2017, 140: 2298-2309).*
International Search Report and Written Opinion for corresponding Application No. PCT/US2020/055849 (mailed Feb. 25, 2021).
Rodrigues et al., "Tumour Exosomal CEMIP Protein Promotes Cancer Cell Colonization in Brain Metastasis," Nat. Cell. Biol. 21(11):1-32 (2019).
Ren et al., "Emerging Treatment Strategies for Breast Cancer Brain Metastasis: From Translational Therapeutics to Real-World Experience," Therapeutic Adv in Med. Oncology 12:1758835920936151 (2020).
Ding et al., "Proteomic Profiling of Serum Exosomes From Patients With Metastatic Gastric Cancer," Front. Oncol. 10:1113 (2020).
International Preliminary Report on Patentability in corresponding PCT application PCT/US2020/055849 (Apr. 19, 2022).
Kodack et al., "Emerging Strategies for Treating Brain Metastases from Breast Cancer," Cancer Cell. 27(2):163-175 (2015).

* cited by examiner

*Primary Examiner* — Sean E Aeder
(74) *Attorney, Agent, or Firm* — Troutman Pepper Locke LLP (Rochester)

(57) ABSTRACT

The present disclosure is directed to a method that involves selecting a subject having a primary tumor and obtaining, from the selected subject, a sample containing exosomes derived from primary tumor cells. The exosomes are isolated from the sample and expression levels of cell migration-inducing and hyaluronan-binding protein (CEMIP) are detected in the isolated exosomes.

19 Claims, 44 Drawing Sheets

Specification includes a Sequence Listing.

e

Exosome pre-treatment

PBS    231 Parental    231 BrT1

231 Parental d e f g c d

CEMIP

▹ 180 kDa
▹ 135 kDa

ACTB

▹ 48 kDa b

| | Sample Name | Subset Name | Count |
|---|---|---|---|
| ▨ | anti-CEMIP-GaMAx647_WT 15_007.fcs | Single Cells | 25159 |
| ▨ | anti-CEMIP-GaMAx647_KO18_005.fcs | Single Cells | 14498 |
| ▨ | anti-CEMIP-GaMAx647_KO13_004.fcs | Single Cells | 15611 |
| ▨ | anti-CEMIP-GaMAx647_KO11_003.fcs | Single Cells | 17472 |
| ▨ | anti-CEMIP-GaMAx647_KO8_001.fcs | Single Cells | 17540 |
| ▨ | unst_WT 15_016.fcs | Single Cells | 19664 |

METHODS FOR DETECTING AND INHIBITING BRAIN METASTASIS

This application is a national stage application under 35 U.S.C. § 371 of International Application No. PCT/US2020/055849, filed Oct. 15, 2020, which claims priority benefit of U.S. Provisional Patent Application Ser. No. 62/915,391, filed Oct. 15, 2019, which are hereby incorporated by reference in their entirety.

The instant application contains a computer readable Sequence Listing which has been submitted electronically in ASCII format ("Sequence Listing ASCII") and is hereby incorporated by reference in its entirety. The Sequence Listing ASCII, created on May 27, 2022, is named 147402.008521_ST25.txt and is 87,740 bytes in size. No new matter is being introduced.

This invention was made with government support under W81XWH-13-1-0427 awarded by the Department of Defense. The government has certain rights in the invention.

FIELD

The present application relates to methods of detecting and inhibiting metastasis.

BACKGROUND

Despite advances in understanding the molecular determinants that drive metastasis, metastatic entry and adaptation to specific organs, particularly the brain, remain poorly understood. The incidence of brain metastasis (BrM) is ten-fold higher than all primary brain tumours combined (Maher et al., "Brain Metastasis: Opportunities in Basic and Translational Research," *Cancer Res* 69:6015-6020 (2009)). Brain metastases most commonly arise from lung and breast cancer, have poor prognosis and high mortality, and lack effective therapy (Eichler et al., "The Biology of Brain Metastases-Translation to New Therapies," *Nat Rev Clin Oncol* 8:344-356 (2011)). Hence, identifying tumour-intrinsic properties and/or drivers of the crosstalk between tumour cells and the brain microenvironment that can be targeted to prevent and/or treat BrM is critical.

The present disclosure is directed to overcoming these and other limitations in the art.

SUMMARY

A first aspect of the disclosure is directed to a method that involves selecting a subject having a primary tumor and obtaining, from the selected subject, a sample containing exosomes derived from primary tumor cells. The exosomes are isolated from the sample and expression levels of cell migration-inducing and hyaluronan-binding protein (CEMIP) are detected in the isolated exosomes.

Another aspect of the disclosure is directed to a method of identifying a subject's risk of developing metastatic brain disease. This method involves selecting a subject having a primary tumor, and isolating, from the subject, a sample comprising primary tumor cells, primary tumor cell derived exosomes, or both. This method further involves detecting CEMIP expression in said isolated sample and identifying the subject's risk of developing metastatic brain disease based on said detecting.

Another aspect of the present disclosure is directed to a method of inhibiting metastatic brain disease in a subject. This method involves selecting a subject having a primary tumor, wherein expression level of CEMIP in primary tumor cells or exosomes derived from primary tumor cells is increased relative to CEMIP expression levels in non-tumor cells or exosomes derived from non-tumor cells, respectively. This method further involves administering, to the selected subject, a brain metastasis prophylactic treatment suitable for inhibiting metastatic brain disease.

Another aspect of the present disclosure is directed to a method of inhibiting metastatic brain disease in a subject. This method involves selecting a subject having a primary tumor, wherein expression level of CEMIP in primary tumor cells or exosomes derived from primary tumor cells is increased relative to CEMIP expression levels in non-tumor cells or exosomes derived from non-tumor cells, respectively, and administering, to the selected subject, a CEMIP inhibitor in an amount effective to inhibit metastatic brain disease.

The development of effective therapies against brain metastasis is currently hindered by a limited understanding of the molecular mechanisms driving it. Described herein is the contribution of tumor-secreted exosomes to brain metastatic colonization based on the demonstration that preconditioning the brain microenvironment with exosomes from brain metastatic cells enhances cancer cell outgrowth. Proteomic analysis identified cell migration-inducing and hyaluronan-binding protein (CEMIP) as elevated in exosomes from brain metastatic, but not lung or bone metastatic cells. CEMIP depletion in tumor cells impaired brain metastasis, disrupting invasion and tumor cell association with the brain vasculature, phenotypes rescued by pre-conditioning the brain microenvironment with CEMIP$^+$ exosomes. Moreover, uptake of CEMIP$^+$ exosomes by brain endothelial and microglial cells induced endothelial cell branching and inflammation in the perivascular niche by upregulating Ptgs2, Tnf, and Ccl/Cxcl cytokines, known to promote brain vascular remodeling and metastasis. CEMIP was elevated in tumor tissues and exosomes from patients with brain metastasis and predicted brain metastasis progression and patient survival. Collectively, these findings indicate that targeting of exosomal CEMIP will provide an effective means for inhibiting brain metastatic disease in susceptible patients.

BRIEF DESCRIPTION OF THE DRAWINGS

FIG. 1A is an illustration of organotropic metastatic derivatives (Yoneda, et al., "A Bone-seeking Clone Exhibits Different Biological Properties From the MDA-MB-231 Parental Human Breast Cancer Cells and a Brain-seeking Clone *In Vivo and In Vitro,*" *J Bone Miner Res* 16:1486-1495 (2001); Bos et al., "Genes that mediate breast cancer metastasis to the brain," *Nature* 459: 1005-1009 (2009); Kang et al., "A Multigenic Program Mediating Breast Cancer Metastasis to Bone," *Cancer Cell* 3:537-549 (2003); Gupta et al., "Identifying Site-specific Metastasis Genes and Functions," *Cold Spring Harb Symp Quant Biol* 70:149-158 (2005); Minn, et al., "Genes that Mediate Breast Cancer Metastasis to Lung," *Nature* 436:518-524 (2005); Zhou et al., "Cancer-secreted miR-105 Destroys Vascular Endothelial Barriers to Promote Metastasis," *Cancer Cell* 25:501-515 (2014), which are hereby incorporated by reference in their entirety) of MDA-MB-231 breast cancer cell model (parental (gray) and brain (purple), lung (orange), and bone (green) metastatic) and respective cell-derived exosomes analyzed. A schematic of the brain slice ex vivo model optimized for the study of exosome-mediated cancer cell brain colonization is shown. FIG. 1B is a schematic of the brain slice model used to study

Figure 1A:
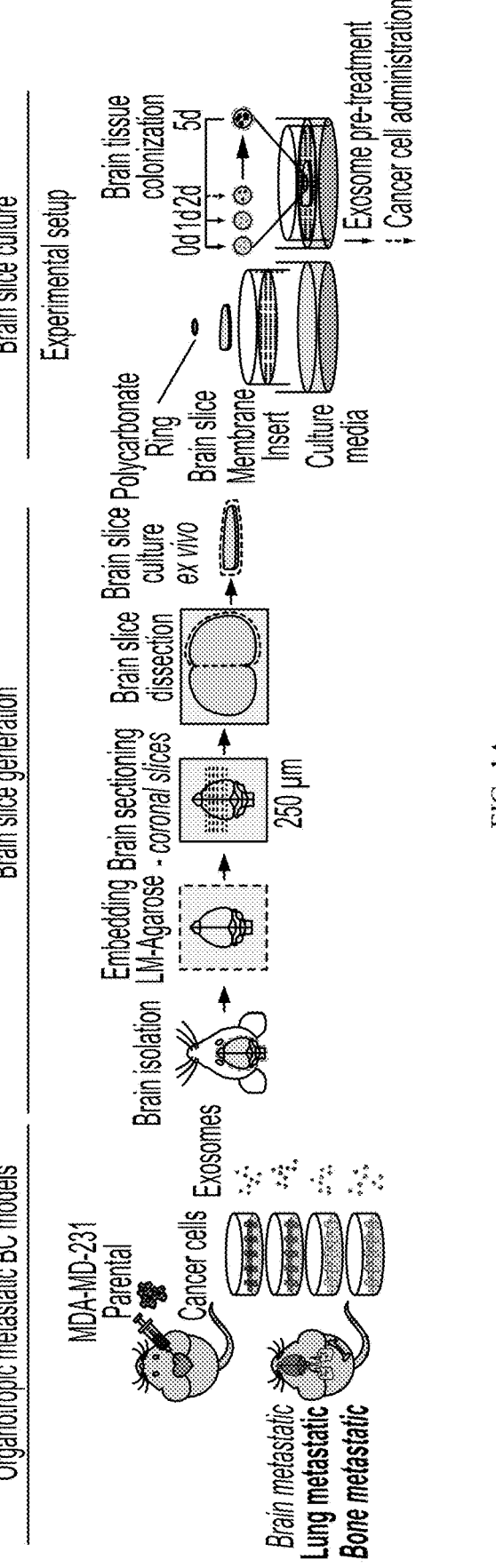
FIGS. 1A-1E show a brain slice model to study the role of tumour exosomes in metastatic colonization.
Figures 1B, 1C, 1D:
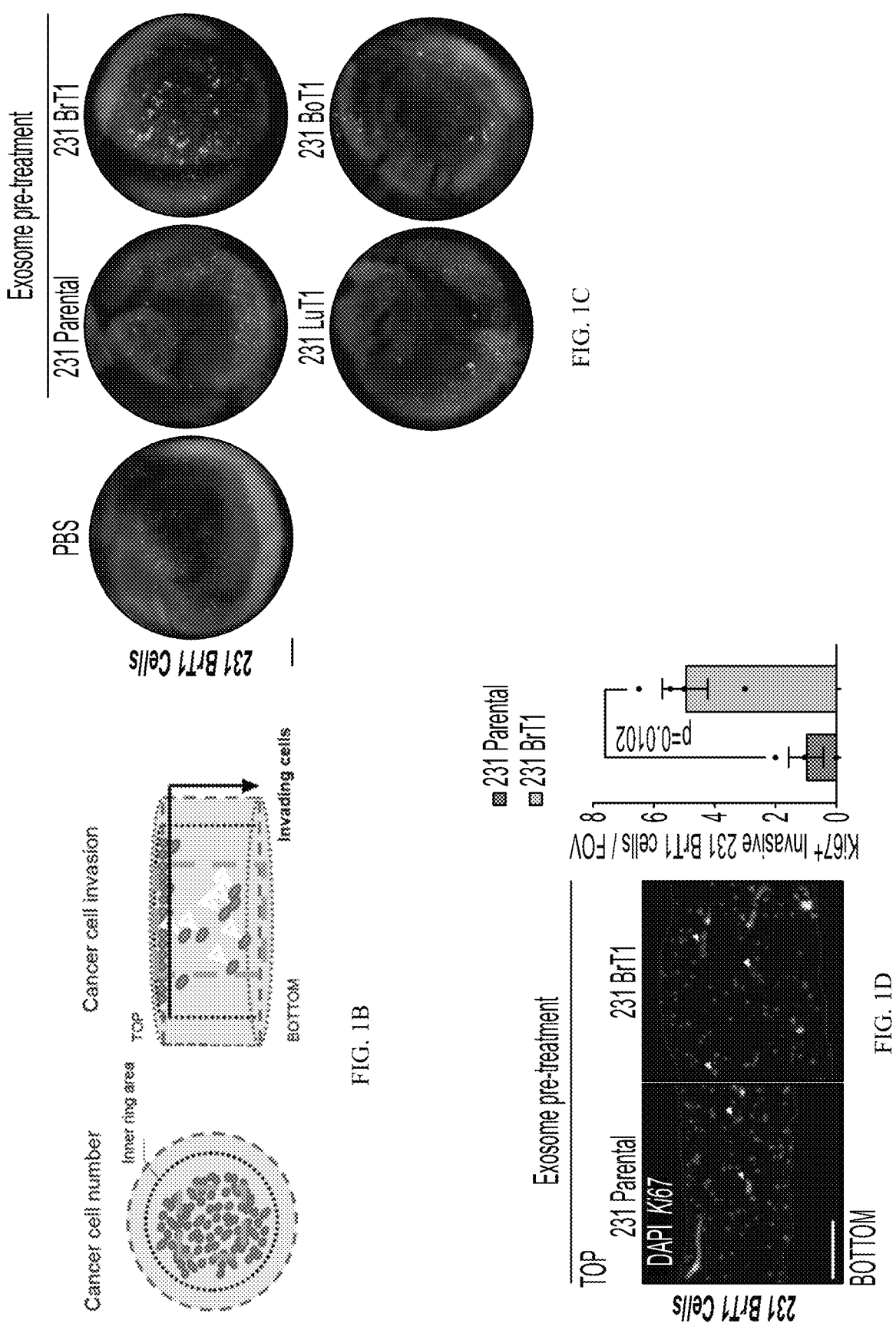
Figure 1E:
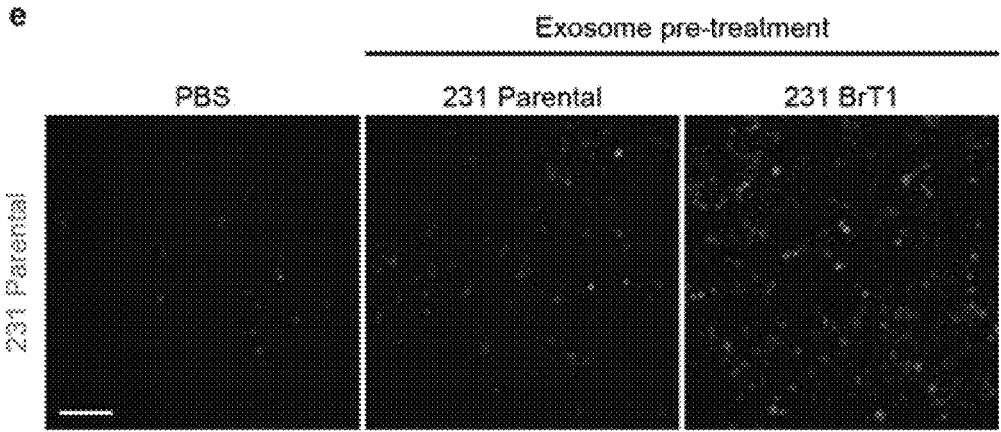
Figure 1E:
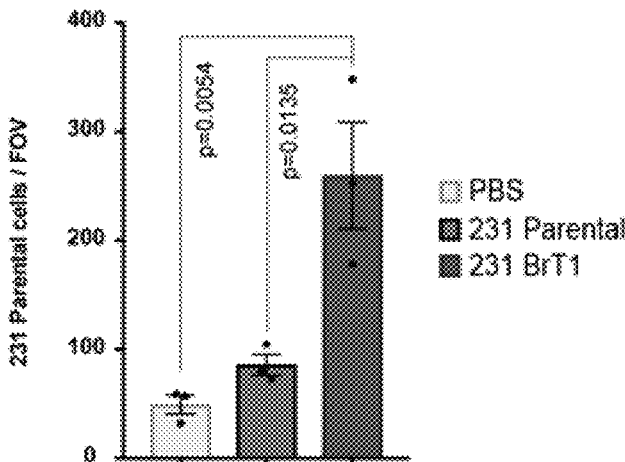
Figure 1F:
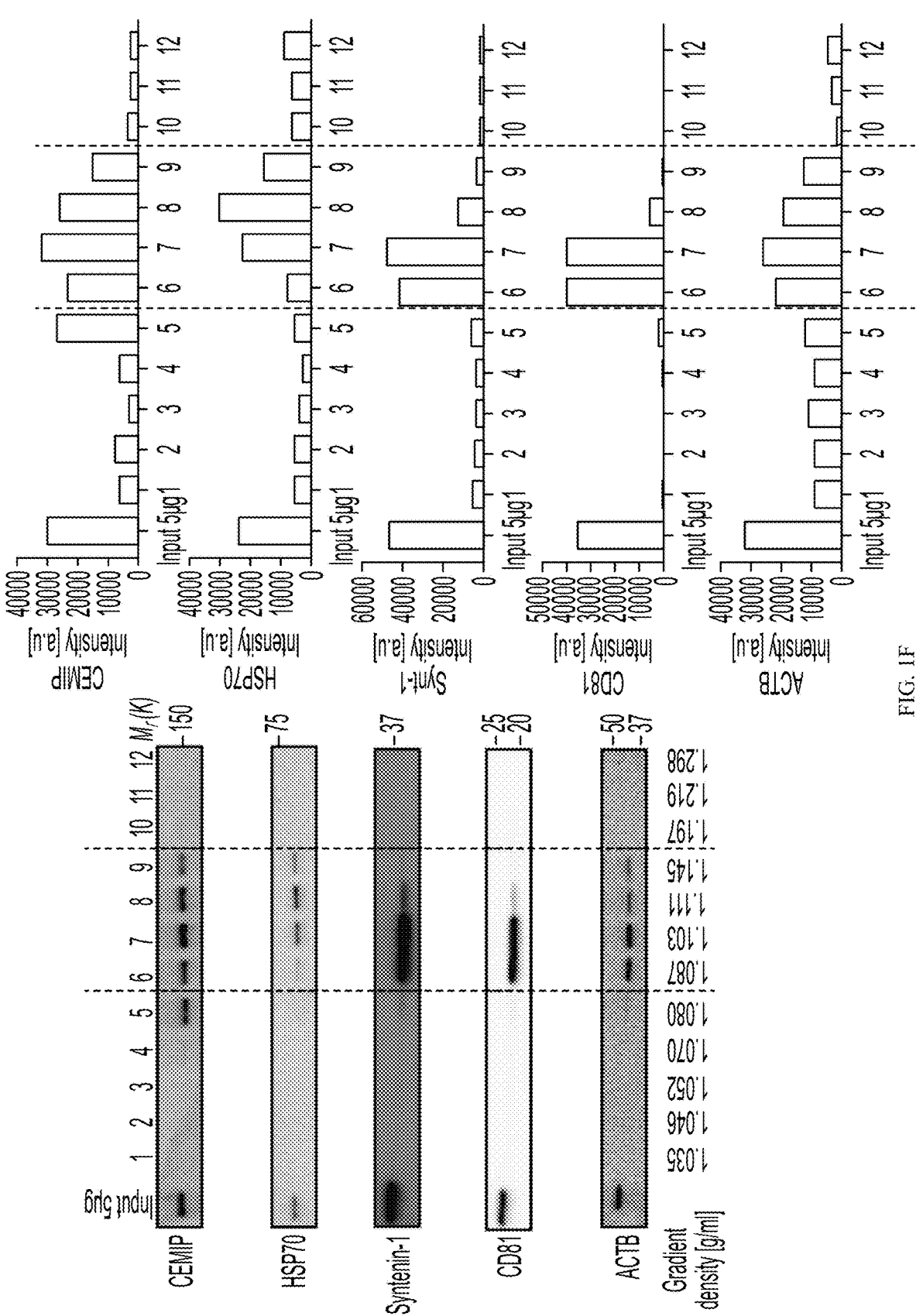

3 the effects of exosome pre-treatment on the brain microenvironment and cancer cell phenotypes (left, cancer cell number—whole brain slice mount; and right, cancer cell invasion-brain slice transversal section). Invading cells (white arrows) inside the region of interest, denoted by the blue square, are comprised of all cancer cells below the first layer of brain cells on the top of the brain slice. FIG. 1C shows representative whole slice fluorescence images of BrT1 GFP+ cells growing on top of brain slices pre-treated with exosomes or PBS. FIG. 1D, left, are representative immunofluorescence microscopy images of proliferating Ki-67+ BrT1 GFP+ cells invading brain slices pre-treated with exosomes. White and red arrows indicate invading Ki-67− or Ki-67+ cells, respectively. On the right, quantification of Ki-67+ invading cancer cell number is shown. FIG. 1E, top, shows representative fluorescence images of 231 parental mCherry+ cells growing on top of brain slices pre-treated with exosomes or PBS. On the bottom, quantification of 231 parental mCherry+ cell number is shown. FIG. 1F, left, is an immunoblot of CEMIP, small EV and exosomal markers (HSP70, Syntenin-1 and CD81) and ACTB in fractions obtained by OptiPrep™ density gradient ultracentrifugation (Freitas et al., "Different Isolation Approaches Lead to Diverse Glycosylated Extracellular Vesicle Populations," *J Extracell Vesicles* 8:1621131 (2019), which is hereby incorporated by reference in its entirety) of BrT1 exosomes. On the right, densitometry quantification of protein expression in the initial exosome population (Input) and across fractions with different density, given in arbitrary units [a.u.], is shown. Small EV and exosome-containing fractions are shown between dashed lines. The number of cells per FOV are averages±SEM, from n=3, 4. (FIG. 1D) and n=3 (FIG. 1E) individual brain slices, scoring two fields per slice. A representative experiment of three (FIGS. 1D-1E) or four (FIG. 1F) independent biological replicates is shown. Brain slice images (FIG. 1B) are representative of three independent biological replicates. Brain slice sections are stained with DAPI (blue), and dotted blue lines delineate the top and bottom limits of the brain slice (FIG. 1D). Scale bars, 500 μm (FIG. 1B) and 100 μm (FIGS. 1D-1E). Error bars depict mean±SEM. P values were calculated by ANOVA (FIG. 1E) or two-sided Student's t-test (FIG. 1D). See FIG. 6 for unprocessed blots. See Table 1 for statistics source data.

Figure 2A:
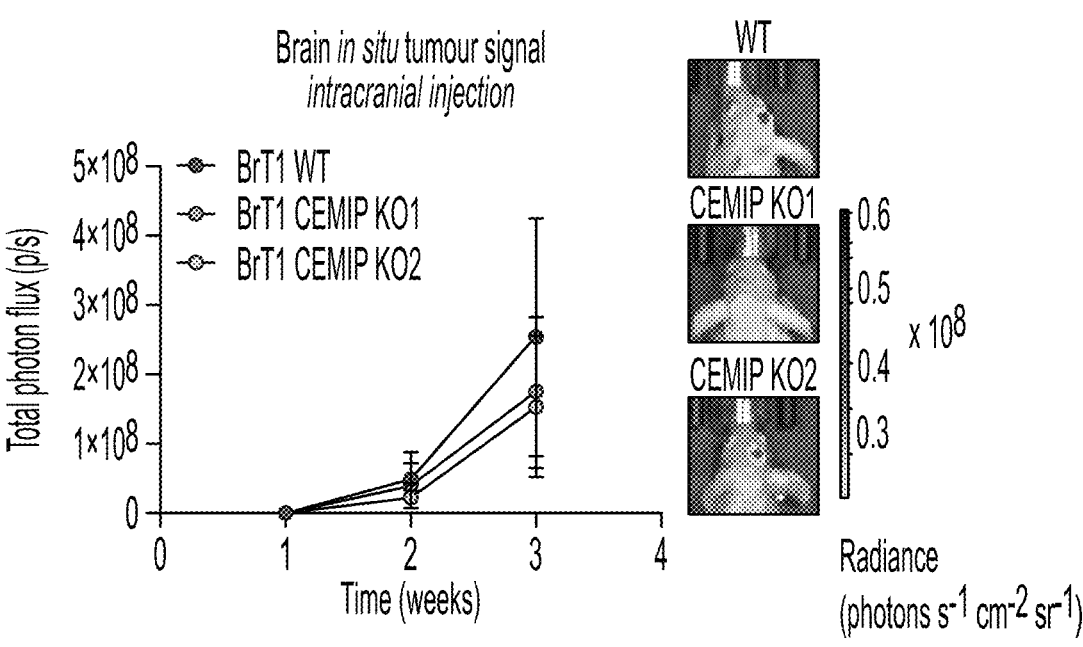
Figure 2B:
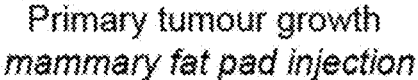
Figure 2B:
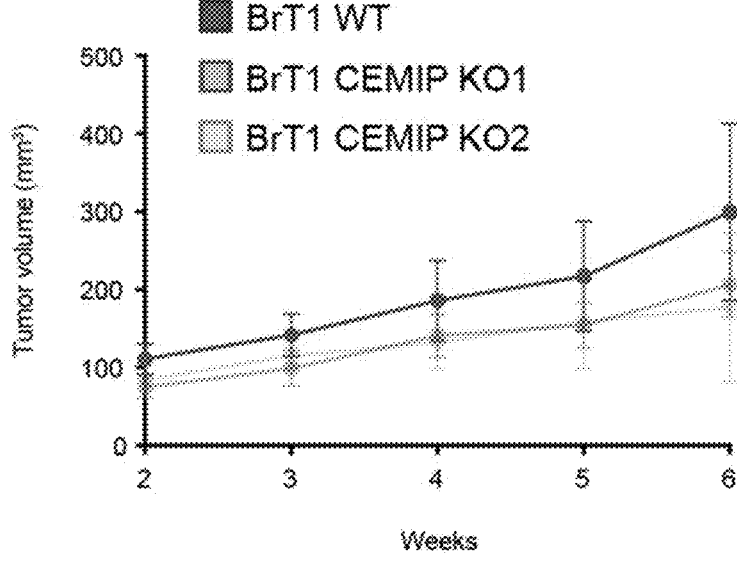

4 ranial injection of GFP-labelled BrT1 WT or BrT1 CEMIP-KO luciferase-positive cells is shown. On the right, a representative IVIS image of brain signal at week 3 is shown. FIG. 2B shows quantification of primary tumour growth (Wapnir et al., "The inverse relationship between microvessel counts and tumor volume in breast cancer," *Breast J* 7:184-188 (2001), which is hereby incorporated by reference in its entirety) in mice injected with BrT1 WT or BrT1 CEMIP-KO cells. One experiment with n=5 mice per experimental group was performed (FIGS. 2A-2B). See Table 1 for statistics source data.

Figure 3A:
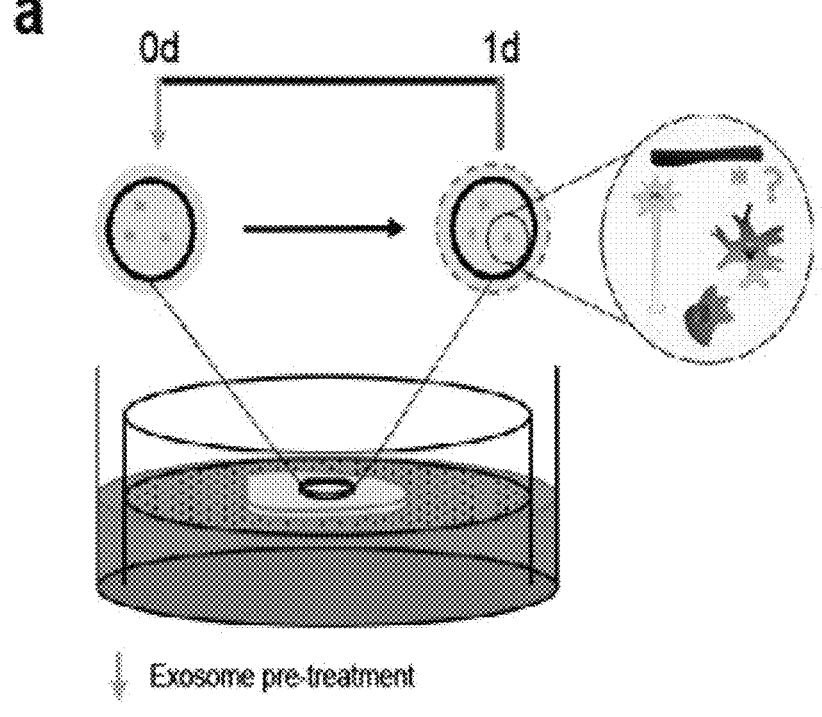
Figures 3B, 3C:
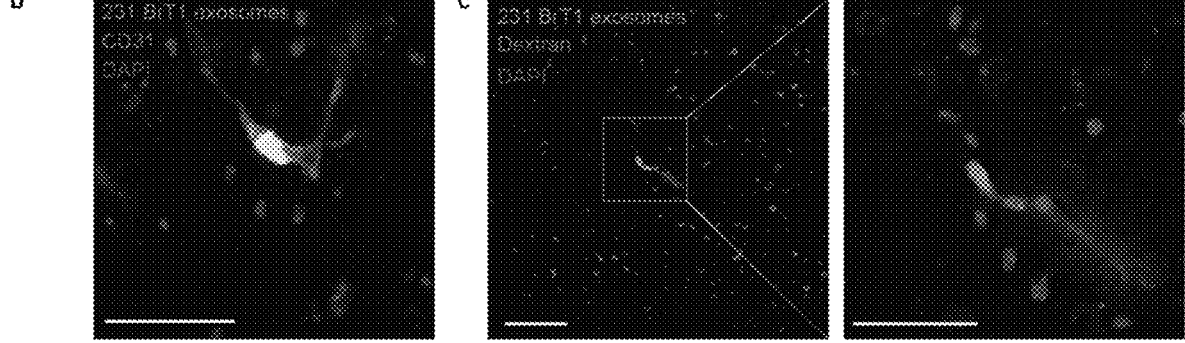
Figure 3D:
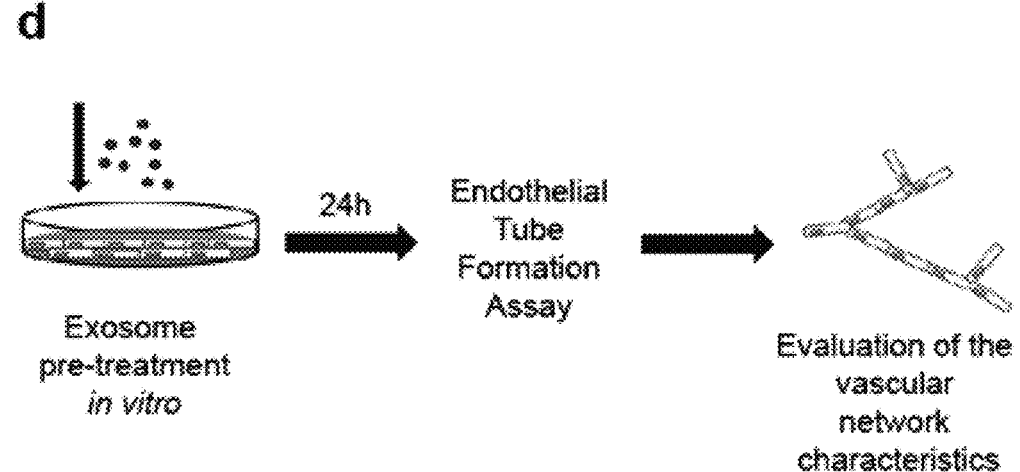
Figure 3E:
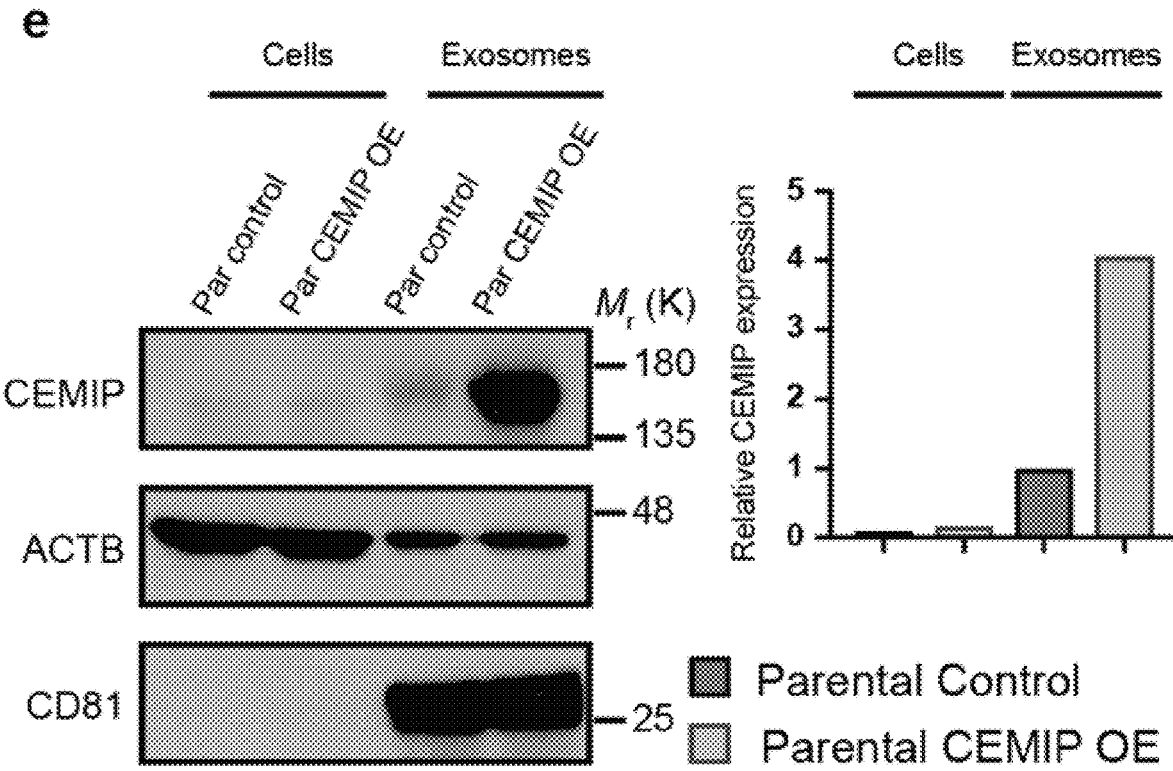
Figure 3F:
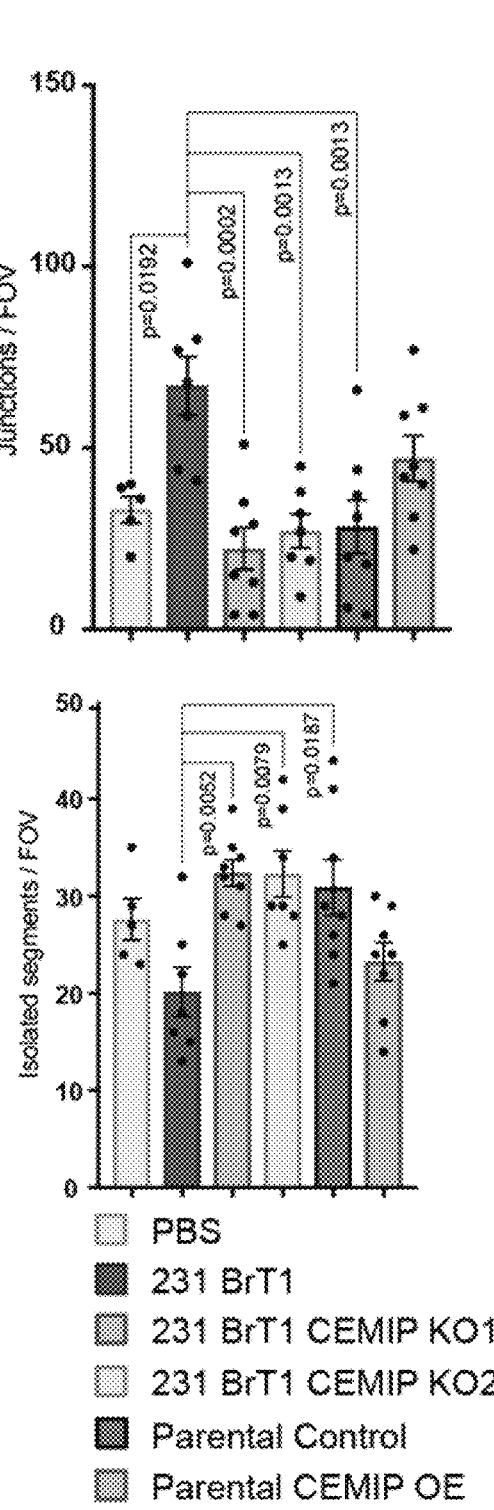

FIGS. 3A-3J show exosomal CEMIP affects BrEC biology and induces vascular remodeling. FIG. 3A is a schematic of the brain slice model setup for the study of exosome interaction with brain microenvironment resident cells. FIG. 3B is a representative fluorescence image of BrT1 exosomes (green) interacting with CD31+ BrECs (red) in vivo 24 hours post-intracardiac injection of labelled exosomes. FIG. 3B is a representative fluorescence image of BrT1 exosomes (green) and associated extravasated rhodamine-labelled Dextran (red) in the brain 24 hours post-intracardiac injection of labelled exosomes (right, enlarged inset). FIG. 3D shows a schematic of the ETF assay setup for studying exosome-dependent vascular network formation by isolated BrECs (Lis et al., "Conversion of Adult Endothelium to Immunocompetent Haematopoietic Stem Cells," *Nature* 545, 439-445 (2017); Seandel et al., "Generation of a Functional and Durable Vascular Niche by the Adenoviral E4ORF1 Gene," *Proc Natl Acad Sci USA* 105:19288-19293 (2008), which are hereby incorporated by reference in their entirety). FIG. 3E, left, shows an immunoblot of CEMIP expression in cells and exosomes of 231 parental Control and 231 parental CEMIP overexpressing (OE) models generated (Campeau et al., "A versatile viral system for expression and depletion of proteins in mammalian cells," *PLOS One* 4:e6529 (2009); Dull et al., "A Third-generation Lentivirus Vector with a Conditional Packaging System," *J Virol* 72:8463-8471 (1998), which are hereby incorporated by reference in their entirety). ACTB and the exosomal marker CD81 are shown below. On the right, densitometry quantification of CEMIP expression normalized to expression in 231 parental Control exosomes is shown. CEMIP expression was normalized to ACTB expression for each sample. FIG. 3F shows quantification of junction (top) and isolated seg-

TABLE 1

| | | | Total cells | | | | |
|---|---|---|---|---|---|---|---|
| | Tukey's multiple comparisons test | Mean Diff. | 95.00% CI of diff. | Significant? | Summary | Adjusted P Value | |
| ANOVA | PBS vs. Par | −23.67 | −74.21 to 26.88 | No | ns | 0.6701 | |
| | PBS vs. Br1 | −159.8 | −210.4 to −109.3 | Yes | **** | <0.0001 | |
| | PBS vs. Lu1 | 0.6111 | −49.94 to 51.16 | No | ns | >0.9999 | |
| | PBS vs. Bo1 | −35 | −85.55 to 15.55 | No | ns | 0.2952 | |
| | Par vs. Br1 | −136.2 | −186.7 to −85.62 | Yes | **** | <0.0001 | |
| | Par vs. Lu1 | 24.28 | −26.27 to 74.82 | No | ns | 0.6488 | |
| | Par vs. Bo1 | −11.33 | −61.88 to 39.21 | No | ns | 0.9674 | |
| | Br1 vs. Lu1 | 160.4 | 109.9 to 211.0 | Yes | **** | <0.0001 | |
| | Br1 vs. Bo1 | 124.8 | 74.29 to 175.4 | Yes | **** | <0.0001 | |
| | Lu1 vs. Bo1 | −35.61 | −86.16 to 14.94 | No | ns | 0.2789 | |

Figure 3G:
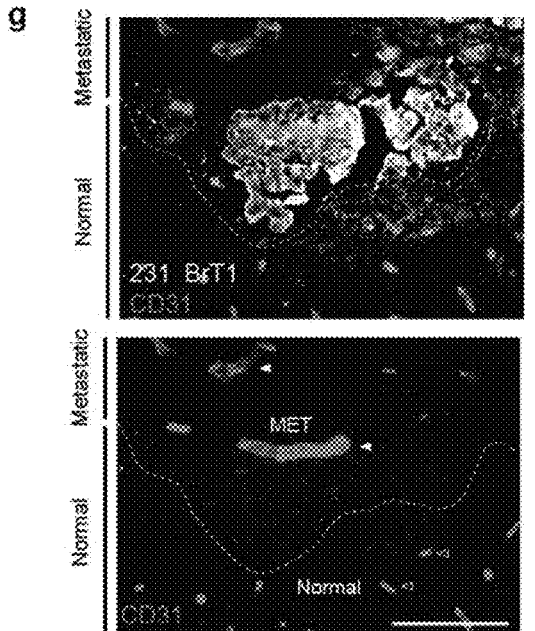
Figure 3G:
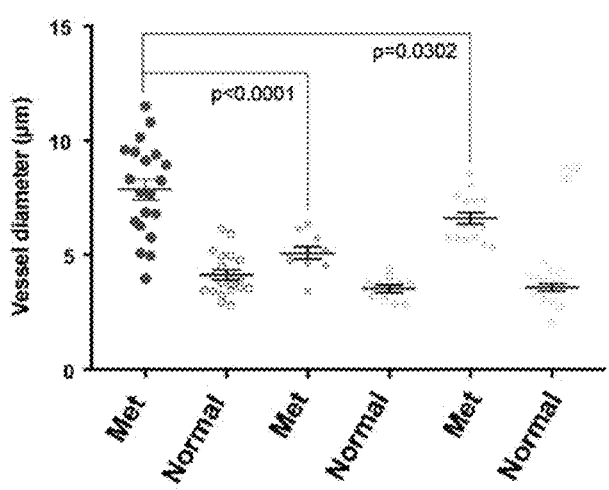

FIGS. 2A-2B show CEMIP loss does not affect primary tumour growth or in situ growth in the brain. FIG. 2A, left, shows quantification of brain metastatic in situ growth in mice intracranially injected with BrT1 WT or BrT1 CEMIP-KO cells. Cranial bioluminescence signal (Total photon flux-photons/second (p/s)) in mice over 3-weeks post-intracment (bottom) number in the vasculature formed upon pre-treatment with exosomes or PBS. FIG. 3G, left, is a representative fluorescence image of tumour vasculature (red) in BrT1 brain metastases (white). On the right, quantification of metastatic tumour and normal vessel diameter in brains from mice injected intracardiacally with BrT1 WT,

6

Figure 3H:
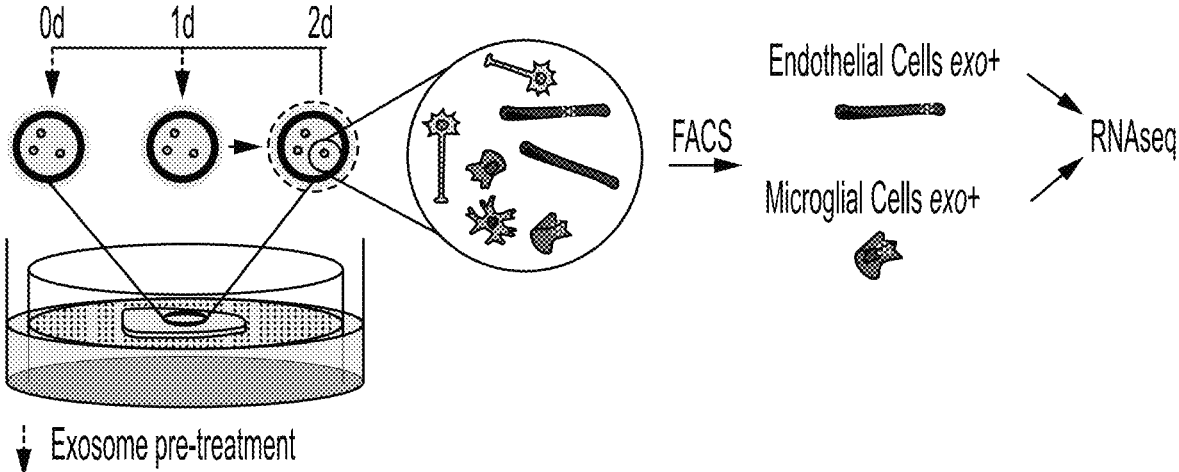
Figure 3I:
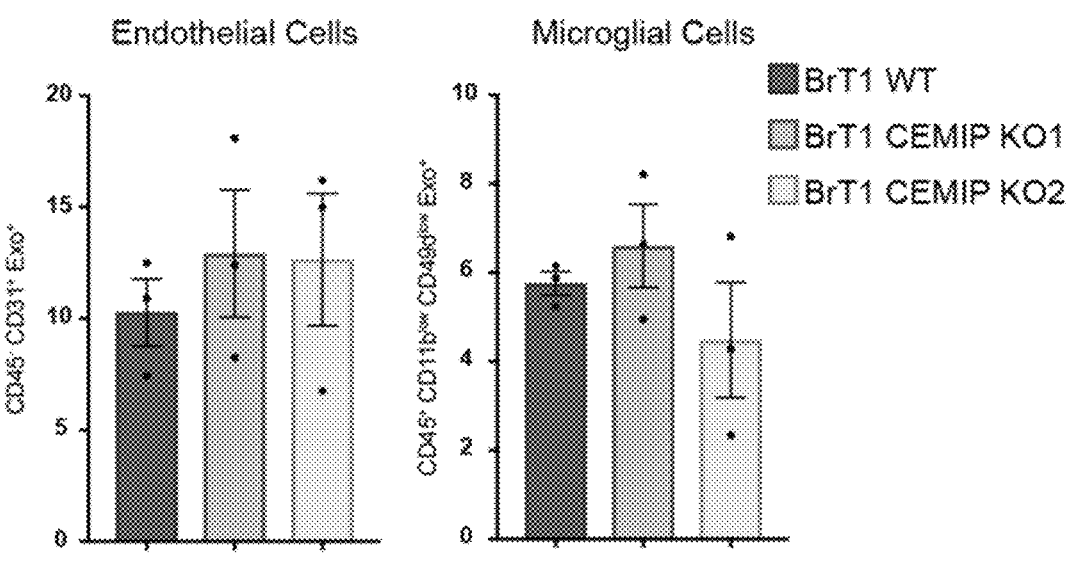
Figure 3J:
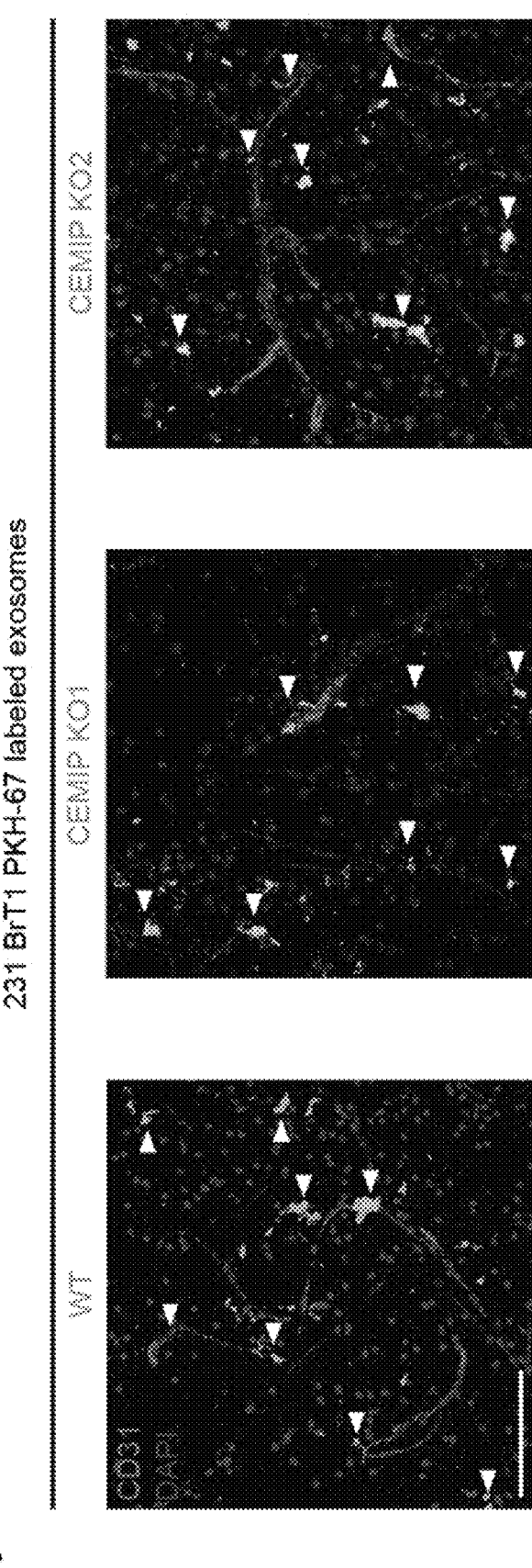

BrT1 CEMIP-KO1 or -KO2 cells is shown. FIG. 3H shows a schematic of the brain slice model setup for studying exosome-induced gene expression changes in stromal cells of the brain. Brain slices were pre-treated with BrT1 WT, BrT1 CEMIP-KO1 or -KO2 cell-derived fluorescently-labelled exosomes. FIG. 3I shows flow cytometry analysis of exosome uptake. Percentage of exosome-positive (Exo⁺) endothelial (CD45⁻ CD31⁺) and microglial (CD45⁺ CD11b^{low} CD49d^{low})[13] cells in brain slices is shown. FIG. 3J shows representative confocal images of the adhesion of fluorescently-labelled BrT1 WT, BrT1 CEMIP-KO1 or -KO2 exosomes with endothelial cells (CD31+) in the brain slice. Arrows indicate co-localization of exosomes (green) with endothelial cells (red). For in vivo experiments, n=4 mice were analyzed per group (FIG. 3G). Individual vessel diameter was obtained from the average of three measurements along the extension of the vessel. Metastatic tumour and normal brain vascular diameters were scored in up to 5 individual metastatic lesions across two sagittal sections from different brain areas per individual presenting brain metastases (FIG. 3G). The number of junctions and isolated segments per FOV are averages±SEM, from n=5, 7, 8, 7, 8, 8 individual μ-slide angiogenesis chamber wells (FIG. 3F), scoring a representative field per μ-slide well. A representative experiment is shown from three independent biological replicates (FIGS. 3E-3F). Graphs depicting endothelial and microglial cell exosome uptake and tumour vasculature diameter (FIG. 3I and FIG. 3G) display the average of three and two independent biological replicates, respectively. Immunofluorescence images of in vivo exosome uptake by BrECs, vascular leakiness and confocal images of the interaction and BrEC exosome uptake in the brain slice (FIGS. 3B, 3C and 3J) are representative of three independent biological replicates. Scale bars, 50 μm (FIG. 3B), 50 μm and 100 μm (FIG. 3C), 100 μm (FIG. 3G) and 75 μm (FIG. 3J). Error bars depict mean±SEM. P values were calculated by ANOVA (FIG. 3F, 3G, 3I). See FIG. 6 for unprocessed blots. See Table 1 for statistics source data.

Figure 4A:
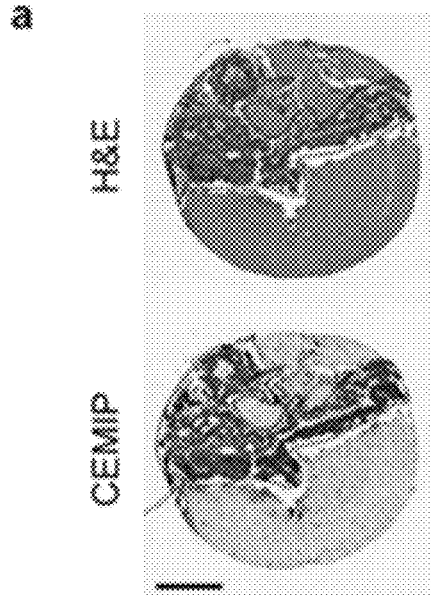
Figure 4B:
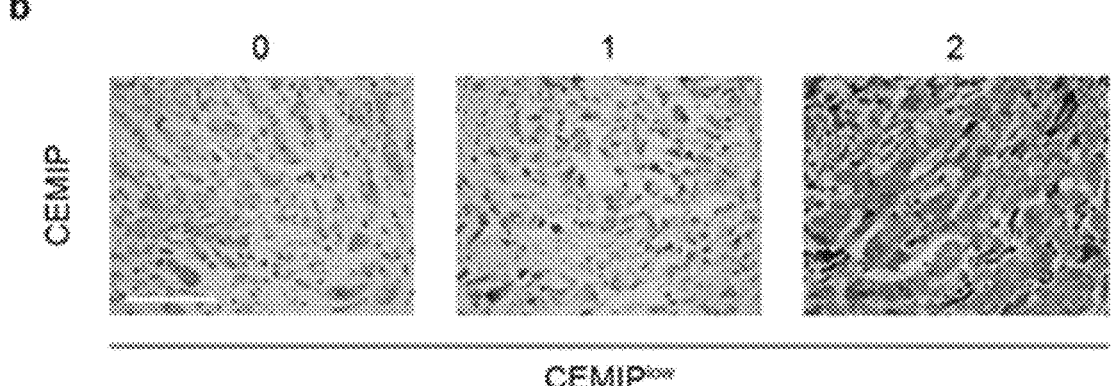
Figure 4C:
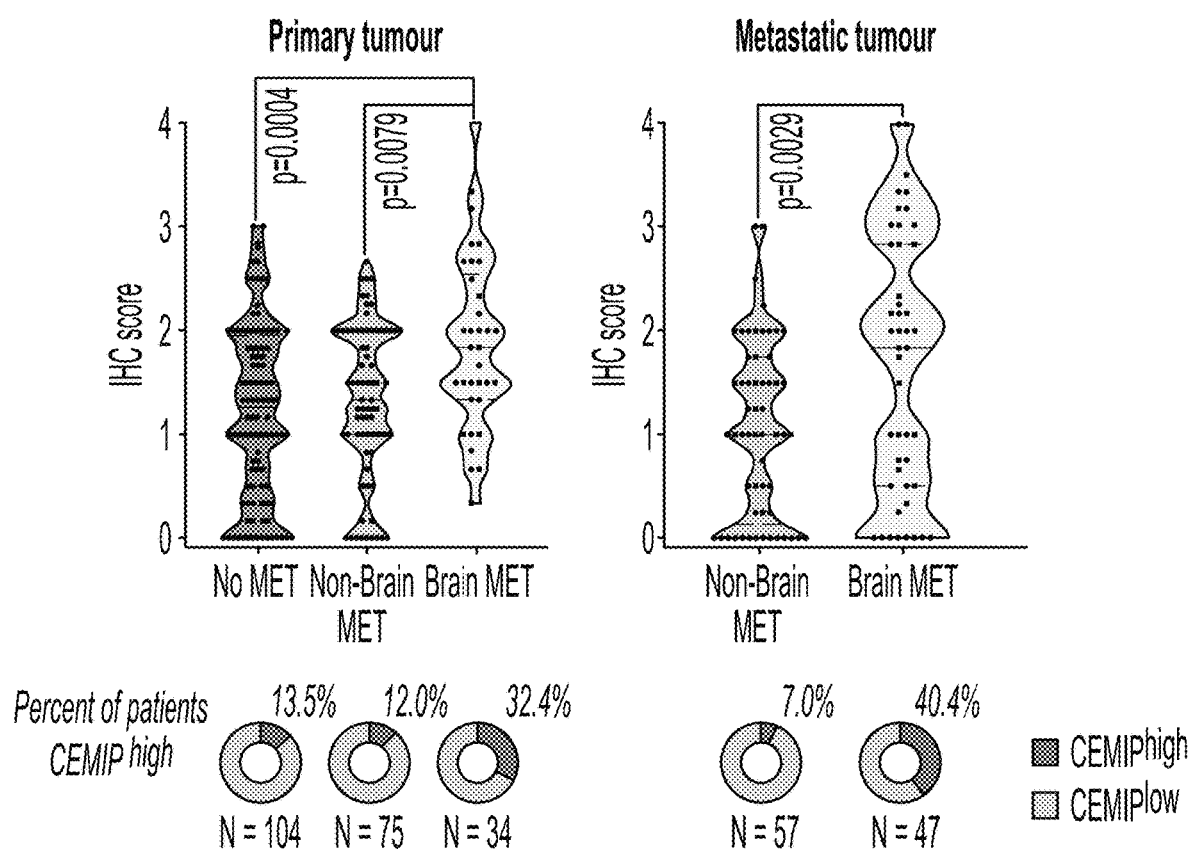
Figure 4D:
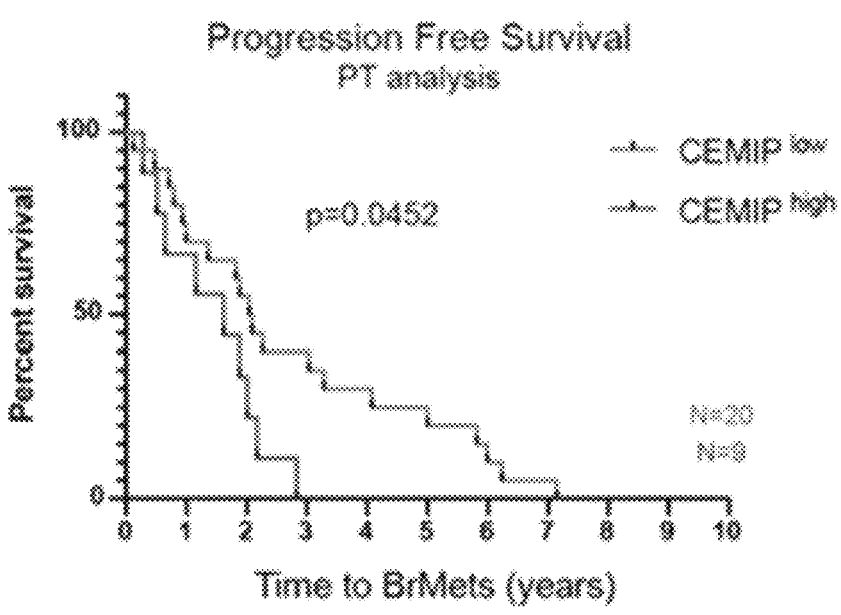

FIGS. 4A-4D show CEMIP is a prognostic biomarker of brain metastasis in patients. FIG. 4A is a representative image of a lung cancer brain metastatic tumour patient sample analyzed by H&E (top) and CEMIP immunohistochemistry (bottom). The metastatic tumor is outlined by the black dashed line. FIG. 4B shows representative immunohistochemistry images illustrating CEMIP expression for each scoring category in patient tumour samples. Samples with no (0) or low (1 and 2) CEMIP staining were considered CEMIP^{low} (green). Samples displaying high expression (3 and 4) were considered CEMIP^{high} (red). FIG. 4C, top, shows quantification of CEMIP expression by immunohistochemistry in primary tumour (left) and metastatic tumour (right) from patients with or without brain metastasis. On the bottom, the percentage of CEMIP^{high} cases and information on total number of samples evaluated in each group is shown. PT (Minimum: 0.00, 0.00, 0.33; Maximum: 3.00, 2.67, 4.00; and Median: 1.25, 1.33, 1.83), and MET (Minimum: 0, 0; Maximum: 3, 4; and Median: 1.00, 1.83). FIG. 4D is a progression-free survival Kaplan-Meier curve for brain metastasis patients depicting time to brain metastasis based on primary tumour CEMIP expression, low (green) or high expression (red). Scale bars, 50 μm (FIG. 4A), and 300 μm (FIG. 4B). Human data consists of n=317 total unique tumour samples (213 primary and 104 metastatic) from 278 breast and lung cancer patients (FIGS. 4A-4C). Immunohistochemistry score represents the average intensity in tumour cores analyzed (1-3 per sample) on a scale from 0 to 4 (FIG. 4B). Dashed line across violin plots depicts quartiles and full line depicts median (FIG. 4C). P values were calculated by ANOVA and two-sided Student's t-test (FIG. 4C), or Log-rank (Mantel-Cox) test (FIG. 4D). See Table 1 for statistics source data.

Figure 5A:
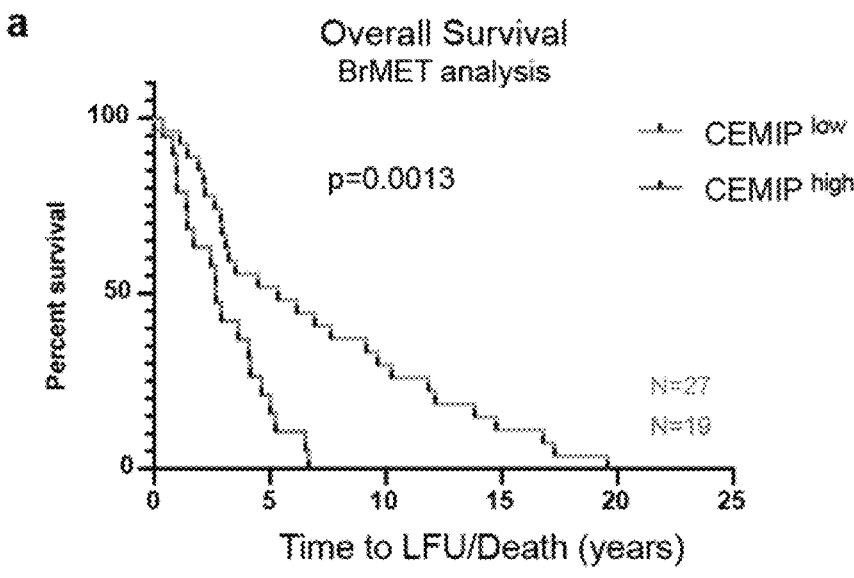
Figure 5B:
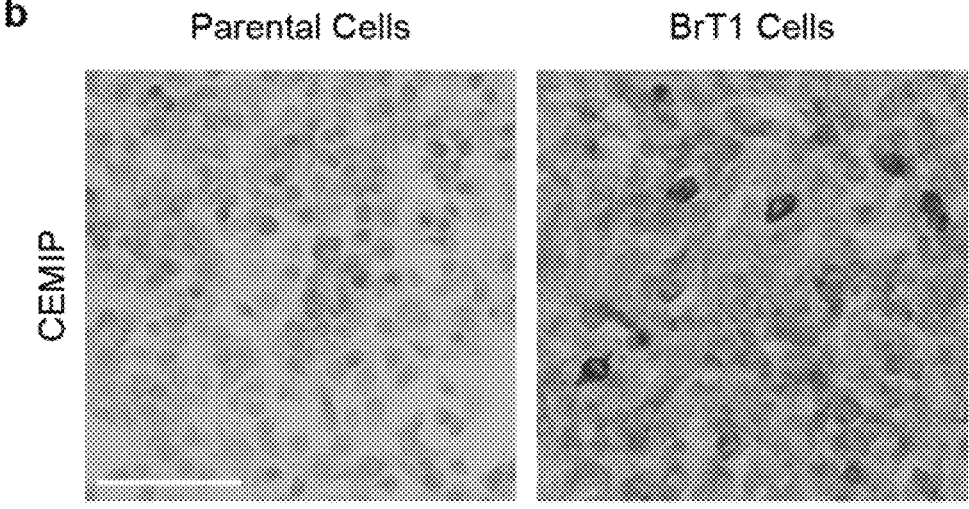
Figure 5C:
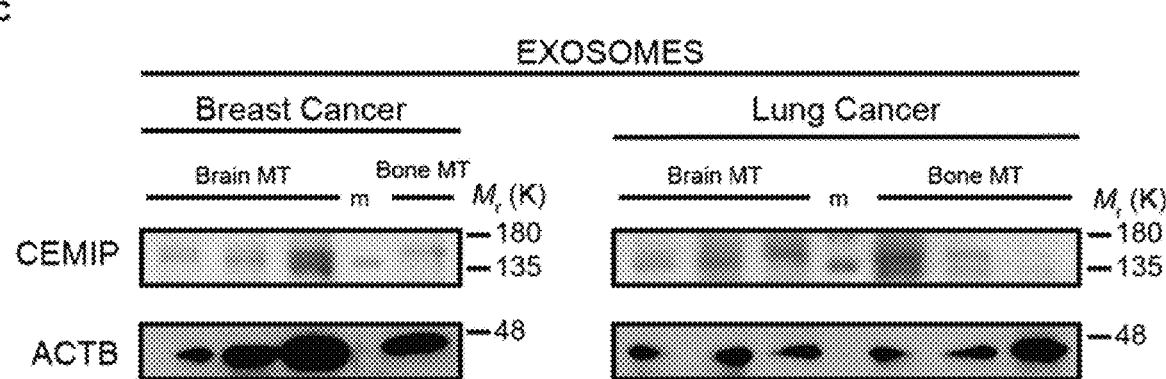
Figure 5D:
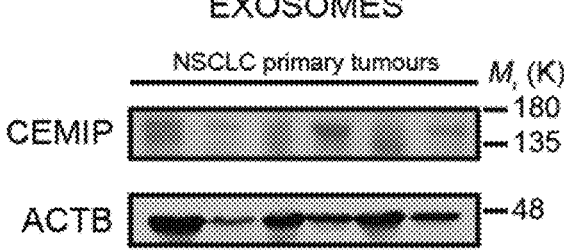

FIGS. 5A-5D show CEMIP is a biomarker of BrM and is present in exosomes from patients. FIG. 5A is a Kaplan-Meier survival curve for brain metastasis patients depicting time to last follow up (LFU) or death from time of primary tumour diagnosis based on low (green) or high (red) CEMIP expression in brain metastatic tumour. FIG. 5B is a representative image of CEMIP expression in 231 parental and BrT1 cells in vitro by immunohistochemistry. FIG. 5C is an immunoblot of CEMIP expression in exosomes collected from culture of human brain and bone metastatic tissue explants resected from patients. ACTB was used as loading control. Marker indicated by m. FIG. 5D is an immunoblot of CEMIP expression in exosomes collected from culture of human non-small cell lung cancer primary tumour tissue resected from patients. ACTB was used as a loading control. IHC images (FIG. 5B) and immunoblots (FIGS. 5C-5D) are representative of one experiment. Scale bars, 100 μm (FIG. 5B). P values was calculated by Log-rank (Mantel-Cox) test (FIG. 5A). See FIG. 6 for unprocessed blots. See Table 1 for statistics source data.

Figure 6:
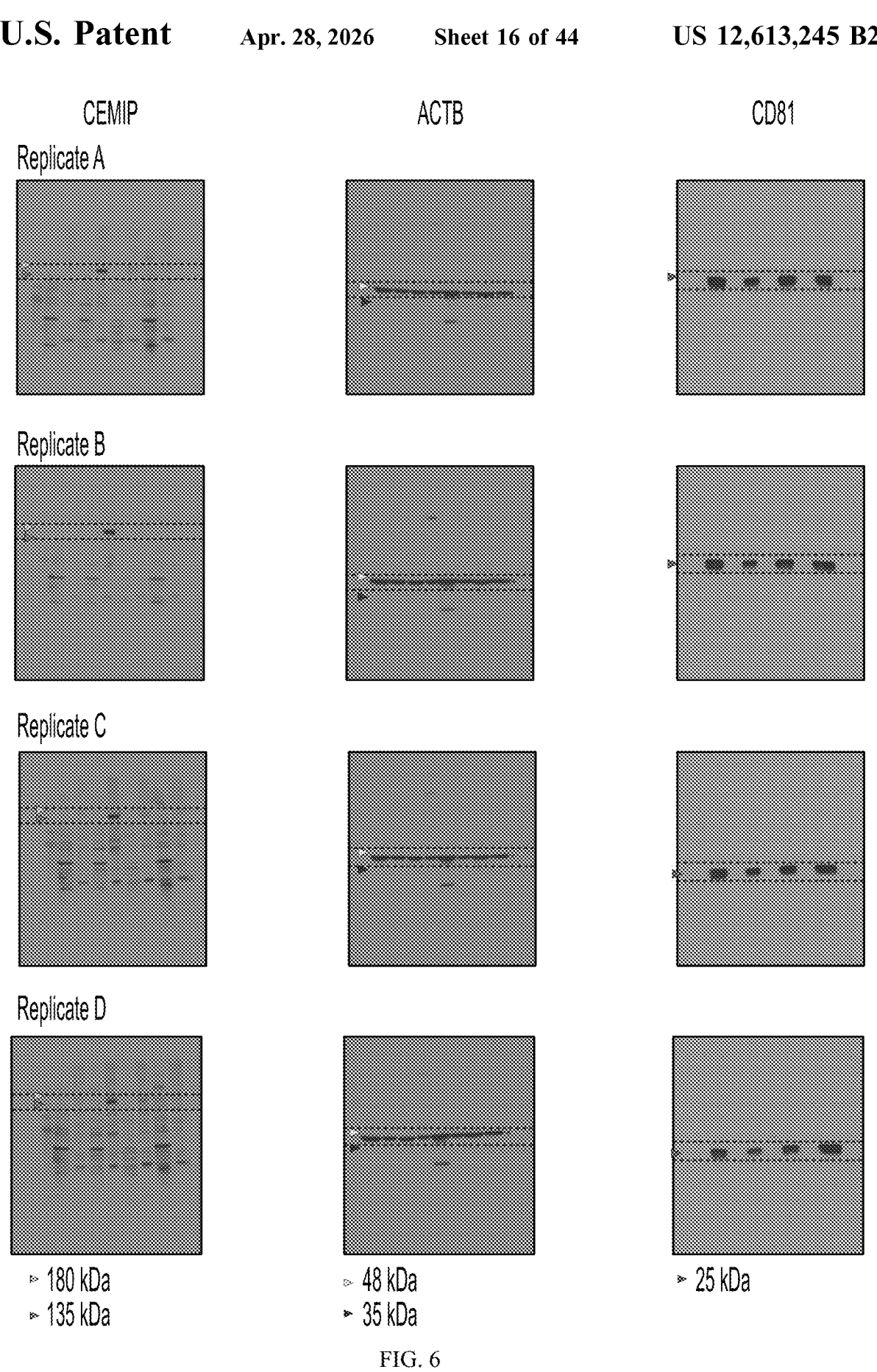
Figure 6:
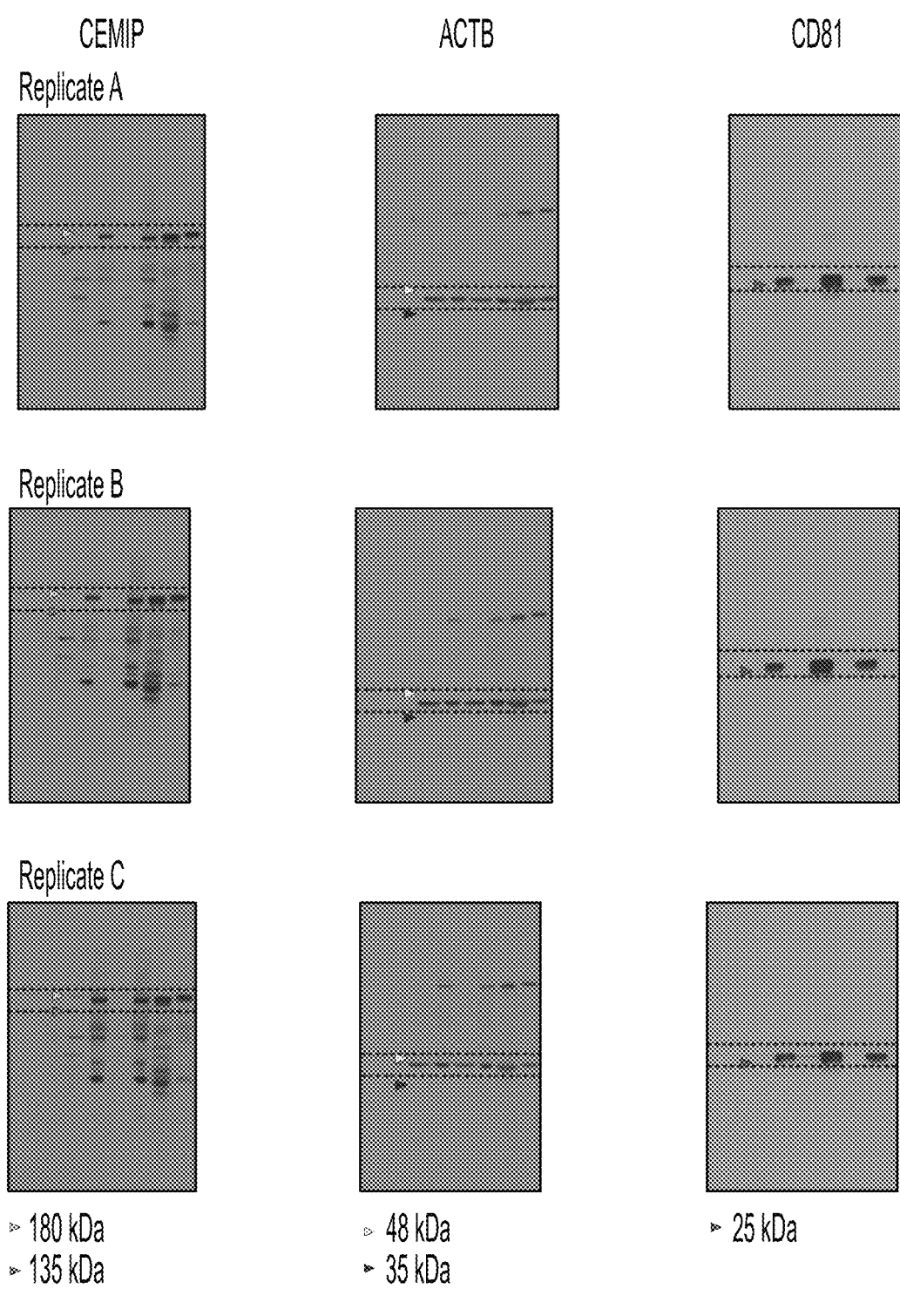
Figure 6:
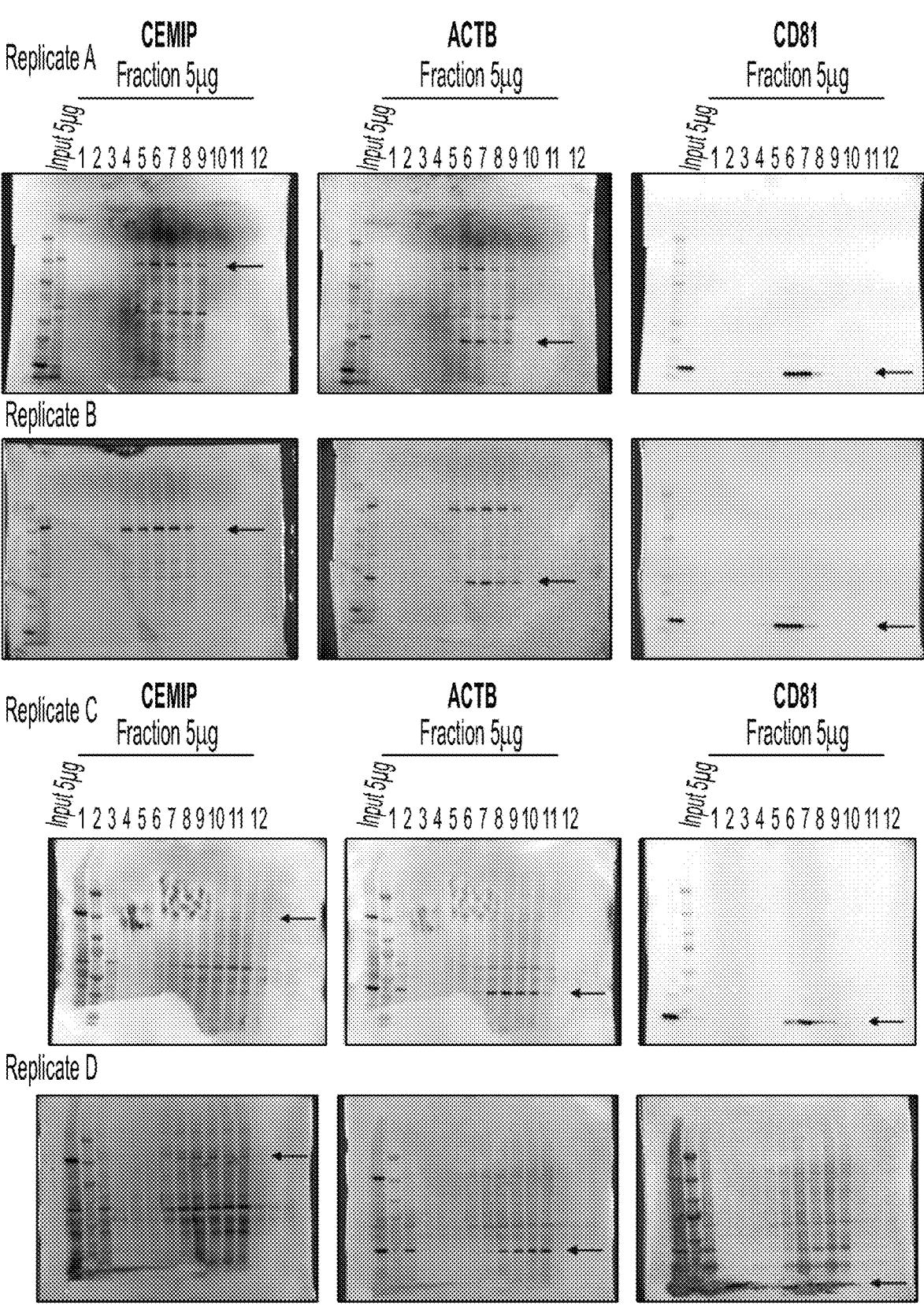
Figure 6:
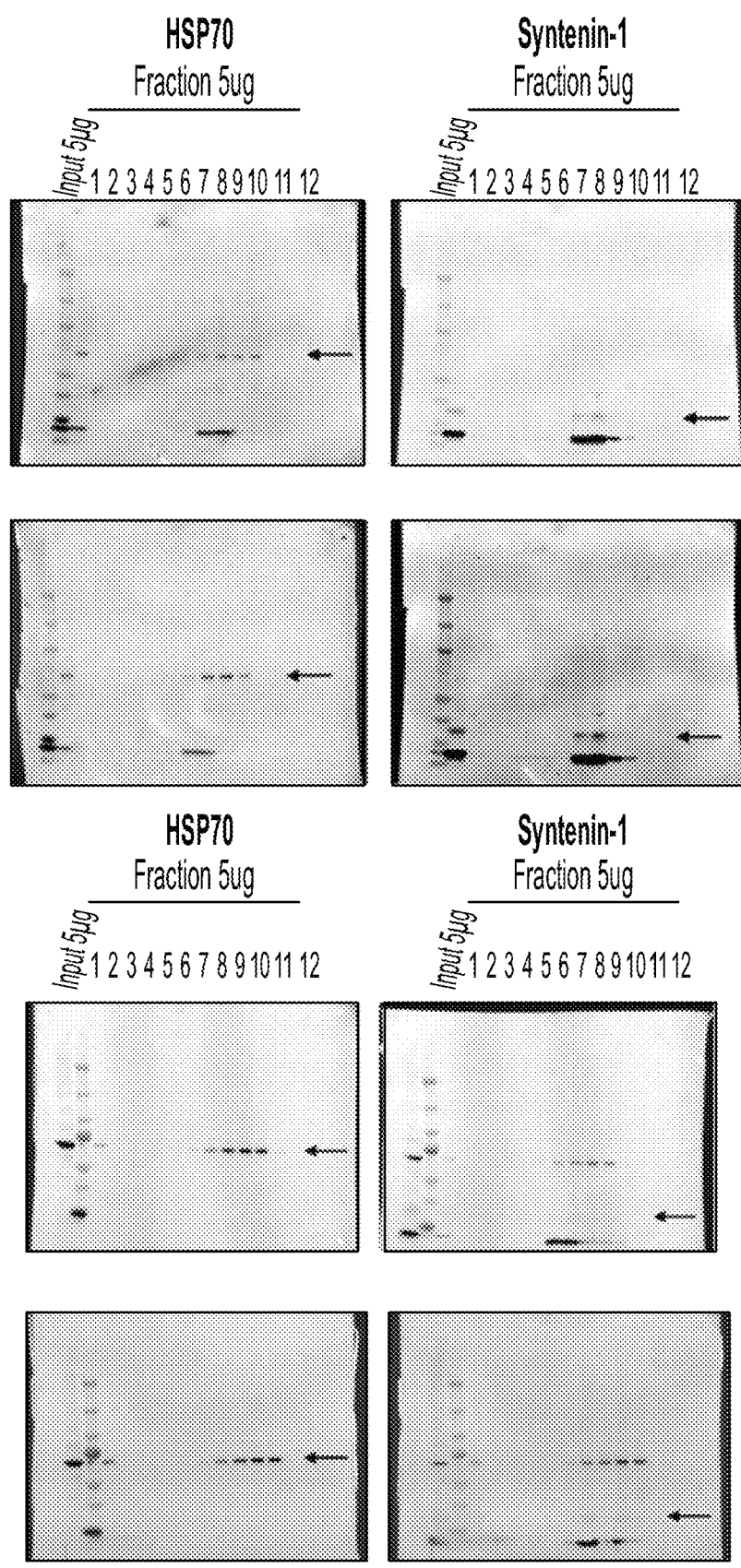
Figure 6:
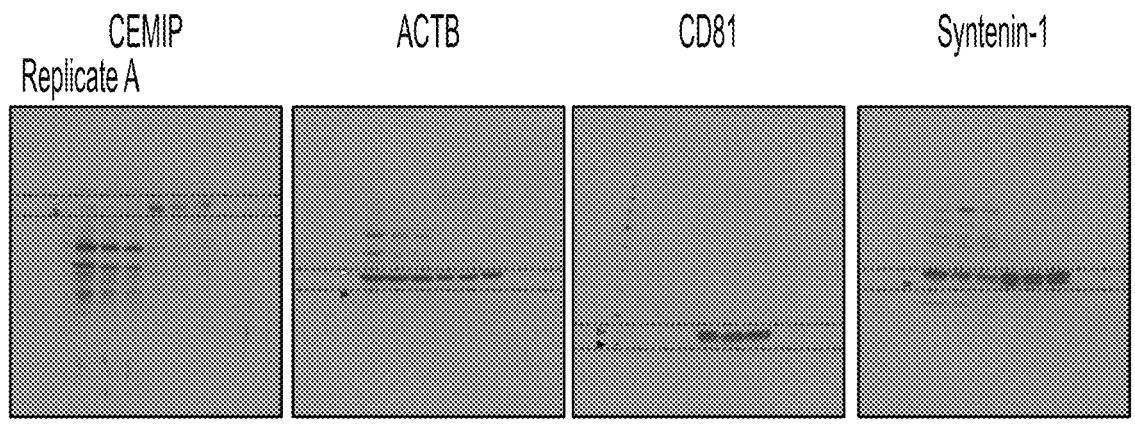
Figure 6:
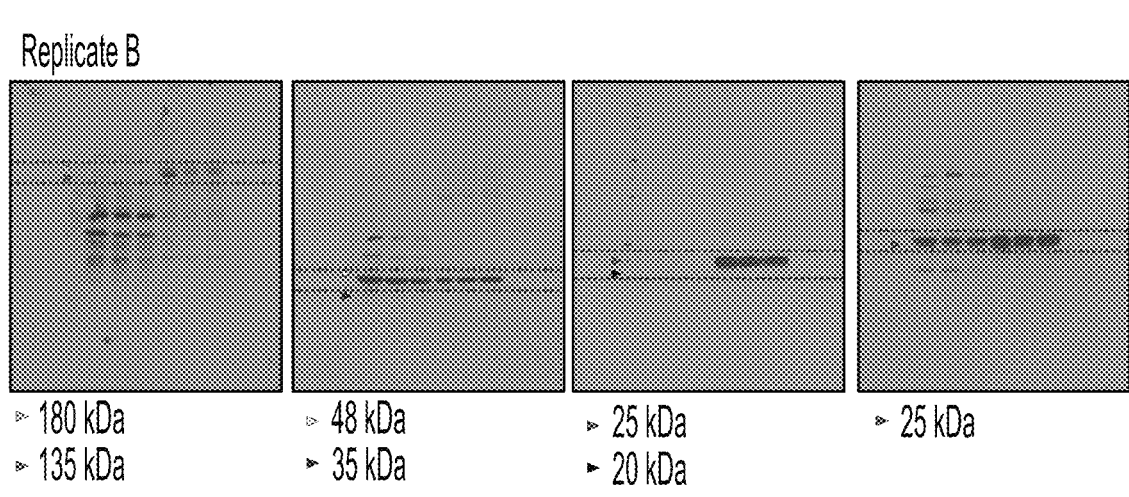
Figure 6:
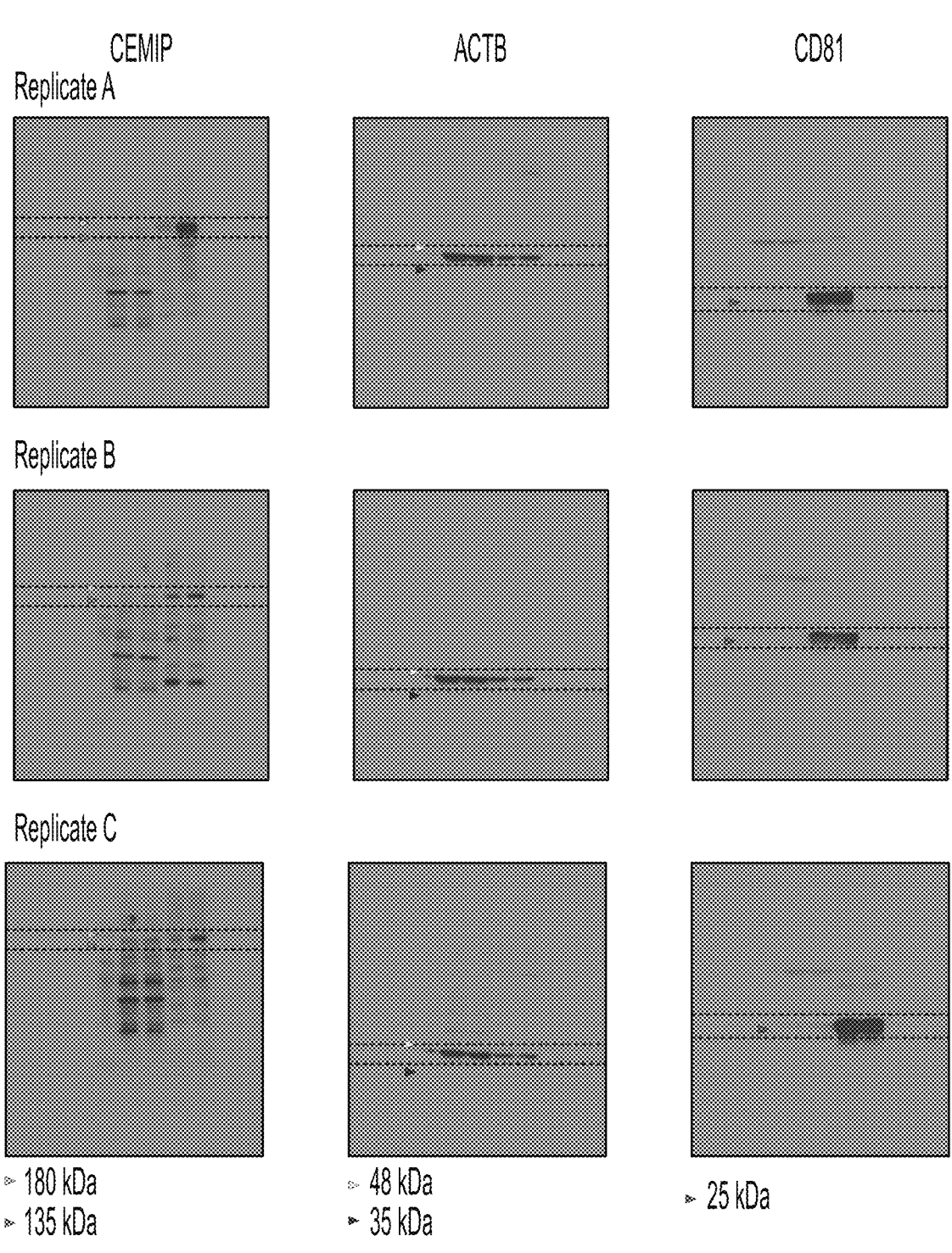
Figure 6:
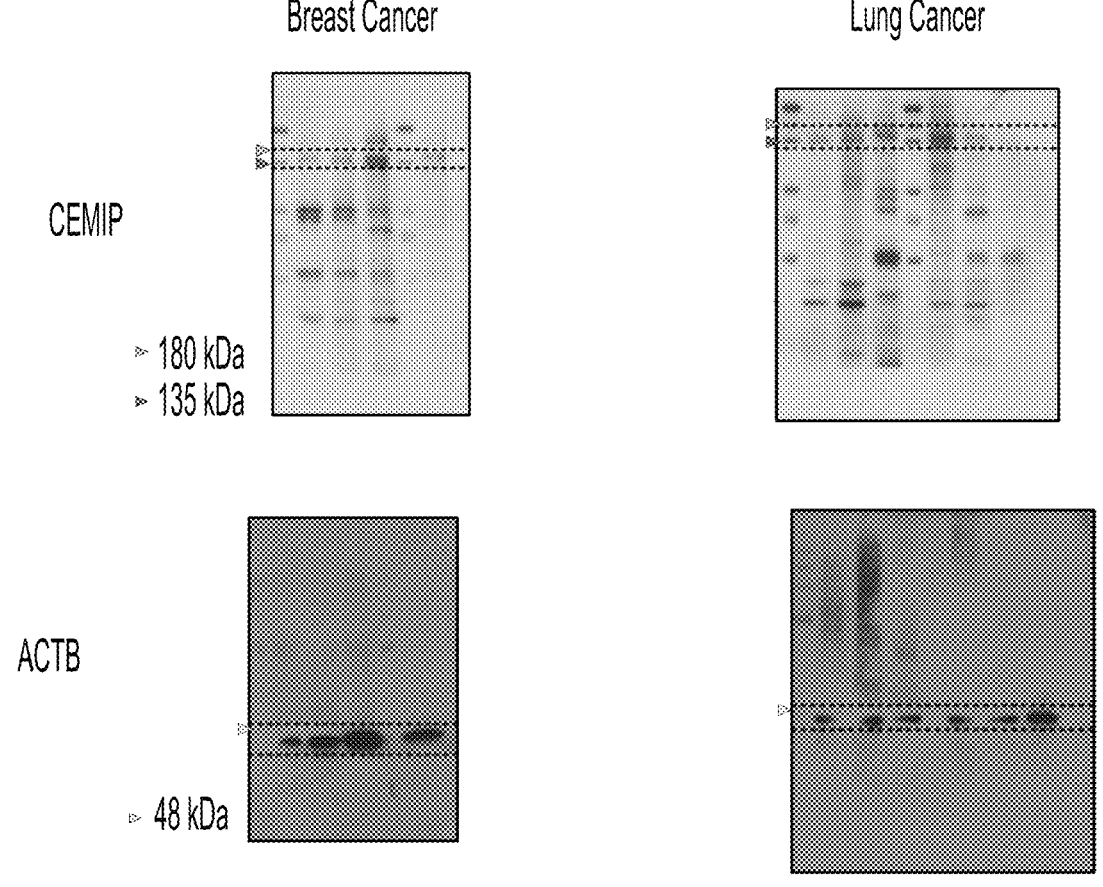
Figure 6:
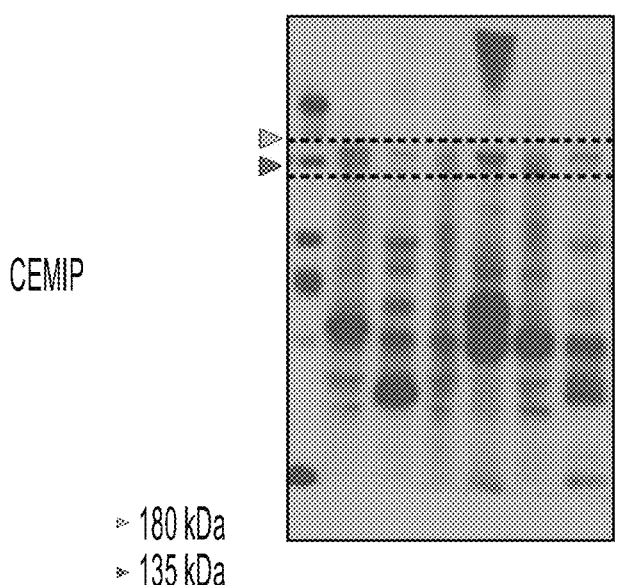
Figure 6:
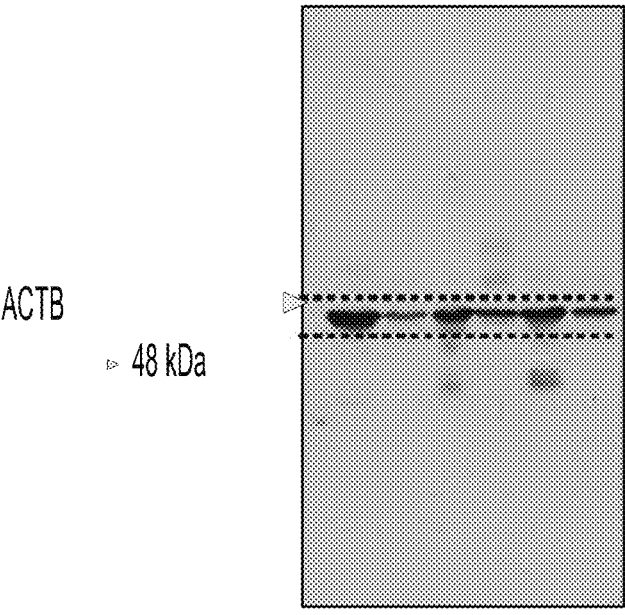
Figure 7A:
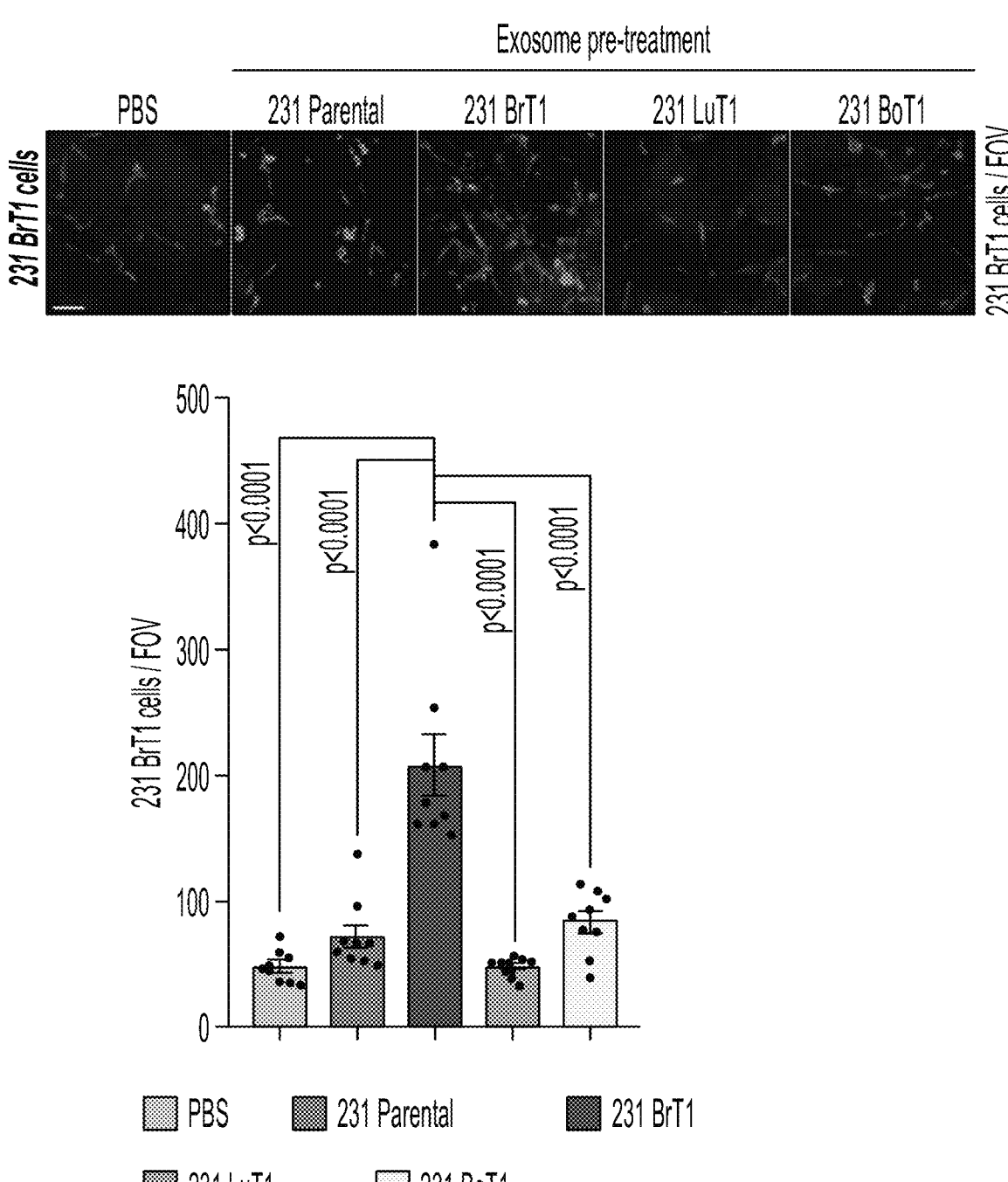
Figure 7B:
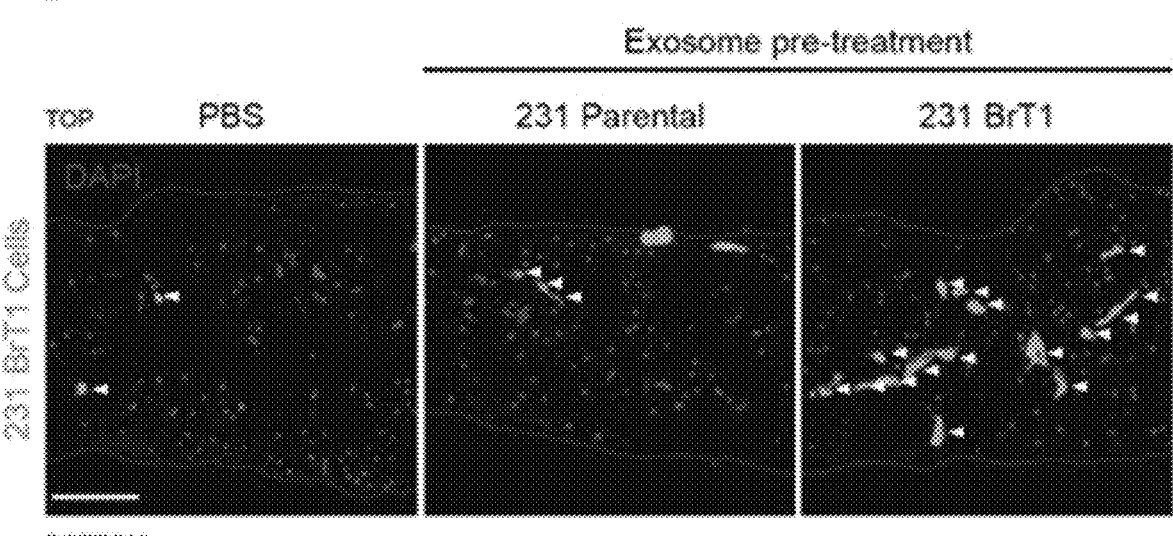
Figure 7B:
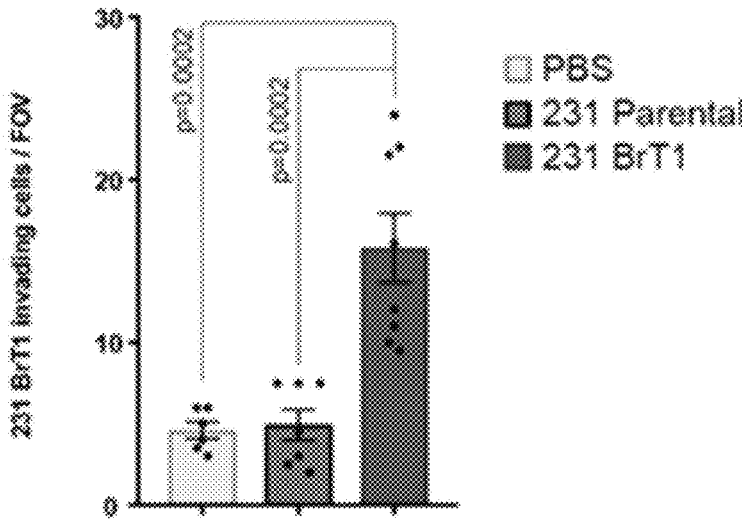
Figure 7C:
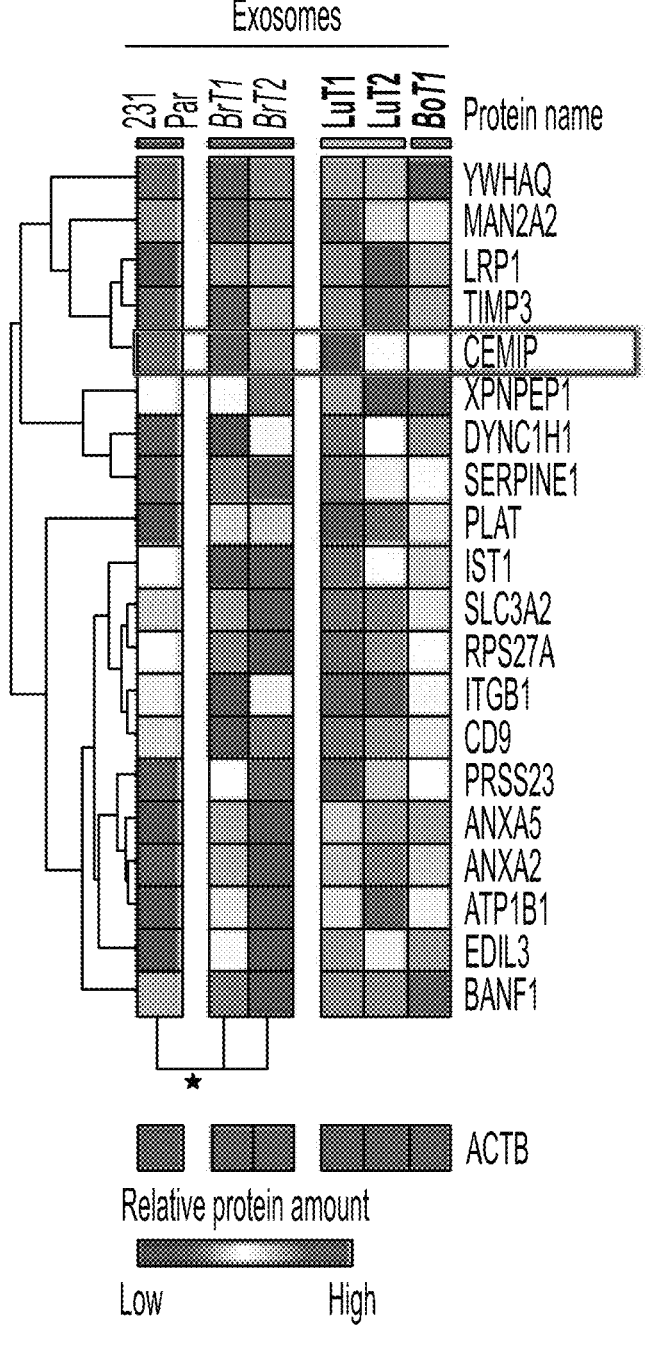
Figure 7D:
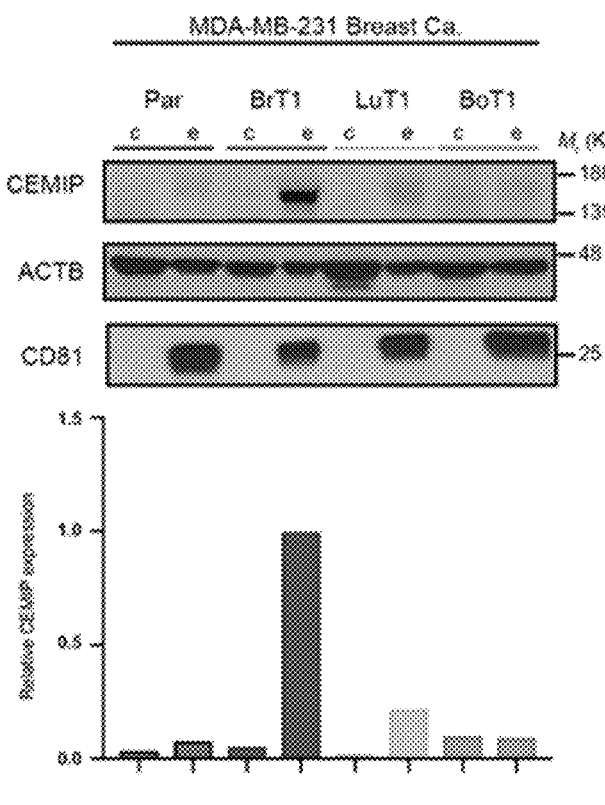

FIG. 6 shows Western blot replicates for FIG. 7D (Replicate C is shown in figure).

Figure 7E:
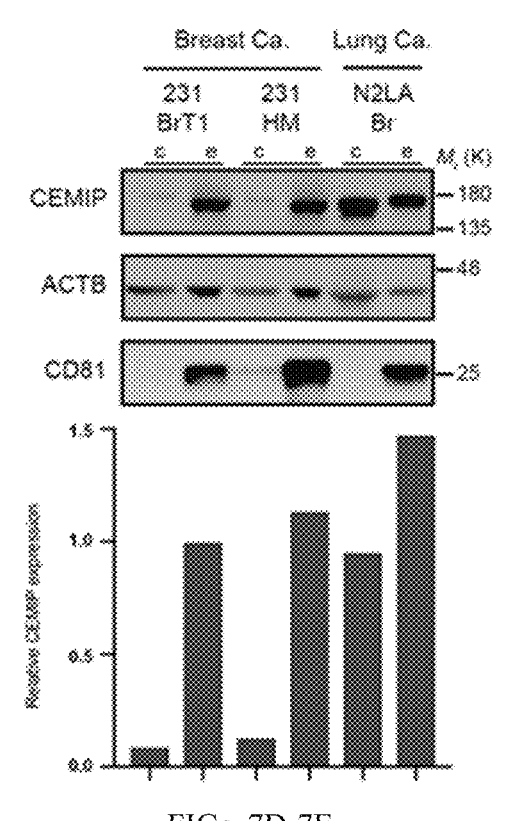

FIGS. 7A-7D show exosomes from brain metastatic cells support brain metastatic colonization and are enriched in CEMIP protein. FIG. 7A, top, shows representative images of 231 BrT1-GFP+ cells growing on top of brain slices pre-treated with exosomes or PBS. On the bottom, quantification of cancer cell number is shown. FIG. 7B, top, shows representative images of 231 BrT1-GFP+ cells invading brain slices pre-treated with exosomes or PBS. Brain slice sections were stained with DAPI (blue); dotted blue lines delineate the top and bottom limit of the brain slice. On the bottom, quantification of invading cancer cell number is shown. FIG. 7C is a heatmap of 20 differentially expressed exosomal proteins and β-Actin (ACTB) based on the quantitative mass spectrometry label-free quantification (LFQ) values (technical triplicates, *FDR—false discovery rate <0.05 by ANOVA). Hierarchical clustering (one minus the sample Spearman's rank of correlation between observations) was performed on protein expression levels. FIG. 7D, top, shows CEMIP, ACTB (loading control), and CD81 (exosomal marker) immunoblot in cells and exosomes from organ-specific metastasis models. Bottom, densitometry quantification of CEMIP. FIG. 7E, top, shows CEMIP, ACTB (loading control), and CD81 (exosomal marker) immunoblot in cells and exosomes from human cancer cell brain metastasis models. At the bottom, densitometry quantification of CEMIP is shown. The number of cells per field of view (FOV) are averages±SEM, from n=9 individual brain slices (FIG. 7A), or n=6, 7, 8 individual brain slices (FIG. 7B), scoring two fields per slice (FIGS. 7A-7B). The heatmap depicting differentially expressed proteins in BrT-derived exosomes displays average of three independent exosome sample replicates (FIG. 7C). Densitometry graphs show CEMIP expression normalized to CEMIP expression in BrT1 exosomes, and CEMIP expression was normalized to ACTB for each sample (FIGS. 7D-7E). A representative experiment of three (FIGS. 7A, 7B, and 7E) or four (FIG. 7D) independent biological replicates is shown. Scale bars, 100 μm (FIGS. 7A-7B). Error bars depict mean±standard error of the mean (SEM). P values were calculated by ANOVA (FIGS. 7A-7B). See FIG. 6 for unprocessed blots. See Table 1 for statistics source data.

Figure 8A:
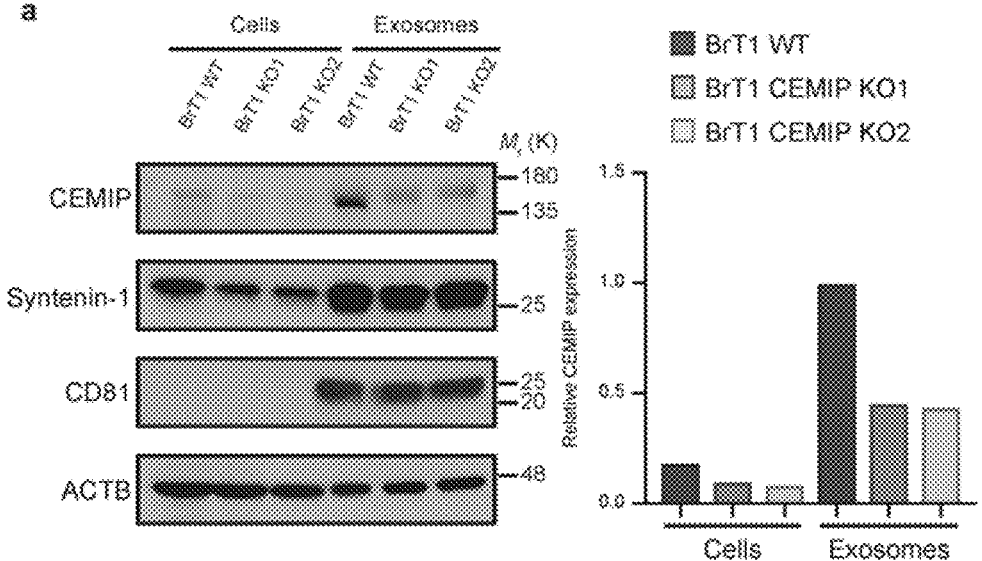
Figure 8B:
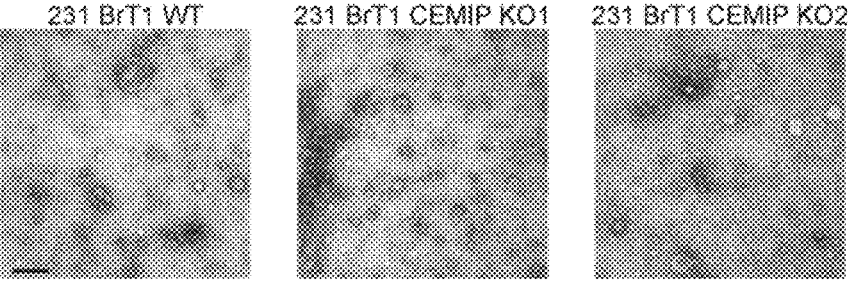
Figure 8C:
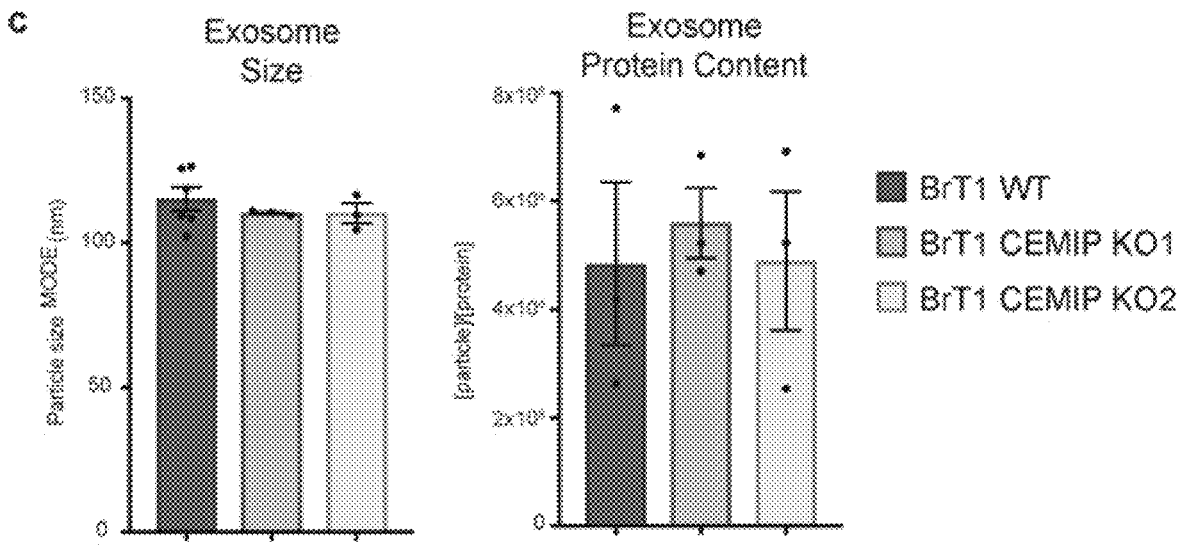
Figure 8D:
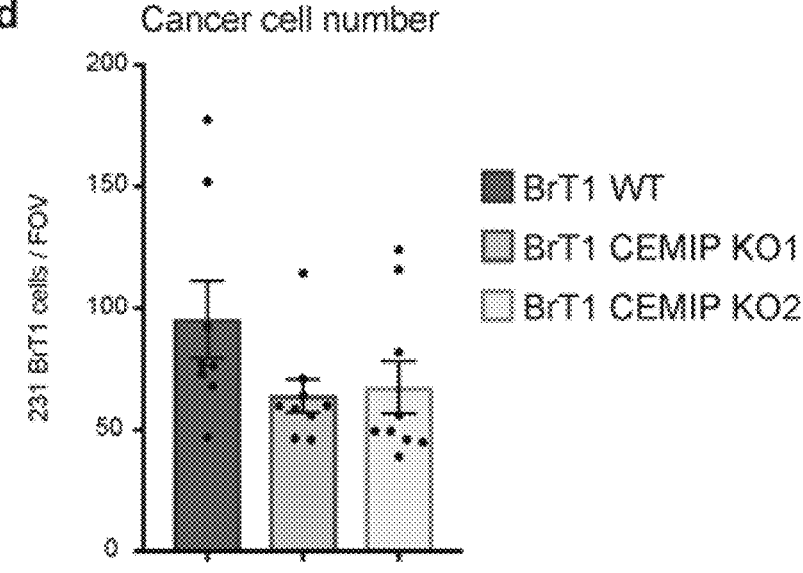
Figures 8E, 8F, 8G, 8H:
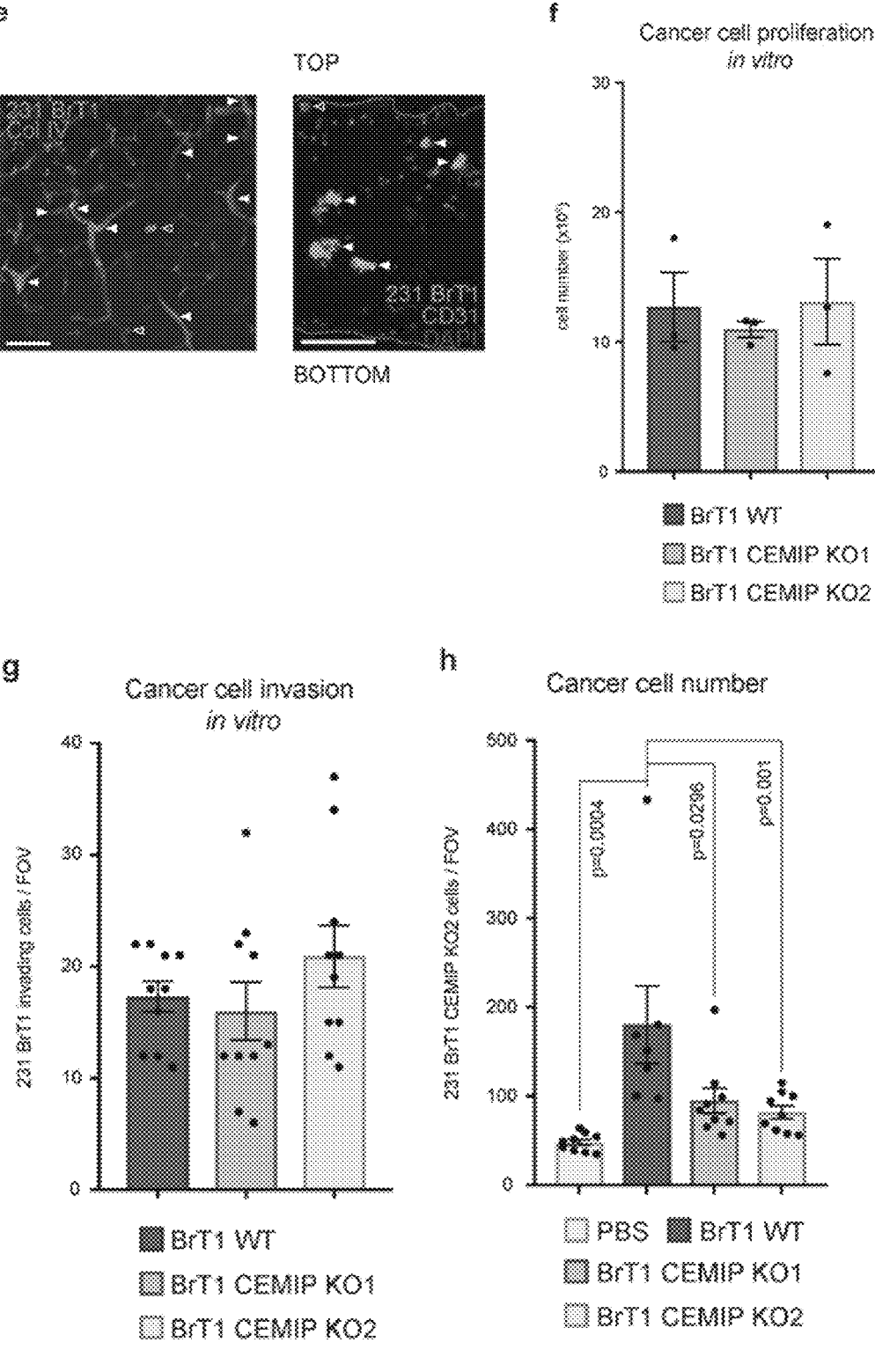

FIGS. 8A-8H show exosomal CEMIP modulates the brain vascular niche to support metastasis. FIG. 8A, left, is an immunoblot of CEMIP expression in cell and exosomal protein extracts from BrT1 WT and BrT1 CEMIP knockout (KO1 and KO2) cells. Immunoblotting for exosomal markers (Syntenin-1 and CD81) and ACTB is shown below. On the right, densitometry quantification of CEMIP normalized to the CEMIP expression in BrT1 WT exosomes is shown. CEMIP expression was normalized to ACTB expression for each sample. FIG. 8B shows transmission electron microscopy (TEM) of BrT1 WT and BrT1 CEMIP-KO1 and -KO2 exosomes. FIG. 8C shows size distribution and protein content analysis of BrT1 WT and BrT1 CEMIP-KO1 and -KO2 exosomes. Exosome size (mode, nm) and number were evaluated by NanoSight particle tracking. Protein content per exosome ([particle]/[protein]) was assessed by factoring in the protein concentration. FIG. 8D shows quantification of BrT1 WT and 231 BrT1 CEMIP-KO1 and -KO2 GFP+ cell number on top of brain slices. FIG. 8E, left, is a representative fluorescence microscopy image of BrT1 GFP+ cells growing on top of the brain slice. On the right, a representative fluorescence microscopy image of BrT1 GFP+ cells invading the brain slice in transversal section is shown. FIG. 8F shows quantification of proliferation of BrT1 WT and BrT1 CEMIP-KO1 and -KO2 cells in vitro over three days. FIG. 8G shows quantification of transwell Matrigel invasion of BrT1 WT and BrT1 CEMIP-KO1 and -KO2 cells in vitro over 24 hours. FIG. 8H shows quantification of BrT1 KO2 GFP+ cells on top of brain slices pre-treated with exosomes or PBS. The number of cells per FOV are averages±SEM, from n=8, 9, 9 (FIG. 8D), n=9, 7, 9, 9 (FIG. 8H) individual brain slices, scoring two fields per slice; and the number of invading cells per FOV are averages±SEM, from n=3 individual transwell cultures (FIG. 8G), scoring a representative field per transwell membrane. One of three (FIGS. 8A-8C, 8D, 8H) independent biological replicates is shown. Graphs depicting in vitro proliferation and invasion (FIGS. 8F-8G) display three independent biological replicates. TEM images and immunofluorescence brain slice images (FIGS. 8B and 8E) are representative of three independent biological replicates. Scale bars, 200 nm (FIG. 8B), and 100 μm (FIG. 8E). Error bars depict mean±SEM. P values were calculated by ANOVA (FIGS. 8C-8D, and FIGS. 8F-8H). See FIG. 6 for unprocessed blots. See Table 1 for statistics source data.

Figure 9A:
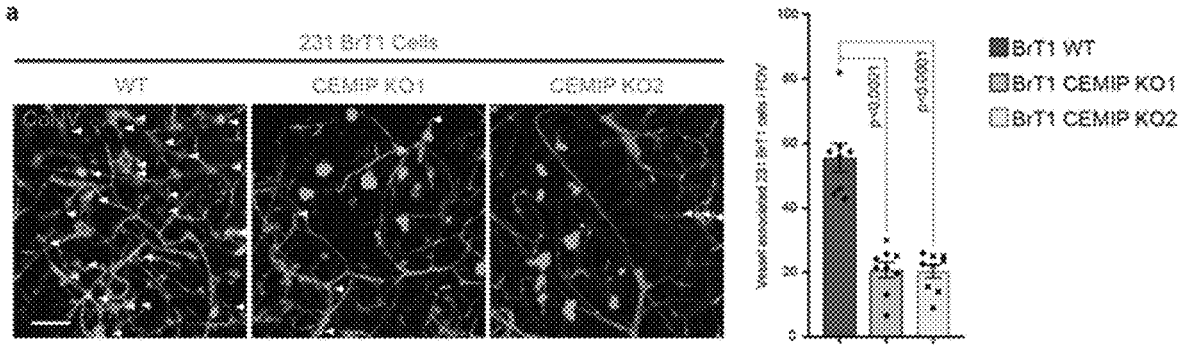
Figure 9B:
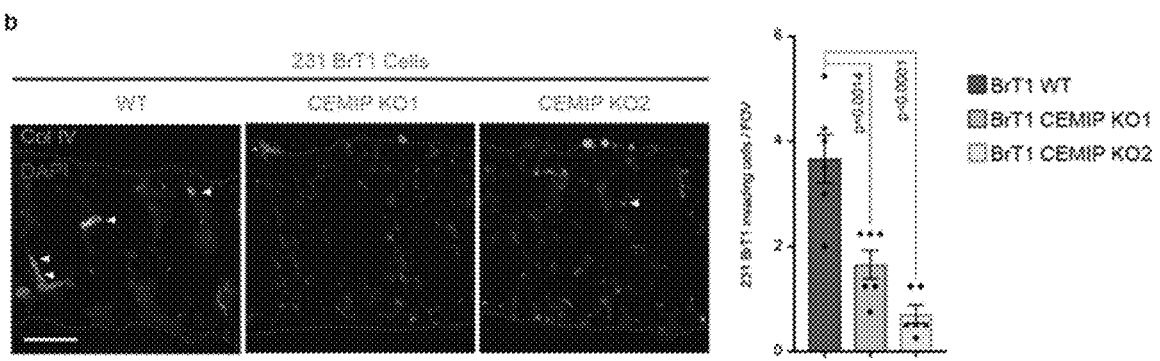
Figure 9C:
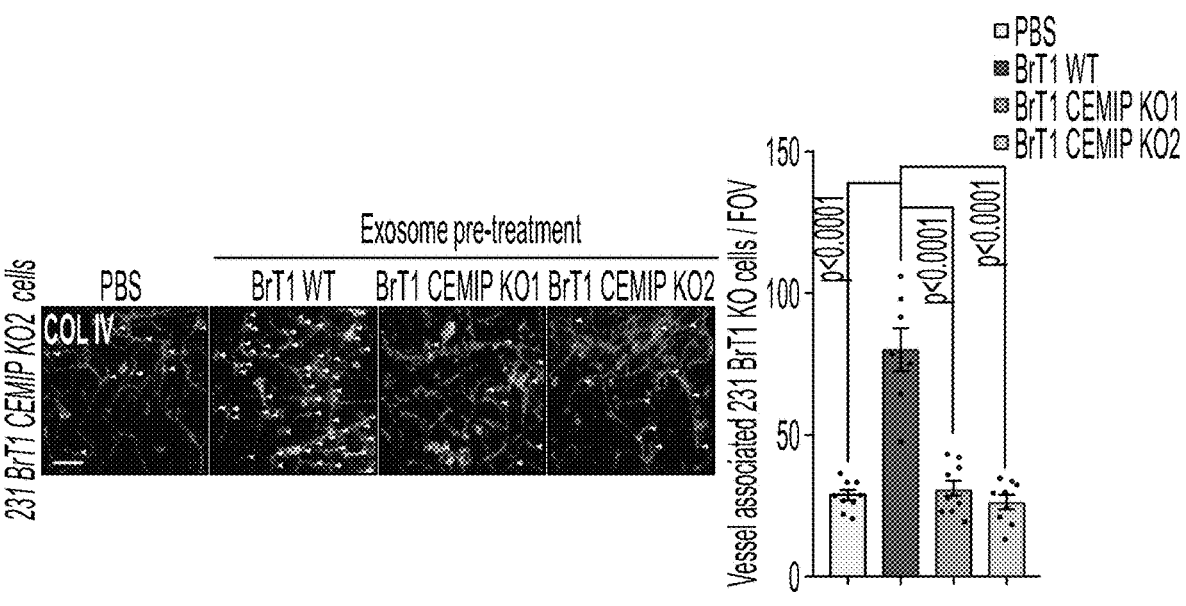
Figure 9D:
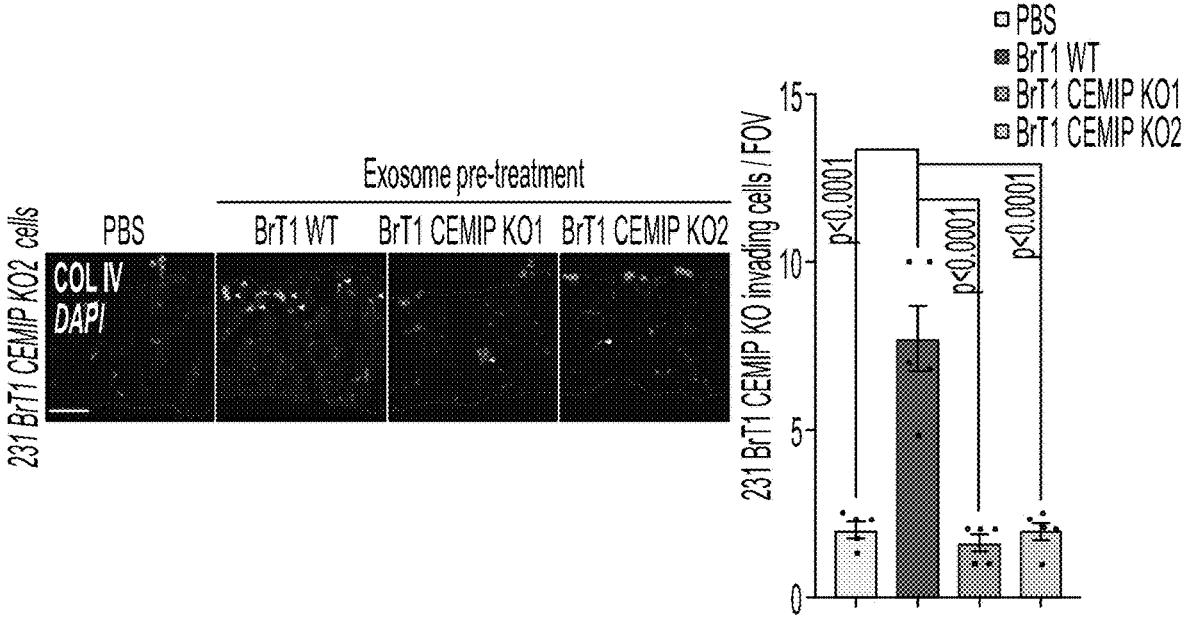

FIGS. 9A-9D show exosomal CEMIP modulates the brain vascular niche to support vascular co-option and invasion. FIG. 9A, left, shows representative fluorescence microscopy images of vessel association of GFP-expressing BrT1 wild-type (WT, control cells with WT CEMIP expression) or GFP-expressing BrT1 CEMIP knockout (KO1 and KO2) cells growing on top of brain slices. Brain vasculature is shown by Col IV+ staining (red, all fluorescent images in FIG. 9A-9D). Cells with spindle-like morphology and spread along vasculature (white arrows) were considered vessel-associated. On the right, quantification of vessel-associated cancer cell number is shown. FIG. 9B, left, shows representative fluorescence microscopy images of BrT1 WT, BrT1 CEMIP-KO1, cells invading brain slices. Cancer cells were considered invasive when migrating inwards past the top cell layer of the brain slice (white arrows). Dotted blue lines delineate the top and bottom limits of the slice. On the right, quantification of invading cancer cell number is shown. FIG. 9C, left, shows representative fluorescence microscopy images of vessel association of BrT1 CEMIP-KO2 GFP cells growing on top of brain slices pre-treated with exosomes or PBS. White arrows indicate vasculature-associated cancer cells. On the right, quantification of vessel-associated cancer cell number is shown. FIG. 9D, left, shows representative fluorescence microscopy images of BrT1 CEMIP-KO2 GFP and CEMIP-KO2 GFP+++ cells invading (white arrows) brain slices pre-treated with exosomes or PBS. Dotted blue lines delineate the top and bottom limits of the brain slice. On the right, quantification of invading cancer cell number is shown. The number of cells per FOV are from n=8, 9, 9 (FIG. 9A), n=6 (FIG. 9B), n=9, 7, 9, 9 (FIG. 9C), or n=5 (FIG. 9D) individual brain slices, scoring two fields per slice. A representative experiment is shown from three (FIGS. 9A-9D) independent biological replicates. Brain slice sections are stained with DAPI, shown in blue (FIGS. 9B, 9D). Scale bar, 100 μm (FIGS. 9A-9D). Error bars depict mean±SEM. P values were calculated by ANOVA (FIGS. 9A-9D). See Table 1 for statistics source data.

Figure 10A:
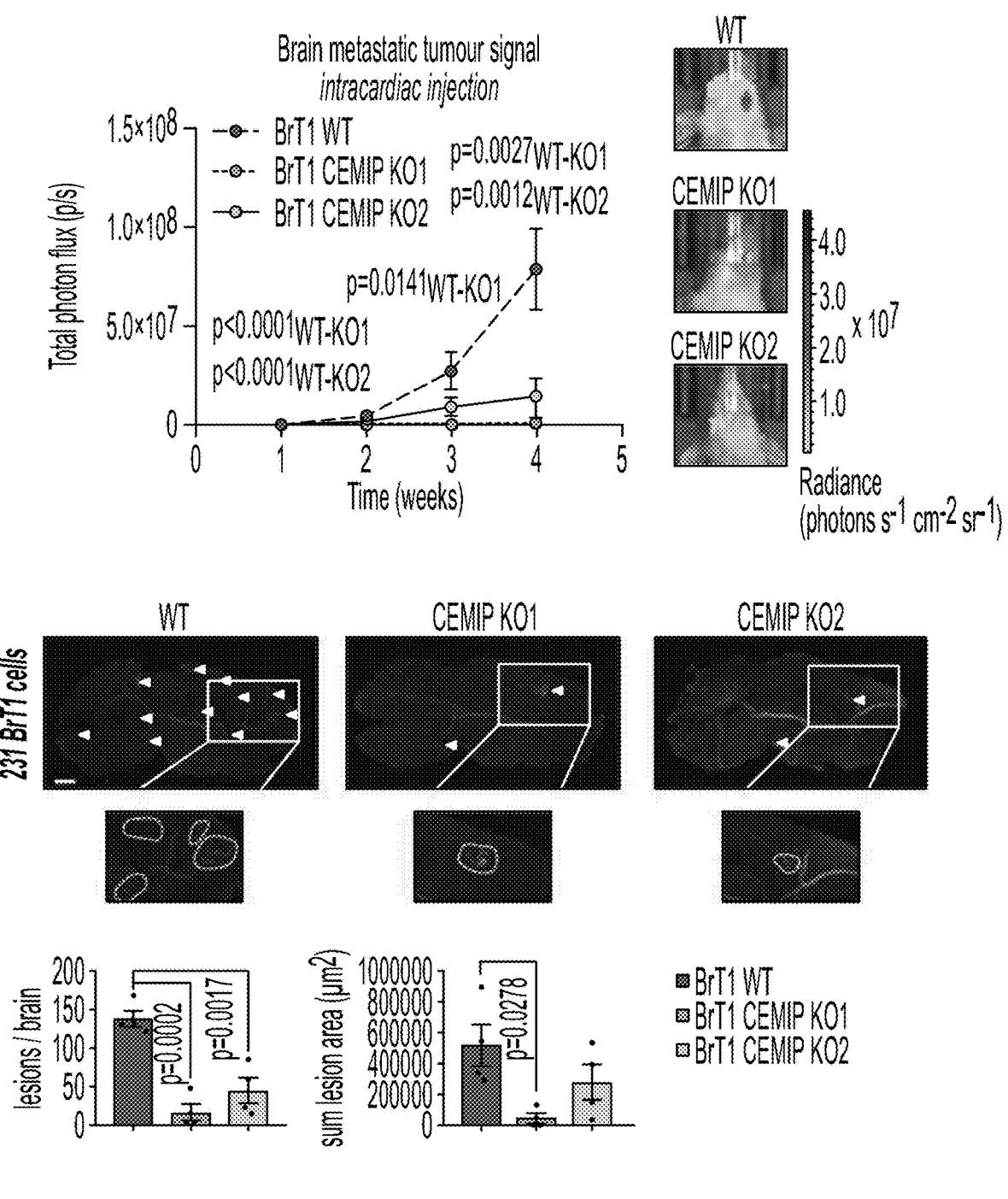
Figure 10B:
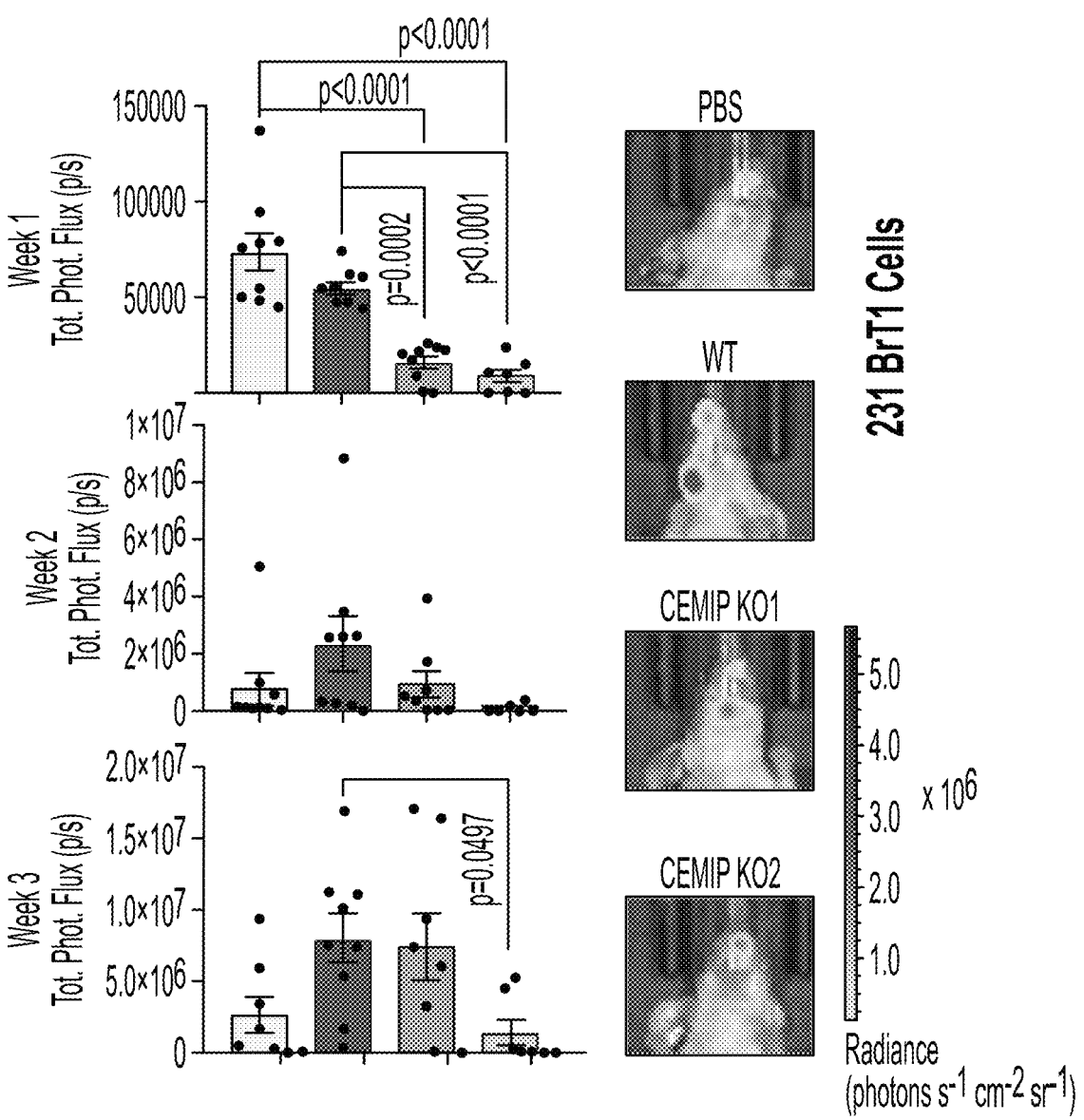
Figure 10B:
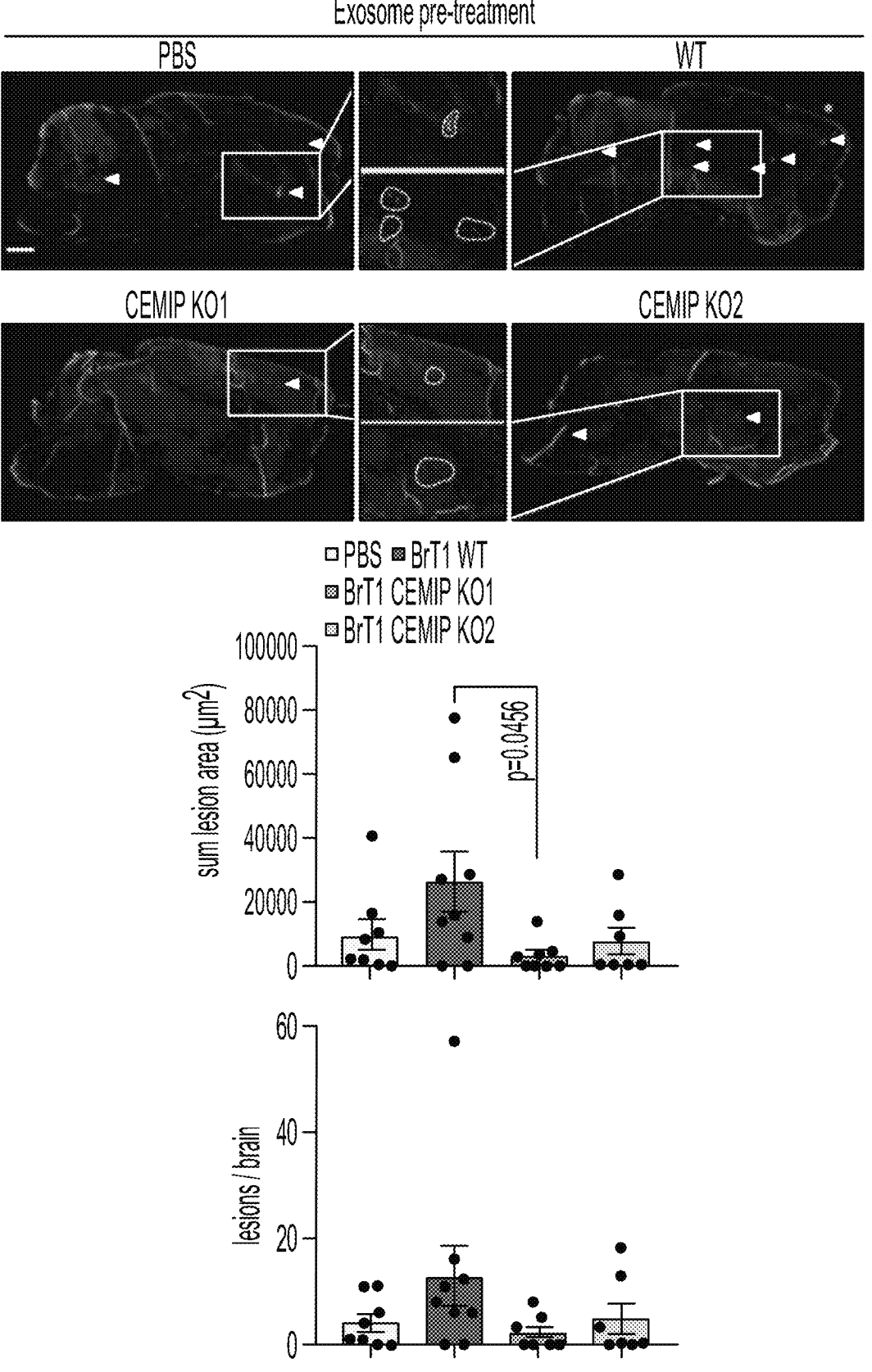

FIGS. 10A-10B show exosomal CEMIP supports brain metastasis in vivo. FIG. 10A shows quantification of brain metastasis in mice intracardiacally injected with BrT1 WT or CEMIP-KO cells. On the left, cranial bioluminescence signal (Total photon flux–photons/second (p/s)) in mice over 4 weeks post-intracardiac injection of GFP-labelled BrT1 WT or BrT1 CEMIP-KO luciferase-positive cells and representative IVIS image of brain signal at week 4 are shown. On the right, representative immunofluorescence images of whole brain sagittal sections from mice with brain metastatic lesions after 4 weeks (green, white arrows) are shown. Quantification of the number of lesions per brain (left graph) and total brain metastatic lesion area (μm², right graph) is shown below the immunofluorescence images. The number of lesions and total metastatic area per brain represent averages±SEM, scored from lesions in two sagittal brain sections from different brain areas per mouse, and n=4, 5, 5 mice per group. FIG. 10B shows quantification of brain metastasis in mice pre-educated with exosomes or PBS. On the left, cranial bioluminescence signal (Total photon flux–photons/second (p/s)) of mice educated for 3 weeks with exosomes or PBS, followed by intracardiac injection of GFP-labelled BrT1 luciferase-positive cells, and representative IVIS image of brain signals at week 3 post-cell injection is shown. Enlarged inset, middle, representative images of whole brain sagittal sections from mice showing GFP+ brain metastases (green, white arrows) 3 weeks post-cell injection. On the right, quantification of total brain metastatic lesion area (μm², upper graph) and number of lesions per brain (lower graph), representing averages±SEM scored from lesions in two sagittal brain sections representative of different brain areas per mouse, with n=9, 9, 9, 7 mice per group is shown. Scale bar, 1 mm (FIGS. 10A-10B). Error bars depict mean±SEM. P values were calculated by ANOVA (FIGS. 10A-10B). One representative experiment of two is shown (FIGS. 10A-10B). See Table 1 for statistics source data.

Figure 11A:
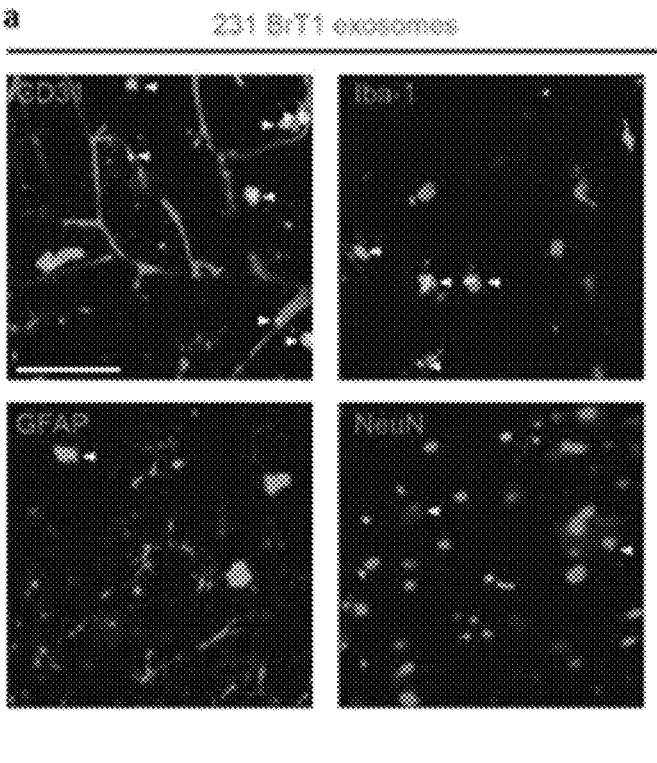
Figure 11B:
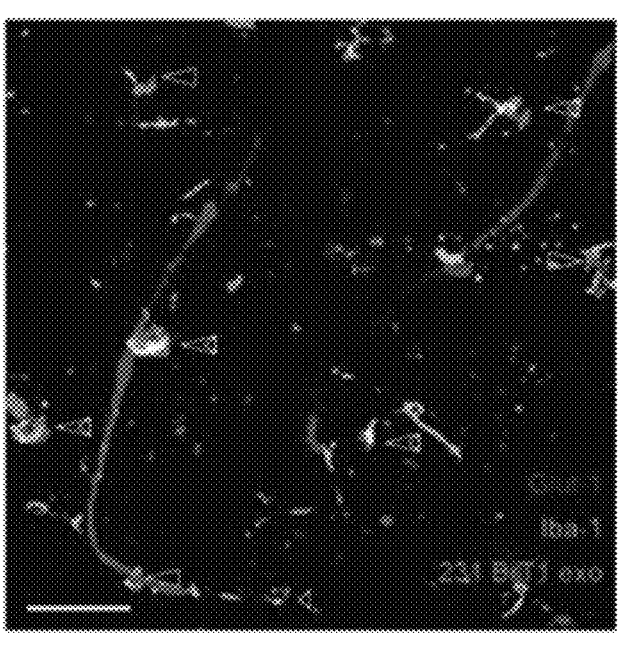
Figure 11C:
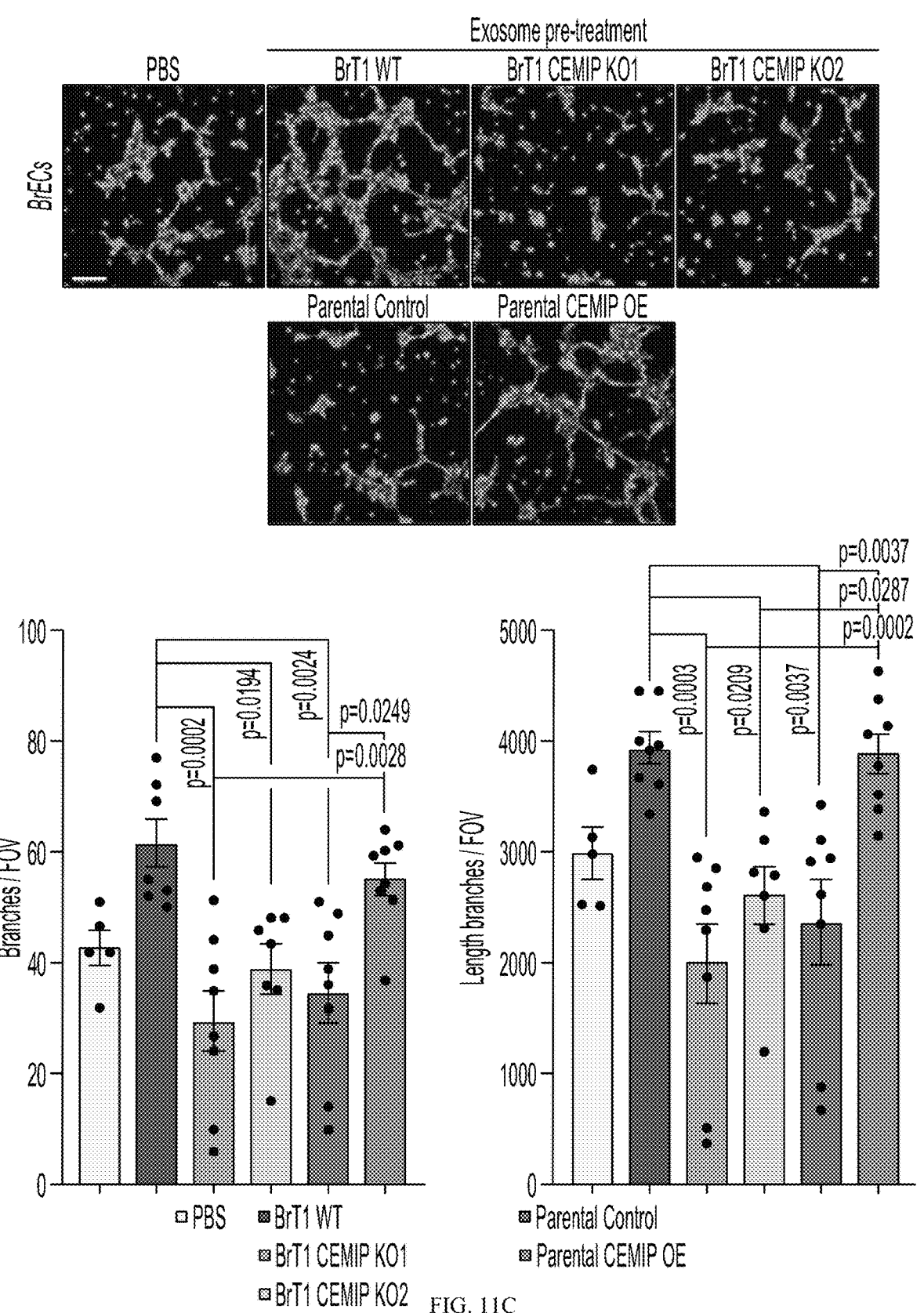
Figure 11D:
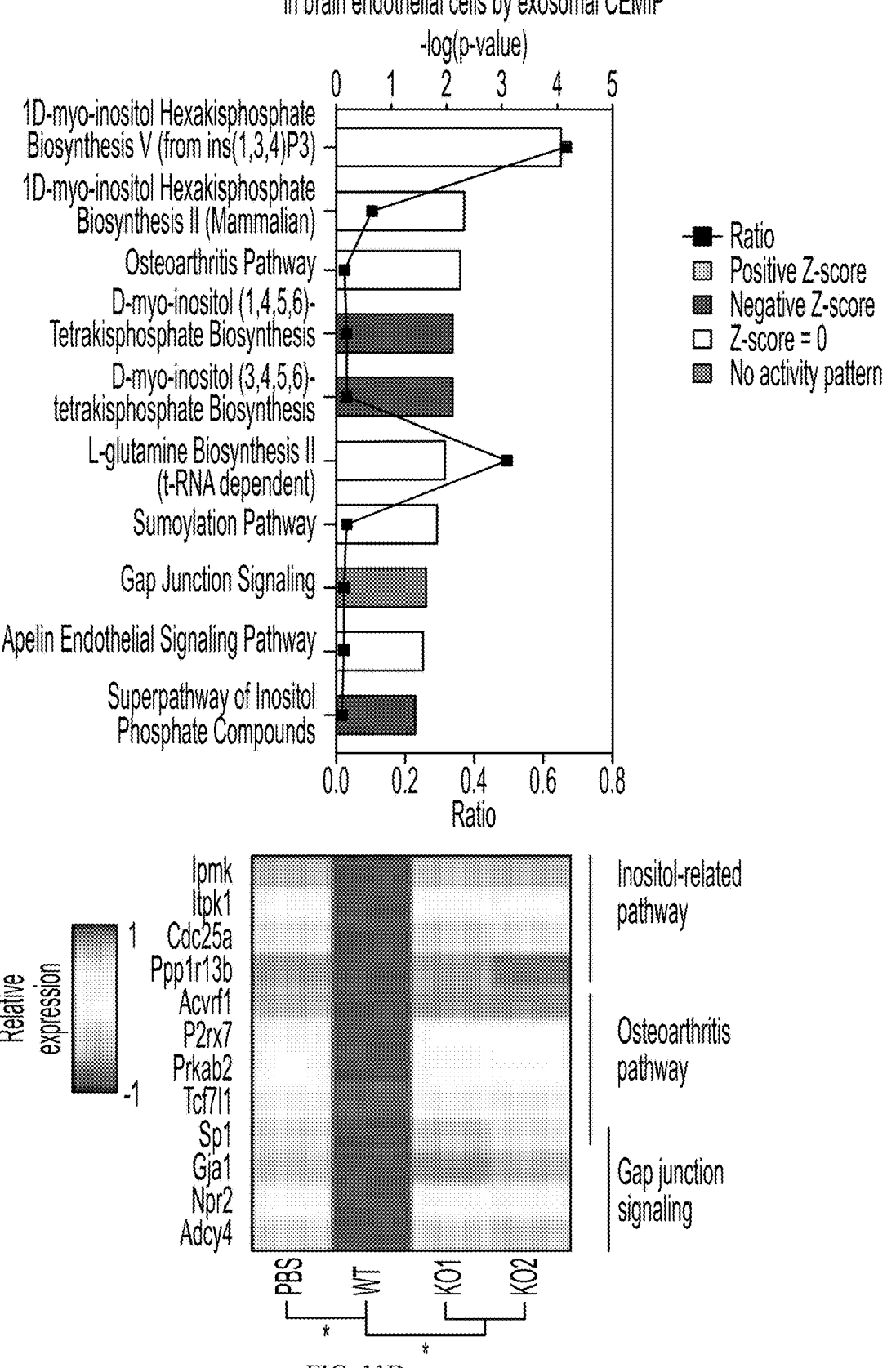
Figure 11D:
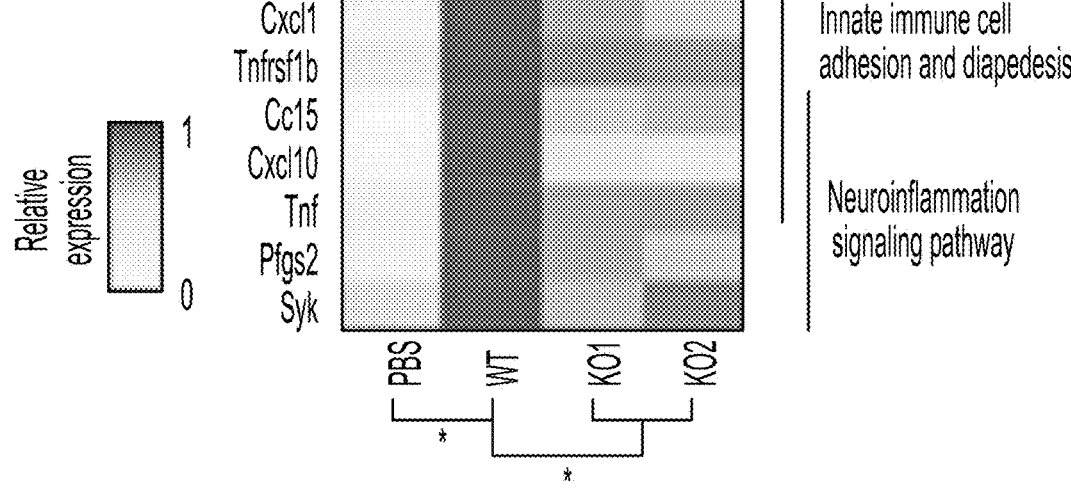

FIGS. 11A-11D show exosomal CEMIP uptake by BrECs and microglia induces vascular remodeling and inflammation in the brain vascular niche. FIG. 11A shows representative images of fluorescently-labelled 231 BrT1 exosomes (green) and brain endothelial cells (BrECs, CD31+), microglia (Iba1+), astrocytes (GFAP+), or neurons (NeuN+) (all in red). White arrows indicate co-localization of exosomes and the indicated cell type. FIG. 11B is a representative confocal microscopy image of Glut1+ BrECs (blue, long arrows) and Iba1+ microglia (green, short arrows) interacting with fluorescently-labelled BrT1 exosomes (red). Double arrows depict joint interaction of BrECs and microglia with exosomes. FIG. 11C, top, show representative images of calcein AM-loaded BrEC vascular networks (green) formed in vitro upon pre-treatment with exosomes or PBS. Vascular tree general topology is depicted by identification of the tree's master junctions (red) and master segments (yellow). On the bottom, quantification of vascular network branch number (left graph) and length (right graph) is shown. FIG. 11D, top, shows pathways affected by exosomal CEMIP in BrECs (left) and microglia (right) isolated from exosome-treated brain slices. Z-score indicates activation (orange) or inhibition (blue), and ratio indicates number of genes from the CEMIP list that map to a pathway divided by the total number of genes that map to that same pathway. Associated p-value of the Fisher's exact test is displayed in black. At the bottom, heatmap of differentially expressed genes involved in selected pathways is shown. The number and length of branches per FOV are averages±SEM, from n=5, 7, 8, 7, 8, 8 individual μ-slide wells (FIG. 11C), scoring a representative field per well. One of three independent biological replicates is shown for FIG. 11A, 11B, 11C. The average of three independent biological replicates is displayed in (FIG. 11D). Scale bars, 100 μm (FIG. 11A, 11C) and 50 μm (FIG. 11B). Error bars depict mean±SEM. P values were calculated by ANOVA (FIG. 11C) and Fisher's exact test (chart) or two-sided Student's t-test (heatmap) (FIG. 11D). See Table 1 for statistics source data.

Figure 12:
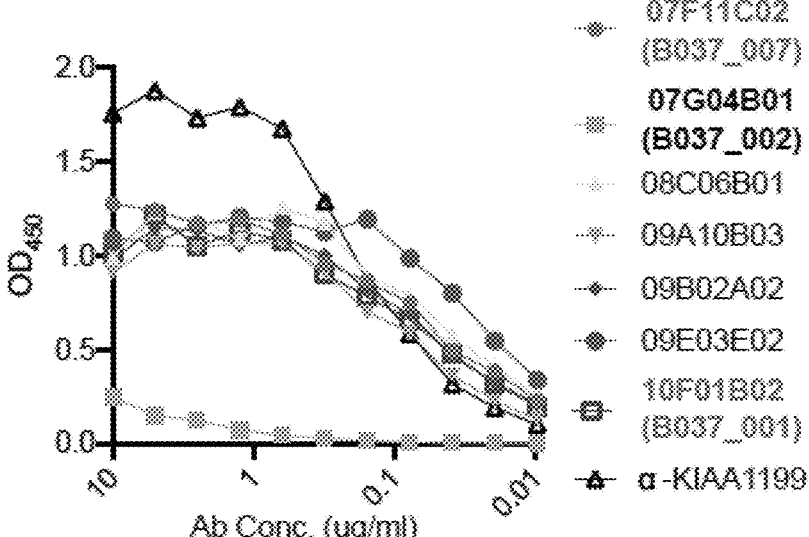

FIG. 12 shows binding of anti-KIAA1199/CEMIP monoclonal antibodies to recombinant protein. Mice were immunized with plasmids containing full length human CEMIP DNA. B cells were isolated from the spleens of immunized mice, and hybridomas were generated. Hybridoma supernatants were screened by ELISA for binding to recombinant KIAA1199/CEMIP protein. Hybridoma from positive hits were subcloned, followed by purification of the monoclonal antibodies and analysis by ELISA using recombinant KIAA1199/CEMIP protein.

Figure 13:
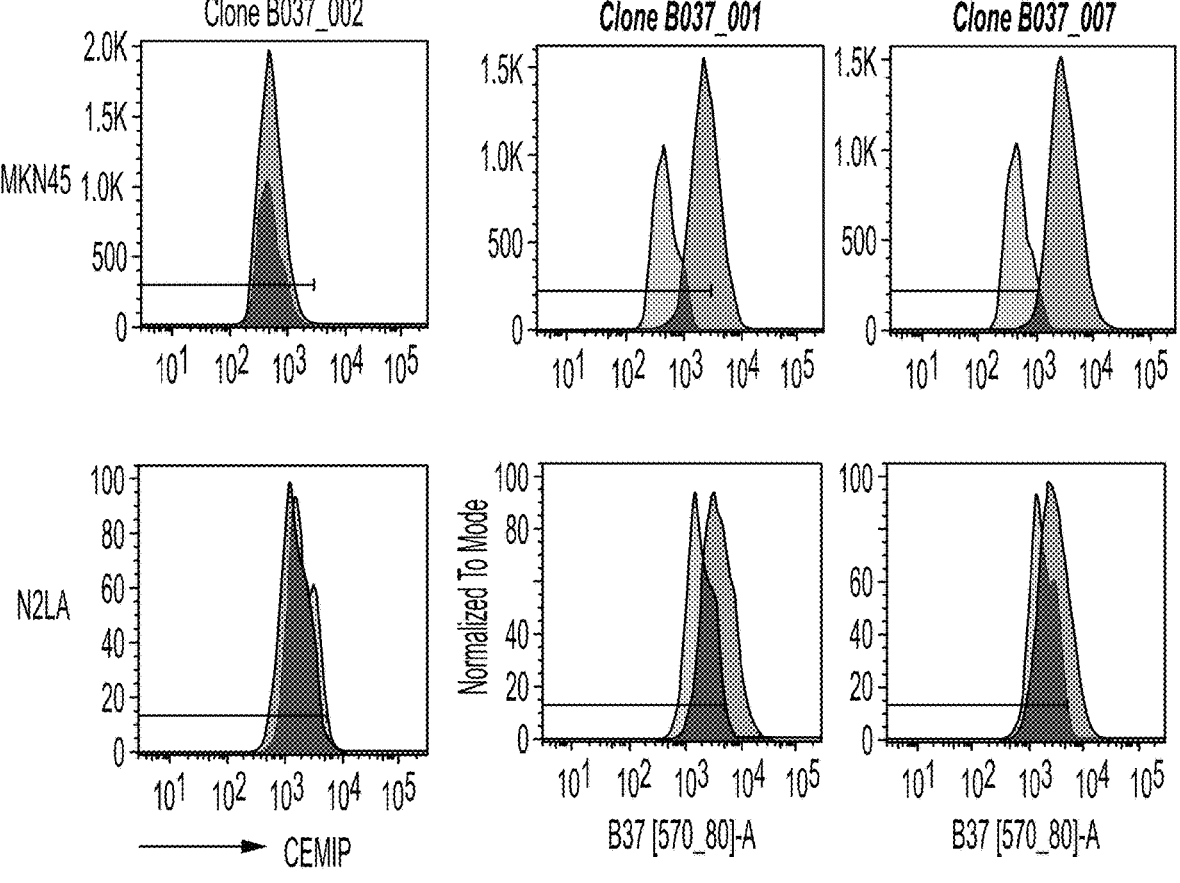

FIG. 13 shows validation of anti-CEMIP/KIAA1199 binding antibodies by flow cytometry. The binding of anti-CEMIP antibodies to native CEMIP expressed on the surface of human MKN45 gastric and N2LA lung cancer cell lines is shown. Two micrograms of indicated antibodies were used to stain 2×105 cells and binding was revealed with an Ax647-labelled goat anti-mouse secondary antibody (Biolegend).

Figure 14:
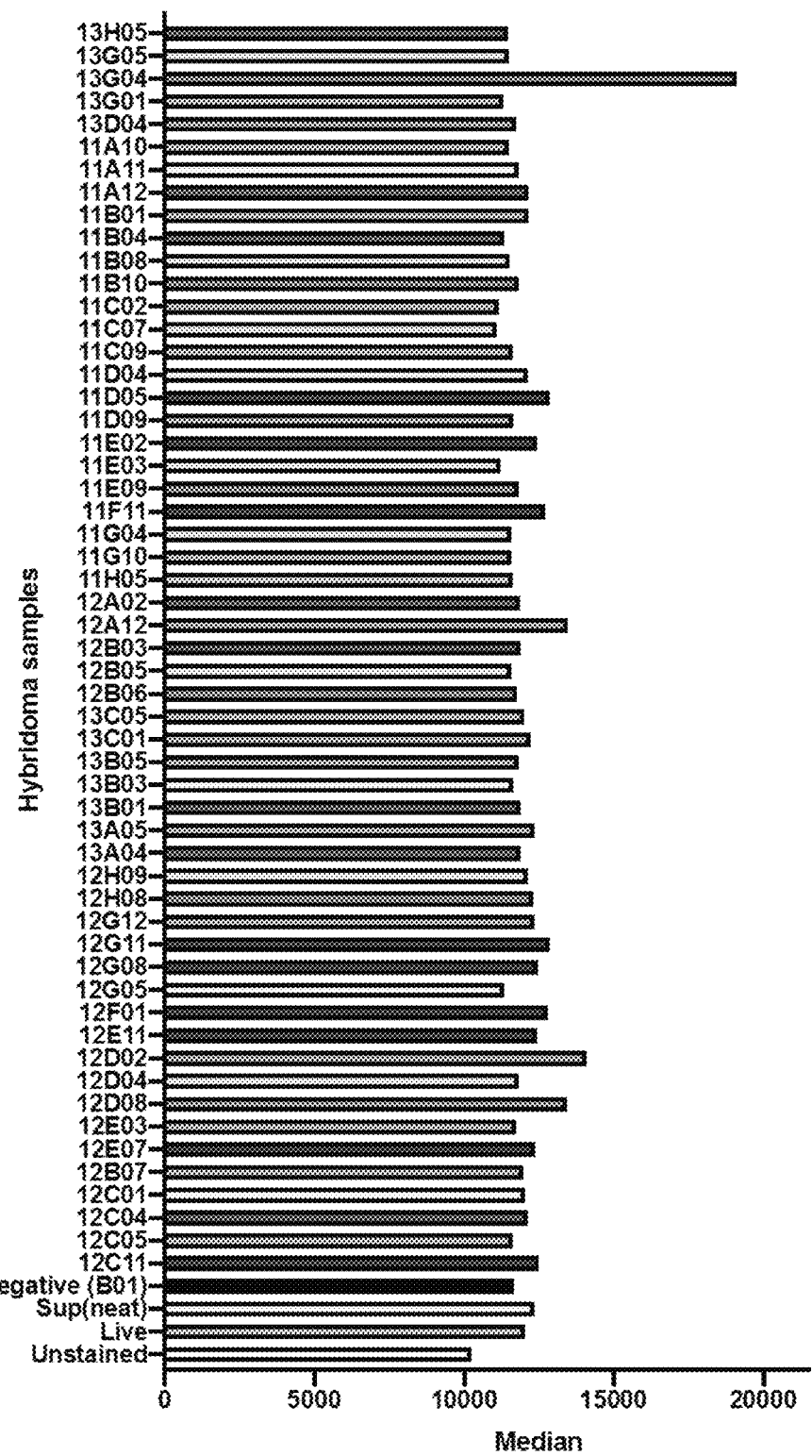

FIG. 14 shows a second phase flow cytometry-based screen for anti-KIAA1199/CEMIP antibodies. Binding of neat exhausted hybridoma supernatants to 2×105 MKN45 cells was detected with an Ax647-labelled goat anti-mouse secondary antibody (Biolegend) using flow cytometry. The y-axis indicates the hybridoma clone name, and the x-axis represents the median fluorescence intensity for the Ax647-labelled goat anti-mouse secondary antibody (Biolegend). Coloured bars indicate hybridoma supernatants that bound above the positive hybridoma control level (10F01B02).

Figure 15:
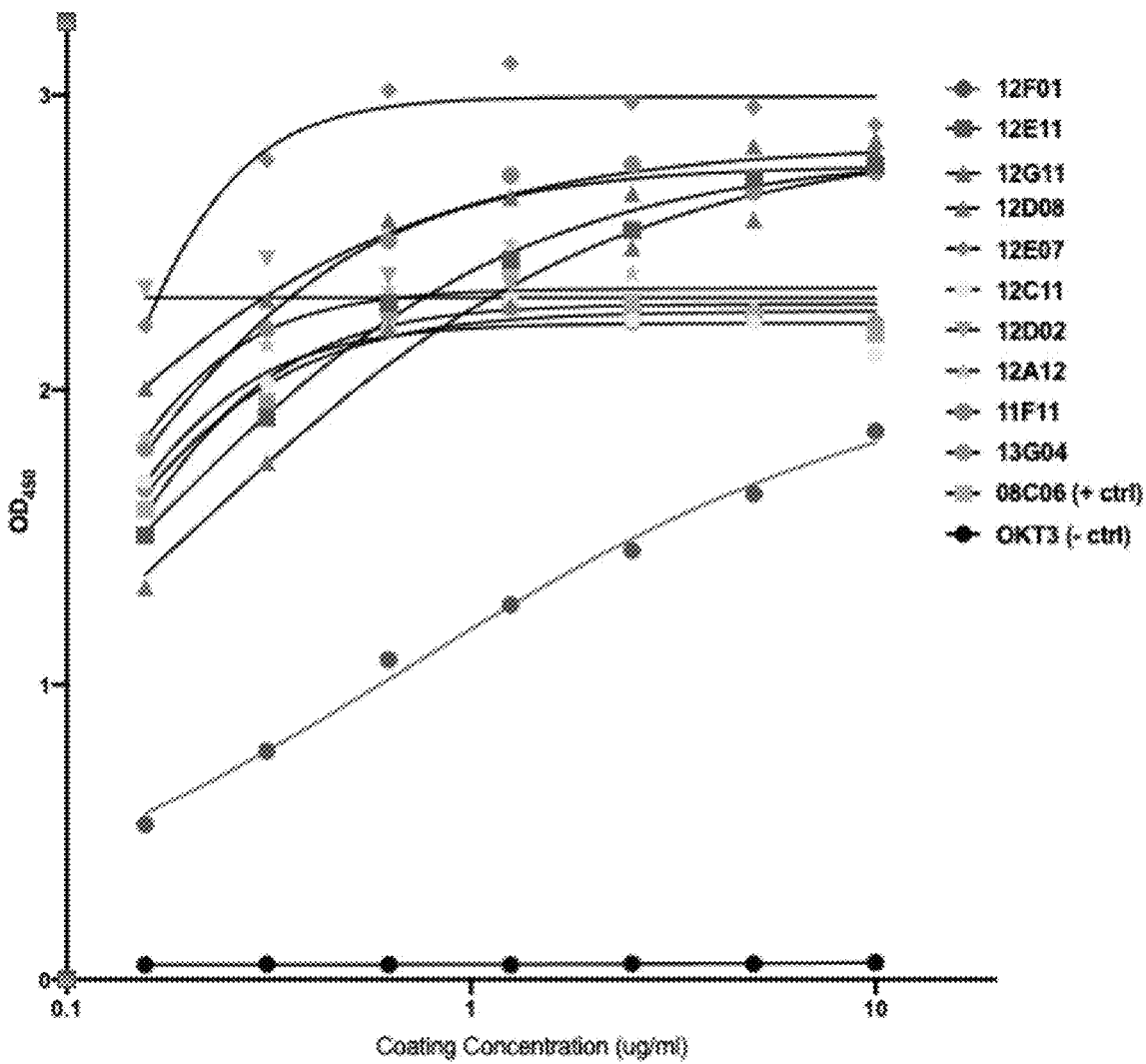

FIG. 15 shows second phase ELISA screen for anti-KIAA1199/CEMIP monoclonal antibodies. Mice were immunized with plasmids containing full length human CEMIP DNA. B cells were isolated from the spleens of immunized mice, and hybridomas were generated and selected from semi-solid media. Clonal hybridoma supernatants were screened by ELISA for binding to recombinant KIAA1199/CEMIP protein. Monoclonal antibodies were purified from the supernatant of hybridoma and analyzed by ELISA using recombinant KIAA1199/CEMIP protein.

Figure 16:
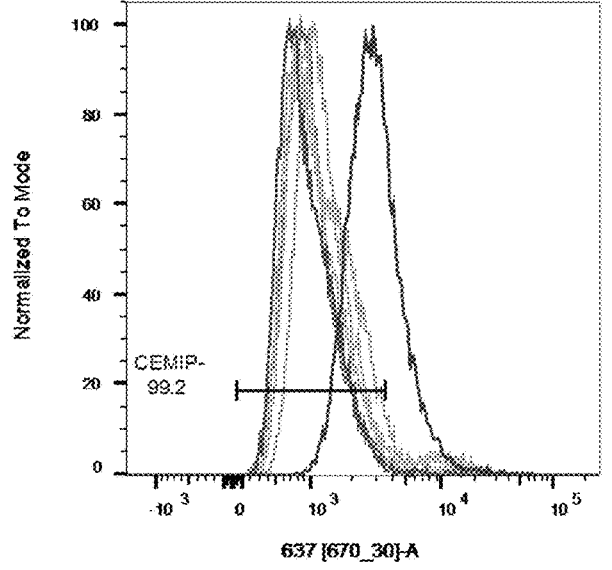

FIG. 16 shows validation of CEMIP/KIAA1199 loss in MKN45 CRISPR/Cas9 clones by flow cytometry. The binding of anti-CEMIP antibodies to native CEMIP expressed on the surface of wild-type and CEMIP/KIAA1199 CRISPR/

Cas9 human MKN45 gastric cell lines is shown. Two micrograms of 10F01B02 anti-CEMIP/KIAA1199 antibody were used to stain 2×105 cells and binding was revealed with an Ax647-labelled goat anti-mouse secondary antibody (Biolegend). This experiment also demonstrates the specificity of the anti-CEMIP/KIAA1199 antibody.

DETAILED DESCRIPTION

The present disclosure relates to methods of early detection and inhibition of brain metastatic disease in patients having a primary tumor.

One aspect of the disclosure relates to a method that involves selecting a subject having a primary tumor and obtaining, from the selected subject, a sample containing exosomes derived from primary tumor cells. The exosomes are isolated from the sample and expression levels of cell migration-inducing and hyaluronan-binding protein (CEMIP) are detected in the isolated exosomes.

Another aspect of the disclosure relates to a method that involves selecting a subject having a primary tumor and obtaining, from the selected subject, a sample containing primary tumor cells. The primary tumor cells are isolated from the sample and expression levels of CEMIP are detected in the isolated primary tumor cells.

CEMIP, also known as KIAA1199, is a Wnt-related protein known for mediating depolymerization of hyaluronic acid via the cell membrane-associated clathrin-coated pit endocytic pathway. As shown herein, CEMIP is enriched in brain metastatic breast and lung tumor derived exosomes and promotes brain metastasis by generating a pro-metastatic environment. The nucleotide sequence encoding CEMIP is known in the art, see e.g., UniProtKB Accession No. Q8WUJ3. The amino acid sequence of CEMIP is provided below as SEQ ID NO: 1

```
                                        SEQ ID NO: 1
          10         20         30         40
MGAAGRQDFL FKAMLTISWL TLTCFPGATS TVAAGCPDQS 50         60         70         80
PELQPWNPGH DQDHHVHIGQ GKTLLLTSSA TVYSIHISEG 90        100        110        120
GKLVIKDHDE PIVLRTRHIL IDNGGELHAG SALCPFQGNF 130        140        150        160
TIILYGRADE GIQPDPYYGL KYIGVGKGGA LELHGQKKLS 170        180        190        200
WTFLNKTLHP GGMAEGGYFF ERSWGHRGVI VHVIDPKSGT 210        220        230        240
VIHSDRFDTY RSKKESERLV QYLNAVPDGR ILSVAVNDEG 250        260        270        280
SRNLDDMARK AMTKLGSKHF LHLGFRHPWS FLTVKGNPSS 290        300        310        320
SVEDHIEYHG HRGSAAARVF KLFQTEHGEY FNVSLSSEWV 330        340        350        360
QDVEWTEWED HDKVSQTKGG EKISDLWKAH PGKICNRPID 370        380        390        400
IQATTMDGVN LSTEVVYKKG QDYRFACYDR GRACRSYRVR 410        420        430        440
FLCGKPVRPK LTVTIDTNVN STILNLEDNV QSWKPGDTLV 450        460        470        480
IASTDYSMYQ AEEFQVLPCR SCAPNQVKVA GKPMYLHIGE
```

-continued

```
            490        500        510        520
EIDGVDMRAE  VGLLSRNIIV MGEMEDKCYP YRNHICNFFD 530        540        550        560
FDTFGGHIKF  ALGFKAAHLE GTELKHMGQQ LVGQYPIHFH 570        580        590        600
LAGDVDERGG  YDPPTYIRDL SIHHTFSRCV TVHGSNGLLI 610        620        630        640
KDVVGYNSLG  HCFFTEDGPE ERNTFDHCLG LLVKSGTLLP 650        660        670        680
SDRDSKMCKM  ITEDSYPGYI PKPRQDCNAV STFWMANPNN 690        700        710        720
NLINCAAAGS  EETGFWFIFH HVPTGPSVGM YSPGYSEHIP 730        740        750        760
LGKFYNNRAH  SNYRAGMIID NGVKTTEASA KDKRPFLSII 770        780        790        800
SARYSPHQDA  DPLKPREPAI IRHFIAYKNQ DHGAWLRGGD 810        820        830        840
VWLDSCRFAD  NGIGLTLASG GTFPYDDGSK QEIKNSLFVG 850        860        870        880
ESGNVGTEMM  DNRIWGPGGL DHSGRTLPIG QNFPIRGIQL 890        900        910        920
YDGPINIQNC  TFRKFVALEG RHTSALAFRL NNAWQSCPHN 930        940        950        960
NVTGIAFEDV  PITSRVFFGE PGPWFNQLDM DGDKTSVFHD 970        980        990       1000
VDGSVSEYPG  SYLTKNDNWL VRHPDCINVP DWRGAICSGC 1010       1020       1030       1040
YAQMYIQAYK  TSNLRMKIIK NDFPSHPLYL EGALTRSTHY 1050       1060       1070       1080
QQYQPVVTLQ  KGYTIHWDQT APAELAIWLI NFNKGDWIRV 1090       1100       1110       1120
GLCYPRGTTF  SILSDVHNRL LKQTSKTGVF VRTLQMDKVE 1130       1140       1150       1160
QSYPGRSHYY  WDEDSGLLFL KLKAQNEREK FAFCSMKGCE 1170       1180       1190       1200
RIKIKALIPK  NAGVSDCTAT AYPKFTERAV VDVPMPKKLF 1210       1220       1230       1240
GSQLKTKDHF  LEVKMESSKQ HFFHLWNDFA YIEVDGKKYP 1250       1260       1270       1280
SSEDGIQVVV  IDGNQGRVVS HTSFRNSILQ GIPWQLFNYV 1290       1300       1310       1320
ATIPDNSIVL  MASKGRYVSR GPWTRVLEKL GADRGLKLKE 1330       1340       1350       1360
QMAFVGFKGS  FRPIWVTLDT EDHKAKIFQV VPIPVVKKKK L
```

In accordance with all aspects of the present disclosure, a "subject" encompasses any animal, but preferably a mammal, e.g., human, non-human primate, a dog, a cat, a horse, a cow, or a rodent. More preferably, the subject or patient is a human. In accordance with this aspect of the present disclosure, the subject has a primary tumor that is susceptible to metastasis. For example and without limitation, the subject has a primary breast tumor, lung tumor, melanoma, renal tumor, gastrointestinal tumor, e.g., colorectal tumor, esophageal tumor, small intestine tumor, stomach tumor, bladder tumor, liver tumor, pancreatic tumor, and prostate tumor.

In accordance with this aspect of the disclosure, a sample containing exosomes is obtained from the subject. In one embodiment, the sample contains exosomes derived from primary tumor cells. "Exosomes" are nanovesicles released from a variety of different cells, including tumor cells (i.e., "tumor-derived exosomes"). These small vesicles (30-120 nm in diameter) derive from large multivesicular endosomes and are secreted into the extracellular milieu. The precise mechanisms of exosome release/shedding remain unclear; however, this release is an energy-requiring phenomenon, modulated by extracellular signals. Exosomes appear to form by invagination and budding from the limiting membrane of late endosomes, resulting in vesicles that contain cytosol and that expose the extracellular domain of membrane-bound cellular proteins on their surface. Using electron microscopy, studies have shown fusion profiles of multivesicular endosomes with the plasma membrane, leading to the secretion of the internal vesicles into the extracellular environment. The rate of exosome release is significantly increased in most neoplastic cells and occurs continuously. Increased release of exosomes and their accumulation appear to be important in the malignant transformation process.

In accordance with the methods of the present disclosure, exosomes can be isolated or obtained from most biological fluids including, without limitation, blood, serum, plasma, ascites, cyst fluid, pleural fluid, peritoneal fluid, cerebral spinal fluid, tears, urine, saliva, sputum, nipple aspirates, lymph fluid, fluid of the respiratory, intestinal, and genitourinary trances, breast milk, intra-organ system fluid, or combinations thereof.

An enriched population of exosomes can be obtained from a biological sample using methods known in the art. For example, exosomes may be concentrated or isolated from a biological sample using size exclusion chromatography, density gradient centrifugation, differential centrifugation (Raposo et al. "B lymphocytes Secrete Antigen-presenting Vesicles," *J Exp Med* 183(3): 1161-72 (1996), which is hereby incorporated by reference in its entirety), anion exchange and/or gel permeation chromatography (for example, as described in U.S. Pat. No. 6,899,863 to Dhellin et al., and U.S. Pat. No. 6,812,023 to Lamparski et al., which are hereby incorporated by reference in their entirety), sucrose density gradients or organelle electrophoresis (for example, as described in U.S. Pat. No. 7,198,923), magnetic activated cell sorting (MACS) (Taylor et al., "MicroRNA Signatures of Tumor-derived Exosomes as Diagnostic Biomarkers of Ovarian Cancer," *Gynecol Oncol* 110(1): 13-21 (2008), which is hereby incorporated by reference in its entirety), nanomembrane ultrafiltration (Cheruvanky et al., "Rapid Isolation of Urinary Exosomal Biomarkers using a Nanomembrane Ultrafiltration Concentrator," *Am J Physiol Renal Physiol* 292(5): F1657-61 (2007), which is hereby incorporated by reference in its entirety), immunoabsorbent capture, affinity purification, microfluidic separation, or combinations thereof.

Exosomes isolated from a bodily fluid (i.e., peripheral blood, cerebrospinal fluid, urine) can be enriched for those originating from a specific organ or cell type, for example, lung, pancreas, stomach, intestine, bladder, kidney, ovary, testis, skin, colorectal, breast, prostate, brain, esophagus, liver, placenta, and fetal cells. Because the exosomes often carry surface molecules from their donor cells, surface molecules may be used to identify, isolate and/or enrich for exosomes from a specific donor cell type. In this way, exosomes originating from distinct cell populations can be analyzed for their protein content. For example, tumor (malignant and non-malignant) exosomes carry tumor-associated surface molecules, and these exosomes can be isolated and/or enriched via these specific tumor-associated surface molecules. In one example, the tumor-associated surface molecule is epithelial-cell-adhesion-molecule (Ep-CAM), which is specific to exosomes from carcinomas of lung, colorectal, breast, prostate, head and neck, and hepatic origin, but not of hematological cell origin (Balzar et al, "The Biology of the 17-1A Antigen (Ep-CAM)," *J Mol Med* 77(10): 699-712 (1999); Went et al. "Frequent EpCam Protein Expression in Human Carcinomas," *Hum Pathol* 35(1): 122-8 (2004), which are hereby incorporated by reference in their entirety). In another example, the surface molecule is CD24, which is a glycoprotein specific to urine microvesicles (Keller et al, "CD24 is a Marker of Exosomes Secreted into Urine and Amniotic Fluid," *Kidney Int* 72(9): 1095-102 (2007), which is hereby incorporated by reference in its entirety). In yet another example, the surface molecule is CD70, carcinoembryonic antigen (CEA), EGFR, EGFRvIII and other variants, Fas ligand, TRAIL, transferrin receptor, p38.5, p97 and HSP72. Alternatively, tumor specific exosomes may be characterized by the lack of surface markers, such as the lack of CD45, CD80 and CD86 expression.

The isolation of exosomes from specific cell types can be accomplished, for example, by using antibodies, aptamers, aptamer analogs, or molecularly imprinted polymers specific for a desired surface molecule. In one embodiment, the surface molecule is specific for a cancer type, e.g., a breast tumor cell specific surface molecule, a lung tumor cell specific surface molecule, a melanoma specific surface molecule, a renal tumor cell surface molecule, a prostate tumor cell surface molecule, etc. In another embodiment, the surface molecule is specific for a cell type which is not necessarily cancerous. One example of a method of exosome separation based on cell surface molecule is provided in U.S. Pat. No. 7,198,923, which is hereby incorporated by reference in its entirety. As described in, e.g., U.S. Pat. No. 5,840,867 to Toole and U.S. Pat. No. 5,582,981 to Toole, which are hereby incorporated by reference in their entirety, aptamers and their analogs specifically bind surface molecules and can be used as a separation tool for retrieving cell type-specific exosomes. Molecularly imprinted polymers also specifically recognize surface molecules as described in, e.g., U.S. Pat. Nos. 6,525,154, 7,332,553 and 7,384,589, which are hereby incorporated by reference in their entirety, and are a tool for retrieving and isolating cell type-specific exosomes.

Upon isolation of the exosomes and or primary tumor cells, expression levels of CEMIP are detected. In accordance with all aspects of the present disclosure, exosomal and primary tumor cell "expression levels" is intended to encompass production of any product by a gene including but not limited to transcription of mRNA and translation of polypeptides, peptides, and peptide fragments. Measuring or detecting expression levels encompasses assaying, measuring, quantifying, scoring, or detecting the amount, concentration, or relative abundance of a gene product. It is recognized that a method of evaluating expression of one type of gene product, such as a polypeptide, may not be suitable for assaying another type of gene product, such as a nucleic acid. It is recognized that methods of assaying a gene product include direct measurements and indirect measurements. One skilled in the art is capable of selecting an appropriate method of evaluating expression of a particular gene product.

In accordance with this aspect and other aspects of the disclosure relating to detecting expression levels of CEMIP in the sample, suitable methods for detecting CEMIP include, but are not limited to, measuring protein expression levels. Methods for detecting and measuring protein expression levels generally involve an immunoassay, where the exosomal sample is contacted with one or more detectable binding reagents that is suitable for measuring protein expression, e.g., a labeled antibody that binds to the protein of interest, i.e., CEMIP, or a primary antibody that binds to CEMIP used in conjunction with a secondary antibody. CEMIP antibodies suitable for detecting CEMIP protein expression levels are known in the art, see e.g., anti-human CEMIP antibodies available from Novus Biologicals, LifeSpan BioSciences, Inc., Invitrogen, and Abclonal. The one or more binding reagents bound to CEMIP (i.e., a binding reagent-CEMIP complex) in the sample is detected and the amount of labeled binding reagent that is detected and normalized to total protein in the sample, serves as an indicator of the amount or expression level of CEMIP present in the sample.

Suitable immunoassays for detecting protein expression level in an exosome sample that are commonly employed in the art include, for example and without limitation, western blot, immunoprecipitation, enzyme-linked immunosorbent assay (ELISA), radioimmunoassay (RIA), fluorescent activated cell sorting (FACS), immunoradiometric assay, gel diffusion precipitation reaction, immunodiffusion assay, in situ immunoassay, imaging mass cytometry, complement fixation assay, and immunoelectrophoresis assay. In accordance with this aspect of the disclosure, the measured CEMIP protein level in the sample can further be compared to the CEMIP protein expression level measured in a reference exosomal sample, e.g., a non-tumor exosome sample from the same subject, to determine the level of CEMIP expression in the tumor-derived exosomal sample relative to a non-tumor derived exosomal sample.

In another embodiment, exosomal CEMIP expression levels are measured using one-dimensional and two-dimensional electrophoretic gel analysis, high performance liquid chromatography (HPLC), reverse phase HPLC, Fast protein liquid chromatograph (FPLC), mass spectrometry (MS), tandem mass spectrometry, liquid crystal-MS (LC-MS) surface enhanced laser desorption/ionization (SELDI), MALDI, and/or protein sequencing In accordance with this aspect of the disclosure, CEMIP expression levels, particularly in primary tumor cells, can also or alternatively be measured by detecting and quantifying CEMIP nucleic acid levels using a nucleic acid detection assay. In one embodiment, RNA, e.g., mRNA, levels are measured. RNA is preferably reverse-transcribed to synthesize complementary DNA (cDNA), which is then amplified and detected or directly detected. The detected cDNA is measured and the levels of cDNA serve as an indicator of the RNA or mRNA levels present in a sample. Reverse transcription may be performed alone or in combination with an amplification step, e.g., reverse transcription polymerase chain reaction (RT-PCR), which may be further modified to be quantitative, e.g., quantitative RT-PCR as described in U.S. Pat. No. 5,639,606, which is hereby incorporated by reference in its entirety.

It may be beneficial or otherwise desirable to extract RNA from the primary tumor cells prior to or for analysis. RNA molecules can be isolated from cells and the concentration (i.e., total RNA) quantified using any number of procedures, which are well-known in the art, the particular extraction procedure chosen based on the particular biological sample.

In some instances, with some techniques, it may also be possible to analyze the nucleic acid without extraction from the cells.

In one embodiment, mRNA is analyzed directly without an amplification step. Direct analysis may be performed with different methods including, but not limited to, nanostring technology (Geiss et al. "Direct Multiplexed Measurement of Gene Expression with Color-Coded Probe Pairs," *Nat Biotechnol* 26(3): 317-25 (2008), which is hereby incorporated by reference in its entirety). Nanostring technology enables identification and quantification of individual target molecules in a biological sample by attaching a color coded fluorescent reporter to each target molecule. This approach is similar to the concept of measuring inventory by scanning barcodes. Reporters can be made with hundreds or even thousands of different codes allowing for highly multiplexed analysis. In another embodiment, direct analysis can be performed using immunohistochemical techniques.

In another embodiment, it may be beneficial or otherwise desirable to reverse transcribe and amplify the RNA prior to detection/analysis. Methods of nucleic acid amplification, including quantitative amplification, are commonly used and generally known in the art. Quantitative amplification will allow quantitative determination of relative amounts of RNA in the cells.

Nucleic acid amplification methods include, without limitation, polymerase chain reaction (PCR) (U.S. Pat. No. 5,219,727, which is hereby incorporated by reference in its entirety) and its variants such as in situ polymerase chain reaction (U.S. Pat. No. 5,538,871, which is hereby incorporated by reference in its entirety), quantitative polymerase chain reaction (U.S. Pat. No. 5,219,727, which is hereby incorporated by reference in its entirety), nested polymerase chain reaction (U.S. Pat. No. 5,556,773), self sustained sequence replication and its variants (Guatelli et al. "Isothermal, In vitro Amplification of Nucleic Acids by a Multienzyme Reaction Modeled after Retroviral Replication," *Proc Natl Acad Sci USA* 87(5): 1874-8 (1990), which is hereby incorporated by reference in its entirety), transcriptional amplification and its variants (Kwoh et al. "Transcription-based Amplification System and Detection of Amplified Human Immunodeficiency Virus type 1 with a Bead-Based Sandwich Hybridization Format," Proc Natl Acad Sci USA 86(4): 1173-7 (1989), which is hereby incorporated by reference in its entirety), Qb Replicase and its variants (Miele et al. "Autocatalytic Replication of a Recombinant RNA." *J Mol Biol* 171(3): 281-95 (1983), which is hereby incorporated by reference in its entirety), cold-PCR (Li et al. "Replacing PCR with COLD-PCR Enriches Variant DNA Sequences and Redefines the Sensitivity of Genetic Testing." *Nat Med* 14(5): 579-84 (2008), which is hereby incorporated by reference in its entirety) or any other nucleic acid amplification method known in the art. Depending on the amplification technique that is employed, the amplified molecules are detected during amplification (e.g., real-time PCR) or subsequent to amplification using detection techniques known to those of skill in the art. Suitable nucleic acid detection assays include, for example and without limitation, northern blot, microarray, serial analysis of gene expression (SAGE), next-generation RNA sequencing (e.g., deep sequencing, whole transcriptome sequencing, exome sequencing), gene expression analysis by massively parallel signature sequencing (MPSS), immune-derived colorimetric assays, and mass spectrometry (MS) methods (e.g., MassARRAY® System).

Another aspect of the disclosure relates to a method of identifying a subject's risk of developing metastatic brain disease. The method involves selecting a subject having a primary tumor and isolating, from the subject, a sample comprising primary tumor cells, primary tumor cell derived exosomes, or both. CEMIP expression is detected in the isolated sample and the subject's risk of developing metastatic brain disease is identified based on this detection.

As described supra, suitable subjects are subjects having a primary tumor that is susceptible to metastasis. Virtually all cancers have the potential to metastasize. The metastases may occur to any site, however some cancers preferentially metastasize to particular organs. For example, lung, breast, head and neck, cervical, and bladder tumors frequently metastasize to particular organs. Specifically, lung cancer metastasizes to brain, bone, liver, adrenal glands, pleura, subcutaneous tissue, kidney, lymph nodes, cerebrospinal fluid, pancreas, and bone marrow. Breast cancer metastasizes to lymph nodes, breast, abdominal viscera, lungs, bones, liver, adrenal glands, brain, meninges, pleura, and cerebrospinal fluid. Head and neck cancer metastasizes to lung, esophagus, upper digestive tracts, lymph nodes, oral and nose cavity. Cervical cancer metastasizes to bladder, rectum, pelvic wall, lymph nodes, and paracervical spaces. Bladder cancer metastasizes to the prostate, uterus, vagina, bowel, pelvic wall, lymph nodes, and perivesical fat. In accordance with this aspect of the disclosure, a sample comprising primary tumor cells or primary tumor cell derived exosomes can be obtained from a biopsy of the primary tumor. In another embodiment, the sample is a liquid biopsy sample containing primary tumor cells and/or primary tumor cell derived exosomes. Other samples comprising primary tumor cells and/or tumor derived exosomes include, without limitation, blood, serum, ascites, cyst fluid, pleural fluid, peritoneal fluid, cerebral spinal fluid, tears, urine, saliva, sputum, nipple aspirates, lymph fluid, fluid of the respiratory, intestinal, and genitourinary trances, breast milk, intra-organ system fluid, or combinations thereof.

Suitable methods for isolating tumor cell-derived exosomes from a sample are described supra. Similar methods of isolation and enrichment can be employed for isolating primary tumor cells from a sample, e.g., primary tumor cells express tumor-associated surface molecules and these cells can be isolated and/or enriched via selection of these specific tumor-associated surface molecules.

Suitable methods of measuring protein expression levels of CEMIP are described supra.

In accordance with this aspect of the present disclosure, the exosomal and/or primary tumor cell expression levels of CEMIP are compared to a "control" expression level of CEMIP to identify whether a subject is at risk for metastatic brain disease. In one embodiment, the control expression level of CEMIP is the average expression level of CEMIP in exosomal and/or cell samples taken from a cohort of healthy individuals (i.e., the average CEMIP expression level in non-cancerous exosome and cell samples). In another embodiment, the control expression level is the average expression level of CEMIP in exosomes and/or tumor cells taken from individuals having a primary tumor, e.g., a breast tumor, that never metastasized to the brain. In another embodiment, the control expression level of CEMIP is the average CEMIP expression level in exosome and/or tumor cells taken from the subject being tested, but at an earlier time point (e.g., a pre-cancerous time point). In all of these embodiments, an increased expression level of CEMIP in the sample from the subject relative to the control exosomal expression level identifies the subject as having an increased risk of developing metastatic brain disease.

An "increased expression level" refers to an expression level (i.e., protein or gene expression level) that is higher than the control level. For example, an increased expression level is at least 5%, at least 10%, at least 20%, at least 30%, at least 40%, at least 50%, at least 60%, at least 70%, at least 80%, at least 90%, at least 100% higher than the control expression level. An increased expression level is one that is at least 2-fold, at least 3-fold, at least 5-fold, at least 10-fold, at least 50-fold or at least 100-fold higher than the control expression level.

In one embodiment, an increase in primary tumor cell expression level of CEMIP relative to CEMIP expression level in non-tumor cells identifies an increased risk of developing brain metastatic disease for the subject. In another embodiment, an increase in primary tumor cell derived exosomal expression level of CEMIP relative to CEMIP expression level in non-tumor cell derived exosomes identifies an increased risk of developing brain metastatic disease for said subject.

In another embodiment, the control expression level of CEMIP is the average expression level of CEMIP in exosomal or tumor cell samples taken from individuals having a primary tumor, e.g., a breast or lung tumor, gastrointestinal cancers, e.g., colorectal tumors, esophageal tumors, small intestine tumors, stomach tumors, bladder tumors, liver tumors, pancreatic tumors, brain tumor, etc. that later metastasized. Alternatively, the control expression level of CEMIP is the average expression level of CEMIP in exosomal or tumor cell samples taken from individuals with metastatic disease. In accordance with this embodiment, when the exosomal or tumor cell expression level of CEMIP in the subject being tested is the same as or higher the control expression level, the subject is identified as having an increased risk of developing brain metastatic disease. Alternatively, when the exosomal or tumor cell expression level of CEMIP in the subject being tested is lower than the control expression level, the subject is identified as having a low risk of developing brain metastatic disease.

Another aspect of the disclosure relates to a method of inhibiting metastatic brain disease in a subject. The method involves selecting a subject having a primary tumor, wherein expression level of CEMIP in primary tumor cells or exosomes derived from primary tumor cells is increased relative to CEMIP expression levels in non-tumor cells or exosomes derived from non-tumor cells, respectively. A brain metastasis prophylactic treatment suitable for inhibiting metastatic brain disease is administered to the selected subject in an amount effective to inhibit metastatic brain disease in the subject.

Suitable methods for isolating tumor cell derived exosomes and measuring gene and protein expression levels of CEMIP are described supra.

The term "prophylactic treatment" refers to administration of a therapy to a patient having a primary tumor which is likely to metastasize to the brain, where the therapy is administered in manner effective to prevent or inhibit the metastasis from occurring. Prophylactic treatment as used herein also encompasses treatment that is effective to delay, slow, or lessen the severity of metastasis of the primary tumor to the brain.

In one embodiment, a suitable brain metastasis prophylactic treatment is whole brain radiation therapy (Bovi J., "Prevention of Brain Metastases," *Front. Neurol.* 9: 758 (2018), which is hereby incorporated by reference in its entirety).

In another embodiment, a suitable brain metastasis prophylactic treatment may include one more inhibitors of human epidermal growth factor receptor 2 (HER2). A suitable inhibitor of HER2 shown to inhibit brain metastases that can be administered in accordance with the methods of the present application is a monoclonal antibody that binds to HER2/neu, such as trastuzumab or trastuzumab-anns (Grossi et al., "Efficacy of Intracerebral Microinfusion of Trastuzumab in an Athymic Rat Model of Intracerebral Metastatic Breast Cancer," *Clin. Cancer Res.* 9(15):5514-20 (2003), which is hereby incorporated by reference in its entirety).

Another suitable brain metastasis prophylactic treatment includes an inhibitor of PTGS2/COX2. A suitable PTGS2/COX2 inhibitor shown to be useful in treating brain metastases, and thus can be administered in accordance with the methods of the present application is Celecoxib (Cerchietti et al., "Phase I/II Study of Selective Cyclooxygenase-2 Inhibitor Celecoxib as a Radiation Sensitizer in Patients with Unresectable Brain Metastases," *J. Neurooncol.* 71(1): 73-81 (2005), which is hereby incorporated by reference in its entirety).

Another brain metastasis prophylactic treatment may include an inhibitor of vascular endothelial growth factor receptor (VEGFR). A suitable inhibitor of VEGFR shown to inhibit brain metastases that can be administered in accordance with the methods disclosed herein includes PTK787/Z 222584 (Vatalanib), which binds to and inhibits the protein kinase domain of VEGFR (Kim et al., "Vascular Endothelial Growth Factor Expression Promotes the Growth of Breast Cancer Brain Metastases in Nude Mice," *Clinical & Experimental Metastasis* 21:107-18 (2004), which is hereby incorporated by reference in its entirety).

Another brain metastasis prophylactic treatment may include an inhibitor of histone deacetylase (HDAC). A suitable HDAC inhibitor shown to inhibit brain metastases that can be administered in accordance with the methods disclosed herein is Vorinostat, also known as suberanilohydroxamic acid, which binds to the active site of HDAC and acts as a zinc chelator (see Baschnagel et al., "Vorinostat enhances the radiosensitivity of a breast cancer brain metastatic cell line grown in vitro and as intracranial xenografts," *Mol. Cancer Ther.* 8(6): 1589-95 (2009), which is hereby incorporated by reference in its entirety).

Another brain metastasis prophylactic treatment may include an inhibitor of phosphodiesterase 5 (PDE5). A suitable inhibitor of PDE5 shown to inhibit brain metastases that can be administered in accordance with the methods disclosed herein is vardenafil (see Hu et al., "Phosphodiesterase Type 5 Inhibitors Increase Herceptin Transport and Treatment Efficacy in Mouse Metastatic Brain Tumor Models," *PloS One* 19:5(4)1-10 (2010), which is hereby incorporated by reference in its entirety).

Another brain metastasis prophylactic treatment may include an inhibitor of proto-oncogene B-Raf. A suitable inhibitor of B-raf shown to inhibit brain metastases that can be administered in accordance with the methods disclosed herein is the kinase inhibitor pazopanib (see Gril et al.; "Effect of lapatinib on the outgrowth of metastatic breast cancer cells to the brain," *Journal of the National Cancer Institute* 100:1092-1103 (2008), which is hereby incorporated by reference in its entirety).

Another brain metastasis prophylactic treatment may include an inhibitor of polo-like kinase 1 (Plk1). A suitable inhibitor of Plk1 shown to inhibit brain metastases that can be administered in accordance with the methods disclosed herein is the imidazotriazine derivative, GSK461364A, an ATP kinase inhibitor that is highly specific for Plk1 (see Qian, et al. "Inhibition of Polo-like kinase 1 Prevents the Growth of Metastatic Breast Cancer Cells in the Brain," *Clin. Exp. Metastasis* 28(8): 899-908 (2011), which is hereby incorporated by reference in its entirety).

Another brain metastasis prophylactic treatment may include an inhibitor of microtubule function. A suitable microtubule inhibitor shown to inhibit brain metastases that can be administered in accordance with the methods disclosed herein is TPI 287, a third generation taxane that binds to tubulin and stabilizes microtubules (see Fitzgerald et al., "TPI-287, a New Taxane Family Member, Reduces the Brain Metastatic Colonization of Breast Cancer Cells," *Mol. Cancer Ther.* 11:1969-67 (2012), which is hereby incorporated by reference in its entirety).

Another brain metastasis prophylactic treatment may include an inhibitor of phosphatidylinositide 3-kinase (PI3K). A suitable PI3K inhibitor shown to inhibit brain metastases that can be administered in accordance with the methods disclosed herein includes BKM-120, which is a dimorpholino pyrimidine derivative capable of penetrating the blood-brain barrier (Nanni et al., "Multiorgan metastasis of human HER-2+ breast cancer in Rag2–/–; Il2rg–/– mice and treatment with PI3K inhibitor," *PLOS One* 7(6): e39626 (2012), which is hereby incorporated by reference in its entirety).

Another brain metastasis prophylactic treatment may include an inhibitor of epidermal growth factor receptor (EGFR). A suitable inhibitor of EGFR shown to inhibit brain metastases that can be administered in accordance with the methods disclosed herein includes TAK-285, which is a dual erbB kinase inhibitor that specifically targets EGFR and HER2 (see Nakayama et al., "Antitumor Activity of TAK-285, an Investigational, Non-Pgp Substrate HER2/EGFR Kinase Inhibitor, in Cultured Tumor Cells, Mouse and Rat Xenograft Tumors, and in an HER2-Positive Brain Metastasis Model," *Journal of Cancer* 4:557-65 (2013), which is hereby incorporated by reference in its entirety). Another suitable inhibitor EGFR for use in accordance with the methods disclosed herein is the quinazoline derivative, icotinib.

Another brain metastasis prophylactic treatment may include an inhibitor of angiopoietin-2 (Ang-2). A suitable inhibitor of Ang-2 shown to inhibit brain metastases that can be administered in accordance with the methods disclosed herein includes trebananib, a neutralizing peptibody that binds to Ang1 and Ang2 (see Avraham et al., "Angiopoietin-2 Mediates Blood-brain Barrier Impairment and Colonization of Triple-Negative Breast Cancer Cells in Brain," *J. Pathol.* 232(3): 369-81 (2014), which is hereby incorporated by reference in its entirety).

Another brain metastasis prophylactic treatment may include an inhibitor of cathepsin S. A suitable cathepsin S inhibitor shown to inhibit brain metastases that can be administered in accordance with the methods disclosed herein is VBY-999 (see Sevenich et al., "Analysis of tumour- and stroma-supplied proteolytic networks reveals a brain-metastasis-promoting role for cathepsin S," *Nat. Cell Biol.* 16(9):876-88 (2014), which is hereby incorporated by reference in its entirety).

Another brain metastasis prophylactic treatment may include an inhibitor of ALK. Suitable ALK inhibitors shown to inhibit brain metastases that can be administered in accordance with the methods disclosed herein include alectinib and crixotinib.

Another suitable brain metastasis prophylactic treatment may also or alternatively include a chemotherapeutic agent. One suitable chemotherapeutic agent utilized for the prevention of brain metastasis is methotrexate. Other chemotherapeutic agents suitable for use as prophylactic treatment of brain metastasis include alkylating agents (e.g., chlorambucil, cyclophosphamide, CCNU, melphalan, procarbazine, thiotepa, BCNU, and busulfan), antimetabolites (e.g., methotrexate, 6-mercaptopurine, and 5-fluorouracil), anthracyclines (e.g., daunorubicin, doxorubicin, idarubicin, epirubicin, and mitoxantrone), antitumor antibiotics (e.g., bleomycin, monoclonal antibodies (e.g., Alemtuzumab, Bevacizumab, Cetuximab, Gemtuzumab, Ibritumomab, Panitumumab, Rituximab, Tositumomab, and Trastuxmab), platiniums (e.g., cisplatin and oxaliplatin) or plant alkaloids (e.g., topoisomerase inhibitors, vinca alkaloids, taxanes, and epipodophyllotoxins).

Another suitable brain metastasis prophylactic treatment may also or alternatively include an anti-angiogenic or anti-vasculogenic therapeutic. Suitable anti-angiogenic or anti-vasculogenic therapeutics for inhibiting brain metastatic disease include, without limitation a vascular endothelial growth factor (VEGF) inhibitor, basic fibroblast growth factor (bFGF) inhibitor, vascular endothelial growth factor receptor (VEGFR) antagonist, platelet-derived growth factor receptor (PDGFR) antagonist, fibroblast growth factor receptor (FGFR) antagonist, Angiopoietin receptor (Tie-2) antagonist, epidermal growth factor receptor (EGFR, ErbB) antagonist, or any combination thereof. A number of suitable small molecule angiogenic inhibitors are known in the art and are under clinical development (see e.g., Wu et al., "Anti-Angiogenic Therapeutic Drugs for the Treatment of Human Cancer," *J Cancer Molecules* 4(2):37-45 (2008) and Bissell et al., "Why Don't We Get More Cancer? A Proposed Role of the Microenvironment in Restraining Cancer Progression," *Nat. Med.* 17(3):320-329 (2011), which are hereby incorporated by reference in their entirety). These angiogenic inhibitors include, without limitation, Endostatin (an endothelial cell proliferation and angiogenesis inhibitors), Gefitinib (an ErbB inhibitor), Lapatinib (a dual ErbB1/ErbB2 inhibitor), Erlotinib (HER1/EGFR inhibitor), Canertinib (a pan-ErbB inhibitor), Vatalanib (VEGF receptor inhibitor), Imatinib (multi-targeted inhibitor of Bcr-Abl, c-kit, and PDGF-R inhibitor), Sunitinib (multi-targeted inhibitor of VEGFR, PDGFR, Kit, Flt3, Tet and CSFIR), Sorafenib (multi-targeted inhibit of VEGFR and PDGFR), Pazopanib (a multi-targeted inhibitor of VEGFR-1, VEGFR-2, VEGFR-3, PDGF-α, PDGFR-β, and c-kit). Alternatively, the anti-vasculogenic therapeutic is a monoclonal antibody. Suitable antibody therapeutics include, without limitation, Bevacizumab (VEGF antibody), IMC-1C11 (VEGFR-2 antibody), mF4-31C1 (VEGFR-3 antibody), and Vitaxin (integrin αvβ3 antibody).

Another suitable brain metastasis prophylactic treatment may also or alternatively include a stromal inhibitor. Suitable stromal inhibitors for use in the present method are known in the art (see Bissell et al., "Why Don't We Get More Cancer? A Proposed Role of the Microenvironment in Restraining Cancer Progression," *Nat. Med.* 17(3):320-329 (2011), which is hereby incorporated by reference in its entirety) and include, without limitation, MK-2461 (a small molecule inhibit of c-MET kinase), Anastrazole (an aromatase inhibitor), AMD070 (a CXCR4 inhibitor), IPI-926 (a hedgehog pathway inhibitor), AVE1642 (a humanized monoclonal antibody targeting insulin-like growth factor-1 receptor), BGJ398 (a small molecule inhibitor of fibroblast growth factor receptors), Celecoxib (a COX-2 inhibitor), MK0822 (a cathepsin K inhibitor), Bortezomib (a 26S proteasome complex inhibitor), Zoledronate (a small-molecule pyrophosphate analog that inhibits the differentiation of myeloid cells and affects tumor-associated macrophages), Denosumab (a human monoclonal antibody the binds RANKL), and PG545, a heparan sulfate mimetic that inhibits heparanase activity.

In practicing the methods of the present application, the administering step is carried out to achieve inhibition of metastasis or metastatic disease progression. Such administration can be carried out systemically or via direct or local administration to the primary tumor site and/or to the brain. By way of example, suitable modes of systemic administration include, without limitation orally, topically, transdermally, parenterally, intradermally, intramuscularly, intraperitoneally, intravenously, subcutaneously, or by intranasal instillation, by intracavitary or intravesical instillation, intraocularly, intraarterialy, intralesionally, or by application to mucous membranes. Suitable modes of local administration include, without limitation, catheterization, implantation, direct injection, dermal/transdermal application, or portal vein administration to relevant tissues, or by any other local administration technique, method or procedure generally known in the art. By way of example, intra-ommaya and intrathecal administration are suitable modes for direct administration into the brain for existing metastases. The mode of affecting delivery of agent will vary depending on the type of prophylactic agent (e.g., an antibody or small molecule).

The brain metastasis prophylactic treatment of the present application may be orally administered, for example, with an inert diluent, or with an assimilable edible carrier, or it may be enclosed in hard or soft shell capsules, or it may be compressed into tablets, or they may be incorporated directly with the food of the diet. Brain metastasis prophylactic treatments may also be administered in a time release manner incorporated within such devices as time-release capsules or nanotubes. Such devices afford flexibility relative to time and dosage. For oral therapeutic administration, the agents of the present application may be incorporated with excipients and used in the form of tablets, capsules, elixirs, suspensions, syrups, and the like. Such compositions and preparations should contain at least 0.1% of the agent, although lower concentrations may be effective and indeed optimal. The percentage of the agent in these compositions may, of course, be varied and may conveniently be between about 2% to about 60% of the weight of the unit.

When the brain metastasis prophylactic treatment is administered parenterally, solutions or suspensions of the agent can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions. Under ordinary conditions of storage and use, these preparations contain a preservative to prevent the growth of microorganisms.

Pharmaceutical formulations of the brain metastasis prophylactic therapeutics suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

In addition to the formulations described previously, the brain metastasis prophylactic therapeutic may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

Effective doses of brain metastasis prophylactic therapeutics, for the prevention or inhibition of brain metastatic disease vary depending upon many different factors, including type and stage of the primary cancer, means of administration, target site, physiological state of the patient, other medications or therapies administered, and physical state of the patient relative to other medical complications. Treatment dosages need to be titrated to optimize safety and efficacy.

Another aspect of the present disclosure relates to a method of treating brain cancer in a subject. The method involves selecting a subject having a primary brain tumor, wherein expression level of CEMIP in primary tumor cells or exosomes derived from primary tumor cells is increased relative to CEMIP expression levels in non-tumor cells or exosomes derived from non-tumor cells, respectively. A CEMIP inhibitor in an amount effective to treat the brain cancer cz is then administered to the selected subject.

Another aspect of the present disclosure relates to a method of inhibiting metastatic brain disease in a subject. The method involves selecting a subject having a primary tumor, wherein expression level of CEMIP in primary tumor cells or exosomes derived from primary tumor cells is increased relative to CEMIP expression levels in non-tumor cells or exosomes derived from non-tumor cells, respectively. A CEMIP inhibitor in an amount effective to inhibit metastatic brain disease is then administered to the selected subject.

As described above, an "increased expression level" refers to an expression level (i.e., protein or gene expression level) that is higher than the control level (e.g., the CEMIP expression level in non-tumor cells or exosomes derived from non-tumor cells). For example, an increased expression level of CEMIP is at least 10%, at least 20%, at least 30%, at least 40%, at least 50%, at least 80%, at least 100%, at least 2-fold, at least 3-fold, at least 5-fold, at least 10-fold, at least 50-fold or at least 100-fold higher than the control expression level.

In some embodiments, the treatment is administered as a part of an adjuvant therapy regime. In particular, this involves chemotherapy, hormone therapy, radiation therapy, immunotherapy, or a targeted therapy together with an agent that inhibits CEMIP prior to and/or after surgery. In addition, the present method may be used to treat patients after primary surgery who may not otherwise receive treatment, i.e. those patients with primary complete resection of the primary tumor without evidence of residual or distant disease in order to prevent metastatic spread.

In one embodiment, the CEMIP inhibitor is an anti-CEMIP antibody, a CEMIP binding fragment thereof, or an anti-CEMIP antibody derivative (collectively referred to herein as "CEMIP antibody-based molecule").

An anti-CEMIP antibody of the present disclosure is an intact immunoglobulin as well as a molecule having an epitope-binding fragment thereof that binds to a portion of the amino acid sequence of SEQ ID NO: 1 and inhibits the function and/or activity of the CEMIP protein. Such functions and/or activities include pre-conditioning the brain microenvironment for metastasis and cancer cell outgrowth, increasing invasion and tumor cell association with the brain vasculature, and inducing endothelial cell branching and inflammation in the perivascular niche. As used herein, the terms "fragment", "region", and "domain" are generally intended to be synonymous, unless the context of their use indicates otherwise. Full CEMIP antibodies typically comprise a tetramer which is usually composed of at least two heavy (H) chains and at least two light (L) chains. Each heavy chain is comprised of a heavy chain variable ($V_H$) region and a heavy chain constant ($C_H$) region, usually comprised of three domains ($C_H1$, $C_H2$ and $C_H3$ domains). Heavy chains can be of any isotype, including IgG (IgG1, IgG2, IgG3 and IgG4 subtypes), IgA (IgA1 and IgA2 subtypes), IgM and IgE. Each light chain is comprised of a light chain variable ($V_L$) region and a light chain constant ($C_L$) region. The heavy and/or light chain variable regions are responsible for CEMIP recognition and binding, while the heavy and light chain constant regions may mediate the binding of the immunoglobulin to host tissues or factors, including various cells of the immune system (e.g., effector cells) and the first component (Clq) of the classical complement system. The $V_H$ and $V_L$ regions can be further subdivided into regions of hypervariability, termed "complementarity determining regions," or "CDRs," that are interspersed with regions of more conserved sequence, termed "framework regions" (FR). Antibodies that bind CEMIP protein are known in the art, see e.g., Fink et al., "Induction of KIAA1199/CEMIP is Associated with Colon Cancer Phenotype and Poor Patient Survival," *Oncotarget* 6(31): 30500-30515 (2015), which is hereby incorporated by reference in its entirety.

CEMIP antibody fragments (including Fab and (Fab)₂ fragments) that exhibit epitope-binding ability can be obtained, for example, by protease cleavage of intact antibodies. Single domain antibody fragments possess only one variable domain (e.g., $V_L$ or $V_H$). Examples of the epitope-binding fragments encompassed within the present application include (i) Fab' or Fab fragments, which are monovalent fragments containing the $V_L$, $V_H$, $C_L$ and $C_H1$ domains; (ii) F(ab')₂ fragments, which are bivalent fragments comprising two Fab fragments linked by a disulfide bridge at the hinge region; (iii) Fd fragments consisting essentially of the $V_H$ and $C_H1$ domains; (iv) Fv fragments consisting essentially of a $V_L$ and $V_H$ domain, (v) dAb fragments (Ward et al. "Binding Activities Of A Repertoire Of Single Immunoglobulin Variable Domains Secreted From *Escherichia coli*," *Nature* 341:544-546 (1989) which is hereby incorporated by reference in its entirety), which consist essentially of a $V_H$ or $V_L$ domain and also called domain antibodies (Holt et al. "Domain Antibodies: Proteins For Therapy," *Trends Biotechnol.* 21(11):484-490 (2003), which is hereby incorporated by reference in its entirety); (vi) camelid or nanobodies (Revets et al. "Nanobodies As Novel Agents For Cancer Therapy," *Expert Opin. Biol. Ther.* 5(1):111-124 (2005), which is hereby incorporated by reference in its entirety) and (vii) isolated complementarity determining regions (CDR). An epitope-binding fragment may contain 1, 2, 3, 4, 5 or all 6 of the CDR domains of such antibody.

Such antibody fragments are obtained using conventional techniques known to those of skill in the art. For example, F(ab')2 fragments may be generated by treating an antibody with pepsin. The resulting F(ab')2 fragment may be treated to reduce disulfide bridges to produce Fab' fragments. Fab fragments may be obtained by treating an IgG antibody with papain and Fab' fragments may be obtained with pepsin digestion of IgG antibody. A Fab' fragment may be obtained by treating an F(ab')₂ fragment with a reducing agent, such as dithiothreitol. Antibody fragment may also be generated by expression of nucleic acids encoding such fragments in recombinant cells (see e.g., Evans et al. "Rapid Expression of An Anti-Human C5 Chimeric Fab Utilizing A Vector That Replicates In COS And 293 Cells," *J. Immunol. Meth.* 184:123-38 (1995), which is hereby incorporated by reference in its entirety). For example, a chimeric gene encoding a portion of an F(ab')₂ fragment could include DNA sequences encoding the CH1 domain and hinge region of the heavy chain, followed by a translational stop codon to yield such a truncated antibody fragment molecule. Suitable fragments capable of binding to a desired epitope may be readily screened for utility in the same manner as an intact antibody.

CEMIP antibody derivatives include those molecules that contain at least one epitope-binding domain of an antibody, and are typically formed using recombinant techniques. One exemplary antibody derivative includes a single chain Fv (scFv). A scFv is formed from the two domains of the Fv fragment, the $V_L$ region and the $V_H$ region, which are encoded by separate gene. Such gene sequences or their encoding cDNA are joined, using recombinant methods, by a flexible linker (typically of about 10, 12, 15 or more amino acid residues) that enables them to be made as a single protein chain in which the $V_L$ and $V_H$ regions associate to form monovalent epitope-binding molecules (see e.g., Bird et al. "Single-Chain Antigen-Binding Proteins," *Science* 242:423-426 (1988); and Huston et al. "Protein Engineering Of Antibody Binding Sites: Recovery Of Specific Activity In An Anti-Digoxin Single-Chain Fv Analogue Produced In *Escherichia coli*," *Proc. Natl. Acad. Sci.* (*U.S.A.*) 85:5879-5883 (1988), which are hereby incorporated by reference in their entirety). Alternatively, by employing a flexible linker that is too short (e.g., less than about 9 residues) to enable the $V_L$ and $V_H$ regions of a single polypeptide chain to associate together, one can form a bispecific antibody.

In another embodiment, the CEMIP antibody-based molecule is an antibody derivative. In some embodiments, the antibody derivative is a divalent or bivalent single-chain variable fragment, engineered by linking two scFvs together either in tandem (i.e., tandem scFv), or such that they dimerize to form diabodies (Holliger et al. "'Diabodies': Small Bivalent And Bispecific Antibody Fragments," *Proc. Natl. Acad. Sci.* (*U.S.A.*) 90(14), 6444-8 (1993), which is hereby incorporated by reference in its entirety). In yet another embodiment, the CEMIP antibody derivative is a trivalent single chain variable fragment, engineered by linking three scFvs together, either in tandem or in a trimer formation to form triabodies. In another embodiment, the CEMIP antibody derivative is a tetrabody single chain variable fragment. In another embodiment, the antibody is a "linear antibody" which is an antibody comprising a pair of tandem Fd segments ($V_H$-$C_H1$-$V_H$-$C_H1$) that form a pair of antigen binding regions (see Zapata et al. *Protein Eng.* 8(10): 1057-1062 (1995), which is hereby incorporated by reference in its entirety). In another embodiment, the antibody derivative is a minibody, consisting of the single-chain Fv regions coupled to the $C_H3$ region (i.e., scFv-$C_H3$).

These and other useful antibody fragments and derivatives in the context of the present application are discussed further herein. It also should be understood that the term antibody-based molecule, unless specified otherwise, also includes antibody-like polypeptides, such as chimeric antibodies and humanized antibodies, and antibody fragments retaining the ability to specifically bind to the antigen (epitope-binding fragments) provided by any known technique, such as enzymatic cleavage, peptide synthesis, and recombinant techniques.

An antibody as generated herein may be of any isotype. As used herein, "isotype" refers to the immunoglobulin class (for instance IgG1, IgG2, IgG3, IgG4, IgD, IgA, IgE, or IgM) that is encoded by heavy chain constant region genes. The choice of isotype typically will be guided by the desired effector functions, such as antibody-dependent cellular cytotoxicity (ADCC) induction. Exemplary isotypes are IgG1, IgG2, IgG3, and IgG4. Either of the human light chain constant regions, kappa or lambda, may be used. If desired, the class of a CEMIP antibody of the present invention may be switched by known methods. For example, an antibody of the present invention that was originally IgM may be class switched to an IgG antibody of the present invention. Further, class switching techniques may be used to convert one IgG subclass to another, for instance from IgG1 to IgG2. Thus, the effector function of the antibodies of the present invention may be changed by isotype switching to, e.g., an IgG1, IgG2, IgG3, IgG4, IgD, IgA, IgE, or IgM antibody for various therapeutic uses.

In some embodiments, the antibody-based molecules of the present invention are "humanized," particularly if they are to be employed for therapeutic purposes. The term "humanized" refers to a chimeric molecule, generally prepared using recombinant techniques, having an antigen-binding site derived from an immunoglobulin from a non-human species and a remaining immunoglobulin structure based upon the structure and/or sequence of a human immunoglobulin. The antigen-binding site may comprise either complete non-human antibody variable domains fused to human constant domains, or only the complementarity determining regions (CDRs) of such variable domains grafted to appropriate human framework regions of human variable domains. The framework residues of such humanized molecules may be wild-type (e.g., fully human) or they may be modified to contain one or more amino acid substitutions not found in the human antibody whose sequence has served as the basis for humanization. Humanization lessens or eliminates the likelihood that a constant region of the molecule will act as an immunogen in human individuals, but the possibility of an immune response to the foreign variable region remains (LoBuglio, A. F. et al. "Mouse/Human Chimeric Monoclonal Antibody In Man: Kinetics And Immune Response," Proc. Natl. Acad. Sci. USA 86:4220-4224 (1989), which is hereby incorporated by reference in its entirety). Another approach focuses not only on providing human-derived constant regions, but modifying the variable regions so as to reshape them as closely as possible to human form. The variable regions of both heavy and light chains contain three complementarity-determining regions (CDRs) which vary in response to the antigens in question and determine binding capability. The CDRs are flanked by four framework regions (FRs) which are relatively conserved in a given species and which putatively provide a scaffolding for the CDRs. When non-human antibodies are prepared with respect to a particular antigen, the variable regions can be "reshaped" or "humanized" by grafting CDRs derived from non-human antibody on the FRs present in the human antibody to be modified. Suitable methods for humanizing the non-human antibody described herein are known in the art see e.g., Sato, K. et al., Cancer Res 53:851-856 (1993); Riechmann, L. et al., "Reshaping Human Antibodies for Therapy," Nature 332:323-327 (1988); Verhoeyen, M. et al., "Reshaping Human Antibodies: Grafting An Antilysozyme Activity," Science 239:1534-

1536 (1988); Kettleborough, C. A. et al., "Humanization Of A Mouse Monoclonal Antibody By CDR-Grafting: The Importance Of Framework Residues On Loop Conformation," Protein Engineering 4:773-3783 (1991); Maeda, H. et al., "Construction Of Reshaped Human Antibodies With HIV-Neutralizing Activity," Human Antibodies Hybridoma 2:124-134 (1991); Gorman, S. D. et al., "Reshaping A Therapeutic CD4 Antibody," Proc. Natl. Acad. Sci. USA 88:4181-4185 (1991); Tempest, P. R. et al., "Reshaping A Human Monoclonal Antibody To Inhibit Human Respiratory Syncytial Virus Infection In Vivo," Bio/Technology 9:266-271 (1991); Co, M. S. et al., "Humanized Antibodies For Antiviral Therapy," Proc. Natl. Acad. Sci. USA 88:2869-2873 (1991); Carter, P. et al., "Humanization Of An Anti-p185her2 Antibody For Human Cancer Therapy," Proc. Natl. Acad. Sci. USA 89:4285-4289 (1992); and Co, M. S. et al., "Chimeric And Humanized Antibodies With Specificity For The CD33 Antigen," J. Immunol. 148:1149-1154 (1992), which are hereby incorporated by reference in their entirety. In some embodiments, humanized CEMIP antibodies of the present invention preserve all CDR sequences (for example, a humanized antibody containing all six CDRs from the mouse antibody). In other embodiments, humanized CEMIP antibodies of the present invention have one or more CDRs (one, two, three, four, five, six) which are altered with respect to the original antibody. Methods of humanizing an antibody are well-known in the art and suitable for humanizing the antibodies of the present invention (see, e.g., U.S. Pat. No. 5,225,539 to Winter; U.S. Pat. Nos. 5,530,101 and 5,585,089 to Queen and Selick; U.S. Pat. No. 5,859,205 to Robert et al.; U.S. Pat. No. 6,407,213 to Carter; and U.S. Pat. No. 6,881,557 to Foote, which are hereby incorporated by reference in their entirety).

Suitable CEMIP-antibody based molecule for use in the methods described herein comprise the amino acid sequence of any one, any two, any three, any four, any five, or any six CDRs as provided in Tables 1 and 2 herein.

In one aspect, the antibody-based molecule that binds to CEMIP comprises a heavy chain variable region, where the heavy chain variable region comprises: (i) a complementarity-determining region 1 (CDR-H1) comprising an amino acid sequence of any one of SEQ ID NOs: 2-8 or a modified amino acid sequence of any one of SEQ ID NOs: 2-8, said modified sequence having at least 80% sequence identity to any one of SEQ ID NOs: 2-8; (ii) a complementarity-determining region 2 (CDR-H2) comprising an amino acid sequence of any one of SEQ ID NOs: 9-15 or a modified amino acid sequence of any one of SEQ ID NOs: 9-15, said modified sequences having at least 80% sequence identity to any one of SEQ ID NOs: 9-15; and (iii) a complementarity-determining region 3 (CDR-H3) comprising an amino acid sequence of any one of SEQ ID NOs: 16-22, or a modified amino acid sequence of any one of SEQ ID NO: 16-22, said modified sequence having at least 80% sequence identity to any one of SEQ ID NOs: 16-22.

In some embodiments, the antibody-based molecule that binds to human CEMIP comprises a heavy chain variable region comprising the CDR-H1 of SEQ ID NO: 2, the CDR-H2 of SEQ ID NO: 9, and the CDR-H3 of SEQ ID NO: 16.

In some embodiments, the antibody-based molecule that binds to human CEMIP comprises a heavy chain variable region comprising the CDR-H1 of SEQ ID NO: 3, the CDR-H2 of SEQ ID NO: 10, and the CDR-H3 of SEQ ID NO: 17.

In some embodiments, the antibody-based molecule that binds to human CEMIP comprises a heavy chain variable region comprising the CDR-H1 of SEQ ID NO: 4, the CDR-H2 of SEQ ID NO: 11, and the CDR-H3 of SEQ ID NO: 18.

In some embodiments, the antibody-based molecule that binds to human CEMIP comprises a heavy chain variable region comprising the CDR-H1 of SEQ ID NO: 5, the CDR-H2 of SEQ ID NO: 12, and the CDR-H3 of SEQ ID NO: 19.

In some embodiments, the antibody-based molecule that binds to human CEMIP comprises a heavy chain variable region comprising the CDR-H1 of SEQ ID NO: 6, the CDR-H2 of SEQ ID NO: 13, and the CDR-H3 of SEQ ID NO: 20.

In some embodiments, the antibody-based molecule that binds to human CEMIP comprises a heavy chain variable region comprising the CDR-H1 of SEQ ID NO: 7, the CDR-H2 of SEQ ID NO: 14, and the CDR-H3 of SEQ ID NO: 21.

In some embodiments, the antibody-based molecule that binds to human CEMIP comprises a heavy chain variable region comprising the CDR-H1 of SEQ ID NO: 8, the CDR-H2 of SEQ ID NO: 15, and the CDR-H3 of SEQ ID NO: 22.

The sequences of the heavy chain CDR sequences of the CEMIP antibodies disclosed herein for use in the methods described herein are provided in Table 8 below mining region 3 (CDR-L3) having an amino acid sequence of any one of SEQ ID NOs: 37-43, or a modified amino acid sequence of any one of SEQ ID NO: 37-43, said modified sequence having at least 80% sequence identity to any one of SEQ ID NO: 37-43.

In some embodiments, the light chain variable region of the CEMIP antibody based molecule disclosed herein comprises a light chain variable region comprising the CDR-L1 of SEQ ID NO: 23, the CDR-L2 of SEQ ID NO: 30, and the CDR-L3 of SEQ ID NO: 37.

In some embodiments, the light chain variable region of the CEMIP antibody based molecule disclosed herein comprises a light chain variable region comprising the CDR-L1 of SEQ ID NO: 24, the CDR-L2 of SEQ ID NO: 31, and the CDR-L3 of SEQ ID NO: 38.

In some embodiments, the light chain variable region of the CEMIP antibody based molecule disclosed herein comprises a light chain variable region comprising the CDR-L1 of SEQ ID NO: 25, the CDR-L2 of SEQ ID NO: 32, and the CDR-L3 of SEQ ID NO: 39.

In some embodiments, the light chain variable region of the CEMIP antibody based molecule disclosed herein comprises a light chain variable region comprising the CDR-L1 of SEQ ID NO: 26, the CDR-L2 of SEQ ID NO: 33, and the CDR-L3 of SEQ ID NO: 40.

TABLE 8

| Heavy Chain CDR Sequences of CEMIP Antibodies | | | | | |
|---|---|---|---|---|---|
| | HCDR1 | | HCDR2 | | HCDR3 | |
| mAb name | Sequence | SEQ ID NO: | Sequence | SEQ ID NO: | Sequence | SEQ ID NO: |
| cAb4853 07F11C02 | SFGMH | 2 | YISSASNTIYYADTVKG | 9 | RDWDLYAMDY | 16 |
| cAb4854 10F01B02 | SFGMH | 3 | YISSASNTIYYADTVKG | 10 | RNWDLYAMDY | 17 |
| cAb4855 01F11A01 | TSGMGVG | 4 | HIWWNDEKYYNAALKS | 11 | ITGAWFPY | 18 |
| cAb5775 12D02 | AYTMN | 5 | LINPYNGGTTYNQKFKG | 12 | YDYGYAMDY | 19 |
| cAb5776 12A12 | AYTMN | 6 | LINPYNGGTTYNQKFKG | 13 | YDYGYAMDY | 20 |
| cAb5777 12D08 | DTYMH | 7 | NIDPANGHTKYAPKFQG | 14 | SNDYDVDFDY | 21 |
| cAb5778 13G04 | AYTMN | 8 | LINPYNGGTTYNQKFKG | 15 | YYGGRGWYFDV | 22 |

In some embodiments, the CEMIP antibody-based molecules for use in the methods described herein further comprise a light chain variable region. The light chain variable region comprises (i) a complementarity-determining region 1 (CDR-L1) having an amino acid sequence of any one of SEQ ID NOs: 23-29, or a modified amino acid sequence of any one of SEQ ID NO: 23-29, said modified sequence having at least 80% sequence identity to any one of SEQ ID NO: 23-29; (ii) a complementarity-determining region 2 (CDR-L2) having an amino acid sequence of any one of SEQ ID NOs: 30-36, or a modified amino acid sequence of any one of SEQ ID NO: 30-36, said modified sequence having at least 80% sequence identity to any one of SEQ ID NO: 30-36; and (iii) a complementarity-deter- In some embodiments, the light chain variable region of the CEMIP antibody based molecule disclosed herein comprises a light chain variable region comprising the CDR-L1 of SEQ ID NO: 27, the CDR-L2 of SEQ ID NO: 34, and the CDR-L3 of SEQ ID NO: 41.

In some embodiments, the light chain variable region of the CEMIP antibody based molecule disclosed herein comprises a light chain variable region comprising the CDR-L1 of SEQ ID NO: 28, the CDR-L2 of SEQ ID NO: 35, and the CDR-L3 of SEQ ID NO: 42.

In some embodiments, the light chain variable region of the CEMIP antibody based molecule disclosed herein comprises a light chain variable region comprising the CDR-L1 of SEQ ID NO: 29, the CDR-L2 of SEQ ID NO: 36, and the CDR-L3 of SEQ ID NO: 43.

The sequences of the light chain CDR sequences are provided in Table 9 below.

grouped separately as aliphatic-hydroxyl; (4) aromatic (phenylalanine, tyrosine, tryptophan); (5) amide (asparagine, glutamine); and (6) sulfur-containing (cysteine and methionine) (Stryer (ed.), Biochemistry, 2nd ed, WH Freeman and Co., 1981, which is hereby incorporated by reference in its

TABLE 9

Light Chain CDR Sequences of CEMIP Antibodies

| mAb name | LCDR1 Sequence | SEQ ID NO: | LCDR2 Sequence | SEQ ID NO: | LCDR3 Sequence | SEQ ID NO: |
|---|---|---|---|---|---|---|
| cAb4853 07F11C02 | KASQNVGTAVA | 23 | SASNRHT | 30 | QQYSSSPT | 37 |
| cAb4854 10F01B02 | KANQNVGTAVA | 24 | STSNRDT | 31 | QQYRNYPT | 38 |
| cAb4855 01F11A01 | RASQHISEYLH | 25 | YGSQSIS | 32 | QNGHSFPYT | 39 |
| cAb5775 12D02 | RSSQSIVHRNGNTYLE | 26 | KVSNRFS | 33 | FQGSHVPWT | 40 |
| cAb5776 12A12 | RSSQSIVHRSGNTYLE | 27 | KVSNRFS | 34 | FQGSHVPWT | 41 |
| cAb5777 12D08 | KSSQSLLNSRTRKNYL A | 28 | WASTRES | 35 | KQSYNLYT | 42 |
| cAb5778 13G04 | RASKSVSTSGYSYVH | 29 | LASNLES | 36 | QNSRELPYT | 43 |

Suitable amino acid modifications to the heavy chain CDR sequences and/or the light chain CDR sequences of the CEMIP antibody-based molecule disclosed herein include, for example, conservative substitutions or functionally equivalent amino acid residue substitutions that result in variant CDR sequences having similar or enhanced binding characteristics to those of the CDR sequences disclosed herein as described above. Encompassed by the present disclosure are CDRs of Table 8 and 9 containing 1, 2, 3, 4, 5, or more amino acid substitutions (depending on the length of the CDR) that maintain or enhance CEMIP binding of the antibody. The resulting modified CDRs are at least 70%, at least 75%, at least 80%, at least 85%, at least 90%, at least 95% similar in sequence to the CDRs of Tables 8 and 9. Suitable amino acid modifications to the heavy chain CDR sequences of Table 8 and/or the light chain CDR sequences of Table 9 include, for example, conservative substitutions or functionally equivalent amino acid residue substitutions that result in variant CDR sequences having similar or enhanced binding characteristics to those of the CDR sequences of Table 8 and Table 9. Conservative substitutions are those that take place within a family of amino acids that are related in their side chains. Genetically encoded amino acids can be divided into four families: (1) acidic (aspartate, glutamate); (2) basic (lysine, arginine, histidine); (3) non-polar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. Alternatively, the amino acid repertoire can be grouped as (1) acidic (aspartate, glutamate); (2) basic (lysine, arginine histidine), (3) aliphatic (glycine, alanine, valine, leucine, isoleucine, serine, threonine), with serine and threonine optionally entirety). Non-conservative substitutions can also be made to the heavy chain CDR sequences of Table 8 and the light chain CDR sequences of Table 9. Non-conservative substitutions involve substituting one or more amino acid residues of the CDR with one or more amino acid residues from a different class of amino acids to improve or enhance the binding properties of CDR. The amino acid sequences of the heavy chain variable region CDRs of Table 8 and/or the light chain variable region CDRs of Table 9 may further comprise one or more internal neutral amino acid insertions or deletions that maintain or enhance CEMIP binding.

In some embodiments, the antibody-based molecule that binds to human CEMIP for use in the methods as described herein comprises a heavy chain variable region comprising the CDR-H1 of SEQ ID NO: 2, the CDR-H2 of SEQ ID NO: 9, and the CDR-H3 of SEQ ID NO: 16, and a light chain variable region comprising the CDR-L1 of SEQ ID NO: 23, the CDR-L2 of SEQ ID NO: 30, and the CDR-L3 of SEQ ID NO: 37.

In some embodiments, the antibody-based molecule that binds to human CEMIP comprises a heavy chain variable region comprising the CDR-H1 of SEQ ID NO: 3, the CDR-H2 of SEQ ID NO: 10, and the CDR-H3 of SEQ ID NO: 17, and a light chain variable region comprising the CDR-L1 of SEQ ID NO: 24, the CDR-L2 of SEQ ID NO: 31, and the CDR-L3 of SEQ ID NO: 38.

In some embodiments, the antibody-based molecule that binds to human CEMIP comprises a heavy chain variable region comprising the CDR-H1 of SEQ ID NO: 4, the CDR-H2 of SEQ ID NO: 11, and the CDR-H3 of SEQ ID NO: 18, and a light chain variable region comprising the CDR-L1 of SEQ ID NO: 25, the CDR-L2 of SEQ ID NO: 32, and the CDR-L3 of SEQ ID NO: 39.

In some embodiments, the antibody-based molecule that binds to human CEMIP comprises a heavy chain variable region comprising the CDR-H1 of SEQ ID NO: 5, the CDR-H2 of SEQ ID NO: 12, and the CDR-H3 of SEQ ID NO: 19, and a light chain variable region comprising the CDR-L1 of SEQ ID NO: 26, the CDR-L2 of SEQ ID NO: 33, and the CDR-L3 of SEQ ID NO: 40.

In some embodiments, the antibody-based molecule that binds to human CEMIP comprises a heavy chain variable region comprising the CDR-H1 of SEQ ID NO: 6, the CDR-H2 of SEQ ID NO: 13, and the CDR-H3 of SEQ ID NO: 20, and a light chain variable region comprising the CDR-L1 of SEQ ID NO: 27, the CDR-L2 of SEQ ID NO: 34, and the CDR-L3 of SEQ ID NO: 41.

In some embodiments, the antibody-based molecule that binds to human CEMIP comprises a heavy chain variable region comprising the CDR-H1 of SEQ ID NO: 7, the CDR-H2 of SEQ ID NO: 14, and the CDR-H3 of SEQ ID NO: 21, and a light chain variable region comprising the CDR-L1 of SEQ ID NO: 28, the CDR-L2 of SEQ ID NO: 35, and the CDR-L3 of SEQ ID NO: 42.

In some embodiments, the antibody-based molecule that binds to human CEMIP comprises a heavy chain variable region comprising the CDR-H1 of SEQ ID NO: 8, the CDR-H2 of SEQ ID NO: 15, and the CDR-H3 of SEQ ID NO: 22, and a light chain variable region comprising the CDR-L1 of SEQ ID NO: 29, the CDR-L2 of SEQ ID NO: 36, and the CDR-L3 of SEQ ID NO: 43.

The CEMIP antibody-based molecules for use in the methods as described herein may comprises a variable light (VL) chain, a variable heavy (VH) chain, or a combination of VL and VH chains. In some embodiments, the VH chain of the CEMIP antibody-based molecule comprises any one of the VH amino acid sequences provided in Table 10 below, or an amino acid sequence that is at least 60%, at least 65%, at least 70%, at least 75%, at least 80%, at least 85%, at least 90%, at least 95% identical to any one of the VH amino acid sequences listed in Table 10. In some embodiments, the VL chain of the CEMIP antibody-based molecule comprises any one of the VL amino acid sequences provided in Table 3 below, or an amino acid sequence that is at least 60%, at least 65%, at least 70%, at least 75%, at least 80%, at least 85%, at least 90%, at least 95% identical to any one of the VL amino acid sequences listed in Table 10.

TABLE 10

| CEMIP Antibody Variable Heavy (VH) and Variable Light (VL) Sequences | | | |
|---|---|---|---|
| mAb name | Region | Sequence | SEQ ID NO: |
| cAb4853 | VH IgG2a | DVQLVESGGGLVQPGGSRKLSCAASGFAFSSFGMHWVR QAPERGLEWVAYISSASNTIYYADTVKGRFTISRDNPKS TLFLQMTSLRSEDTAIYYCAKRDWDLYAMDYWGQGTS VTVSS | 44 |
| | VL kappa | DIVMTQSQKFLSTSVGDRVTITCKASQNVGTAVAWYQQ KPGQSPELLIYSASNRHTGVPARFTGSGSGTDFTLTITNM QSEDLADYFCQQYSSSPTFGGGTKLESK | 45 |
| cAb4854 | VH IgG2a | DVQLVESGGGLVQPGGSRKLSCAASGFPFSSFGMHWVR QAPDKGLEWVAYISSASNTIYYADTVKGRFTVSRDNPK NTLFLQMTSLRSEDTAIYYCTKRNWDLYAMDYWGQGT SVTVSS | 46 |
| | VL kappa | DIVMTQSQKFMSTSVGDRVSITCKANQNVGTAVAWYQ QKPGQSPKLLIYSTSNRDTGVPDRFTGSGSGTDFTLTINY IQSEDLADYFCQQYRNYPTFGGGTKLEIK | 47 |
| cAb4855 | VH IgG2a | QVTLKESGPGILQPSQTLSLTCSFSGFSLSTSGMGVGWIR QPSGKGLEWLAHIWWNDEKYYNAALKSRLTISKDTSKN QVFLKIASVDAADTATYYCARITGAWFPYWGQGTLVTV SA | 48 |
| | VL kappa | DIVMTQSPATLSVTPGDRVSLSCRASQHISEYLHWYQQK SHESPRLLIKYGSQSISGIPSRFSGSGSGSDFTLNINSVEPE DVGVYYCQNGHSFPYTFGGGTKLEIK | 49 |
| cAb5775 | VH IgG1 | EVQLQQSGPELVKPGASMKISCKASGYSFTAYTMNWVK QSHGENLEWIGLINPYNGGTTYNQKFKGKATLTVDKSS STAYMELLSLTSEDSAVYYCASYDYGYAMDYWGQGTS VTVSS | 50 |
| | VL kappa | DVLMTQTPLSLPVSLGDQASISCRSSQSIVHRNGNTYLE WYLQKPGQSPKLLIYKVSNRFSGVPDRFSGSGSGTDFTL KISRVEAEDLGVYYCFQGSHVPWTFGGGTKLEIK | 51 |
| cAb5776 | VH IgG1 | EVQLQQSGPELVKPGVSMKISCKASGYSFTAYTMNWVK QSHGENLEWIGLINPYNGGTTYNQKFKGKATLTVDKSS STAYMELLSLTSEDSAVYYCASYDYGYAMDYWGQGTS VTVSS | 52 |
| | VL kappa | DVLMTQTPLSLPVSLGDQASISCRSSQSIVHRSGNTYLE WYLQKPGQSPKLLIYKVSNRFSGVPDRFSGSGSGTDFTL KISRVEAEDLGVYYCFQGSHVPWTFGGGTKLEIK | 53 |
| cAb5777 | VH IgG2a | EVQLQQSGAELVKPGASVKLSCTASGFNIKDTYMHWV KQRPEQGLIWIGNIDPANGHTKYAPKFQGKATITADTSS NTAYLQLSSLTSEDTAVYYCARSNDYDVDFDYWGQGT TLTVSS | 54 |
| | VL kappa | DIVMSQSPSSLAVSAGEKVTMSCKSSQSLLNSRTRKNYL AWYQQKPGQSPKLLIYWASTRESGVPDRFTGSGSGTDF SLTISSVQAEDLAVYYCKQSYNLYTFGGGTKLEIK | 55 |

TABLE 10-continued

CEMIP Antibody Variable Heavy (VH) and Variable Light (VL) Sequences

| mAb name | Region | Sequence | SEQ ID NO: |
|---|---|---|---|
| cAb5778 | VH IgG1 | EVHLQQSGPELVKPGASMKISCKASGYSFTAYTMNWVK QSHGKNLEWIGLINPYNGGTTYNQKFKGKATLTVDKSS STAYMELLSLTSEDSAVYYCASYYGGRGWYFDVWGAG TSVTVSS | 56 |
| | VL kappa | DIVLTQSPASLAVSLGQRATISCRASKSVSTSGYSYVHW YQQKPGQPPKLLIYLASNLESGVPARFSGSGSGTDFTLNI HPVEEEDAATYYCQNSRELPYTFGGGTKLEMK | 57 |

In some embodiments, the CEMIP antibody-based molecule disclosed herein for use in the methods as described herein comprises a heavy chain variable region comprising an amino acid sequence that is at least 80% identical to SEQ ID NO: 44 and a light chain variable region comprising an amino acid sequence that is at least 80% identical to SEQ ID NO: 45.

In some embodiments, the CEMIP antibody-based molecule disclosed herein comprises a heavy chain variable region comprising an amino acid sequence that is at least 80% identical to SEQ ID NO: 46 and a light chain variable region comprising an amino acid sequence that is at least 80% identical to SEQ ID NO: 47.

In some embodiments, the CEMIP antibody-based molecule disclosed herein comprises a heavy chain variable region comprising an amino acid sequence that is at least 80% identical to SEQ ID NO: 48 and a light chain variable region comprising an amino acid sequence that is at least 80% identical to SEQ ID NO: 49.

In some embodiments, the CEMIP antibody-based molecule disclosed herein comprises a heavy chain variable region comprising an amino acid sequence that is at least 80% identical to SEQ ID NO: 50 and a light chain variable region comprising an amino acid sequence that is at least 80% identical to SEQ ID NO: 51.

In some embodiments, the CEMIP antibody-based molecule disclosed herein comprises (v) a heavy chain variable region comprising an amino acid sequence that is at least 80% identical to SEQ ID NO: 52 and a light chain variable region comprising an amino acid sequence that is at least 80% identical to SEQ ID NO: 53.

In some embodiments, the CEMIP antibody-based molecule disclosed herein comprises a heavy chain variable region comprising an amino acid sequence that is at least 80% identical to SEQ ID NO: 54 and a light chain variable region comprising an amino acid sequence that is at least 80% identical to SEQ ID NO: 55.

In some embodiments, the CEMIP antibody-based molecule disclosed herein comprises a heavy chain variable region comprising an amino acid sequence that is at least 80% identical to SEQ ID NO: 56 and a light chain variable region comprising an amino acid sequence that is at least 80% identical to SEQ ID NO: 57.

In some embodiments, the CEMIP antibody-based molecule for use in the methods as described herein comprises a heavy chain variable region comprising an amino acid sequence that is at least 80% identical to SEQ ID NO: 44 and a light chain variable region comprising an amino acid sequence that is at least 80% identical to SEQ ID NO: 45, a heavy chain constant region comprising an amino acid sequence that is at least 80% identical to SEQ ID NO: 72, and a light chain constant region comprising an amino acid sequence that is at least 80% identical to SEQ ID NO: 73. This antibody is referred to herein as cAb4853.

In some embodiments, the CEMIP antibody-based molecule for use in the methods as described herein comprises a heavy chain variable region comprising an amino acid sequence that is at least 80% identical to SEQ ID NO: 46, a light chain variable region comprising an amino acid sequence that is at least 80% identical to SEQ ID NO: 47, a heavy chain constant region comprising an amino acid sequence that is at least 80% identical to SEQ ID NO: 74, and a light chain constant region comprising an amino acid sequence that is at least 80% identical to SEQ ID NO: 75. This antibody is referred to herein as cAb4854.

In some embodiments, the CEMIP antibody-based molecule for use in the methods as described herein comprises a heavy chain variable region comprising an amino acid sequence that is at least 80% identical to SEQ ID NO: 48 and a light chain variable region comprising an amino acid sequence that is at least 80% identical to SEQ ID NO: 49, a heavy chain constant region comprising an amino acid sequence that is at least 80% identical to SEQ ID NO: 76, and a light chain constant region comprising an amino acid sequence that is at least 80% identical to SEQ ID NO: 77. This antibody is referred to herein as cAb4855.

In some embodiments, the CEMIP antibody-based molecule for use in the methods as described herein comprises a heavy chain variable region comprising an amino acid sequence that is at least 80% identical to SEQ ID NO: 50 and a light chain variable region comprising an amino acid sequence that is at least 80% identical to SEQ ID NO: 51, a heavy chain constant region comprising an amino acid sequence that is at least 80% identical to SEQ ID NO: 78, and a light chain constant region comprising an amino acid sequence that is at least 80% identical to SEQ ID NO: 79. This antibody is referred to herein as cAb5775.

In some embodiments, the CEMIP antibody-based molecule for use in the methods as described herein comprises (v) a heavy chain variable region comprising an amino acid sequence that is at least 80% identical to SEQ ID NO: 52 and a light chain variable region comprising an amino acid sequence that is at least 80% identical to SEQ ID NO: 53, a heavy chain constant region comprising an amino acid sequence that is at least 80% identical to SEQ ID NO: 80, and a light chain constant region comprising an amino acid sequence that is at least 80% identical to SEQ ID NO: 81. This antibody is referred to herein as cAb5776.

In some embodiments, the CEMIP antibody-based molecule for use in the methods as described herein comprises a heavy chain variable region comprising an amino acid sequence that is at least 80% identical to SEQ ID NO: 54 and a light chain variable region comprising an amino acid sequence that is at least 80% identical to SEQ ID NO: 55, a heavy chain constant region comprising an amino acid sequence that is at least 80% identical to SEQ ID NO: 82, and a light chain constant region comprising an amino acid sequence that is at least 80% identical to SEQ ID NO: 83. This antibody is referred to herein as cAb5777.

In some embodiments, the CEMIP antibody-based molecule for use in the methods as described herein comprises a heavy chain variable region comprising an amino acid sequence that is at least 80% identical to SEQ ID NO: 56 and a light chain variable region comprising an amino acid sequence that is at least 80% identical to SEQ ID NO: 57, a heavy chain constant region comprising an amino acid sequence that is at least 80% identical to SEQ ID NO: 84, and a light chain constant region comprising an amino acid sequence that is at least 80% identical to SEQ ID NO: 85. This antibody is referred to herein as cAb5778.

In some embodiments, the CEMIP antibody is administered to a subject in need thereof as described herein in the form of a polynucleotide encoding the antibody. Accordingly, suitable polynucleotides encoding the CEMIP antibody of the present invention comprise a sequence encoding any one, any two, any three, any four, any five, or any six of the CDRs described supra, including the heavy chain CDRs of SEQ ID NOs: 2-22, and the light chain CDRs of SEQ ID NOs: 23-43.

In some embodiments, the polynucleotide comprises a nucleotide sequence encoding a VH domain, where the VH domain comprises the CDR-H1 of SEQ ID NO: 2, the CDR-H2 of SEQ ID NO: 9, and the CDR-H3 of SEQ ID NO: 16. An exemplary nucleotide sequence comprises the nucleotide sequence of SEQ ID NO: 58, and nucleotide sequences having at least 80%, at least 85%, at least 90%, at least 95%, at least 96%, 97%, 98%, or 99% sequence similarity to the nucleotide sequence of SEQ ID NO: 58.

In some embodiments, the polynucleotide comprises a nucleotide sequence encoding a VH domain, where the VH domain comprises the CDR-H1 of SEQ ID NO: 3, the CDR-H2 of SEQ ID NO: 10, and the CDR-H3 of SEQ ID NO: 17. An exemplary nucleotide sequence comprises the nucleotide sequence of SEQ ID NO: 60, and nucleotide sequences having at least 80%, at least 85%, at least 90%, at least 95%, at least 96%, 97%, 98%, or 99% sequence similarity to the nucleotide sequence of SEQ ID NO: 60.

In some embodiments, the polynucleotide comprises a nucleotide sequence encoding a VH domain, where the VH domain comprises the CDR-H1 of SEQ ID NO: 4, the CDR-H2 of SEQ ID NO: 11, and the CDR-H3 of SEQ ID NO: 18. An exemplary nucleotide sequence comprises the nucleotide sequence of SEQ ID NO: 62, and nucleotide sequences having at least 80%, at least 85%, at least 90%, at least 95%, at least 96%, 97%, 98%, or 99% sequence similarity to the nucleotide sequence of SEQ ID NO: 62.

In some embodiments, the polynucleotide comprises a nucleotide sequence encoding a VH domain, where the VH domain comprises the CDR-H1 of SEQ ID NO: 5, the CDR-H2 of SEQ ID NO: 12, and the CDR-H3 of SEQ ID NO: 19. An exemplary nucleotide sequence comprises the nucleotide sequence of SEQ ID NO: 64, and nucleotide sequences having at least 80%, at least 85%, at least 90%, at least 95%, at least 96%, 97%, 98%, or 99% sequence similarity to the nucleotide sequence of SEQ ID NO: 64.

In some embodiments, the polynucleotide comprises a nucleotide sequence encoding a VH domain, where the VH domain comprises the CDR-H1 of SEQ ID NO: 6, the CDR-H2 of SEQ ID NO: 13, and the CDR-H3 of SEQ ID NO: 20. An exemplary nucleotide sequence comprises the nucleotide sequence of SEQ ID NO: 66, and nucleotide sequences having at least 80%, at least 85%, at least 90%, at least 95%, at least 96%, 97%, 98%, or 99% sequence similarity to the nucleotide sequence of SEQ ID NO: 66.

In some embodiments, the polynucleotide comprises a nucleotide sequence encoding a VH domain, where the VH domain comprises the CDR-H1 of SEQ ID NO: 7, the CDR-H2 of SEQ ID NO: 14, and the CDR-H3 of SEQ ID NO: 21. An exemplary nucleotide sequence comprises the nucleotide sequence of SEQ ID NO: 68, and nucleotide sequences having at least 80%, at least 85%, at least 90%, at least 95%, at least 96%, 97%, 98%, or 99% sequence similarity to the nucleotide sequence of SEQ ID NO: 68.

In some embodiments, the polynucleotide comprises a nucleotide sequence encoding a VH domain, where the VH domain comprises the CDR-H1 of SEQ ID NO: 8, the CDR-H2 of SEQ ID NO: 15, and the CDR-H3 of SEQ ID NO: 22. An exemplary nucleotide sequence comprises the nucleotide sequence of SEQ ID NO: 70, and nucleotide sequences having at least 80%, at least 85%, at least 90%, at least 95%, at least 96%, 97%, 98%, or 99% sequence similarity to the nucleotide sequence of SEQ ID NO: 70.

Exemplary nucleotide sequences of CEMIP VH domains described herein are provided in Table 11 below.

In some embodiments, the polynucleotides suitable for administering a subject in need thereof in accordance with the methods described herein comprises a nucleotide sequence encoding a VL domain. In some embodiments, the polynucleotide comprises a nucleotide sequence encoding a VL domain, where the VL domain comprises the CDR-L1 of SEQ ID NO: 23, the CDR-L2 of SEQ ID NO: 30, and the CDR-L3 of SEQ ID NO: 37. An exemplary nucleotide sequence comprises the nucleotide sequence of SEQ ID NO: 59, and nucleotide sequences having at least 80%, at least 85%, at least 90%, at least 95%, at least 96%, 97%, 98%, or 99% sequence similarity to the nucleotide sequence of SEQ ID NO: 59.

In some embodiments, the polynucleotide comprises a nucleotide sequence encoding a VL domain, where the VL domain comprises the CDR-L1 of SEQ ID NO: 24, the CDR-L2 of SEQ ID NO: 31, and the CDR-L3 of SEQ ID NO: 38. An exemplary nucleotide sequence comprises the nucleotide sequence of SEQ ID NO: 61, and nucleotide sequences having at least 80%, at least 85%, at least 90%, at least 95%, at least 96%, 97%, 98%, or 99% sequence similarity to the nucleotide sequence of SEQ ID NO: 61.

In some embodiments, the polynucleotide comprises a nucleotide sequence encoding a VL domain, where the VL domain comprises the CDR-L1 of SEQ ID NO: 25, the CDR-L2 of SEQ ID NO: 32, and the CDR-L3 of SEQ ID NO: 39. An exemplary nucleotide sequence comprises the nucleotide sequence of SEQ ID NO: 63, and nucleotide sequences having at least 80%, at least 85%, at least 90%, at least 95%, at least 96%, 97%, 98%, or 99% sequence similarity to the nucleotide sequence of SEQ ID NO: 63.

In some embodiments, the polynucleotide comprises a nucleotide sequence encoding a VL domain, where the VL domain comprises the CDR-L1 of SEQ ID NO: 26, the CDR-L2 of SEQ ID NO: 33, and the CDR-L3 of SEQ ID NO: 40. An exemplary nucleotide sequence comprises the nucleotide sequence of SEQ ID NO: 65, and nucleotide sequences having at least 80%, at least 85%, at least 90%, at least 95%, at least 96%, 97%, 98%, or 99% sequence similarity to the nucleotide sequence of SEQ ID NO: 65.

In some embodiments, the polynucleotide comprises a nucleotide sequence encoding a VL domain, where the VL domain comprises the CDR-L1 of SEQ ID NO: 27, the CDR-L2 of SEQ ID NO: 34, and the CDR-L3 of SEQ ID NO: 41. An exemplary nucleotide sequence comprises the nucleotide sequence of SEQ ID NO: 67, and nucleotide sequences having at least 80%, at least 85%, at least 90%, at least 95%, at least 96%, 97%, 98%, or 99% sequence similarity to the nucleotide sequence of SEQ ID NO: 67.

In some embodiments, the polynucleotide comprises a nucleotide sequence encoding a VL domain, where the VL domain comprises the CDR-L1 of SEQ ID NO: 28, the CDR-L2 of SEQ ID NO: 35, and the CDR-L3 of SEQ ID NO: 42. An exemplary nucleotide sequence comprises the nucleotide sequence of SEQ ID NO: 69, and nucleotide sequences having at least 80%, at least 85%, at least 90%, at least 95%, at least 96%, 97%, 98%, or 99% sequence similarity to the nucleotide sequence of SEQ ID NO: 69.

In some embodiments, the polynucleotide comprises a nucleotide sequence encoding a VL domain, where the VL domain comprises the CDR-L1 of SEQ ID NO: 29, the CDR-L2 of SEQ ID NO: 36, and the CDR-L3 of SEQ ID NO: 43. An exemplary nucleotide sequence comprises the nucleotide sequence of SEQ ID NO: 71, and nucleotide sequences having at least 80%, at least 85%, at least 90%, at least 95%, at least 96%, 97%, 98%, or 99% sequence similarity to the nucleotide sequence of SEQ ID NO: 71.

Exemplary nucleotide sequences of CEMIP VL domains described herein are provided in Table 11 below.

TABLE 11

| CEMIP Antibody Variable Heavy (VH) and Variable Light (VL) DNA Sequences | | | |
|---|---|---|---|
| mAb/Fab name | Region | Sequence | SEQ ID NO: |
| cAb4853 | VH | GATGTGCAGCTGGTGGAGTCTGGGGGAGGCTTAGTGCAGCCT GGAGGGTCCCGGAAACTCTCCTGTGCAGCCTCTGGATTCGCTT TCAGTAGCTTTGGAATGCACTGGGTTCGTCAGGCTCCAGAGA GGGGGCTGGAGTGGGTCGCATACATTAGTAGTGCCAGCAATA CCATCTACTATGCAGACACAGTGAAGGGCCGATTCACCATCTC CAGAGACAATCCCAAGAGCACCCTGTTCCTGCAAATGACCAG TCTAAGGTCTGAGGACACGGCCATTTATTACTGTGCAAAGCG AGACTGGGACCTCTATGCTATGGACTACTGGGGTCAAGGAAC CTCAGTCACCGTCTCGTCA | 58 |
| | VL | GACATTGTGATGACCCAGTCTCAAAAATTCTTGTCCACATCAG TGGGAGACAGGGTCACCATCACCTGCAAGGCCAGTCAGAATG TGGGAACTGCTGTTGCCTGGTATCAACAGAAACCAGGGCAAT CTCCTGAACTTCTGATTTACTCGGCATCCAATCGGCACACTGG AGTCCCTGCTCGCTTCACAGGCAGTGGATCTGGGACAGATTTC ACTCTCACCATCACCAATATGCAGTCTGAAGACCTGGCAGATT ATTTCTGCCAGCAATATAGTAGCTCGCCGACATTCGGTGGAGG CACCAAGTTGGAATCCAAA | 59 |
| cAb4854 | VH | GATGTGCAGCTGGTGGAGTCTGGGGGAGGCTTAGTGCAGCCT GGAGGGTCCCGGAAACTCTCCTGTGCAGCCTCTGGATTCCCTT TCAGTAGCTTTGGAATGCACTGGGTTCGTCAGGCTCCAGACAA GGGACTGGAGTGGGTCGCATACATTAGTAGTGCCAGTAATAC CATCTACTATGCTGACACAGTGAAGGGCCGATTCACCGTCTCC AGAGACAATCCCAAGAACACCCTGTTCCTGCAAATGACCAGT CTAAGGTCTGAGGACACGGCCATTTATTACTGTACAAAGCGA AATTGGGACCTCTATGCTATGGACTACTGGGGTCAAGGAACC TCAGTCACCGTCTCCTCA | 60 |
| | VL | GACATTGTGATGACCCAGTCTCAAAAATTCATGTCCACATCAG TGGGAGACAGGGTCAGCATCACCTGCAAGGCCAATCAGAATG TGGGTACTGCTGTAGCCTGGTATCAACAGAAACCAGGACAAT CTCCTAAACTACTGATTTATTCGACATCCAATCGGGACACTGG AGTCCCTGACCGCTTCACAGGCAGTGGATCTGGGACAGATTTC ACTCTCACCATCAACTATATTCAATCTGAAGACCTGGCAGATT ATTTCTGCCAGCAATATAGAAATTATCCGACGTTCGGTGGAGG CACCAAGCTGGAAATCAAA | 61 |
| cAb4855 | VH | CAGGTTACTCTGAAAGAGTCTGGCCCTGGGATATTGCAGCCCT CCCAGACCCTCAGTCTGACTTGTTCTTTCTCTGGGTTTTCACTG AGCACTTCTGGTATGGGTGTAGGCTGGATTCGTCAGCCTTCAG GGAAGGGTCTGGAGTGGCTGGCACACATTTGGTGGAATGATG AGAAATACTATAACGCAGCCCTGAAGAGCCGGCTCACAATCT CCAAGGATACCTCCAAAAACCAGGTTTTCCTCAAGATCGCCA GTGTGGACGCTGCAGATACTGCCACATACTACTGTGCTCGCAT CACTGGTGCCTGGTTTCCTTATTGGGGCCAAGGGACTCTGGTC ACTGTCTCTGCA | 62 |
| | VL | GACATTGTGATGACTCAGTCTCCAGCCACCCTGTCTGTGACTC CAGGAGATAGAGTCTCTCTTTCCTGCAGGGCCAGTCAGCATAT TAGCGAATACTTACACTGGTATCAACAAAAATCACACGAGTC TCCAAGGCTTCTCATCAAATATGGTTCCCAATCCATCTCTGGG ATCCCCTCCAGGTTCAGTGGCAGTGGATCAGGGTCAGATTTCA CTCTCAATATCAACAGTGTGGAACCTGAAGATGTTGGAGTGT ATTACTGTCAAAATGGTCACAGCTTTCCGTACACGTTCGGAGG GGGGACCAAGCTGGAAATAAAA | 63 |
| cAb5775 | VH | GAGGTCCAGCTGCAACAGTCTGGACCTGAGCTGGTGAAGCCT GGAGCCTCAATGAAGATATCTTGCAAGGCTTCTGGTTACTCAT TCACTGCCTACACCATGAACTGGGTGAAGCAGAGCCATGGAG | 64 |

TABLE 11-continued

CEMIP Antibody Variable Heavy (VH) and Variable Light (VL) DNA Sequences

| mAb/Fab name | Region | Sequence | SEQ ID NO: |
|---|---|---|---|
| | | AGAACCTTGAGTGGATTGGACTTATTAATCCTTATAATGGTGG TACTACCTACAACCAGAAGTTCAAGGGCAAGGCCACATTAAC TGTAGACAAGTCATCCAGCACAGCCTACATGGAGCTCCTCAG TCTGACATCTGAGGACTCTGCAGTCTATTACTGTGCATCATAT GATTACGGCTATGCTATGGACTACTGGGGTCAAGGAACCTCA GTCACCGTCTCCTCA | |
| | VL | GATGTTTTGATGACCCAAACTCCACTCTCCCTGCCTGTCAGTC TTGGAGATCAAGCCTCCATCTCTTGCAGATCTAGTCAGAGCAT TGTACATAGAAATGGAAACACCTATCTAGAATGGTACCTGCA GAAACCAGGCCAGTCTCCAAAGCTCCTGATCTACAAAGTTTCC AACCGATTTTCTGGGGTCCCAGACAGGTTCAGTGGCAGTGGA TCAGGGACAGATTTCACACTCAAGATCAGCAGAGTGGAGGCT GAGGATCTGGGAGTTTATTACTGCTTTCAAGGTTCACATGTTC CGTGGACGTTCGGTGGAGGCACCAAGCTGGAAATCAAA | 65 |
| cAb5776 | VH | GAGGTCCAGCTGCAACAGTCTGGACCTGAGCTGGTGAAGCCT GGAGTTTCAATGAAGATATCCTGCAAGGCTTCTGGTTACTCAT TCACTGCCTACACTATGAATTGGGTGAAGCAGAGTCATGGAG AGAACCTTGAGTGGATTGGACTTATTAATCCTTATAATGGTGG TACTACCTACAACCAGAAGTTCAAGGGCAAGGCCACATTAAC TGTAGACAAGTCATCCAGCACAGCCTACATGGAGCTCCTCAG TCTGACATCTGAGGACTCTGCAGTCTATTACTGTGCATCATAT GATTACGGCTATGCTATGGACTACTGGGGTCAAGGAACCTCA GTCACCGTCTCCTCA | 66 |
| | VL | GATGTTTTGATGACCCAAACTCCACTCTCCCTGCCTGTCAGTC TTGGAGATCAAGCCTCCATCTCTTGCAGATCTAGTCAGAGCAT TGTACATCGTAGTGGAAACACCTATTTAGAATGGTACCTGCAG AAACCAGGCCAGTCTCCAAAGCTCCTGATCTACAAAGTTTCCA ACCGATTTTCTGGGGTCCCAGACAGGTTCAGTGGCAGTGGATC AGGGACAGATTTCACACTCAAGATCAGCAGAGTGGAGGCTGA GGATCTGGGAGTTTATTACTGCTTTCAAGGTTCACATGTTCCG TGGACGTTCGGTGGAGGCACCAAGTTGGAAATCAAA | 67 |
| cAb5777 | VH | GAGGTTCAACTGCAGCAGTCTGGGGCAGAGCTTGTGAAGCCA GGGGCCTCAGTCAAGTTGTCCTGCACAGCTTCTGGCTTCAACA TTAAAGACACCTATATGCACTGGGTGAAACAGAGGCCTGAGC AGGGCCTGATTTGGATTGGAAACATTGATCCTGCGAATGGTC ATACTAAATATGCCCCGAAGTTCCAGGGCAAGGCCACTATCA CAGCAGACACATCCTCCAACACAGCCTACCTGCAGCTCAGCA GCCTGACATCTGAGGACACTGCCGTCTATTACTGTGCTAGATC TAATGATTACGACGTCGACTTTGACTACTGGGGCCAAGGCAC CACTCTCACAGTCTCCTCA | 68 |
| | VL | GACATTGTGATGTCACAGTCTCCATCCTCCCTGGCTGTGTCAG CAGGAGAGAAGGTCACTATGAGCTGCAAATCCAGTCAGAGTC TGCTCAACAGTAGAACCCGAAAGAACTACTTGGCTTGGTACC AGCAGAAACCAGGGCAGTCTCCTAAACTGCTGATCTACTGGG CATCCACTAGGGAATCTGGGGTCCCTGATCGCTTCACAGGCA GTGGATCTGGGACAGATTTCAGTCTCACCATCAGCAGTGTGCA GGCTGAAGACCTGGCAGTTTATTACTGCAAGCAATCTTATAAT CTATACACGTTCGGAGGGGGGACCAAGCTGGAAATAAAA | 69 |
| cAb5778 | VH | GAGGTCCACCTGCAACAGTCTGGACCTGAGCTGGTGAAGCCT GGAGCTTCAATGAAGATATCCTGCAAGGCTTCTGGTTACTCCT TCACTGCCTACACCATGAACTGGGTGAAACAGAGCCATGGAA AGAACCTTGAGTGGATTGGACTTATTAATCCTTACAATGGTGG TACTACCTACAACCAGAAATTCAAGGGCAAGGCCACATTAAC TGTAGACAAGTCATCCAGCACAGCCTACATGGAGCTCCTCAG TCTGACATCTGAGGACTCTGCAGTCTATTACTGTGCTTCTTACT ACGGTGGTAGGGGCTGGTACTTCGATGTCTGGGGCGCAGGGA CCTCGGTCACCGTCTCCTCA | 70 |
| | VL | GACATTGTGCTGACACAGTCTCCTGCTTCCTTAGCTGTATCTCT GGGGCAGAGGGCCACCATCTCATGCAGGGCCAGCAAAAGTGT CAGTACATCTGGCTATAGTTATGTTCACTGGTACCAACAGAAA CCAGGACAGCCACCCAAACTCCTCATCTATCTTGCATCCAACC TAGAATCTGGGGTCCCTGCCAGGTTCAGTGGCAGTGGGTCTG GGACAGACTTCACCCTCAACATCCATCCTGTGGAGGAGGAAG ATGCTGCAACCTATTACTGTCAGAATAGTAGGGAACTTCCGTA CACGTTCGGAGGGGGGACCAAGCTGGAAATGAAA | 71 |

In some embodiments, the isolated polynucleotide encoding the CEMIP antibody based molecule encodes any one of the VH and/or VL domain sequences as provided in Table 10 infra.

In some embodiments, a suitable polynucleotide encoding the CEMIP antibody of the present disclosure encodes a heavy chain variable region comprising an amino acid sequence that is at least 80% identical to SEQ ID NO: 44 and a light chain variable region comprising an amino acid sequence that is at least 80% identical to SEQ ID NO: 45. An exemplary polynucleotide of this embodiment comprises the nucleotide sequences of SEQ ID NOs: 58 and 59. In some embodiments, the exemplary polynucleotide encoding the CEMIP antibody further includes one or more of a nucleotide sequence encoding a heavy chain constant region (CH), and nucleotide sequence encoding a heavy chain signal peptide, a nucleotide sequence encoding the light chain constant region (CL), and a nucleotide sequence encoding light chain signal peptide. Exemplary nucleotide sequences are provided in Table 13 below (see nucleotides sequences for cAb4853).

In some embodiments, a suitable polynucleotide encoding the CEMIP antibody of the present disclosure encodes a heavy chain variable region comprising an amino acid sequence that is at least 80% identical to SEQ ID NO: 46 and a light chain variable region comprising an amino acid sequence that is at least 80% identical to SEQ ID NO: 47. An exemplary polynucleotide of this embodiment comprises the nucleotide sequences of SEQ ID NOs: 60 and 61. In some embodiments, the exemplary polynucleotide encoding the CEMIP antibody further includes one or more of a nucleotide sequence encoding a heavy chain constant region (CH), and nucleotide sequence encoding a heavy chain signal peptide, a nucleotide sequence encoding the light chain constant region (CL), and a nucleotide sequence encoding light chain signal peptide. Exemplary nucleotide sequences are provided in Table 13 below (see nucleotides sequences for cAb4854).

In some embodiments, a suitable polynucleotide encoding the CEMIP antibody of the present disclosure encodes a heavy chain variable region comprising an amino acid sequence that is at least 80% identical to SEQ ID NO: 48 and a light chain variable region comprising an amino acid sequence that is at least 80% identical to SEQ ID NO: 49. An exemplary polynucleotide of this embodiment comprises the nucleotide sequences of SEQ ID NOs: 62 and 63. In some embodiments, the exemplary polynucleotide encoding the CEMIP antibody further includes one or more of a nucleotide sequence encoding a heavy chain constant region (CH), and nucleotide sequence encoding a heavy chain signal peptide, a nucleotide sequence encoding the light chain constant region (CL), and a nucleotide sequence encoding light chain signal peptide. Exemplary nucleotide sequences are provided in Table 13 below (see nucleotides sequences for cAb4855).

In some embodiments, a suitable polynucleotide encoding the CEMIP antibody of the present disclosure encodes a heavy chain variable region comprising an amino acid sequence that is at least 80% identical to SEQ ID NO: 50 and a light chain variable region comprising an amino acid sequence that is at least 80% identical to SEQ ID NO: 51. An exemplary polynucleotide of this embodiment comprises the nucleotide sequences of SEQ ID NOs: 64 and 65. In some embodiments, the exemplary polynucleotide encoding the CEMIP antibody further includes one or more of a nucleotide sequence encoding a heavy chain constant region (CH), and nucleotide sequence encoding a heavy chain signal peptide, a nucleotide sequence encoding the light chain constant region (CL), and a nucleotide sequence encoding light chain signal peptide. Exemplary nucleotide sequences are provided in Table 13 below (see nucleotides sequences for cAb5775).

In some embodiments, a suitable polynucleotide encoding the CEMIP antibody of the present disclosure encodes a heavy chain variable region comprising an amino acid sequence that is at least 80% identical to SEQ ID NO: 52 and a light chain variable region comprising an amino acid sequence that is at least 80% identical to SEQ ID NO: 53. An exemplary polynucleotide of this embodiment comprises the nucleotide sequences of SEQ ID NOs: 66 and 67. In some embodiments, the exemplary polynucleotide encoding the CEMIP antibody further includes one or more of a nucleotide sequence encoding a heavy chain constant region (CH), and nucleotide sequence encoding a heavy chain signal peptide, a nucleotide sequence encoding the light chain constant region (CL), and a nucleotide sequence encoding light chain signal peptide. Exemplary nucleotide sequences are provided in Table 13 below (see nucleotides sequences for cAb5776).

In some embodiments, a suitable polynucleotide encoding the CEMIP antibody of the present disclosure encodes a heavy chain variable region comprising an amino acid sequence that is at least 80% identical to SEQ ID NO: 54 and a light chain variable region comprising an amino acid sequence that is at least 80% identical to SEQ ID NO: 55. An exemplary polynucleotide of this embodiment comprises the nucleotide sequences of SEQ ID NOs: 68 and 69. In some embodiments, the exemplary polynucleotide encoding the CEMIP antibody further includes one or more of a nucleotide sequence encoding a heavy chain constant region (CH), and nucleotide sequence encoding a heavy chain signal peptide, a nucleotide sequence encoding the light chain constant region (CL), and a nucleotide sequence encoding light chain signal peptide. Exemplary nucleotide sequences are provided in Table 13 below (see nucleotides sequences for cAb5777).

In some embodiments, a suitable polynucleotide encoding the CEMIP antibody of the present disclosure encodes a heavy chain variable region comprising an amino acid sequence that is at least 80% identical to SEQ ID NO: 56 and a light chain variable region comprising an amino acid sequence that is at least 80% identical to SEQ ID NO: 57. An exemplary polynucleotide of this embodiment comprises the nucleotide sequences of SEQ ID NOs: 70 and 71. In some embodiments, the exemplary polynucleotide encoding the CEMIP antibody further includes one or more of a nucleotide sequence encoding a heavy chain constant region (CH), and nucleotide sequence encoding a heavy chain signal peptide, a nucleotide sequence encoding the light chain constant region (CL), and a nucleotide sequence encoding light chain signal peptide. Exemplary nucleotide sequences are provided in Table 13 below (see nucleotides sequences for cAb5778).

The nucleic acid molecules described herein include isolated polynucleotides, portions of expression vectors or portions of linear DNA sequences, including linear DNA sequences used for in vitro transcription/translation, and vectors compatible with prokaryotic, eukaryotic or filamentous phage expression, secretion, and/or display of the antibodies or binding fragments thereof described herein.

The polynucleotides of the disclosure may be produced by chemical synthesis such as solid phase polynucleotide synthesis on an automated polynucleotide synthesizer and assembled into complete single or double stranded molecules. Alternatively, the polynucleotides of the invention may be produced by other techniques such a PCR followed by routine cloning. Techniques for producing or obtaining polynucleotides of a given sequence are well known in the art.

The polynucleotides of the disclosure may comprise at least one non-coding sequence, such as a promoter or enhancer sequence, intron, polyadenylation signal, a cis sequence facilitating RepA binding, and the like. The polynucleotide sequences may also comprise additional sequences encoding for example a linker sequence, a marker or a tag sequence, such as a histidine tag or an HA tag to facilitate purification or detection of the protein, a signal sequence, a fusion protein partner such as RepA, Fc portion, or bacteriophage coat protein such as pIX or pIII.

Another embodiment of the disclosure is directed to a vector comprising at least one polynucleotide encoding the CEMIP antibody-based molecule as described herein. Such vectors include, without limitation, plasmid vectors, viral vectors, including without limitation, vaccina vector, lenti-viral vector, adenoviral vector, adeno-associated viral vector, vectors for baculovirus expression, transposon based vectors or any other vector suitable for introduction of the polynucleotides described herein into a given organism or genetic background by any means to facilitate expression of the encoded antibody polypeptide. In one embodiment, the polynucleotide sequence encoding the heavy chain variable domain, alone or together with the polynucleotide sequence encoding the light chain variable domain as described herein, are combined with sequences of a promoter, a translation initiation segment (e.g., a ribosomal binding sequence and start codon), a 3? untranslated region, poly-adenylation signal, a termination codon, and transcription termination to form one or more expression vector constructs.

In one embodiment, the vector is an adenoviral-associated viral (AAV) vector. A number of therapeutic AAV vectors suitable for delivery of the polynucleotides encoding antibodies described herein to the central nervous system are known in the art. See e.g., Deverman et al., "Gene Therapy for Neurological Disorders: Progress and Prospects," Nature Rev. 17:641-659 (2018), which in hereby incorporated by reference in its entirety. Suitable AAV vectors include serotypes AAV1, AAV2, AAV3, AAV4, AAV5, AAV6, AAV7, AAV8, AAV9, AAV10, or AAV11 in their native form or engineered for enhanced tropism. AAV vectors known to have tropism for the CNS that are particularly suited for therapeutic expression of the CEMIP antibodies described herein include, AAV1, AAV2, AAV4, AAV5, AAV8 and AAV9 in their native form or engineered for enhanced tropism. In one embodiment, the AAV vector is an AAV2 vector. In another embodiment, the AAV vector is an AAV5 vector (Vitale et al., "Anti-tau Conformational scFv MC1 Antibody Efficiently Reduces Pathological Tau Species in Adult JNPL3 Mice," Acta Neuropathol. Commun. 6:82 (2018), which is hereby incorporate by reference in its entirety), optionally containing the GFAP or CAG promoter and the Woodchuck hepatitis virus (WPRE) post-transla-tional regulatory element. In another embodiment, the AAV vector is an AAV9 vector (Haiyan et al., "Targeting Root Cause by Systemic scAAV9-hIDS Gene Delivery: Func-tional Correction and Reversal of Severe MPSII in Mice," Mol. Ther. Methods Clin. Dev. 10:327-340 (2018), which is hereby incorporated by reference in its entirety). In another embodiment, the AAV vector is an AAVrh10 vector (Liu et al., "Vectored Intracerebral Immunizations with the Anti-Tau Monoclonal Antibody PHF1 Marchkedly Reduces Tau Pathology in Mutant Transgenic Mice," J. Neurosci. 36(49): 12425-35 (2016), which is hereby incorporated by reference in its entirety).

In another embodiment the AAV vector is a hybrid vector comprising the genome of one serotype, e.g., AAV2, and the capsid protein of another serotype, e.g., AAV1 or AAV3-9 to control tropism. See e.g., Broekman et al., "Adeno-associ-ated Virus Vectors Serotyped with AAV8 Capsid are More Efficient than AAV-1 or -2 Serotypes for Widespread Gene Delivery to the Neonatal Mouse Brain," Neuroscience 138: 501-510 (2006), which is hereby incorporated by reference in its entirety. In one embodiment, the AAV vector is an AAV2/8 hybrid vector (Ising et al., "AAV-mediated Expres-sion of Anti-Tau ScFv Decreases Tau Accumulation in a Mouse Model of Tauopathy," J. Exp. Med. 214(5): 1227 (2017), which is hereby incorporated by reference in its entirety). In another embodiment the AAV vector is an AAV2/9 hybrid vector (Simon et al., "A Rapid Gene Deliv-ery-Based Mouse Model for Early-Stage Alzheimer Dis-ease-Type Tauopathy," J. Neuropath. Exp. Neurol. 72(11): 1062-71 (2013), which is hereby incorporated by reference in its entirety).

In another embodiment, the AAV vector is one that has been engineered or selected for its enhanced CNS transduc-tion after intraparenchymal administration, e.g., AAV-DJ (Grimm et al., J. Viol. 82:5887-5911 (2008), which is hereby incorporated by reference in its entirety); increased trans-duction of neural stem and progenitor cells, e.g., SCH9 and AAV4.18 (Murlidharan et al., J. Virol. 89: 3976-3987 (2015) and Ojala et al., Mol. Ther. 26:304-319 (2018), which are hereby incorporated by reference in their entirety); enhanced retrograde transduction, e.g., rAAV2-retro (Muller et al., Nat. Biotechnol. 21:1040-1046 (2003), which is hereby incorporated by reference in its entirety); selective transduc-tion into brain endothelial cells, e.g., AAV-BRI (Korbelin et al., EMBO Mol. Med. 8: 609-625 (2016), which is hereby incorporated by reference in its entirety); or enhanced trans-duction of the adult CNS after IV administration, e.g., AAV-PHP.B and AAVPHP.eB (Deverman et al., Nat. Bio-technol. 34: 204-209 (2016) and Chan et al., Nat. Neurosci. 20: 1172-1179 (2017), which are hereby incorporated by reference in their entirety.

In accordance with this embodiment, the expression vec-tor construct encoding the CEMIP antibody-based molecule can include the polynucleotide sequence encoding the heavy chain polypeptide, a fragment thereof, a variant thereof, or combinations thereof. The expression construct can also include a nucleic acid sequence encoding the light chain polypeptide, a fragment thereof, a variant thereof, or com-binations thereof.

The expression construct also typically comprises a pro-moter sequence suitable for driving expression of the CEMIP antibody-based molecule. Suitable promoter sequences include, without limitation, the elongation factor 1-alpha promoter (EF1a) promoter, a phosphoglycerate kinase-1 promoter (PGK) promoter, a cytomegalovirus immediate early gene promoter (CMV), a chimeric liver-specific promoter (LSP), a cytomegalovirus enhancer/chicken beta-actin promoter (CAG), a tetracycline respon-sive promoter (TRE), a transthyretin promoter (TTR), a simian virus 40 promoter (SV40) and a CK6 promoter. Other promoters suitable for driving gene expression in mamma-lian cells that are known in the art are also suitable for incorporation into the expression constructs disclosed herein.

The expression construct can further encode a linker sequence. The linker sequence can encode an amino acid sequence that spatially separates and/or links the one or more components of the expression construct (heavy chain and light chain components of the encoded antibody).

In therapeutic applications, pharmaceutical antibody compositions are administered to a subject suspected of, or already suffering from brain metastasis in an amount sufficient to cure, or at least partially arrest or alleviate, one or more symptoms of the condition and its complications. An amount adequate to accomplish this is defined as a therapeutically- or pharmaceutically-effective dose. In both prophylactic and therapeutic regimes, agents are usually administered in several dosages until a sufficient response has been achieved. An effective dose of the composition of the present application, for the treatment of the above described conditions will vary depending upon many different factors, including means of administration, target site, physiological state of the patient, whether the patient is human or an animal, other medications administered, and whether treatment is prophylactic or therapeutic.

In accordance with the prophylactic and therapeutic methods described herein, compositions comprising any one of the CEMIP antibody-based molecules are administered in a dosage ranging from about 0.0001 to 100 mg/kg, and more usually 0.01 to 10 mg/kg of the recipient's body weight. For example, a CEMIP antibody or binding fragment thereof is administered in a dosage of 1, 2, 3, 4, 5, 6, 7, 8, 9 or 10 mg/kg, or higher, for example 15, 20, 25, 30, 35, 40, 45, 50, 55, 60, 65, 70, 75, 80, 85, 90, 95, or 100 mg/kg. An exemplary treatment regime entails administration once per every two weeks or once a month or once every 3 to 6 months. In some methods, two or more antibodies with different binding specificities are administered simultaneously, in which case the dosage of each antibody administered falls within the ranges indicated. Intervals between single dosages can be weekly, monthly or yearly. Intervals can also be irregular as indicated by measuring blood levels of antibody in the patient. Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

The mode of administration of the antibody, binding fragment thereof, or pharmaceutical composition described herein may be any suitable route that delivers the compositions to the host, such as parenteral administration, e.g., intradermal, intramuscular, intraperitoneal, intravenous or subcutaneous, pulmonary; transmucosal (oral, intranasal, intravaginal, rectal); using a formulation in a tablet, capsule, solution, powder, gel, particle; and contained in a syringe, an implanted device, osmotic pump, cartridge, micropump; or other means appreciated by the skilled artisan, as well known in the art. Site specific administration may be achieved by, for example, intrarticular, intrabronchial, intraabdominal, intracapsular, intracartilaginous, intracavitary, intracelial, intracerebellar, intracerebroventricular, intracolic, intracervical, intragastric, intrahepatic, intracardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravascular, intravesical, intralesional, vaginal, rectal, buccal, sublingual, intranasal, or transdermal delivery.

Administration can be systemic or local. In one embodiment, it may be desirable to administer the antibodies of the application locally to the area in need of treatment; this may be achieved by, for example, and not by way of limitation, local infusion, by injection, or by means of an implant, said implant being of a porous or non-porous material, including membranes and matrices, such as sialastic membranes, polymers, fibrous matrices (e.g., Tissuel®), or collagen matrices.

In another embodiment, compositions containing the antibody or binding fragment thereof are delivered in a controlled release or sustained release system. In one embodiment, a pump is used to achieve controlled or sustained release. In another embodiment, polymeric materials can be used to achieve controlled or sustained release of the antibody compositions described herein. Examples of polymers used in sustained release formulations include, but are not limited to, poly(2-hydroxy ethyl methacry-late), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. The polymer used in a sustained release formulation is preferably inert, free of leachable impurities, stable on storage, sterile, and biodegradable. Also, the use of liposomes, microcapsules or microspheres, inclusion complexes, or other types of carriers known in the art are also contemplated.

In yet another embodiment, a controlled or sustained release system can be placed in proximity of the prophylactic or therapeutic target, thus requiring only a fraction of the systemic dose. Controlled and/or release systems for delivery of antibodies known in the art are suitable for use and delivery of compositions containing the antibodies and binding fragments thereof as described herein, see e.g., Song et al, "Antibody Mediated Lung Targeting of Long-Circulating Emulsions," *PDA Journal of Pharmaceutical Science & Technology* 50:372-397 (1995); Cleek et al, "Biodegradable Polymeric Carriers for a bFGF Antibody for Cardiovascular Application," *Pro. Int'l. Symp. Control. Rel. Bioact. Mater.* 24:853-854 (1997); and Lam et al., "Microencapsulation of Recombinant Humanized Monoclonal Antibody for Local Delivery," *Proc. Int'l. Symp. Control Rel. Bioact. Mater.* 24:759-760 (1997), each of which is incorporated herein by reference in their entireties.

In embodiments where the pharmaceutical composition comprises polynucleotides encoding the antibody or binding fragment thereof as described herein, the nucleic acid can be administered in vivo to promote expression of its encoded antibody, by constructing it as part of an appropriate nucleic acid expression vector and administering it so that it becomes intracellular, e.g., by use of a retroviral vector (see e.g., U.S. Pat. No. 4,980,286 to Morgan et al., which is hereby incorporated by reference in its entirety), or by direct injection, or by use of microparticle bombardment (see e.g., a gene gun; Biolistic, Dupont), or coating with lipids or cell-surface receptors or transfecting agents, or by administering it in linkage to a homeobox-like peptide which is known to enter the nucleus (see e.g., Joliot et al, *Proc. Natl. Acad. Sci. USA* 88: 1864-1868 (1991), which is hereby incorporated by reference in its entirety). Alternatively, a nucleic acid can be introduced intracellularly and incorporated within host cell DNA for expression by homologous recombination.

The polynucleotide compositions can result in the generation of the antibody in the subject within at least about 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 20 hours, 25 hours, 30 hours, 35 hours, 40 hours, 45 hours, 50 hours, or 60 hours of administration of the composition to the subject. The composition can result in generation of the synthetic antibody in the subject within at least about 1 day, 2 days, 3 days, 4 days, 5 days, 6 days, 7 days, 8 days, 9 days, or 10 days of administration of the composition to the subject. The composition can result in generation of the antibody in the subject within about 1 hour to about 6 days, about 1 hour to about 5 days, about 1 hour to about 4 days, about 1 hour to about 3 days, about 1 hour to about 2 days, about 1 hour to about 1 day, about 1 hour to about 72 hours, about 1 hour to about 60 hours, about 1 hour to about 48 hours, about 1 hour to about 36 hours, about 1 hour to about 24 hours, about 1 hour to about 12 hours, or about 1 hour to about 6 hours of administration of the composition to the subject.

The composition, when administered to the subject in need thereof, can result in the persistent generation of the antibody in the subject. The composition can result in the generation of the antibody in the subject for at least about 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days, or 60 days.

If the methods described herein involve intranasal administration of the antibody composition, the composition can be formulated in an aerosol form, spray, mist or in the form of drops. In particular, prophylactic or therapeutic agents for use according to the present application can be conveniently delivered in the form of an aerosol spray presentation from pressurized packs or a nebulizer, with the use of a suitable propellant (e.g., dichlorodifluoromethane, trichloro-fluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

If the methods described herein involve oral administration of the antibody compositions described herein, the compositions can be formulated orally in the form of tablets, capsules, cachets, gelcaps, solutions, suspensions, and the like. Tablets or capsules can be prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets may be coated by methods well-known in the art.

Liquid preparations for oral administration may take the form of, but not limited to, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate.

Formulations for injection may be presented in unit dosage form (e.g., in ampoules or in multi-dose containers) with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle (e.g., sterile pyrogen-free water) before use. The methods of the application may additionally comprise of administration of compositions formulated as depot preparations. Such long acting formulations may be administered by implantation (e.g., subcutaneously or intramuscularly) or by intramuscular injection. Thus, for example, the compositions may be formulated with suitable polymeric or hydrophobic materials (e.g., as an emulsion in an acceptable oil) or ion exchange resins, or as sparingly soluble derivatives (e.g., as a sparingly soluble salt).

Most of the chemotherapeutic agents currently in use in treating cancer possess functional groups that are amenable to chemical crosslinking directly with an amine or carboxyl group for drug conjugation purposes. For example, free amino groups are available on methotrexate, doxorubicin, daunorubicin, cytosinarabinoside, cisplatin, vindesine, mitomycin, and bleomycin while free carboxylic acid groups are available on methotrexate, melphalan, and chlorambucil. These functional groups, that is free amino and carboxylic acids, are targets for a variety of homo-bifunctional and hetero-bifunctional chemical crosslinking agents which can crosslink these drugs directly to a free amino group of a nanoparticle or antibody. Specific procedures for performing such conjugation with chemotherapeutic agents have been described and are known in the art. By way of example, conjugation of chlorambucil with antibodies is described by Flechner, "The Cure and Concomitant Immunization of Mice Bearing Ehrlich Ascites Tumors by Treatment With an Antibody—Alkylating Agent Complex," *European Journal of Cancer* 9:741-745 (1973); Ghose et al., "Immunochemotherapy of Cancer with Chlorambucil-Carrying Antibody," *British Medical Journal* 3:495-499 (1972); and Szekerke et al., "The Use of Macromolecules as Carriers of Cytotoxic Groups (part II) Nitrogen Mustard—Protein Complexes," *Neoplasma* 19:211-215 (1972), which are hereby incorporated by reference in their entirety. Procedures for conjugating daunomycin and adriamycin to antibodies are described by Hurwitz et al., "The Covalent Binding of Daunomycin and Adriamycin to Antibodies, With Retention of Both Drug and Antibody Activities," *Cancer Research* 35:1175-1181 (1975) and Arnon et al. *Cancer Surveys* 1:429-449 (1982), which are hereby incorporated by reference in their entirety. Coupling procedures as also described in EP 86309516.2, which is hereby incorporated by reference in its entirety.

The amount can be determined by a physician with consideration of individual differences in age, weight, tumor type and size, extent of infection or metastasis, and condition of the patient (subject). It can generally be stated that a pharmaceutical composition comprising the T cells described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., "Use of Tumor-Infiltrating Lymphocytes and Interleukin-2 in the Immunotherapy of Patients with Metastatic Melanoma. A Preliminary Report," *New Eng. J. of Med.* 319:1676 (1988), which is hereby incorporated by reference in its entirety). The optimal dosage and treatment regime for a particular patient can readily be determined by one skilled in the art of medicine by monitoring the patient for signs of disease and adjusting the treatment accordingly.

The administration of CAR T cells may be carried out in any convenient manner, including by aerosol inhalation, injection, ingestion, transfusion, implantation or transplantation. The CAR T cells may be administered to a patient subcutaneously, intradermally, intratumorally, intranodally, intramedullary, intramuscularly, by intravenous (i.v.) injection, or intraperitoneally.

The dosage of the above treatments to be administered to a patient will vary with the precise nature of the condition being treated and the recipient of the treatment. The scaling of dosages for human administration can be performed according to art-accepted practices.

Another aspect of the present disclosure is directed to a method of identifying a subject's risk of developing metastatic brain disease that involves in vitro or in vivo detection of CEMIP, and in particular exosomal expression of CEMIP. Detecting the presence of a CEMIP protein or peptide in a subject using the antibodies or antibody fragments thereof as described herein can be achieved by obtaining a biological sample from the subject (e.g., blood, urine, cerebral spinal fluid, ocular lacrimal secretion, saliva, feces, nasal brushings and tissue or organ biopsy), contacting the biological sample with the diagnostic antibody reagent, and detecting binding of the diagnostic antibody reagent to a CEMIP protein or peptide if present in the sample from the subject. Assays for carrying out the detection of a CEMIP protein/peptide in a biological sample using a diagnostic antibody are well known in the art and include, without limitation, ELISA, immunohistochemistry, SIMOA (single molecule array), and Western blot. Suitable CEMIP antibodies are described herein.

In accordance with this and other embodiments described herein, the CEMIP antibody or binding fragments described herein are coupled to a detectable label. The label can be any detectable moiety known and used in the art. Suitable labels include, without limitation, radioisotopes or radionuclides (e.g., $^3$H, $^{14}$C, $^{35}$S, $^{90}$Y, $^{99}$Tc, $^{111}$In, $^{125}$I, $^{131}$I, $^{177}$Lu, $^{166}$Ho, or $^{153}$Sm); fluorescent labels (e.g., FITC, rhodamine, lanthanide phosphors), enzymatic labels (e.g., horseradish peroxidase, luciferase, alkaline phosphatase); chemiluminescent markers; biotinyl groups; predetermined polypeptide epitopes recognized by a secondary reporter (e.g., leucine zipper pair sequences, binding sites for secondary antibodies, metal binding domains, epitope tags); and magnetic agents, such as gadolinium chelates.

Detecting the presence of CEMIP proteins or peptides in a subject using the diagnostic antibody reagent of the present application can also be achieved using in vivo imaging techniques. In vivo imaging involves administering to the subject the antibody or binding fragments thereof described herein, and detecting the binding of the antibody or binding fragment thereof to the CEMIP protein in vivo.

In one embodiment, the CEMIP antibody is a radiolabeled anti-CEMIP antibody or CEMIP- or anti-CEMIP-bound nanoparticle conjugated to an anti-CEMIP antibody.

Suitable radionuclides for use in labelling anti-CEMIP antibodies include, without limitation, $^{80}$Re, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{188}$Rd, $^{166}$Dy, $^{166}$Ho, $^{149}$Pm, $^{151}$Pm, $^{153}$Sm, $^{159}$Gd, $^{172}$Tm, $^{169}$Yb, $^{175}$Yb, $^{177}$Lu, $^{105}$Rh, $^{111}$Ag, $^{131}$I, $^{177m}$Sn, $^{225}$Ac, $^{227}$Th, $^{211}$At, and combinations thereof.

Procedures for labeling antibodies with radioactive isotopes are generally known in the art. For example, there are a wide range of moieties which can serve as chelating ligands and which can be derivatized to an anti-CEMIP antibody. Procedures for iodinating biological agents, such as antibodies, and binding portions thereof, are described by Hunter and Greenwood, "Preparation of Iodine-131 Labelled Human Growth Hormone of High Specific Activity," *Nature* 144:496-496 (1962), David et al., "Protein Iodination With Solid State Lactoperoxidase," *Biochemistry* 13:1014-1021 (1974), and U.S. Pat. No. 3,867,517 to Ling and U.S. Pat. No. 4,376,110 to David, which are hereby incorporated by reference in their entirety. Other procedures for iodinating biological agents are described by Greenwood et al., "The Preparation of I-131-Labelled Human Growth Hormone of High Specific Radioactivity," *Biochem. J.* 89:114-123 (1963); Marchalonis, "An Enzymic Method for the Trace Iodination of Immunoglobulins and Other Proteins," *Biochem. J.* 113:299-305 (1969); and Morrison et al., "Use of Lactoperoxidase Catalyzed Iodination in Immunochemical Studies," *Immunochemistry* 8:289-297 (1971), which are hereby incorporated by reference in their entirety. Procedures for $^{99m}$Tc-labeling are described by Rhodes, B. et al. in Burchiel, S. et al. (eds.), Tumor Imaging: The Radioimmunochemical Detection of Cancer, New York: Masson 111-123 (1982) and the references cited therein, which are hereby incorporated by reference in their entirety. Procedures suitable for In-labeling biological agents are described by Hnatowich et al., "The Preparation of DTPA-coupled Antibodies Radiolabeled With Metallic Radionuclides: an Improved Method," *J. Immul. Methods* 65:147-157 (1983), Hnatowich et al., "Coupling Antibody With DTPA—an Alternative to the Cyclic Anhydride," *Int. J. Applied Radiation* 35:554-557 (1984), and Buckley et al., "An Efficient Method For Labelling Antibodies With $^{111}$In," *F.E.B.S.* 166:202-204 (1984), which are hereby incorporated by reference in their entirety.

Diagnostic antibodies or similar reagents can be administered by intravenous injection into the body of the patient, or directly into the brain by intracranial injection or by drilling a hole through the skull. The dosage of antibody should be within the same ranges as for treatment methods. In accordance with this embodiment, the antibody or binding fragment is coupled to an imaging agent to facilitate in vivo imaging. The imaging agent can be any agent known to one of skill in the art to be useful for imaging, preferably being a medical imaging agent. Examples of medical imaging agents include, but are not limited to, single photon emission computed tomography (SPECT) agents, positron emission tomography (PET) agents, magnetic resonance imaging (MRI) agents, nuclear magnetic resonance imaging (NMR) agents, x-ray agents, optical agents (e.g., fluorophores, bioluminescent probes, near infrared dyes, quantum dots), ultrasound agents and neutron capture therapy agents, computer assisted tomography agents, two photon fluorescence microscopy imaging agents, and multi-photon microscopy imaging agents. Exemplary detectable markers include radioisotypes (e.g., $^{18}$F, $^{11}$C, $^{13}$N, $^{64}$Cu, $^{124}$I, $^{76}$Br, $^{82}$Rb, $^{68}$Ga $^{99m}$Tc, $^{111}$In, $^{201}$Tl or $^{15}$O, which are suitable for PET and/or SPECT use) and ultra-small superparamagnetic particles of iron oxide (USPIO) which are suitable for MRI.

Diagnosis of a brain metastasis is performed by comparing the number, size, and/or intensity of detected CEMIP proteins/peptides in a sample from the subject or in the subject, to corresponding baseline values. An appropriate baseline value can be the average level of CEMIP protein/peptide found in a population of undiseased individuals. Alternatively, an appropriate baseline value may be the level of CEMIP in the same subject determined at an earlier time.

The diagnostic methods described herein can also be used to monitor a subject's response to therapy. In this embodiment, detection of CEMIP proteins or peptides in the subject is determined prior to the commencement of treatment. The level of CEMIP protein or peptide in the subject at this timepoint is used as a baseline value. At various times during the course of treatment the detection of CEMIP protein/peptide is repeated, and the measured values thereafter compared with the baseline values. A decrease in values relative to baseline signals a positive response to treatment.

A related aspect of the disclosure is directed to a method of identifying a subject's risk for developing a condition mediated by a CEMIP protein or peptide. This method involves detecting, in the subject, the presence of an CEMIP protein or peptide using a diagnostic reagent comprising the antibody or binding fragment thereof described herein, and identifying the subject's risk of developing a condition mediated by the CEMIP protein or peptide based on the results of the detecting step.

Methods of detecting the presence of a CEMIP protein/peptide in the subject or in a sample from the subject include the in vitro and in vivo methods described supra. In one embodiment, the subject is not exhibiting any definitive signs or symptoms of brain metastasis, and employment of this method serves as an early diagnostic. In another embodiment, the subject is not exhibiting any signs or symptoms of brain metastasis, but has a genetic predisposition to a condition and employment of this method serves to predict the likelihood that the individual will develop brain metastasis in the future. In either embodiment, appropriate therapeutic and/or prophylactic intervention can be employed, e.g., administration of a therapeutic compositions containing the antibodies or binding fragments thereof in an amount effective to slow or prevent the onset or progression of brain metastasis.

Another aspect of the present disclosure is directed to a diagnostic kit that comprises the antibody or binding fragment thereof as described herein and a detectable label.

A suitable detectable label is any moiety attached to an antibody or an analyte to render the reaction between the antibody and the analyte detectable. A label can produce a signal that is detectable by visual or instrumental means. Various labels include signal-producing substances, such as chromogens, fluorescent compounds, chemiluminescent compounds, radioactive compounds, and the like. Representative examples of detectable labels include moieties that produce light, e.g., acridinium compounds, and moieties that produce fluorescence, e.g., fluorescein. In this regard, the moiety itself may not be detectable, but becomes detectable upon reaction with yet another moiety.

Other suitable detectable labels include radioactive labels (e.g., H, I, S, C, P, and P), enzymatic labels (e.g., horseradish peroxidase, alkaline peroxidase, glucose 6-phosphate dehydrogenase, and the like), chemiluminescent labels (e.g., acridinium esters, thioesters, or sulfonamides; luminol, isoluminol, phenanthridinium esters, and the like), fluorescent labels (such as fluorescein (e.g., 5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, and the like)), rhodamine, phycobiliproteins, R-phycoerythrin, quantum dots (e.g., zinc sulfide-capped cadmium selenide), a thermometric label, or an immuno-polymerase chain reaction label.

EXAMPLES

The following examples are provided to illustrate embodiments of the present application, but they are by no means intended to limit its scope.

Materials and Methods for Examples

Cell lines. The breast cancer cell line MDA-MB-231 (parental) was purchased from ATCC. The following MDA-MB-231 organotropic derivative cell lines were provided: 231BR (brain-tropic, BrT1) by P. Steeg (NCI); 831 (brain-tropic, BrT2), 4175 (lung-tropic, LuT1) and 1833 (bone-tropic, BoT1) by J. Massagué (MSKCC); 4173 (lung-tropic, LuT2) by A. Minn (University of Pennsylvania); and MDA-MB-231-HM (brain-tropic) by S. Wang (UC San Diego) (FIG. 1A). The brain metastatic derivative N2LA-BR of the lung cancer cell line N2LA was generated from a metastatic lung cancer patient by V. Rajasekhar (MSKCC). Breast and lung cancer cells were cultured in DMEM or RPMI, respectively, with 10% fetal bovine serum (FBS), and Penicillin/Streptomycin. For exosome isolation from culture supernatants, cells were cultured in exosome-depleted FBS (Peinado et al., "Melanoma Exosomes Educate Bone Marrow Progenitor Cells Toward a Pro-Metastatic Phenotype Through MET," *Nat Med* 18:883-891 (2012); Costa-Silva et al., "Pancreatic Cancer Exosomes Initiate Pre-Metastatic Niche Formation in the Liver," *Nat Cell Biol* 17:816-826 (2015); Hoshino et al., "Tumour Exosome Integrins Determine Organotropic Metastasis," Nature 527:329-335, (2015), which are hereby incorporated by reference in their entirety). Cells were maintained in a humidified 37° C. incubator with 5% $CO_2$. Cell lines routinely tested negative for *mycoplasma*.

Exosome Purification, Labelling, and Characterization. Exosomes from cell lines were purified by ultracentrifugation (Peinado., "Melanoma Exosomes Educate Bone Marrow Progenitor Cells Toward a Pro-metastatic Phenotype Through MET," *Nat Med* 18:883-891 (2012); Costa-Silva et al., "Pancreatic Cancer exosomes initiate pre-metastatic niche formation in the liver," *Nat Cell Biol* 17:816-826 (2015); Hoshino et al., "Tumour Exosome Integrins Determine Organotropic Metastasis," *Nature* 527:329-335 (2015), which are hereby incorporated by reference their entirety.)

Cell culture supernatant was centrifuged at 500×g for 10 minutes and then at 12,000×g for 20 minutes. Exosomes were collected by ultracentrifugation of this supernatant at 100,000×g for 70 minutes and the pellet washed by resuspending in PBS and re-ultracentrifuging at 100,000×g for 70 minutes. For imaging, exosomes were fluorescently-labelled using PKH67 or PKH26 lipophilic membrane dyes (Sigma) or CellVue Maroon (Polysciences) and PBS-washed (Peinado et al., "Melanoma Exosomes Educate Bone Marrow Progenitor Cells Toward a Pro-Metastatic Phenotype Through MET," *Nat Med* 18:883-891 (2012); Costa-Silva et al., "Pancreatic Cancer Exosomes Initiate Pre-Metastatic Niche Formation in the Liver," *Nat Cell Biol* 17:816-826 (2015); Hoshino et al., "Tumour Exosome Integrins Determine Organotropic Metastasis," *Nature* 527:329-335, (2015), which are hereby incorporated by reference in their entirety). Unlabelled or labelled exosomes were resuspended in PBS for experiments.

Exosome protein concentration was determined by BCA assay (Pierce, Thermo Scientific). Exosome size and particle number were analyzed using the DS500 nanoparticle characterization system (NanoSight, Malvern Instruments) (Hoshino et al., "Tumour Exosome Integrins Determine Organotropic Metastasis," *Nature* 527:329-335, (2015), which is hereby incorporated by reference in its entirety). Exosomes were imaged by negative stain transmission electron microscopy (Zhang et al., "Identification of Distinct Nanoparticles and Subsets of Extracellular Vesicles by Asymmetric Flow Field-Flow Fractionation," *Nat Cell Biol* 20:332-343 (2018), which is hereby incorporated by reference in its entirety).

Brain slice assay. Organotypic brain slice cultures were adapted from a previously described protocol for generation of mouse brain cortical slices to study neuron development14. Brains from 6-8 week-old athymic NCr nude (Taconic) or outbred Foxn–/– (Jackson Laboratories, #007850) female mice were dissected in complete HBSS (HBSS supplemented with HEPES (pH 7.4, 2.5 mM); D-glucose (30 mM); CaCl2 (1 mM); MgSO4 (1 mM); and NaHCO3 (4 mM)), after whole-body PBS perfusion. Fresh brains were embedded in microwave-preheated 4% low melting agarose (Lonza) in complete HBSS once the agarose cooled to 37° C. Once solidified, embedded brains were cut into 250 µm coronal slices (bregma –2 mm to +2 mm) using a VT 12000s vibratome (Leica). Slices were dissected across the midline separating brain hemispheres, generating symmetric halves. Brain slices damaged during sectioning/handling were discarded. Slices generated from different positions across the brain anterior-posterior axis were distributed equally to ensure experimental groups contained an identical collection of slices representative of the brain region sectioned. Groups of three half-brain slices were placed flat on top of 0.4 µm pore polycarbonate (PC) membrane cell culture inserts (#Z353086 Sigma or #140660 Thermo Scientific) in 6-well plates with media (DMEM with 25% complete HBSS, 5% FBS, L-glutamine (1 mM), Penicillin/Streptomycin, and Normocin (Invivogen, 50 µg/mL)) in the bottom well. To establish and ensure a well-defined region for exosome and cancer cell administration to brain slices, a sterilized transparent PC ring (Small Parts) with a 3 mm inner diameter was placed on top of each slice. Rings were centrally positioned so that the inner-limit of the ring was within the slice boundaries.

For exosome and cancer cell administration, 3 µL of PBS-resuspended exosomes (5 µg), 7,500 BrT1 cells, or 20,000 parental cells were added inside the rings. For colonization studies, slices were pre-treated with PBS or exosomes for two consecutive days prior to adding cells to ensure that exosome-induced changes resulted from effects on the brain microenvironment. Cancer cells were added 24 hours after exosome treatment and incubated for 72 hours. Brain slices were maintained in a humidified 37° C. incubator with 5% $CO_2$ for up to 5 days, changing media every two days. At endpoint, slices were washed with PBS before fixation in 2% paraformaldehyde for 2 hours at 4° C. Tissue processing and immunofluorescence are described below.

Tumour cell colonization was quantified by averaging the number of cancer cells growing on top of slices. Cell invasion was quantified by averaging the number of invading cancer cells observed below the first layer of brain cells on transversal sections of slices. Tumour cell interaction with vessels in the brain microenvironment was measured by quantifying the average number of spindle-like cells growing on top of slices in association with vessels. Cancer cells were counted manually with the multi-point tool in ImageJ software (version 1.52a).

For exosome adhesion and uptake, co-localization of exosomes and resident brain cells was evaluated after one treatment with fluorescently-labelled exosomes (5 µg). Slices were incubated with exosomes for 12 hours for adhesion studies or 24 hours for uptake studies, and then washed, fixed, and processed for immunofluorescence.

Proteomics. Mass spectrometry of exosomes was performed at the Rockefeller University Proteomics Resource Center, as described (Hoshino et al., "Tumour exosome integrins determine organotropic metastasis," *Nature* 527: 329-335 (2015), which is hereby incorporated by reference in its entirety). Data were quantified and searched against Human Uniprot database (July 2014) using MaxQuant (version 1.5.0.9). Perseus software (version 1.5.0.9) was used for bioinformatics and statistical analysis. Protein abundances were expressed as LFQ (label free quantitation) values. Only proteins quantified in at least two of three replicates in at least one group were retained, and missing values were imputed. An ANOVA test was performed and corrected for multiple hypotheses testing using a permutation-based FDR threshold of 0.05. GENE-E software was used for heatmap generation and data display.

Immunoblotting. Exosomes and cells lysed with RIPA buffer plus protease inhibitor cocktail were diluted with sample buffer, run on Novex 4-12% Tris-Glycine Gels (Life Technologies), and transferred onto PVDF membrane. Proteins were detected with primary antibodies and HRP-conjugated secondaries (Jackson Immunoresearch), and imaged by enhanced chemiluminescence. Antibodies can be found in Table 2. For CEMIP quantification, the ratio between the CEMIP and ACTB band intensities for each sample was measured using ImageJ software.

TABLE 2

| Antibody List | | | | |
| --- | --- | --- | --- | --- |
| Application | Antibody/Protein recognized | Vendor | Product reference | Antibody dilution |
| Immunoblot | CEMIP | Novus biologicals | 4575.00.02 | 1:5000 |
| | HSP70 | System Biosciences | EXOAB-Hsp70A-1 | 1:1000 |

TABLE 2-continued

Antibody List

| Application | Antibody/Protein recognized | Vendor | Product reference | Antibody dilution |
|---|---|---|---|---|
| | Syntenin-1 | Santa Cruz biotechnology | sc-100336 | 1:200 |
| | CD81 | Santa Cruz biotechnology | sc-166029 | 1:1000 |
| | ACTB [unconjugated] | Cell Signaling | 4967L | 1:1000 |
| | ACTB [peroxidase-conjugated] | Sigma | A3854 | 1:20000 |
| | Mouse/Rabbit Whole IgG [peroxidase-conjugated] | Jackson ImmunoResearch Laboratories | | 1:5000 |
| Immunofluorescence | GFP | Aves labs | GFP-1020 | 1:200 |
| | mCherry | abcam | ab205402 | 1:200 |
| | Collagen IV | abcam | ab6586 | 1:500 |
| | PECAM-1/CD31 | Santa Cruz biotechnology | sc-18916 | 1:50 |
| | Glut-1 | abcam | ab40084 | 1:100 |
| | Iba-1 | Wako | 019-19741 | 1:200 |
| | GFAP | abcam | ab7260 | 1:500 |
| | NeuN | Millipore | ABN90 | 1:500 |
| | Ki-67 | abcam | ab66155 | 1:500 |
| | Mouse/Rat/Chicken/Rabbit IgG [fluorochrome-conjugated] | Life technologies | A11001, A11008, A11036, A11039, A11077, A21244, A21247, A27040 | 1:500 |
| | Mouse IgG [fluorochrome-conjugated] | Vector laboratories | CI-2000 | 1:500 |
| Immunohistochemistry | CEMIP | abcam | ab76849 | 1:100 |
| FACS | CD45 | EBioscience | 56-0451-82 | 1:100 |
| | CD31 | BD Biosciences | 561073 | 1:40 |
| | CD11b | BD Biosciences | 550993 | 1:200 |
| | CD49d | Biolegend | 103618 | 1:100 |

Primer List

| Application | Primer name | Primer sequence | Notes |
|---|---|---|---|
| CEMIP knockout | CEMIP gRNA KO1 CEMIP gRNA KO2 | CGTACCAACGGGCCCCTCCG (SEQ ID NO: 114) GCGGCTTGGACCATAGCGGA (SEQ ID NO: 115) | |
| CEMIP overexpression | CEMIP forward CEMIP reverse | 5'-ACGTACTCGAGCACCATGGGAGCTGCTGGGAGGCA-3' (SEQ ID NO: 116) 5'-ACGTGCTAGCCTACAACTTCTTCTTCTTCAC-3' (SEQ ID NO: 117) | with 5' PspXI restriction site with 3' NheI restriction site |

Exosome OptiPrep™ density gradient. To prepare the discontinuous iodixanol gradient, 40% (w/v), 20% (w/v), 10% (w/v) and 5% (w/v) iodixanol solutions were made by diluting OptiPrep™ (60% (w/v) aqueous iodixanol from Sigma) with 0.25 M sucrose/10 mM Tris, pH 7.5. Three milliliters of 40% iodixanol solution were added to a 14×95 mm ultra-clear tube (Beckman Coulter), followed by layering 3 mL each of 20% and 10% solutions and 2.5 mL of 5% solution. Exosomes in 500 uL of PBS were overlaid onto the top of the gradient. A portion of the exosome sample was saved as input. The gradient was centrifuged at 100,000×g for 16 hours at 10° C. using a SW-40 Ti Rotor. Twelve 1 mL gradient fractions were collected from top to bottom, diluted with PBS, centrifuged at 100,000×g for 3 hours at 10° C., and resuspended in RIPA buffer. Density was determined by measuring the weight of each fraction (g/mL) (FIG. 1F).

Mouse studies. Mouse work was performed in accordance with institutional, IACUC and AAALAS guidelines (Weill Cornell Medicine animal protocol 0709-666A) and the study is compliant with all relevant ethical regulations regarding animal research. Animals were monitored for stress, illness or abnormal tissue growth, and euthanized if health deteriorated. Mice that died before the experimental endpoint were excluded from the analysis. Experiments used 6-8 week-old athymic NCr nude or outbred Foxn$^{-/-}$ mice. At endpoints, mice were euthanized, perfused with PBS, and tissues were collected. No statistical method was used to pre-determine sample size and no method of randomization was used to allocate animals to experimental groups.

For in vivo exosome distribution, brains were collected 24 hours post-intracardiac injection of fluorescently-labelled exosomes (10 µg). Uptake by brain cells was evaluated by immunofluorescence. To evaluate exosome-induced vascular leakiness, Texas-Red-lysine fixable dextran 70,000 MW (Invitrogen) (2 mg) was retro-orbitally injected 23 hours after treatment with PKH67-labelled exosomes (10 µg). One hour post-dextran injection, brain tissue was collected for analysis of extravasated dextran and exosome localization.

For experimental brain metastasis, $1 \times 10^4$ GFP-labelled and/or luciferase-expressing BrT1 cells in PBS were intracardiacally injected. For experimental brain metastasis in situ growth, $1 \times 10^5$ GFP/luciferase-expressing BrT1 cells in 2 µL of PBS were intracranially injected in the right brain hemisphere using a low-volume Hamilton syringe and stereotactic apparatus. Cells were injected at a rate of 0.2 µL/min, at 2.5 mm depth from the surface of the brain and coordinates 0.1 mm posterior and 2.0 mm lateral to the bregma. For orthotopic primary tumour growth, $1 \times 10^6$ BrT1 cells in Matrigel (Corning) were injected into the 4th mammary fat pad.

For experimental brain metastasis exosome education, exosomes (10 µg) were retro-orbitally injected every other day for three weeks, mimicking continuous and systemic exosome release by primary tumours (Peinado et al., "Melanoma Exosomes Educate Bone Marrow Progenitor Cells Toward a Pro-Metastatic Phenotype Through MET," *Nat Med* 18:883-891 (2012); Hoshino et al., "Tumour Exosome Integrins Determine Organotropic Metastasis," *Nature* 527: 329-335 (2015), which are hereby incorporated by reference in their entirety). One day after the last treatment, mice were intracardiacally injected with $1 \times 10^4$ BrT1 GFP/luciferase-expressing cells in PBS.

IVIS SpectrumCT bioluminescence imaging system (PerkinElmer) was used for in vivo brain metastasis imaging. In vivo cranial bioluminescence was analyzed by total cranial photon flux (p/s) quantification using Living Image software (Caliper Life Sciences). Negative p/s values were considered zero. Brain metastases in sagittal brain sections were analyzed by histological evaluation and quantification of lesion number and total brain metastatic lesion area, scoring two whole brain sagittal sections from different brain areas per mouse, stained with anti-GFP and DAPI or H&E. Tumour cell clusters with 10 or more cells were considered as metastatic foci. Orthotopic primary tumour size was measured manually with a vernier caliper. Tumour volume was calculated using the formula for an ellipsoid, $V = \pi/6$ (L×W×H) (FIG. 2B).

Tumour vasculature caliber was determined by measuring vessel diameter within metastatic foci and neighboring normal brain regions, in two whole brain sagittal sections from different brain areas per individual using ImageJ software. Vessel diameter was calculated as the average of three measurements along the vessel, scoring up to five different tumour/normal vessels per individual, evaluating metastatic foci within the same size range across groups.

Tissue Processing and Immunostaining. For histological analysis of exosome and brain metastasis, freshly dissected brains were embedded and frozen in in Tissue-tek OCT (Electron Microscopy Sciences). Lungs and other organs were fixed in 4% paraformaldehyde overnight at 4° C. before freezing in OCT.

For immunofluorescence, cryosections were permeabilized in PBS with 0.25% Triton X-100 (PBS-T), blocked in PBS-T with 3% bovine serum albumin and 5% normal goat serum and incubated overnight at 4° C. in blocking solution with primary antibodies (Table 2). Samples were incubated with secondary antibodies conjugated to AMCA, Alexa Fluor 488, 568 or 647, DAPI-stained, and mounted with Prolong Diamond antifade (Invitrogen). For histological analysis of brain metastasis with H&E, brains were fixed in 4% paraformaldehyde overnight at 4° C. and processed for paraffin embedding. Sections were stained and mounted with VectaMount medium (Vector).

For brain slices, the PC ring was removed and slices were PBS washed. Immunofluorescence was carried out in freefloating conditions using the same protocol for tissue sections. For invasion, fixed slices were washed in PBS, outerring regions were dissected out and tissue was embedded in OCT and frozen. Cryosections perpendicular to the plane of the slice were immunostained as for tissue sections.

CEMIP knockout and overexpression. CEMIP knockout in BrT1 cells was achieved by transfection of cells using Lipofectamine LTX/PLUS (Invitrogen, 15338100) with PX458-DsRed-Cas9 vector carrying gRNAs (Table 2) targeting human CEMIP. Vectors were prepared by MSKCC Gene Editing and Screening Core Facility, and sgRNAs were chosen using Guidescan (MSKCC). DsRed-expressing cells were single cell-sorted into 96-well plates for clonal growth. CEMIP depletion was evaluated by immunoblot and validation of CEMIP gene editing was verified by Sanger sequence identification of complex indels.

CEMIP was overexpressed in 231 parental cells by lentiviral transduction. Full length human CEMIP was PCR-amplified (Table 2) from pcDNA3.2V5DEST_wtKIAA1199 (a gift from Dr. G. Marra, Institute of Molecular Cancer Research, University of Zurich) and subcloned into SalI/XbaI sites of pLentiCMV-blast (provided by E. Campeau, University of Massachusetts Medical School; Addgene #17486) (FIG. 3E). As a control, parental cells were infected with pLentiCMV-blast empty-vector lentivirus. Lentivirus was produced using a third-generation system by co-transfecting HEK-293T cells using Lipofectamine LTX/PLUS with expression cDNA and packaging/envelope plasmids (pRSV-REV, pMD2Lg/pRRE, and pMD2.g, provided by D. Trono, École Polytechnique Fédérale de Lausanne; Addgene #12253, #12251, and #12259). Cells were infected overnight with virus. Stable cell lines were selected with blasticidin, and overexpression was confirmed by immunoblot.

Proliferation and invasion assays. For proliferation, $2 \times 10^6$ BrT1 cells were plated in T175 flasks and counted 72 hours post-seeding. For invasion, cells were serum-starved for 24 hours pre-plating, and $2.5 \times 10^4$ cells were seeded in Matrigel-coated transwell inserts (8-µm pore size, Corning). Cell suspensions were added to inserts containing media with 1% FBS on the top and media with 10% FBS in the bottom chamber and were incubated at 37° C. for 48 hours. Cells that remained in the upper chamber were removed with cotton swabs. Inserts were fixed with 1% paraformaldehyde overnight at 4° C. and mounted with Prolong Gold antifade reagent with DAPI (Invitrogen) for visualization.

Brain endothelial cells. Brain endothelial cells (BrECs) were isolated from young adult C57BL/6J mouse brains with a collagenase/dispase solution and cultured (FIG. 3D). Cells were plated on fibronectin-coated plates (Sigma, 1 mg/mL in PBS) in mEC media. BrECs were selected with puromycin-containing media up to the first passage. BrECs were infected with E4ORF1-carrying lentivirus 96 hours post-isolation to enable robust expansion (FIG. 3D). Accutase was used for cell detachment and endothelial purity was confirmed by expression of VE-Cadherin and CD31 and absence of CD45. BrECs were maintained in a humidified 37° C. incubator under hypoxic conditions (5% $O_2$) and 5% $CO_2$.

For assays, cells were sub-cultured in Advanced DMEM/F12 with 20% exosome-depleted FBS, 1% Antibiotic-Antimycotic (Invitrogen), 1% Glutamax (Life Technologies), 1% Non-essential Amino Acids (Life Technologies), 1% CD Lipid Concentrate (Life Technologies), HEPES (20 mM), Heparin (100 μg/mL), Endothelial cell mitogen (Alfa Aesar, 50 μg/mL), and SB431542 (R&D systems, 5 μM). BrECs were grown to 80% confluence and starved in 5% FBS for 6 hours pre-exosome treatment. The Cultrex In Vitro Angiogenesis Assay tube formation kit (Trevigen) was used for tube formation. $1 \times 10^4$ calcein AM-labelled BrECs, pre-treated for 24 hours with PBS or exosomes (10 μg), were seeded in μ-Slide Angiogenesis chambers (Ibidi) and allowed to form vascular networks for 4 to 6 hours. Images of vascular networks were analyzed with ImageJ's tool "Angiogenesis Analyzer" (by Gilles Carpentier) to quantitate the number of junction elements (corresponding to nodes or groups of fusing nodes—pixels with 3 neighbors), number and length of branches (elements of a ramification delimited by a junction and one extremity) or isolated segments (binary lines that are not branched or connected to other vascular structures) allowed overall assessment of topology and complexity of the vascular meshed network formed.

Image Acquisition. Pictures were taken as follows: with an E800 Eclipse microscope (Nikon) at 400× magnification to analyze in vivo exosome distribution, exosome-induced vascular leakiness, and in vitro CEMIP immunohistochemistry; with an EVOS FL Cell Imaging System microscope (Thermo Scientific) at 260× magnification to analyze ex vivo brain slice exosome uptake, cancer cell colonization and invasion, in vitro BrEC ETF, and in vivo brain metastatic vasculature; with a Panoramic Flash slide scanner (3DHistech) at 20× magnification to analyze brain metastatic colonization in whole brain slices and whole brain sagittal sections; with a TCS SP5-II confocal microscope (Leica Microsystems) to analyze ex vivo exosome adhesion and uptake.

FACS. Brain slices were pre-treated with PBS or PKH67-labelled exosomes (5 μg/slice) for two consecutive days, the outer-ring areas were dissected out and the PC ring removed. Tissue was washed with PBS before Dispase/Collagenase (Roche; Dispase II at 1 U/mL and Collagenase A at 2.5 mg/mL final concentration) digestion for 15 minutes at 37° C. with agitation (70 RPM). Single-cell suspensions were obtained by pipetting and filtering through a 100 μm cell strainer. Cells were washed with MACS buffer (PBS $Ca^{2+}$/$Mg^{2+}$-free, 1% Bovine Serum Albumin, 2 mM EDTA), collected by centrifugation at 300×g for 5 minutes at 4° C., and incubated with Myelin Removal Beads (Miltenyi). Myelin-free cells were resuspended in MACS buffer and incubated with fluorescently-labelled antibodies (Table 2) for 30 minutes at 4° C.: CD45, CD31, CD11b, and CD49d. BrECs were defined as CD45$^-$ CD31$^+$ and microglial cells as CD45$^+$ CD11b$^{low}$ CD49d$^{low}$ (FIG. 3H). Cells were washed with MACS buffer, filtered through a 40 μm strainer and DAPI-stained. Unstained and single-stained cells/beads were used for cell sorter set-up. DAPI+ dead cells were excluded. Sorting was performed on a FACS Aria (Becton Dickinson) and exosome positive BrECs and microglia cells were sorted into RLT buffer (Qiagen) with 2-Mercaptoethanol and frozen. Becton Dickinson Diva Software was used for cell sorting and data acquisition and TreeStar FlowJo 10.5.3 was used for data analysis.

RNA sequencing. RNA was extracted from cells using the RNeasy Micro kit (QIAGEN) and quantified using Qubit 2.0 Fluorometer (Life Technologies). RNA integrity was checked with TapeStation (Agilent Technologies). GENEWIZ, LLC. (South Plainfield, NJ, USA) prepared RNA libraries and performed sequencing on the Illumina HiSeq instrument using HiSeq Control Software. Samples were sequenced using a 2×150 Paired End (PE) configuration. Raw sequence data (.bcl files) generated from Illumina HiSeq was converted into fastq files and de-multiplexed using the Illumina bcl2fastq v. 2.17 program. One mismatch was allowed for index sequence identification. After demultiplexing, sequence data was checked for overall quality and yield. RNA expression analysis methods and code are described in detail at doi: 10.5281/zenodo.3334930, complete all scripts used. Briefly, fastq file quality was evaluated with FastQC, followed by read trimming using Trimmomatic. Reads were aligned to *Mus musculus* GRCm38.p6 using Salmon. DESeq2 assessed differential gene expression among conditions using the Likelihood Ratio Test (LRT) and controlling for replicates. Sample clustering using Principal Component Analysis and sample clustering of variance stabilized transformed read counts identified two outliers—WT replicate C and KO2 replicate A—which were removed from further analysis. A post-hoc binomial Wald test in DESeq2 evaluated differences between PBS, WT, KO1 and KO2. The focal gene set of interest was identified as those genes for which: a) the likelihood ratio test was significant ($p \le 0.05$); b) there were significant expression differences between WT and PBS ($p \le 0.05$); c) WT expression was significantly different from both KO1 and KO2 ($p \le 0.05$ in each contrast); and d) expression was concordantly up- or down-regulated in KO1 and KO2 relative to WT. Log 2(Fold change) values and p values are reported according to the Wald tests. Ingenuity Pathway Analysis (IPA, Qiagen, version 01-13) was used for pathway analysis of gene expression data. RNA-seq data that support the findings of this study have been deposited in the Gene Expression Omnibus (GEO) under accession code GSE136628.

Human studies. Tissue microarray-based studies and fresh tissue studies were conducted in accordance with Weill Cornell Medicine IRB-approved protocols (IRB #0604008488, #1312014589, #0411007570, and #0607008642) with informed consent or with HIPAA waiver of consent. The study is compliant with all relevant ethical regulations regarding research involving human participants. For the archival tissue microarray studies, samples from 317 distinct tumour resections (213 primary tumours and 104 metastatic tumours) over 278 unique patients were used. At the time of their surgery, patients ranged in age from 28 to greater than 89 years. 100% of breast carcinoma samples and 45% of lung carcinoma samples were derived from female patients. All patients used for this study had been diagnosed with invasive breast carcinoma (35% of samples) or non-small cell carcinoma of the lung (65% of samples). Within the lung carcinoma cohort, 72% of patients were diagnosed with adenocarcinoma, 15% with squamous cell carcinoma, and the remainder with non-small cell carcinoma. Additional details regarding human samples analyzed can be found in the results and methods section of the manuscript, the figure legends, and the supplementary source data file on patient samples.

Tissue microarrays from primary tumour (PT) and metastatic tumour (MT) were generated from paraffin-embedded archival samples approved for research use through the Institutional Review Board at Weill Cornell Medicine. Blocks were cored in representative areas and H&E stained to confirm presence of tumour. Immunohistochemistry was performed on a Leica Bond system using the standard protocol F. Heat-mediated antigen retrieval was performed with Sodium Citrate buffer, pH 6 for 30 minutes, then samples were incubated with anti-CEMIP/KIAA1199 for 25 minutes at RT and detected with DAB. Sections were then counterstained with hematoxylin and mounted with Leica Micromount. Tumour cores (1-3 per sample) were scored for CEMIP staining intensity in tumour by two pathologists (D.P. and N.N.) on a scale from zero (no expression) to four (very high expression). For samples with more than one core available, average intensity was calculated. Based on CEMIP expression observed across different tumour samples, pathologists defined a threshold cutoff expression value (CEMIPexp>2) and assigned a binary score (CEMIP$^{low/high}$) to samples. Cases in which brain metastasis coincided with or preceded primary diagnosis or for which there was no information regarding time of primary diagnosis, were excluded from survival analyses. Progression Free Survival was based on CEMIP$^{low/high}$ expression in PT and defined as the duration between PT diagnosis and the earliest brain metastasis detected. Cases with >10 years from PT diagnosis to brain metastasis were omitted from analysis. Overall Survival was based on CEMIP$^{low/high}$ expression in brain MT and defined as the duration between PT diagnosis and patient date of death or last follow-up. Kaplan-Meier survival curves were compared using Log-rank (Mantel-Cox) test. Correlation of PT CEMIP expression with metastatic status (overall metastasis, non-brain metastasis, and brain metastasis) was determined by calculating the Spearman correlation coefficient.

For analysis of exosomes from surgically-resected fresh tumour samples, tissue was received within two hours post-surgery, dissected into 2 mm$^2$ pieces and cultured in serum-free DMEM media with L-glutamine (1 mM) and Penicillin/Streptomycin. Cultures were maintained in a humidified 37° C. incubator with 5% $CO_2$ and exosomes were isolated from the culture supernatant after 24 hours. Exosomal CEMIP expression was analyzed by immunoblot.

Statistics and Reproducibility. Error bars in graphs represent mean±SEM. The number of independent biological replicates for each experiment and the sample size of each experimental group/condition are provided in figure legends. Statistical significance was determined with two-tailed Student's t-test or one-way ANOVA. P<0.05 was considered statistically significant. Variance was similar between compared groups. The experiments were repeated independently with similar results. Prism 8 (version 8.0.2) was used for statistical analysis and graphing (Graphpad software). ImageJ (version 1.52a) was used for image processing and analysis. Photoshop CC (version 20.0.3, Adobe) and Illustrator CC (version 23.0.2, Adobe) were used for image editing and presentation.

Data availability. RNA-seq raw data that support the findings of this study have been deposited in the Gene Expression Omnibus (GEO) under accession code GSE136628. Mass spectrometry raw data have been deposited in ProteomeXchange with the primary accession code PXD015210. RNA sequencing data is shown in Tables 3-6 below, for murine brain endothelial cells and microglia cells isolated from ex vivo brain slices treated with PBS, 231 BrT1 WT, 231 BrT1 CEMIP KO1 and KO2. Patient data is shown in Table 7. Unprocessed scans and replicates for all immunoblots presented in the manuscript are available as FIG. 7.

TABLE 3

Heatmap of significant genes differentially expressed in brain endothelial and microglial cells following BrT1 exosome treatment, relative to WT condition.
Endothelial Cells

| Upregulated genes | PBS | WT | Downregulated genes | PBS | WT |
|---|---|---|---|---|---|
| Syngr1 | 0.003124 | 1 | Map4k2 | −0.000064 | −1 |
| Orm2 | 0.004066 | 1 | Med14 | −0.000099 | −1 |
| Igfbp2 | 0.004284 | 1 | Efr3b | −0.00011 | −1 |
| Car12 | 0.004898 | 1 | Rnf24 | −0.00018 | −1 |
| F5 | 0.012248 | 1 | Zfp46 | −0.00018 | −1 |
| 1500015O10Rik | 0.012453 | 1 | Wdr20 | −0.00019 | −1 |
| Ttr | 0.012736 | 1 | Tmem101 | −0.00025 | −1 |
| Clu | 0.018878 | 1 | Ambra1 | −0.00027 | −1 |
| Il1m | 0.021534 | 1 | Tmem120b | −0.00029 | −1 |
| Mmp3 | 0.059761 | 1 | Ints13 | −0.00033 | −1 |
| Plau | 0.061139 | 1 | Ddx20 | −0.00037 | −1 |
| Cd53 | 0.064122 | 1 | Usp28 | −0.00038 | −1 |
| Lgals3 | 0.084457 | 1 | Smug1 | −0.0004 | −1 |
| Atp1b1 | 0.085936 | 1 | Hectd3 | −0.00046 | −1 |
| Enpp2 | 0.087764 | 1 | Zfp975 | −0.00048 | −1 |
| Ccl5 | 0.091899 | 1 | Fxyd6 | −0.0005 | −1 |
| Ifi202b | 0.117175 | 1 | Vps9d1 | −0.00053 | −1 |
| Scd2 | 0.127722 | 1 | Qser1 | −0.00056 | −1 |
| Irf7 | 0.131648 | 1 | Nif3l1 | −0.00057 | −1 |
| Lenep | 0.139262 | 1 | Xpnpep1 | −0.00059 | −1 |
| Gal | 0.144013 | 1 | 2700097O09Rik | −0.0006 | −1 |
| Sdc4 | 0.145063 | 1 | Farp1 | −0.00064 | −1 |
| Ifi44 | 0.156789 | 1 | Mfsd8 | −0.00071 | −1 |
| Als2cl | 0.173213 | 1 | Zfp119a | −0.00072 | −1 |
| Ttc9 | 0.1821 | 1 | Npr2 | −0.00073 | −1 |
| Asb1 | 0.197988 | 1 | Mpg | −0.00075 | −1 |
| Gbp2 | 0.199549 | 1 | Prrg1 | −0.00078 | −1 |
| Isg15 | 0.203208 | 1 | Dis3l2 | −0.00079 | −1 |

TABLE 3-continued

Heatmap of significant genes differentially expressed in brain endothelial and
microglial cells following BrT1 exosome treatment, relative to WT condition.
Endothelial Cells

| Upregulated genes | PBS | WT | Downregulated genes | PBS | WT |
|---|---|---|---|---|---|
| Timmdc1 | 0.218542 | 1 | Fbxo46 | −0.00081 | −1 |
| Got1 | 0.218568 | 1 | Pgap3 | −0.00082 | −1 |
| Tcf7l1 | 0.231412 | 1 | Trdmt1 | −0.00089 | −1 |
| Ifit3 | 0.235126 | 1 | Rhpn2 | −0.00089 | −1 |
| Slfn2 | 0.238992 | 1 | Eda2r | −0.0009 | −1 |
| Rsad2 | 0.240572 | 1 | Prkab2 | −0.00092 | −1 |
| Gbp3 | 0.240662 | 1 | Crebl2 | −0.00093 | −1 |
| Bst2 | 0.24761 | 1 | Qrsl1 | −0.00117 | −1 |
| Ogfrl1 | 0.256329 | 1 | Aph1b | −0.00122 | −1 |
| Tmem237 | 0.277502 | 1 | Fbxl8 | −0.00165 | −1 |
| Poc1b | 0.293103 | 1 | Myzap | −0.00179 | −1 |
| Alyref2 | 0.297401 | 1 | Zfp169 | −0.00196 | −1 |
| Marcksl1 | 0.31268 | 1 | Med23 | −0.00213 | −1 |
| Lgals3bp | 0.34049 | 1 | Nin | −0.00216 | −1 |
| Ch25h | 0.340732 | 1 | 1110017D15Rik | −0.00217 | −1 |
| Bhlhe41 | 0.345993 | 1 | Lifr | −0.00219 | −1 |
| Serpinb9 | 0.346613 | 1 | Ptpn14 | −0.00232 | −1 |
| Lrg1 | 0.352408 | 1 | Snx27 | −0.00245 | −1 |
| Gm13889 | 0.381592 | 1 | Trmt5 | −0.00253 | −1 |
| Ifitm3 | 0.383959 | 1 | Napepld | −0.00254 | −1 |
| Mthfd1 | 0.386786 | 1 | Hmgcs2 | −0.00274 | −1 |
| H2-K1 | 0.390189 | 1 | Pcdhb7 | −0.00301 | −1 |
| Drosha | 0.394953 | 1 | Phldb1 | −0.00325 | −1 |
| Smc3 | 0.394958 | 1 | Prkcz | −0.0034 | −1 |
| Dhodh | 0.398022 | 1 | Rtp3 | −0.0035 | −1 |
| Cenpc1 | 0.41094 | 1 | Ezh2 | −0.00359 | −1 |
| Ptgs2 | 0.418371 | 1 | Zfp518a | −0.00373 | −1 |
| Herc6 | 0.426473 | 1 | Jam3 | −0.00411 | −1 |
| Creb3l2 | 0.428511 | 1 | Uba6 | −0.00429 | −1 |
| Myc | 0.435402 | 1 | 2610301B20Rik | −0.00441 | −1 |
| Pabpc1 | 0.436831 | 1 | Zfp963 | −0.00454 | −1 |
| Mrpl46 | 0.452756 | 1 | Zdhhc24 | −0.00473 | −1 |
| Sh3bgrl3 | 0.464271 | 1 | Rgs2 | −0.00535 | −1 |
| Ly6e | 0.468036 | 1 | Itpk1 | −0.00541 | −1 |
| Zmynd8 | 0.483705 | 1 | Bbs12 | −0.00585 | −1 |
| Ecm1 | 0.483825 | 1 | Gan | −0.00586 | −1 |
| Fgfr1 | 0.50474 | 1 | Txndc11 | −0.00624 | −1 |
| Stc1 | 0.53205 | 1 | Ablim1 | −0.00727 | −1 |
| Tpi1 | 0.534199 | 1 | Zfp607b | −0.00781 | −1 |
| Eno1 | 0.539196 | 1 | Rtel1 | −0.00914 | −1 |
| Ctsz | 0.539409 | 1 | Hic2 | −0.00985 | −1 |
| Mafg | 0.555021 | 1 | Mthfsd | −0.01135 | −1 |
| Eno1b | 0.557559 | 1 | Top1mt | −0.0122 | −1 |
| Ybx3 | 0.571799 | 1 | Ufsp1 | −0.01301 | −1 |
| Ahcyl2 | 0.573199 | 1 | Sh3rf1 | −0.0145 | −1 |
| Cpe | 0.582685 | 1 | Abcg2 | −0.0189 | −1 |
| Ubfd1 | 0.586624 | 1 | F2rl2 | −0.02127 | −1 |
| Smap2 | 0.587341 | 1 | Map3k14 | −0.0225 | −1 |
| Shisa5 | 0.59866 | 1 | Ptprs | −0.02342 | −1 |
| Gorasp2 | 0.603873 | 1 | Aatk | −0.02443 | −1 |
| Fth1 | 0.635354 | 1 | Kdelc2 | −0.03099 | −1 |
| Rhog | 0.688433 | 1 | Abcd4 | −0.04181 | −1 |
| Pomgnt1 | 0.701046 | 1 | P2rx7 | −0.05168 | −1 |
| Snx9 | 0.708948 | 1 | Nqo2 | −0.05604 | −1 |
| Prelid1 | 0.764442 | 1 | Zfp281 | −0.06585 | −1 |
| Sar1b | 0.779915 | 1 | Lpl | −0.07805 | −1 |
| Mybbp1a | 0.787993 | 1 | Mindy2 | −0.08093 | −1 |
| | | | Dcun1d3 | −0.08354 | −1 |
| | | | Cyp2d22 | −0.14308 | −1 |
| | | | Eif2ak4 | −0.14607 | −1 |
| | | | Amn1 | −0.14665 | −1 |
| | | | Ahsa2 | −0.15009 | −1 |
| | | | Fbxo9 | −0.15029 | −1 |
| | | | Hspa1a | −0.17162 | −1 |
| | | | Zfp266 | −0.17675 | −1 |
| | | | Pex13 | −0.1825 | −1 |
| | | | Cdc25a | −0.18339 | −1 |
| | | | Yy1 | −0.18638 | −1 |
| | | | Tsc22d1 | −0.18767 | −1 |
| | | | Prr5l | −0.20632 | −1 |
| | | | Zfp316 | −0.22759 | −1 |
| | | | Sp1 | −0.22801 | −1 |
| | | | Hspa1b | −0.23391 | −1 |

TABLE 3-continued

Heatmap of significant genes differentially expressed in brain endothelial and
microglial cells following BrT1 exosome treatment, relative to WT condition.
Endothelial Cells

| Upregulated genes | PBS | WT | Downregulated genes | PBS | WT |
|---|---|---|---|---|---|
| | | | Enc1 | −0.23488 | −1 |
| | | | Adcy4 | −0.25228 | −1 |
| | | | Tgfbr1 | −0.2545 | −1 |
| | | | Fem1b | −0.26116 | −1 |
| | | | Phyhd1 | −0.26301 | −1 |
| | | | Efnb2 | −0.28604 | −1 |
| | | | Rybp | −0.29137 | −1 |
| | | | Cyr61 | −0.29519 | −1 |
| | | | Slc20a1 | −0.29904 | −1 |
| | | | Slc39a10 | −0.30111 | −1 |
| | | | Sgms1 | −0.30179 | −1 |
| | | | Csrp2 | −0.30546 | −1 |
| | | | Mfn2 | −0.31039 | −1 |
| | | | Stxbp3 | −0.32013 | −1 |
| | | | Gpcpd1 | −0.32544 | −1 |
| | | | Nedd9 | −0.32832 | −1 |
| | | | Tvp23b | −0.33507 | −1 |
| | | | Kcnj2 | −0.3436 | −1 |
| | | | Pdk4 | −0.37002 | −1 |
| | | | Ocln | −0.3751 | −1 |
| | | | Dcaf5 | −0.37709 | −1 |
| | | | Mafk | −0.38102 | −1 |
| | | | Fbxw8 | −0.38254 | −1 |
| | | | Hipk3 | −0.38846 | −1 |
| | | | Pdlim5 | −0.3978 | −1 |
| | | | Zfand2a | −0.40677 | −1 |
| | | | Gdf15 | −0.4094 | −1 |
| | | | Ptprb | −0.41268 | −1 |
| | | | Vwa1 | −0.41442 | −1 |
| | | | Synm | −0.41564 | −1 |
| | | | Gja1 | −0.41632 | −1 |
| | | | Mpzl1 | −0.42192 | −1 |
| | | | Prom1 | −0.42626 | −1 |
| | | | Lrrc41 | −0.42922 | −1 |
| | | | Scaf8 | −0.44401 | −1 |
| | | | Slc25a33 | −0.44531 | −1 |
| | | | Sh3tc1 | −0.44805 | −1 |
| | | | Sema6d | −0.44933 | −1 |
| | | | Ccdc59 | −0.45262 | −1 |
| | | | Sde2 | −0.46375 | −1 |
| | | | Scarb2 | −0.47647 | −1 |
| | | | Kansl3 | −0.47688 | −1 |
| | | | Ppp1r2 | −0.47693 | −1 |
| | | | Tm4sf1 | −0.48155 | −1 |
| | | | Taz | −0.48868 | −1 |
| | | | Sgk1 | −0.48976 | −1 |
| | | | Plat | −0.48981 | −1 |
| | | | Selenop | −0.49005 | −1 |
| | | | Pacs1 | −0.49301 | −1 |
| | | | Gadd45b | −0.4931 | −1 |
| | | | Pdxdc1 | −0.49868 | −1 |
| | | | Gimap6 | −0.506 | −1 |
| | | | Slc1a1 | −0.50811 | −1 |
| | | | 2510009E07Rik | −0.5111 | −1 |
| | | | Acvrl1 | −0.51155 | −1 |
| | | | Zfp948 | −0.51752 | −1 |
| | | | Tmem204 | −0.51809 | −1 |
| | | | Cggbp1 | −0.52198 | −1 |
| | | | Ipmk | −0.52303 | −1 |
| | | | Cd93 | −0.53501 | −1 |
| | | | Sparcl1 | −0.53826 | −1 |
| | | | Slc25a25 | −0.54129 | −1 |
| | | | Sptbn1 | −0.5453 | −1 |
| | | | Cdc42ep3 | −0.55449 | −1 |
| | | | Ranbp9 | −0.56115 | −1 |
| | | | Mbnl1 | −0.56262 | −1 |
| | | | Ppp1cb | −0.56755 | −1 |
| | | | Apold1 | −0.57406 | −1 |
| | | | Tpra1 | −0.57446 | −1 |
| | | | Pmp | −0.58457 | −1 |
| | | | Lipa | −0.58656 | −1 |
| | | | Fam168b | −0.59236 | −1 |
| | | | Ppp1r13b | −0.60319 | −1 |

TABLE 3-continued

Heatmap of significant genes differentially expressed in brain endothelial and
microglial cells following BrT1 exosome treatment, relative to WT condition.
Endothelial Cells

| Upregulated genes | PBS | WT | Downregulated genes | PBS | WT |
|---|---|---|---|---|---|
| | | | Snap29 | −0.60368 | −1 |
| | | | Dll4 | −0.60581 | −1 |
| | | | Swap70 | −0.60945 | −1 |
| | | | Acly | −0.61016 | −1 |
| | | | Itgb3 | −0.61649 | −1 |
| | | | Lmf2 | −0.63078 | −1 |
| | | | Car4 | −0.63633 | −1 |
| | | | Klhdc3 | −0.64252 | −1 |
| | | | Plk2 | −0.6478 | −1 |
| | | | Arhgap31 | −0.6496 | −1 |
| | | | Clic4 | −0.65454 | −1 |
| | | | Slc38a2 | −0.65599 | −1 |
| | | | Slc30a1 | −0.66373 | −1 |
| | | | Lamc1 | −0.66673 | −1 |
| | | | Kctd12 | −0.671 | −1 |
| | | | Esam | −0.68019 | −1 |
| | | | Hnrnpf | −0.68033 | −1 |
| | | | Sparc | −0.68057 | −1 |
| | | | Adipor1 | −0.68662 | −1 |
| | | | Ubc | −0.69755 | −1 |
| | | | Ankle2 | −0.70299 | −1 |
| | | | Tgm2 | −0.70619 | −1 |
| | | | Tmed2 | −0.72842 | −1 |
| | | | Sumo3 | −0.74904 | −1 |
| | | | Cd81 | −0.75467 | −1 |
| | | | Cds2 | −0.78656 | −1 |
| | | | H3f3b | −0.81354 | −1 |

Microglial Cells

| Upregulated genes | PBS | WT | Downregulated genes | PBS | WT |
|---|---|---|---|---|---|
| Flvcr2 | 0.00014 | 1 | Rassf5 | −0.0002 | −1 |
| Ifnb1 | 0.000179 | 1 | Zfp248 | −0.0002 | −1 |
| Zfp646 | 0.000272 | 1 | Pole2 | −0.00129 | −1 |
| Mgat4a | 0.000322 | 1 | Herc3 | −0.00149 | −1 |
| Ifi205 | 0.000459 | 1 | Zfp119b | −0.00159 | −1 |
| Gbp9 | 0.000471 | 1 | Smpd4 | −0.06704 | −1 |
| Siglec1 | 0.000498 | 1 | Zcwpw1 | −0.07725 | −1 |
| Mfsd8 | 0.000508 | 1 | Mdm4 | −0.19872 | −1 |
| Slfn1 | 0.00069 | 1 | Fbxo11 | −0.24823 | −1 |
| Xk | 0.000841 | 1 | Aldh18a1 | −0.25413 | −1 |
| F2r | 0.000944 | 1 | Plxdc2 | −0.2987 | −1 |
| Nfkbid | 0.000963 | 1 | Sfxn1 | −0.31876 | −1 |
| Akap6 | 0.001005 | 1 | Spp1 | −0.3215 | −1 |
| Gbp10 | 0.001056 | 1 | Fam134b | −0.32982 | −1 |
| Gabpb2 | 0.001088 | 1 | Ap1g2 | −0.33269 | −1 |
| Abtb1 | 0.001132 | 1 | Rp2 | −0.33405 | −1 |
| Poc5 | 0.001406 | 1 | Cox6a2 | −0.33833 | −1 |
| Virma | 0.002084 | 1 | Tbcd | −0.34366 | −1 |
| Irgm2 | 0.003661 | 1 | Atp6v0d2 | −0.34656 | −1 |
| Smug1 | 0.004758 | 1 | Desi2 | −0.34974 | −1 |
| Numa1 | 0.006844 | 1 | Hk1 | −0.42637 | −1 |
| 3830406C13Rik | 0.014239 | 1 | Chchd10 | −0.43046 | −1 |
| Sp100 | 0.019537 | 1 | Gzf1 | −0.44201 | −1 |
| Ccdc88a | 0.029986 | 1 | Pros1 | −0.44892 | −1 |
| Traf3ip1 | 0.036265 | 1 | Echs1 | −0.45072 | −1 |
| Gsap | 0.037446 | 1 | Rnaset2b | −0.45714 | −1 |
| Plau | 0.065593 | 1 | Lta4h | −0.47099 | −1 |
| Ifit3b | 0.066734 | 1 | Tmem87b | −0.4939 | −1 |
| Phf11b | 0.082866 | 1 | Trp53inp2 | −0.51337 | −1 |
| Acod1 | 0.088539 | 1 | Laptm5 | −0.5283 | −1 |
| Siglech | 0.093261 | 1 | Ctsc | −0.54554 | −1 |
| Gm11127 | 0.095349 | 1 | Ctsd | −0.55252 | −1 |
| Usp18 | 0.095802 | 1 | Arpc5l | −0.55526 | −1 |
| Ms4a7 | 0.099166 | 1 | Rhob | −0.56212 | −1 |
| Ccl5 | 0.105219 | 1 | Aldh2 | −0.58949 | −1 |
| H2-T24 | 0.109932 | 1 | Gdf15 | −0.59577 | −1 |

-continued

Microglial Cells

| Upregulated genes | PBS | WT | Downregulated genes | PBS | WT |
|---|---|---|---|---|---|
| Map3k2 | 0.110101 | 1 | Hyou1 | −0.61017 | −1 |
| Rsad2 | 0.115805 | 1 | Gng2 | −0.61314 | −1 |
| Cxcl10 | 0.115913 | 1 | Scoc | −0.6259 | −1 |
| Mettl21a | 0.121395 | 1 | Sgk1 | −0.62697 | −1 |
| Zbp1 | 0.126535 | 1 | Wars | −0.63625 | −1 |
| Cxcl1 | 0.150244 | 1 | Gosr1 | −0.65538 | −1 |
| H2-Q7 | 0.16067 | 1 | Mt2 | −0.66848 | −1 |
| Mmp14 | 0.161915 | 1 | Psat1 | −0.6845 | −1 |
| Sec24b | 0.166457 | 1 | Atp6v1c1 | −0.69792 | −1 |
| Cybb | 0.169295 | 1 | Cd53 | −0.69981 | −1 |
| Ifit1 | 0.170257 | 1 | Uqcrc1 | −0.71079 | −1 |
| Ifi2712a | 0.170889 | 1 | Mif | −0.72989 | −1 |
| Zbtb2 | 0.172798 | 1 | Iqgap1 | −0.7398 | −1 |
| Ifit3 | 0.179724 | 1 | | | |
| Cxcl2 | 0.185589 | 1 | | | |
| Ifi209 | 0.186437 | 1 | | | |
| Uba7 | 0.187695 | 1 | | | |
| Irf7 | 0.19355 | 1 | | | |
| Parp14 | 0.194141 | 1 | | | |
| Slc25a36 | 0.194714 | 1 | | | |
| H2-T23 | 0.203717 | 1 | | | |
| Ccl2 | 0.206392 | 1 | | | |
| Dtx3l | 0.2082 | 1 | | | |
| H2-Q4 | 0.209637 | 1 | | | |
| B430306N03Rik | 0.21228 | 1 | | | |
| Rtp4 | 0.22021 | 1 | | | |
| Ifitm3 | 0.222252 | 1 | | | |
| Parp12 | 0.240724 | 1 | | | |
| Grap | 0.25375 | 1 | | | |
| Cxcl3 | 0.254095 | 1 | | | |
| Faf2 | 0.257311 | 1 | | | |
| Phf11d | 0.261702 | 1 | | | |
| Pim1 | 0.266034 | 1 | | | |
| Irgm1 | 0.273069 | 1 | | | |
| Lgals3bp | 0.276708 | 1 | | | |

-continued

| Microglial Cells | | | | | |
|---|---|---|---|---|---|
| Upregulated genes | PBS | WT | Downregulated genes | PBS | WT |
| Cog1 | 0.279216 | 1 | | | |
| Micall1 | 0.279881 | 1 | | | |
| Ptgs2 | 0.286863 | 1 | | | |
| Cd52 | 0.287811 | 1 | | | |
| Stat2 | 0.28793 | 1 | | | |
| Il1b | 0.293798 | 1 | | | |
| Milr1 | 0.30739 | 1 | | | |
| Kctd12 | 0.313332 | 1 | | | |
| Cxcl16 | 0.330445 | 1 | | | |
| Glrx | 0.338638 | 1 | | | |
| Tnf | 0.345003 | 1 | | | |
| Sbno1 | 0.345844 | 1 | | | |
| Wdr92 | 0.345966 | 1 | | | |
| Rab11fip1 | 0.346441 | 1 | | | |
| Prkab1 | 0.347838 | 1 | | | |
| Fcgr1 | 0.348714 | 1 | | | |
| Ipo13 | 0.351976 | 1 | | | |
| Bst2 | 0.352192 | 1 | | | |
| Adar | 0.36431 | 1 | | | |
| Sod2 | 0.366037 | 1 | | | |
| Slfn8 | 0.372115 | 1 | | | |
| Trex1 | 0.378738 | 1 | | | |
| Herc6 | 0.379431 | 1 | | | |
| Ptpre | 0.383389 | 1 | | | |
| Atf7 | 0.391192 | 1 | | | |
| Slc31a2 | 0.394503 | 1 | | | |
| Bclaf1 | 0.403329 | 1 | | | |
| Heatr3 | 0.415155 | 1 | | | |
| Nrp2 | 0.419777 | 1 | | | |
| Tmem87a | 0.420078 | 1 | | | |
| Ccdc93 | 0.430103 | 1 | | | |
| Zc3hav1 | 0.432219 | 1 | | | |
| Tnfrsf1b | 0.446745 | 1 | | | |
| Slfn2 | 0.447419 | 1 | | | |
| Nfkb2 | 0.448603 | 1 | | | |
| B2m | 0.451333 | 1 | | | |
| Ccrl2 | 0.452961 | 1 | | | |

-continued

| Microglial Cells | | | | | |
|---|---|---|---|---|---|
| Upregulated genes | PBS | WT | Downregulated genes | PBS | WT |
| Plagl2 | 0.459967 | 1 | | | |
| Tnfaip3 | 0.460542 | 1 | | | |
| Ndst2 | 0.461243 | 1 | | | |
| Sart3 | 0.46149 | 1 | | | |
| Rab3gap2 | 0.463537 | 1 | | | |
| Pla2g7 | 0.467256 | 1 | | | |
| Clec4e | 0.469438 | 1 | | | |
| Fbxo9 | 0.475164 | 1 | | | |
| Ints14 | 0.477173 | 1 | | | |
| C5ar1 | 0.480114 | 1 | | | |
| Pkn2 | 0.483711 | 1 | | | |
| Ddx24 | 0.496271 | 1 | | | |
| Tpcn2 | 0.496744 | 1 | | | |
| Shisa5 | 0.497113 | 1 | | | |
| Il1a | 0.498242 | 1 | | | |
| Ier3 | 0.504378 | 1 | | | |
| Keap1 | 0.519773 | 1 | | | |
| Map2k3 | 0.533802 | 1 | | | |
| Irf9 | 0.533973 | 1 | | | |
| Plpp3 | 0.549301 | 1 | | | |
| Sik3 | 0.552849 | 1 | | | |
| Zdhhc7 | 0.55388 | 1 | | | |
| Syk | 0.56568 | 1 | | | |
| Lrch3 | 0.570318 | 1 | | | |
| Nfkbia | 0.572514 | 1 | | | |
| Fig4 | 0.582381 | 1 | | | |
| Fam207a | 0.596037 | 1 | | | |
| Flna | 0.596159 | 1 | | | |
| Hbs1l | 0.612832 | 1 | | | |
| Nmt1 | 0.615463 | 1 | | | |
| Golga3 | 0.61727 | 1 | | | |
| Skiv2l2 | 0.648561 | 1 | | | |
| Atp13a1 | 0.672946 | 1 | | | |
| Lilr4b | 0.678703 | 1 | | | |
| Psen1 | 0.720106 | 1 | | | |
| Rab43 | 0.770255 | 1 | | | |

TABLE 4

Top significant IPA Canonical Pathways - BrEC and microglia - 231 BrT1 exosomes
and exosomal CEMIP specific - List of canonical pathways affected by 231
BrT1 exosome and exosomal CEMIP treatment in BrECs and microglia.

| 231 BrT1 exosome-modulated pathways | 231 BrT1 exosomal CEMIP-modulated pathways |
|---|---|
| Top significant IPA Canonical Pathways - BrEC - 231 BrT1 exosomes and exosomal CEMIP specific | |
| Osteoarthritis Pathway | 1D-myo-inositol Hexakisphosphate Biosynthesis V (from Ins(1,3,4)P3) |
| 1D-myo-inositol Hexakisphosphate Biosynthesis V (from Ins(1,3,4)P3) | 1D-myo-inositol Hexakisphosphate Biosynthesis II (Mammalian) |
| Interferon Signaling | Osteoarthritis Pathway |
| Glucocorticoid Receptor Signaling | D-myo-inositol (1,4,5,6)-Tetrakisphosphate Biosynthesis |
| Protein Kinase A Signaling | D-myo-inositol (3,4,5,6)-tetrakisphosphate Biosynthesis |
| PPARα/RXRα Activation | L-glutamine Biosynthesis II (tRNA-dependent) |
| Coagulation System | Sumoylation Pathway |
| Oleate Biosynthesis II (Animals) | Gap Junction Signaling |
| Acetyl-CoA Biosynthesis III (from Citrate) | Apelin Endothelial Signaling Pathway |
| NRF2-mediated Oxidative Stress Response | Superpathway of Inositol Phosphate Compounds |
| Huntington's Disease Signaling | Inositol Pyrophosphates Biosynthesis |
| Colorectal Cancer Metastasis Signaling | Mitotic Roles of Polo-Like Kinase |
| Glioma Invasiveness Signaling | Endocannabinoid Cancer Inhibition Pathway |
| VDR/RXR Activation | 3-phosphoinositide Degradation |
| Neuroinflammation Signaling Pathway | |
| LXR/RXR Activation | |
| Tight Junction Signaling | |
| Apelin Endothelial Signaling Pathway | |

TABLE 4-continued eNOS Signaling
1D-myo-inositol Hexakisphosphate
Biosynthesis II (Mammalian)
L-glutamine Biosynthesis II (tRNA-
dependent)
Prolactin Signaling
Granulocyte Adhesion and Diapedesis
GP6 Signaling Pathway
IL-17 Signaling
NF-κB Activation by Viruses
P2Y Purigenic Receptor Signaling
Pathway
Production of Nitric Oxide and
Reactive Oxygen Species in
Macrophages
CDP-diacylglycerol Biosynthesis I
L-cysteine Degradation III
Glutamate Degradation II
Aspartate Biosynthesis
Insulin Receptor Signaling
Endothelin-1 Signaling
STAT3 Pathway
Gap Junction Signaling
Antiproliferative Role of TOB in T Cell
Signaling
Estrogen-mediated S-phase Entry
Phosphatidylglycerol Biosynthesis II
(Non-plastidic)
Glycolysis I
IL-8 Signaling
Type II Diabetes Mellitus Signaling
Cholecystokinin/Gastrin-mediated
Signaling
mTOR Signaling
Endocannabinoid Cancer Inhibition
Pathway
Relaxin Signaling
L-cysteine Degradation I
Thrombin Signaling Top significant IPA Canonical Pathways - Microglia - 231 BrT1 exosomes and exosomal CEMIP specific

| | |
|---|---|
| Activation of IRF by Cytosolic Pattern Recognition Receptors | Granulocyte Adhesion and Diapedesis |
| Granulocyte Adhesion and Diapedesis | Role of MAPK Signaling in the Pathogenesis of Influenza |
| Communication between Innate and Adaptive Immune Cells | IL-17A Signaling in Gastric Cells |
| Type I Diabetes Mellitus Signaling | LXR/RXR Activation |
| Role of PKR in Interferon Induction and Antiviral Response | Role of Hypercytokinemia/hyperchemokinemia in the Pathogenesis of Influenza |
| Agranulocyte Adhesion and Diapedesis | Neuroinflammation Signaling Pathway |
| Dendritic Cell Maturation | Pathogenesis of Multiple Sclerosis |
| TNFR2 Signaling | Agranulocyte Adhesion and Diapedesis |
| Neuroinflammation Signaling Pathway | Death Receptor Signaling |
| OX40 Signaling Pathway | Communication between Innate and Adaptive Immune Cells |
| Death Receptor Signaling | PPAR Signaling |
| Role of Hypercytokinemia/hyperchemokinemia in the Pathogenesis of Influenza | Differential Regulation of Cytokine Production in Macrophages and T Helper Cells by IL-17A and IL-17F |
| IL-10 Signaling | Differential Regulation of Cytokine Production in Intestinal Epithelial Cells by IL-17A and IL-17F |
| Role of IL-17A in Arthritis | Role of Pattern Recognition Receptors in Recognition of Bacteria and Viruses |
| PPAR Signaling | TNFR2 Signaling |
| Role of Pattern Recognition Receptors in Recognition of Bacteria and Viruses | Hepatic Fibrosis/Hepatic Stellate Cell Activation |
| Graft-versus-Host Disease Signaling | Production of Nitric Oxide and Reactive Oxygen Species in Macrophages |
| Toll-like Receptor Signaling | Osteoarthritis Pathway |
| Role of MAPK Signaling in the Pathogenesis of Influenza | LPS/IL-1 Mediated Inhibition of RXR Function |
| Crosstalk between Dendritic Cells and Natural Killer Cells | Induction of Apoptosis by HIV1 |
| MIF-mediated Glucocorticoid Regulation | Role of IL-17A in Arthritis |
| Interferon Signaling | T Helper Cell Differentiation |
| IL-6 Signaling | VDR/RXR Activation |
| Acute Phase Response Signaling | IL-15 Signaling |

TABLE 4-continued

| | |
|---|---|
| MIF Regulation of Innate Immunity | Xenobiotic Metabolism Signaling |
| Role of RIG1-like Receptors in Antiviral Innate Immunity | Crosstalk between Dendritic Cells and Natural Killer Cells |
| Phagosome Maturation | IL-17 Signaling |
| Differential Regulation of Cytokine Production in Intestinal Epithelial Cells by IL-17A and IL-17F | Airway Inflammation in Asthma |
| CD40 Signaling | Proline Biosynthesis I |
| TNFR1 Signaling | Role of Macrophages, Fibroblasts and Endothelial Cells in Rheumatoid Arthritis |
| LXR/RXR Activation | Apoptosis Signaling |
| CD27 Signaling in Lymphocytes | Ceramide Signaling |
| Role of Macrophages, Fibroblasts and Endothelial Cells in Rheumatoid Arthritis | Glucocorticoid Receptor Signaling |
| Allograft Rejection Signaling | Cholecystokinin/Gastrin-mediated Signaling |
| Altered T Cell and B Cell Signaling in Rheumatoid Arthritis | Type I Diabetes Mellitus Signaling |
| IL-1 Signaling | HGF Signaling |
| Role of Osteoblasts, Osteoclasts and Chondrocytes in Rheumatoid Arthritis | p38 MAPK Signaling |
| Glucocorticoid Receptor Signaling | Fc Epsilon RI Signaling |
| Induction of Apoptosis by HIV1 | Renin-Angiotensin Signaling |
| HMGB1 Signaling | Airway Pathology in Chronic Obstructive Pulmonary Disease |
| NF-κB Signaling | IL-6 Signaling |
| Aryl Hydrocarbon Receptor Signaling | HMGB1 Signaling |
| Xenobiotic Metabolism Signaling | Prostanoid Biosynthesis |
| Production of Nitric Oxide and Reactive Oxygen Species in Macrophages | Citrulline Biosynthesis |
| Cholecystokinin/Gastrin-mediated Signaling | Aryl Hydrocarbon Receptor Signaling |
| Antigen Presentation Pathway | Type II Diabetes Mellitus Signaling |
| Antioxidant Action of Vitamin C | Hepatic Cholestasis |
| Type II Diabetes Mellitus Signaling | Tight Junction Signaling |
| Hepatic Cholestasis | Acute Phase Response Signaling |
| Osteoarthritis Pathway | Isoleucine Degradation I |
| Differential Regulation of Cytokine Production in Macrophages and T Helper Cells by IL-17A and IL-17F | Germ Cell-Sertoli Cell Junction Signaling |
| Cdc42 Signaling | Superpathway of Citrulline Metabolism |
| Role of PI3K/AKT Signaling in the Pathogenesis of Influenza | Sertoli Cell-Sertoli Cell Junction Signaling |
| fMLP Signaling in Neutrophils | NF-κB Signaling |
| CD28 Signaling in T Helper Cells | B Cell Receptor Signaling |
| Hepatic Fibrosis/Hepatic Stellate Cell Activation | Dendritic Cell Maturation |
| Role of JAK1, JAK2 and TYK2 in Interferon Signaling | ILK Signaling |
| Role of Cytokines in Mediating Communication between Immune Cells | Valine Degradation I |
| Role of NFAT in Regulation of the Immune Response | Fatty Acid α-oxidation |
| IL-17A Signaling in Gastric Cells | Role of Osteoblasts, Osteoclasts and Chondrocytes in Rheumatoid Arthritis |
| B Cell Receptor Signaling | Apelin Liver Signaling Pathway |
| Apoptosis Signaling | Colorectal Cancer Metastasis Signaling |
| Ceramide Signaling | Fatty Acid β-oxidation I |
| Retinoic acid Mediated Apoptosis Signaling | MIF-mediated Glucocorticoid Regulation |
| Airway Pathology in Chronic Obstructive Pulmonary Disease | Role of PKR in Interferon Induction and Antiviral Response |
| 4-1BB Signaling in T Lymphocytes | MIF Regulation of Innate Immunity |
| Pathogenesis of Multiple Sclerosis | IL-9 Signaling |
| LPS/IL-1 Mediated Inhibition of RXR Function | Role of IL-17F in Allergic Inflammatory Airway Diseases |
| Caveolar-mediated Endocytosis Signaling | Graft-versus-Host Disease Signaling |
| Coagulation System | |
| TWEAK Signaling | |
| IL-17A Signaling in Fibroblasts | |
| p38 MAPK Signaling | |
| Systemic Lupus Erythematosus Signaling | |
| TREM1 Signaling | |
| Germ Cell-Sertoli Cell Junction Signaling | |
| IL-17A Signaling in Airway Cells | |
| April Mediated Signaling | |
| Atherosclerosis Signaling | |
| PI3K/AKT Signaling | |
| PPARα/RXRα Activation | |

TABLE 4-continued

B Cell Activating Factor Signaling
Small Cell Lung Cancer Signaling
PI3K Signaling in B Lymphocytes
iNOS Signaling
Role of IL-17F in Allergic Inflammatory
Airway Diseases
LPS-stimulated MAPK Signaling
PEDF Signaling
Autoimmune Thyroid Disease Signaling
CTLA4 Signaling in Cytotoxic T
Lymphocytes
RANK Signaling in Osteoclasts
Gαq Signaling
Inflammasome pathway
PKCθ Signaling in T Lymphocytes
Tec Kinase Signaling
UVA-Induced MAPK Signaling
Fatty Acid α-oxidation
Role of Lipids/Lipid Rafts in the
Pathogenesis of Influenza
Virus Entry via Endocytic Pathways
Pyridoxal 5'-phosphate Salvage Pathway
Lymphotoxin β Receptor Signaling
Eicosanoid Signaling
Signaling by Rho Family GTPases
Protein Kinase A Signaling
iCOS-iCOSL Signaling in T Helper Cells
Rac Signaling
Lipid Antigen Presentation by CD1
Colorectal Cancer Metastasis Signaling
IL-15 Production
T Helper Cell Differentiation
Phagosome Formation
ILK Signaling
Thyroid Hormone Biosynthesis
Glioma Invasiveness Signaling
Adrenomedullin signaling pathway
VDR/RXR Activation
IL-8 Signaling
Cytotoxic T Lymphocyte-mediated
Apoptosis of Target Cells
Gα12/13 Signaling
IL-15 Signaling
Airway Inflammation in Asthma
Angiopoietin Signaling
Phenylethylamine Degradation I
Ascorbate Recycling (Cytosolic)
Glutathione Redox Reactions II
Proline Biosynthesis I
Regulation of IL-2 Expression in
Activated and Anergic T Lymphocytes
Erythropoietin Signaling
IL-17 Signaling
Trehalose Degradation II (Trehalase)
Serine Biosynthesis
Eumelanin Biosynthesis
Fcγ Receptor-mediated Phagocytosis in
Macrophages and Monocytes
NF-κB Activation by Viruses
Relaxin Signaling
Sumoylation Pathway
Salvage Pathways of Pyrimidine
Ribonucleotides
Acute Myeloid Leukemia Signaling Top significant IPA Canonical Pathways - BrEC
and microglia common - 231 BrT1 exosomes and
exosomal CEMIP specific Common pathways in EC and MG
modulated by 231 BrT1 exosome
pre-treatment Single common pathway in EC and MG modulated by
exosomal CEMIP pre-treatment Osteoarthritis Pathway
Interferon Signaling
Glucocorticoid Receptor
Signaling
Protein Kinase A Signaling TABLE 4-continued PPARα/RXRα Activation
Coagulation System
Colorectal Cancer Metastasis
Signaling
Glioma Invasiveness Signaling
VDR/RXR Activation
Neuroinflammation Signaling
Pathway
LXR/RXR Activation
Granulocyte Adhesion and
Diapedesis
IL-17 Signaling
NF-κB Activation by Viruses
Production of Nitric Oxide and
Reactive Oxygen Species in
Macrophages
IL-8 Signaling
Type II Diabetes Mellitus
Signaling
Cholecystokinin/Gastrin-
mediated Signaling
Relaxin Signaling

TABLE 5

Heatmap of significant genes differentially expressed in brain endothelial and
microglial cells following exosomal CEMIP treatment, relative to WT condition.

| Upregulated genes | PBS | WT | KO1 | KO2 | Downregulated genes | PBS | WT | KO1 | KO2 |
|---|---|---|---|---|---|---|---|---|---|
| | | | | | Endothelial Cells | | | | |
| Asb1 | 0.197988 | 1 | 0.15 | 0.01 | Map4k2 | −0.000064 | −1 | 0 | 0 |
| Timmdc1 | 0.218542 | 1 | 0.08 | 0.04 | Med14 | −0.000099 | −1 | 0 | 0 |
| Tcf7l1 | 0.231412 | 1 | 0.16 | 0.31 | Efr3b | −0.00011 | −1 | 0 | 0 |
| Poc1b | 0.293103 | 1 | 0.38 | 0.41 | Zfp46 | −0.00018 | −1 | 0 | 0 |
| Alyref2 | 0.297401 | 1 | 0.22 | 0.39 | Rnf24 | −0.00018 | −1 | 0 | −0.02 |
| Drosha | 0.394953 | 1 | 0.26 | 0.18 | Wdr20 | −0.00019 | −1 | 0 | 0 |
| Smc3 | 0.394958 | 1 | 0.44 | 0.52 | Tmem101 | −0.00025 | −1 | 0 | 0 |
| Zmynd8 | 0.483705 | 1 | 0.57 | 0.26 | Ambra1 | −0.00027 | −1 | 0 | 0 |
| Mafg | 0.555021 | 1 | 0.49 | 0.51 | Tmem120b | −0.00029 | −1 | 0 | 0 |
| Ybx3 | 0.571799 | 1 | 0.76 | 0.7 | Ints13 | −0.00033 | −1 | 0 | 0 |
| Ubfd1 | 0.586624 | 1 | 0.69 | 0.39 | Ddx20 | −0.00037 | −1 | 0 | 0 |
| Shisa5 | 0.59866 | 1 | 0.73 | 0.72 | Usp28 | −0.00038 | −1 | 0 | 0 |
| Gorasp2 | 0.603873 | 1 | 0.54 | 0.81 | Smug1 | −0.0004 | −1 | 0 | 0 |
| Rhog | 0.688433 | 1 | 0.63 | 0.61 | Hectd3 | −0.00046 | −1 | 0 | 0 |
| | | | | | Zfp975 | −0.00048 | −1 | −0.01 | 0 |
| | | | | | Fxyd6 | −0.0005 | −1 | 0 | 0 |
| | | | | | Qser1 | −0.00056 | −1 | 0 | 0 |
| | | | | | Nif3l1 | −0.00057 | −1 | −0.01 | 0 |
| | | | | | Xpnpep1 | −0.00059 | −1 | −0.05 | 0 |
| | | | | | 2700097O09Rik | −0.0006 | −1 | 0 | 0 |
| | | | | | Farp1 | −0.00064 | −1 | 0 | 0 |
| | | | | | Zfp119a | −0.00072 | −1 | 0 | 0 |
| | | | | | Npr2 | −0.00073 | −1 | 0 | −0.02 |
| | | | | | Mpg | −0.00075 | −1 | 0 | 0 |
| | | | | | Dis3l2 | −0.00079 | −1 | 0 | 0 |
| | | | | | Fbxo46 | −0.00081 | −1 | 0 | −0.01 |
| | | | | | Pgap3 | −0.00082 | −1 | 0 | 0 |
| | | | | | Trdmt1 | −0.00089 | −1 | 0 | 0 |
| | | | | | Eda2r | −0.0009 | −1 | 0 | 0 |
| | | | | | Prkab2 | −0.00092 | −1 | −0.02 | 0 |
| | | | | | Qrsl1 | −0.00117 | −1 | 0 | 0 |
| | | | | | Aph1b | −0.00122 | −1 | 0 | 0 |
| | | | | | Fbxl8 | −0.00165 | −1 | 0 | 0 |
| | | | | | Myzap | −0.00179 | −1 | 0 | 0 |
| | | | | | Med23 | −0.00213 | −1 | 0 | 0 |
| | | | | | Nin | −0.00216 | −1 | −0.01 | 0 |
| | | | | | 1110017D15Rik | −0.00217 | −1 | 0 | 0 |
| | | | | | Lifr | −0.00219 | −1 | 0 | 0 |
| | | | | | Ptpn14 | −0.00232 | −1 | −0.02 | −0.02 |
| | | | | | Snx27 | −0.00245 | −1 | 0 | 0 |
| | | | | | Trmt5 | −0.00253 | −1 | 0 | 0 |
| | | | | | Phldb1 | −0.00325 | −1 | −0.02 | −0.01 |
| | | | | | Ezh2 | −0.00359 | −1 | 0 | 0 |
| | | | | | Zfp518a | −0.00373 | −1 | 0 | 0 |

TABLE 5-continued

Heatmap of significant genes differentially expressed in brain endothelial and
microglial cells following exosomal CEMIP treatment, relative to WT condition.

| Upregulated genes | PBS | WT | KO1 | KO2 | Downregulated genes | PBS | WT | KO1 | KO2 |
|---|---|---|---|---|---|---|---|---|---|
| | | | | | Uba6 | −0.00429 | −1 | −0.01 | 0 |
| | | | | | Zfp963 | −0.00454 | −1 | 0 | 0 |
| | | | | | Zdhhc24 | −0.00473 | −1 | 0 | 0 |
| | | | | | Rgs2 | −0.00535 | −1 | 0 | 0 |
| | | | | | Itpk1 | −0.00541 | −1 | 0 | 0 |
| | | | | | Bbs12 | −0.00585 | −1 | 0 | −0.05 |
| | | | | | Gan | −0.00586 | −1 | −0.05 | −0.02 |
| | | | | | Txndc11 | −0.00624 | −1 | −0.01 | −0.01 |
| | | | | | Ablim1 | −0.00727 | −1 | 0 | −0.01 |
| | | | | | Rtel1 | −0.00914 | −1 | 0 | −0.03 |
| | | | | | Mthfsd | −0.01135 | −1 | −0.01 | 0 |
| | | | | | Top1mt | −0.0122 | −1 | −0.01 | −0.01 |
| | | | | | Sh3rf1 | −0.0145 | −1 | −0.09 | −0.01 |
| | | | | | F2rl2 | −0.02127 | −1 | 0 | −0.07 |
| | | | | | Aatk | −0.02443 | −1 | −0.01 | −0.02 |
| | | | | | Kdelc2 | −0.03099 | −1 | −0.03 | −0.02 |
| | | | | | Abcd4 | −0.04181 | −1 | −0.05 | −0.04 |
| | | | | | P2rx7 | −0.05168 | −1 | −0.01 | 0 |
| | | | | | Zfp281 | −0.06585 | −1 | −0.08 | −0.09 |
| | | | | | Mindy2 | −0.08093 | −1 | −0.25 | −0.18 |
| | | | | | Dcun1d3 | −0.08354 | −1 | −0.15 | −0.12 |
| | | | | | Cyp2d22 | −0.14308 | −1 | −0.24 | −0.17 |
| | | | | | Eif2ak4 | −0.14607 | −1 | −0.14 | −0.14 |
| | | | | | Amn1 | −0.14665 | −1 | −0.17 | −0.07 |
| | | | | | Ahsa2 | −0.15009 | −1 | −0.38 | −0.3 |
| | | | | | Fbxo9 | −0.15029 | −1 | −0.16 | −0.14 |
| | | | | | Pex13 | −0.1825 | −1 | −0.19 | −0.2 |
| | | | | | Cdc25a | −0.18339 | −1 | −0.31 | −0.19 |
| | | | | | Yy1 | −0.18638 | −1 | −0.22 | −0.16 |
| | | | | | Prr5l | −0.20632 | −1 | −0.24 | −0.29 |
| | | | | | Sp1 | −0.22801 | −1 | −0.38 | −0.17 |
| | | | | | Adcy4 | −0.25228 | −1 | −0.29 | −0.38 |
| | | | | | Phyhd1 | −0.26301 | −1 | −0.4 | −0.23 |
| | | | | | Efnb2 | −0.28604 | −1 | −0.49 | −0.48 |
| | | | | | Slc20a1 | −0.29904 | −1 | −0.37 | −0.36 |
| | | | | | Csrp2 | −0.30546 | −1 | −0.55 | −0.41 |
| | | | | | Mfn2 | −0.31039 | −1 | −0.32 | −0.45 |
| | | | | | Gpcpd1 | −0.32544 | −1 | −0.55 | −0.43 |
| | | | | | Nedd9 | −0.32832 | −1 | −0.51 | −0.47 |
| | | | | | Ocln | −0.3751 | −1 | −0.54 | −0.32 |
| | | | | | Dcaf5 | −0.37709 | −1 | −0.39 | −0.33 |
| | | | | | Fbxw8 | −0.38254 | −1 | −0.32 | −0.33 |
| | | | | | Gja1 | −0.41632 | −1 | −0.62 | −0.5 |
| | | | | | Prom1 | −0.42626 | −1 | −0.55 | −0.54 |
| | | | | | Lrrc41 | −0.42922 | −1 | −0.54 | −0.68 |
| | | | | | Slc25a33 | −0.44531 | −1 | −0.58 | −0.47 |
| | | | | | Sh3tc1 | −0.44805 | −1 | −0.53 | −0.55 |
| | | | | | Sema6d | −0.44933 | −1 | −0.54 | −0.48 |
| | | | | | Ccdc59 | −0.45262 | −1 | −0.41 | −0.29 |
| | | | | | Scarb2 | −0.47647 | −1 | −0.37 | −0.45 |
| | | | | | Taz | −0.48868 | −1 | −0.38 | −0.33 |
| | | | | | Pacs 1 | −0.49301 | −1 | −0.29 | −0.39 |
| | | | | | Pdxdc1 | −0.49868 | −1 | −0.51 | −0.39 |
| | | | | | 2510009E07Rik | −0.5111 | −1 | −0.53 | −0.39 |
| | | | | | Acvrl1 | −0.51155 | −1 | −0.61 | −0.63 |
| | | | | | Ipmk | −0.52303 | −1 | −0.47 | −0.52 |
| | | | | | Ppp1r13b | −0.60319 | −1 | −0.59 | −0.71 |
| | | | | | Itgb3 | −0.61649 | −1 | −0.64 | −0.52 |
| | | | | | Lmf2 | −0.63078 | −1 | −0.41 | −0.55 |
| | | | | | Arhgap31 | −0.6496 | −1 | −0.82 | −0.7 |
| | | | | | Sumo3 | −0.74904 | −1 | −0.74 | −0.55 |
| | | | | | Microglial Cells | | | | |
| Xk | 0.000841 | 1 | 0 | 0.01 | Zfp248 | −0.0002 | −1 | 0 | 0 |
| Acod1 | 0.088539 | 1 | 0.71 | 0.57 | Zfp119b | −0.00159 | −1 | 0 | 0 |
| Ccl5 | 0.105219 | 1 | 0.61 | 0.66 | Mdm4 | −0.19872 | −1 | −0.27 | −0.18 |
| Map3k2 | 0.110101 | 1 | 0.64 | 0.64 | Fbxo11 | −0.24823 | −1 | −0.56 | −0.38 |
| Cxcl10 | 0.115913 | 1 | 0.53 | 0.45 | Aldh18a1 | −0.25413 | −1 | −0.48 | −0.53 |
| Cxcl1 | 0.150244 | 1 | 0.72 | 0.6 | Echs1 | −0.45072 | −1 | −0.4 | −0.5 |
| Parp14 | 0.194141 | 1 | 0.59 | 0.53 | Trp53inp2 | −0.51337 | −1 | −0.42 | −0.5 |
| Ptgs2 | 0.286863 | 1 | 0.72 | 0.62 | | | | | |
| Tnf | 0.345003 | 1 | 0.73 | 0.74 | | | | | |
| Bst2 | 0.352192 | 1 | 0.74 | 0.79 | | | | | |
| Bclaf1 | 0.403329 | 1 | 0.67 | 0.68 | | | | | |

TABLE 5-continued

Heatmap of significant genes differentially expressed in brain endothelial and microglial cells following exosomal CEMIP treatment, relative to WT condition.

| Upregulated genes | PBS | WT | KO1 | KO2 | Downregulated genes | PBS | WT | KO1 | KO2 |
|---|---|---|---|---|---|---|---|---|---|
| Tnfrsf1b | 0.446745 | 1 | 0.8 | 0.77 | | | | | |
| Ccrl2 | 0.452961 | 1 | 0.78 | 0.68 | | | | | |
| Sart3 | 0.46149 | 1 | 0.74 | 0.71 | | | | | |
| Syk | 0.56568 | 1 | 0.66 | 0.83 | | | | | |
| Fam207a | 0.596037 | 1 | 0.54 | 0.61 | | | | | |
| Hbs11 | 0.612832 | 1 | 0.58 | 0.74 | | | | | |
| Rab43 | 0.770255 | 1 | 0.61 | 0.64 | | | | | |

TABLE 6

Top10 significant Gene Ontology - Biological Processes - BrEC and microglia - exosomal CEMIP specific - List of significant Biological Processes affected by exosomal CEMIP treatment in BrECs and microglia.

Top10 significant Gene Ontology - Biological Processes - BrEC - exosomal CEMIP specific GeneSet Analysis:
Gene Ontology -
Biological Process
* Enriched terms by
p-value < 0.05

| Rank | GO Acc. and Desc. | p-value |
|---|---|---|
| 1 | GO:0010628<br>positive regulation of gene expression | 3.12E−04 |
| 2 | GO: 0048514<br>blood vessel morphogenesis | 3.83E−04 |
| 3 | GO: 0001946<br>lymphangiogenesis | 1.12E−03 |
| 4 | GO: 0048593<br>camera-type eye morphogenesis | 4.13E−03 |
| 5 | GO: 0046022<br>positive regulation of transcription from RNA polymerase II promoter during mitosis | 4.59E−03 |
| 5 | GO: 0045844<br>positive regulation of striated muscle tissue development | 4.59E−03 |
| 5 | GO: 0038203<br>TORC2 signaling | 4.59E−03 |
| 5 | GO: 0039520<br>induction by virus of host autophagy | 4.59E−03 |
| 5 | GO: 0044254<br>multicellular organismal protein catabolic process | 4.59E−03 |
| 5 | GO: 0043132<br>NAD transport | 4.59E−03 |

Top10 significant Gene Ontology - Biological Processes - Microglia - exosomal CEMIP specific GeneSet Analysis:
Gene Ontology -
Biological Process
* Enriched terms by
p-value < 0.05

| Rank | GO Acc. and Desc. | p-value |
|---|---|---|
| 1 | GO: 0006954<br>inflammatory response | 1.16E−06 |
| 2 | GO: 0031622<br>positive regulation of fever generation | 4.56E−06 |
| 3 | GO: 0006952<br>defense response | 1.43E−04 |
| 3 | GO: 0097191<br>extrinsic apoptotic signaling pathway | 1.43E−04 |
| 3 | GO: 0045662<br>negative regulation of myoblast differentiation | 1.43E−04 |
| 6 | GO: 0008630<br>intrinsic apoptotic signaling pathway in response to DNA damage | 4.20E−04 |

TABLE 6-continued

Top10 significant Gene Ontology - Biological Processes - BrEC and microglia -
exosomal CEMIP specific - List of significant Biological Processes
affected by exosomal CEMIP treatment in BrECs and microglia.

| 7 | GO: 0007166 | 7.69E−04 |
| | cell surface receptor signaling pathway | |
| 8 | GO: 0007566 | 8.38E−04 |
| | embryo implantation | |
| 9 | GO: 0045087 | 8.73E−04 |
| | innate immune response | |
| 10 | GO: 0072573 | 8.98E−04 |
| | tolerance induction to lipopolysaccharide | |

Example 1—Tumor Exosome Remodeling of the Brain Microenvironment Fosters Metastasis To overcome hurdles in BrM research posed by limitations of the current pre-clinical models (Lowery et al., "Brain Metastasis: Unique Challenges and Open Opportunities," *Biochim Biophys Acta Rev Cancer* 1867:49-57 (2017), which is hereby incorporated by reference in its entirety) and define the specific contribution of tumour-derived exosomes to brain metastatic colonization, an ex vivo organotypic brain slice culture system (FIG. 1A) (Polleux et al., "The Slice Overlay Assay: a Versatile Tool to Study the Influence of Extracellular Signals on Neuronal Development," *Sci STKE* (2002), which is hereby incorporated by reference in its entirety) was optimized. Brain slices were pre-treated with 5 μg of exosomes from brain-tropic 231-BR (231 BrT1), lung-tropic 4175 (231 LuT1), bone-tropic 1833 (231 BoT1), or parental MDA-MB-231 (231 Parental) human breast cancer metastatic cells (Bos et al., "Genes that Mediate Breast Cancer Metastasis to the Brain," *Nature* 459:1005-1009 (2009); Yoneda et al., "A Bone-Seeking Clone Exhibits Different Biological Properties From the MDA-MB-231 Parental Human Breast Cancer Cells and a Brain-Seeking Clone *In Vivo and In Vitro*," *J Bone Miner Res* 16:1486-1495 (2001) (FIG. 1A), for two consecutive days, then added fluorescently-labelled 231 BrT1 cancer cells, measuring tumour cell colonization three days later (FIG. 1B—cancer cell number). Pre-treatment of brain slices with 231 BrT1-derived exosomes increased colonizing 231 BrT1 cell number four-fold compared to PBS, and two-fold or more compared to pre-treatment with 231 parental and lung- or bone-metastatic exosomes (FIG. 8A), respectively. Pre-treatment with non-brain tropic exosomes did not induce significant cancer cell growth compared to PBS (FIG. 7A and FIG. 1C).

Next, it was asked if pre-conditioning with brain metastatic tumour-derived exosomes impacted brain metastatic cell invasiveness. Three days after tumour cell addition, invading 231 BrT1 cells in transversal sections of brain slices pre-treated with 231 BrT1 or 231 parental-derived exosomes were quantified (FIG. 1B—cancer cell invasion) and determined that 231 BrT1 exosome pre-treatment augmented 231 BrT cell invasiveness three-fold compared to 231 parental-derived exosomes or PBS, respectively (FIG. 7B). Moreover, Ki-67 immunostaining showed that 231 BrT1 exosome pre-treatment bolstered invading 231 BrT1 cell proliferation over four-fold compared to 231 parental exosomes (FIG. 1D). Remarkably, brain slice pre-conditioning with 231 BrT1-derived exosomes also enhanced colonization by 231 parental cells (FIG. 1E), which have limited ability to generate brain metastases (Valiente et al., "Serpins Promote Cancer Cell Survival and Vascular Co-option in Brain Metastasis," *Cell* 156:1002-1016 (2014); Lorger et al., "Capturing Changes in the Brain Microenvironment During Initial Steps of Breast Cancer Brain Metastasis," *Am J Pathol* 176:2958-2971 (2010), which are hereby incorporated by reference in their entirety). Brain slice pre-treatment with 231 BrT1-derived exosomes induced a five-fold and over two-fold increase in colonizing 231 parental cell number compared to PBS or 231 parental exosome pre-treatment, respectively (FIG. 1E). Overall, pre-conditioning brain slices with brain metastatic cell-derived exosomes supported tumour colonization independent of cell-intrinsic brain metastatic potential, suggesting that exosome-mediated brain microenvironment remodeling supports metastatic cell proliferation and invasion.

Example 2—Proteomic Analysis Identifies Exosomal CEMIP as a Brain Metastatic Protein It has previously been shown that tumour exosomes package specific proteins critical for the metastatic process at target organs (Peinado et al., "Melanoma Exosomes Educate Bone Marrow Progenitor Cells Toward a Pro-Metastatic Phenotype Through MET," *Nat Med* 18:883-891 (2012); Costa-Silva B et al., "Pancreatic Cancer Exosomes Initiate Pre-metastatic Niche Formation in the Liver," *Nat Cell Biol* 17:816-826 (2015), which are hereby incorporated by reference in their entirety) and that integrins are abundantly packaged in tumour exosomes that promote lung and liver metastasis (Hoshino et al., "Tumour Exosome Integrins Determine Organotropic Metastasis," *Nature* 527:329-335 (2015), which is hereby incorporated by reference in its entirety). Surprisingly, brain metastatic exosomes packaged few integrins and at low levels (Hoshino et al., "Tumour Exosome Integrins Determine Organotropic Metastasis," *Nature* 527:329-335 (2015), which is hereby incorporated by reference in its entirety), albeit ones whose cellular expression had previously been associated with BrM: α2, α3, β3 and β1 integrins (Carbonell et al., "The Vascular Basement Membrane as "Soil" in Brain Metastasis," *PLOS One* 4 e5857 (2009); Lorger et al., "Activation of Tumor Cell Integrin alphavbeta3 Controls Angiogenesis and Metastatic Growth in the Brain," *Proc Natl Acad Sci USA* 106:10666-10671 (2009), which are hereby incorporated by reference in their entirety). Thus, exosomal molecules other than integrins may support BrM. Quantitative mass spectrometry comparison of exosome proteomes from brain-tropic 231 BrT1 and BrT2 [831] to those of 231 parental, lung-tropic (LuT1 [4175]; LuT2 [4173]) and bone-tropic (BoT1 [1833]) MDA-MB-231 cells revealed that only twenty proteins were differentially expressed in brain tropic exosomes when compared to exosomes from parental cells (FIG. 7C). Among these, CEMIP or KIAA119918, emerged as a prominent exosomal protein in both brain metastatic models, with low or undetectable expression in exosomes from lung and bone metastatic models, suggesting a specific association with BrM potential. CEMIP is involved in hyaluronic acid depolymerization (Yoshida et al., "KIAA1199, a Deafness Gene of Unknown Function, is a New Hyaluronan Binding Protein Involved in Hyaluronan Depolymerization," *Proc Natl Acad Sci USA* 110:5612-5617 (2013), which is hereby incorporated by reference in its entirety), intracellular calcium regulation (Evensen et al., "Unraveling the Role of KIAA1199, a Novel Endoplasmic Reticulum Protein, in Cancer Cell Migration," *J Natl Cancer Inst* 105:1402-1416 (2013), which is hereby incorporated by reference in its entirety) and Wnt signaling (Birkenkamp-Demtroder et al., "Repression of KIAA1199 Attenuates Wnt-signalling and Decreases the Proliferation of Colon Cancer Cells," *Br J Cancer* 105:552-561 (2011), which is hereby incorporated by reference in its entirety), playing multiple roles in cancer progression (Zhang et al., "KIAA1199 and its biological role in human cancer and cancer cells (review)," *Oncol Rep* 31:1503-1508 (2014), which is hereby incorporated by reference in its entirety), inflammation (Yang et al., "KIAA1199 as a Potential Diagnostic Biomarker of Rheumatoid Arthritis Related to Angiogenesis," *Arthritis Res Ther* 17:140 (2015), which is hereby incorporated by reference in its entirety), and interestingly, in normal brain physiology (Yoshino et al., "Distribution and Function of Hyaluronan Binding Protein Involved in Hyaluronan Depolymerization (HYBID, KIAA1199) in the Mouse Central Nervous System," *Neuroscience* 347:1-10 (2017), which is hereby incorporated by reference in its entirety). Western blot quantification of exosomal CEMIP confirmed high abundance in brain metastatic cell-derived exosomes compared to parental and non-brain metastatic cell-derived exosomes (FIG. 7D). Interestingly, CEMIP was enriched ten-fold in 231 BrT1 exosomes relative to 231 BrT1 cells, suggesting selective packaging in exosomes (FIG. 7D).

To investigate CEMIP association with extracellular vesicle (EV) fractions containing exosomes, the 231 BrT1 EV pellet obtained from ultracentrifugation was applied onto an iodixanol/Optiprep density gradient and CEMIP expression was quantified in fractions positive for exosomal and small EV markers Syntenin-1, CD81, and HSP70 (fractions 6-9). CEMIP was detected in fractions 5-9 (FIG. 1F), with the highest CEMIP expression in the exosome-containing fraction 7, corresponding to a density of 1.10 g/mL. This indicates that CEMIP expression is specifically associated with small EVs, that include exosomes and their subpopulations (exosome large, exosome small vesicles and exomere particles) (Zhang et al., "Identification of Distinct Nanoparticles and Subsets of Extracellular Vesicles by Asymmetric Flow Field-flow Fractionation," *Nat Cell Biol* 20:332-343 (2018), which is hereby incorporated by reference in its entirety), as opposed to non-EV protein aggregates or microvesicles. CEMIP was abundant in exosomes from additional orthotopic brain metastatic models: MDA-MB-231-HM breast and N2LA-BR lung cancer (FIG. 7E), further supporting the association of exosomal CEMIP with BrM potential. Taken together, these data identify CEMIP as a protein enriched in exosomes from brain metastatic cancer cells.

Example 3—Exosomal CEMIP Modulates the Brain Vascular Niche to Support Metastasis To determine whether CEMIP is required for exosome-mediated brain colonization, CEMIP in brain metastatic 231 BrT1 cancer cells was targeted using CRISPR/Cas9. Western blot confirmed a significant reduction in CEMIP expression in two 231 BrT1 single cell clones with complex CEMIP indels, KO1 and KO2, and their exosomes, compared to control BrT1 cells (WT) and exosomes (FIG. 8A). Transmission electron microscopy (FIG. 8B) and nanoparticle tracking analysis (FIG. 8C) revealed that CEMIP targeting did not affect exosome morphology or size. In addition, protein levels (BCA protein assay; FIG. 8C) and expression of CD81 or Syntenin-1 (FIG. 8A) remained unaltered in 231 BrT1 CEMIP KO-derived exosomes, suggesting CEMIP loss does not alter exosomal protein packaging.

The functional role of CEMIP in BrM was next investigated. Although the overall cancer cell number on the surface of ex vivo brain slices was not significantly impacted by CEMIP loss (FIG. 8D), 231 BrT1 CEMIP KO and WT cell morphology was distinct. Consistent with previous reports (Valiente et al., "Serpins Promote Cancer Cell Survival and Vascular Co-option in Brain Metastasis," *Cell* 156:1002-1016 (2014); Lorger et al., "Capturing Changes in the Brain Microenvironment During Initial Steps of Breast Cancer Brain Metastasis," *Am J Pathol* 176:2958-2971 (2010); Carbonell et al., "The vascular basement membrane as "soil" in brain metastasis," *PLOS One* 4:e5857 (2009), which are hereby incorporated by reference in their entirety), brain metastatic 231 BrT1 cells presented a spindle-like morphology and when invading, consistently associated with and spread along brain endothelial cells (BrECs) (FIG. 8E—right and left panels, full white arrows), a process known as vascular co-option (Winkler, "Hostile Takeover: How Tumours Hijack Pre-existing Vascular Environments to Thrive," *J Pathol* 242:267-272 (2017), which is hereby incorporated by reference in its entirety). Interestingly, 231 BrT1 CEMIP KO cells were rounder, lost spindle-like morphology (FIG. 9A, full white arrows) and displayed significantly impaired ability to associate with brain vasculature, with a 50% reduction in both co-opting and invading cancer cells compared to 231 BrT1 CEMIP WT cells (FIG. 9A-9B). Despite diminished brain colonizing ability ex vivo, CEMIP ablation did not affect in vitro proliferation or invasion (FIG. 8F-8G) suggesting that CEMIP's role in BrM is dependent on the brain microenvironment. Collectively, these results indicate that CEMIP loss reduces the ability of brain metastatic cells to interact with brain vasculature and successfully invade the brain.

To evaluate the relative contributions of exosomal and cellular CEMIP to BrM, whether exosomal CEMIP was sufficient to rescue brain colonization, invasion and vascular co-option by 231 BrT1 CEMIP KO cells was investigated. Brain slice pre-treatment with 231 BrT1 CEMIP WT-derived exosomes induced a four-fold and two-fold increase in colonizing 231 BrT1 CEMIP KO2 cell number compared to PBS and CEMIP KO exosome pre-treatment, respectively (FIG. 8H). More importantly, brain slice pre-treatment with 231 BrT1 CEMIP WT-derived exosomes restored 231 BrT1 CEMIP KO2 vascular co-option, and their characteristic spindle-like phenotype (FIG. 9C, full white arrows). Whereas 231 BrT1 CEMIP WT-derived exosomes increased cancer cell vascular co-option over two-fold, pre-treatment with CEMIP KO1 or KO2 exosomes did not (FIG. 9C). Moreover, pre-treatment with 231 BrT1 CEMIP WT-derived exosomes increased 231 BrT1 CEMIP KO2 invasion by three-fold compared to PBS and CEMIP KO exosome pre-treatment (FIG. 9D). These results suggest that exosomal CEMIP supersedes cellular CEMIP in promoting adaptation to the brain microenvironment via vascular co-option, ultimately supporting successful invasion and metastatic colonization of the brain.

Example 4-Exosomal CEMIP Supports Brain Colonization In Vivo

Whereas the above illustrated that CEMIP promotes vascular co-option, invasion, and colonization, the data were confined to brain slices and thus bypassed critical steps of the metastatic cascade. Therefore, experimental metastasis assays were used to investigate whether CEMIP mediates BrM in vivo. Loss of cellular CEMIP led to a significant reduction in BrM four weeks following intracardiac injection of 231 BrT1 cells (FIG. 10A). Histology revealed a 70% decrease in brain metastatic foci generated by 231 BrT1 CEMIP KO versus CEMIP WT cells (FIG. 10A—bottom left graph) and a metastatic burden reduction in both CEMIP KO models relative to CEMIP WT, especially in KO1 (FIG. 10A—bottom right graph). However, no significant differences in individual lesion size between CEMIP WT and CEMIP KO cells was observed, suggesting that CEMIP is required during early steps of metastatic colonization. Accordingly, no significant difference was found in tumor outgrowth after intracranial injection upon CEMIP loss FIG. 2A), or in primary tumor growth after mammary fat pad injection (FIG. 2B).

To determine if exosomal CEMIP affects BrM in vivo, it was evaluated if pre-treatment of mice with 10 μg of 231 BrT1 CEMIP WT or CEMIP KO-derived exosomes every other day for three weeks prior to intracardiac injection of 231 BrT1 GFP-luciferase[+] cells enhanced BrM in a CEMIP-dependent manner. Pre-treatment with 231 BrT1 CEMIP WT-derived exosomes significantly boosted BrM compared to CEMIP KO1 and KO2 exosome pre-treatments at week one and two post-injection, ultimately normalizing over time since emerging CEMIP[+] WT cells produce CEMIP[+] exosomes (FIG. 10B—left graphs). Quantification of brain lesions revealed an increase in metastatic foci number and metastatic burden in CEMIP WT exosome pre-treated mice compared to PBS and one of the CEMIP KO exosome pre-treated groups (FIG. 10B—bottomt graphs). Collectively, these data support a pro-metastatic role of exosomal CEMIP in vivo during the early stages of colonization and demonstrate that exosomal CEMIP promotes BrM in vivo.

Example 5-Exosomal CEMIP Induces Remodeling and Inflammation in the Brain Vascular Niche Since the findings suggest a critical role for exosomal CEMIP in the brain vascular niche, it was sought to identify resident cells within the brain involved in this process. Brain slices were treated with 5 μg of fluorescently-labelled 231 BrT1-derived exosomes and exosome uptake by endothelial cells, microglia, astrocytes and neurons was examined, via immunofluorescence, 24 hours post-treatment (FIG. 11A and FIG. 3A). Exosomes co-localized primarily with CD31[+] and Glut1[+] endothelial cells but were also uptaken by Iba1[+] microglia, including perivascular ones, and, to much lower extent, by GFAP[+] astrocytes and NeuN[+] neurons (FIG. 11A-11B). These data are consistent with previous work demonstrating that BrEC predominantly uptake tumour cell-derived exosomes in vivo (Hoshino et al., "Tumour Exosome Integrins Determine Organotropic Metastasis," *Nature* 527:329-335, (2015), which is hereby incorporated by reference in its entirety) (FIG. 3B). In addition, a single intracardiac injection of 10 μg of fluorescently-labelled 231 BrT1-derived exosomes disrupted blood-brain barrier vascular integrity, as evidenced by extravasated high molecular weight dextran in exosome-positive blood vessels (FIG. 3C).

To determine whether exosomal CEMIP pre-conditioning led to vascular remodeling, murine BrEC were treated in vitro with 10 μg of exosomes from CEMIP loss or gain of function models and vascular network formation was evaluated in a 3D endothelial tube formation (ETF) assay 24 hours later (FIG. 3D). To test if high exosomal CEMIP levels were sufficient to support vascular network formation, CEMIP was overexpressed in 231 parental cells (231 parental CEMIP OE) and their exosomes (FIG. 3E). Pre-treatment with 231 parental CEMIP OE and 231 BrT1 CEMIP WT-derived exosomes promoted ETF, increasing the number and size of endothelial cell branches formed compared to 231 parental control and 231 BrT1 CEMIP KO exosomes (FIG. 11C). Consistent with these metrics, pre-treatment with exosomal CEMIP also increased segment junction number and decreased isolated segment number (FIG. 3F). In vivo, in contrast to the surrounding normal brain tissue (empty white arrow), 231 BrT1 brain metastases had altered, morphologically heterogeneous vasculature with enlarged and dilated vessels (FIG. 3G—full white arrows and graph), characteristic of metastatic lesions in the brain (Fidler, "The Role of the Organ Microenvironment in Brain Metastasis," *Semin Cancer Biol* 21:107-112 (2011), which is hereby incorporated by reference in its entirety), while 231 BrT1 CEMIP KO metastatic lesions displayed significantly smaller vessel diameter, similar to the surrounding non-metastatic brain tissue. Collectively, these findings support a functional role for tumour cell-derived exosomal CEMIP in the remodeling of brain vasculature.

To dissect the molecular changes elicited by exosomal CEMIP during brain vascular niche remodeling, the gene expression profiles of brain cells uptaking tumour exosomes, endothelial cells and microglia were analyzed, the latter often observed in close contact with the brain vasculature (FIG. 11B, double white arrow) and known to play critical roles during vascular remodeling and dysfunction (Arnold et al., "The Importance of Microglia in the Development of the Vasculature in the Central Nervous System," *Vasc Cell* 5:4 (2013), which is hereby incorporated by reference in its entirety). Exosome-positive BrEC (CD45[-] CD31[+]) and microglia (CD45[+] CD11b[low] CD49d[low]) were isolated from brain slices pre-conditioned with 5 μg of fluorescently-labelled exosomes from either 231 BrT1 CEMIP WT or 231 BrT1 CEMIP KO cells and analyzed gene expression changes by RNA sequencing (FIG. 3H). No difference was observed between the uptake of fluorescently-labelled 231 BrT1 CEMIP WT or 231 BrT1 CEMIP KO exosomes (FIG. 3I), indicating that gene expression differences are not due to differential binding or uptake of exosomes. Correspondingly, no difference was observed between 231 BrT1 CEMIP WT and CEMIP KO exosome adhesion to CD31+ endothelial cells by immunofluorescence analysis (FIG. 3J).

Analysis of gene expression changes induced by brain metastatic-derived exosomes in both endothelial cells and microglia (Table 3) revealed activation of several signaling pathways related to inflammation and cancer metastasis (Table 4). To identify genes modulated by exosomal CEMIP, the focus was first on genes significantly altered by pre-treatment with 231 BrT1 CEMIP WT-derived exosomes compared to the PBS control and then on the genes that showed significant and concordant difference in expression when compared to pre-treatment with both 231 BrT1 CEMIP KO exosomes. Pre-treatment with 231 BrT1-derived exosomes changed the expression levels of 286 endothelial cell genes and 193 microglial genes (Table 3), with a higher proportion of CEMIP-dependent changes in BrEC versus microglia (119 versus 25 genes, respectively; Table 5). Gene ontology analysis of genes with altered expression upon CEMIP⁺ exosome treatment identified blood vessel morphogenesis and lymphangiogenesis as the second and third most significantly affected processes in BrECs (Table 6), while inflammatory responses were the top most significantly affected biological process in exosome-positive microglia (Table 6). Ingenuity Pathway Analysis (IPA) identified 14 pathways significantly affected by exosomal CEMIP in BrEC, half of which were inositol-related pathways, which CEMIP impacts through intracellular calcium release (Evensen et al., "Unraveling the Role of KIAA1199, a Novel Endoplasmic Reticulum Protein, in Cancer Cell Migration," *J Natl Cancer Inst* 105:1402-1416 (2013); Tran et al., "Calcium Signalling in Endothelial Cells," *Cardiovase Res* 48:13-22 (2000), which are hereby incorporated by reference in their entirety) (Table 4). CEMIP-dependent calcium signaling governs numerous cellular processes relevant for vascular remodeling and angiogenesis, such as cell migration and Wnt signaling (Birkenkamp-Demtroder et al., "Repression of KIAA1199 Attenuates Wnt-signalling and Decreases the Proliferation of Colon Cancer Cells," *Br J Cancer* 105:552-561 (2011); Liebner et al., "Wnt/beta-catenin Signaling Controls Development of the Blood-brain Barrier," *J Cell Biol* 183:409-417 (2008), which are hereby incorporated by reference in their entirety) suggesting these gene expression changes may underlie the exosome-dependent vascular phenotypes that was observed. Other CEMIP-dependent pathways were osteoarthritis (Tcf7l1, Acvrl1, P2rx7, Prkab2 and Sp1), an inflammatory condition modulated by CEMIP as well as gap junction signaling (Gja1, Npr2. Adcy4 and Sp1), and several adhesion molecules (e.g. Efnb2, Nedd9, Itgb3, Acvrl1, Farp1, Synm, Sema6d, Ocln, etc.), with roles in vascular remodeling and endothelial cell-cell contacts (FIG. 11D and Table 3).

In microglia, IPA identified 69 exosomal CEMIP-dependent pathways, related to inflammation, immune regulation through cell adhesion and diapedesis (Ccl5, Cxcl10, Cxcl1, Tnf and Tnfrsf1b) and neuroinflammation (Ccl5, Cxcl10, Ptgs2, Syk and Tnf) (FIG. 12D and Table 4). Taken together, these data demonstrate that exosomal CEMIP affects molecular pathways in BrEC and microglia implicated in BrM that may underlie reshaping of brain vascular niches and brain pre-metastatic niche formation.

Example 6-CEMIP Predicts Brain Metastasis and Survival in Patients

Next, the correlation between CEMIP protein levels in tissues and exosomes collected from cancer patients with brain metastases was investigated. First, CEMIP expression was characterized by immunohistochemistry in tissue microarrays from over 300 samples of primary tumours (PTs) and metastatic tumours (MTs) from breast and lung cancer patients with metastases in the brain, metastases in other organs (e.g. bone, colon, heart, kidney, liver, lung, pleura, skin or stomach) or no metastases. Analysis of brain MTs revealed that tumour CEMIP expression was markedly increased compared to surrounding brain stroma (FIG. 4A). Based on staining intensity, brain MTs were categorized into low (staining score 0-2) or high (staining score >2-4) CEMIP expression (FIG. 4B). Interestingly, analysis of CEMIP expression in PTs revealed that patients with BrM had significantly higher CEMIP expression (CEMIP*high* sample percentage: 32.4 for PTs Brain MET versus 12.0 and 13.5 for PTs Non-Brain MET and No MET, respectively; FIG. 4C; Table 7) than PTs from patients with metastasis to organ sites other than the brain, or without metastasis, indicating PT CEMIP expression levels correlated with BrM but not with non-brain metastasis (Table 7).

TABLE 7

Correlation of CEMIP expression in PTs and metastatic status - Spearman correlation of CEMIP expression in primary tumour samples and metastatic status of patients (any organ metastasis, non-brain metastasis, and brain metastasis).
Correlation of CEMIP expression in PTs and metastatic status

| | METASTASIS | | |
|---|---|---|---|
| CEMIP Expression | Any organ | Non-Brain | Brain |
| Spearman r | 0.1598 | 0.0757 | 0.2956 |
| Significance (2-tailed) | 0.0196 | 0.3137 | 0.0004 |
| Sample size | 213 | 179 | 138 |

Moreover, analysis of brain MTs showed significantly higher CEMIP expression compared to MTs from other organs (FIG. 4C). Consistently, more than 40% of brain MTs analyzed were CEMIP*high*, whereas of all non-brain MTs only 7% were CEMIP*high* (FIG. 4C). Furthermore, for patients that developed brain metastases, high PT CEMIP expression correlated with a shorter latency period for metastasis (FIG. 4D). Moreover, patients with CEMIP*high* brain MTs had significantly poorer survival compared to patients with CEMIP*low* brain MTs (FIG. 5A).

Similar to PTs and MTs of patients with brain metastases, CEMIP expression by immunohistochemistry was higher in cultured brain MT cells (FIG. 5B), whose exosomes expressed high CEMIP by western blot (FIG. 7D). Evaluation of CEMIP expression in exosomes collected from 24-hour cultures of viable human brain MTs, as well as bone MTs, another common site of metastasis, revealed CEMIP in all human brain MT exosomes examined; but only in one of three bone MT-derived exosomes from lung cancer patients (FIG. 5C). Western blot analysis of exosomal CEMIP from surgically resected early stage human NSCLC PTs revealed variable expression across patients, indicating exosomal CEMIP can be detected in PT-derived samples even at early stages and could therefore inform brain metastatic risk (FIG. 5D). Collectively, the patient data demonstrated that CEMIP is expressed by brain MTs and their exosomes and that high CEMIP expression in PTs is associated with shorter latency to brain metastasis and poor patient survival.

Example 7-Generation and Validation of CEMIP/KIAA1199 Neutralizing Antibodies and Testing their Targeting Specificity A series of anti-human CEMIP antibodies was generated in mice and screened. Validation was performed on two human cell lines with high cellular and exosomal KIAA1199 (CEMIP); the gastric cell line MKN45 and the N2LA lung cancer cell line.

Antibodies targeting KIAA1199/CEMIP were generated in Balb/c and A/J mice. Immunogens included a truncated version of KIAA1199/CEMIP protein (amino acids 1-649) and plasmid DNA. DNA immunization is a strategy that is often successful for challenging or problematic antigens such as membrane-associated proteins, multi-pass membrane proteins or large proteins. DNA immunization with a high volume of CEMIP-encoding plasmid permits in vivo antigen production, bypassing immunogen (e.g. peptides and recombinant proteins) synthesis and purification. In this strategy, CEMIP is expressed in vivo by liver cells, and the protein maintains the native structures and goes through appropriate post-translational modifications. These properties contribute to the generation of antibodies binding to the native conformation of the target antigen, which is a crucial feature for developing therapeutic antibodies. After multiple rounds of injections, splenocytes were harvested and fused with myeloma cells to generate hybridoma. Hybridoma supernatants were tested by ELISA using purified KIAA1199/CEMIP protein (aa 1-649). Hybridoma from positive hits (10-fold over background) were subcloned, followed by purification of the monoclonal antibodies from hybridoma supernatant. From this initial phase, 7 anti-KIAA1199/CEMIP antibodies identified were tested by ELISA using purified KIAA1199/CEMIP protein (aa 1-649) (FIG. 12).

Purified monoclonal antibodies were tested in secondary flow-cytometry screens on 2 CEMIPhi cell lines, MKN45 and N2LA (FIG. 13). Flow cytometry is performed on live cells, and antibodies bind to the native cell surface CEMIP/KIAA1199. Three antibody clones with high affinity and specificity for human KIAA1199/CEMIP were identified from the first screen: 07F11C02, 10F01B02 and 01F11A01, and the sequence of these antibodies was obtained (Table 12). One of these clones resulted from the protein immunization and two resulted from the DNA immunization (FIG.

13). Clone 07G04B01 demonstrated no binding to KIAA1199/CEMIP and was used as a negative control in future experiments. These antibodies will be tested for their ability to efficiently block brain-tropic tumor cell outgrowth in vitro, in organotypic cultures as described herein.

In the second phase of the screen, an additional 55 antibodies that bind to recombinant KIAA1199/CEMIP (aa 1-649) in ELISA assays were identified and tested by flow cytometry of exhausted hybridoma supernatants on the MKN45 cell line. These hybridomas were selected from semi-solid medium using a ClonePix instrument, resulting in monoclonality without the need for subcloning. Supernatant production from hybridomas producing binders was scaled up and antibodies were purified, tested and titrated by flow cytometry. Of the 55 clones screened, 29 were found to bind at levels higher than the negative control antibody (07G04B01) and of these 29, 13 clones, 13G04, 11D05, 11E02, 11F11, 12A12, 12G11, 12G08, 12F01, 12E11, 12D02, 12D08, 12E07, 12C11 were found to bind at levels higher than the positive control antibody (10F01B02), and were selected for further characterization (FIG. 14). These 13 purified antibodies as well as additional controls were re-screened by ELISA versus known KIAA1199-binding antibody and an irrelevant control (FIG. 15). The 4 antibodies with the highest anti-CEMIP/KIAA1199 binding based on these 2 assays, 12D02, 12D08, 12A12 and 13G04, were sequenced (Table 12).

TABLE 12

| mAb/Fab name | Region | Sequence | SEQ ID NO: |
|---|---|---|---|
| | Amino Acid Sequences of Exemplary Antibodies of the Disclosure |
| cAb4853 07F11C02 | $V_H$ IgG2a | DVQLVESGGGLVQPGGSRKLSCAASGFAFSSFGMHWVRQA PERGLEWVAYISSASNTIYYADTVKGRFTISRDNPKSTLFLQ MTSLRSEDTAIYYCAKRDWDLYAMDYWGQGTSVTVSS | 44 |
| | $C_H$ | AKTTAPSVYPLAPVCGDTTGSSVTLGCLVKGYFPEPVTLTW NSGSLSSGVHTFPAVLQSDLYTLSSSVTVTSSTWPSQSITCNV AHPASSTKVDKKIEPRGPTIKPCPPCKCPAPNLLGGPSVFIFPP KIKDVLMISLSPIVTCVVVDVSEDDPDVQISWFVNNVEVHTA QTQTHREDYNSTLRVVSALPIQHQDWMSGKEFKCKVNNKD LPAPIERTISKPKGSVRAPQVYVLPPPEEEMTKKQVTLTCMV TDFMPEDIYVEWTNNGKTELNYKNTEPVLDSDGSYFMYSKL RVEKKNWVERNSYSCSVVHEGLHNHHTTKSFSRTPGK | 72 |
| | $V_L$ kappa | DIVMTQSQKFLSTSVGDRVTITCKASQNVGTAVAWYQQKPG QSPELLIYSASNRHTGVPARFTGSGSGTDFTLTITNMQSEDLA DYFCQQYSSSPTFGGGTKLESK | 45 |
| | $C_L$ | RADAAPTVSIFPPSSEQLTSGGASVVCFLNNFYPKDINVKWKI DGSERQNGVLNSWTDQDSKDSTYSMSSTLTLTKDEYERHNS YTCEATHKTSTSPIVKSFNRNEC | 73 |
| cAb4854 10F01B02 | $V_H$ IgG2a | DVQLVESGGGLVQPGGSRKLSCAASGFPFSSFGMHWVRQAP DKGLEWVAYISSASNTIYYADTVKGRFTVSRDNPKNTLFLQ MTSLRSEDTAIYYCTKRNWDLYAMDYWGQGTSVTVSS | 46 |
| | $C_H$ | AKTTAPSVYPLAPVCGDTTGSSVTLGCLVKGYFPEPVTLTW NSGSLSSGVHTFPAVLQSDLYTLSSSVTVTSSTWPSQSITCNV AHPASSTKVDKKIEPRGPTIKPCPPCKCPAPNLLGGPSVFIFPP KIKDVLMISLSPIVTCVVVDVSEDDPDVQISWFVNNVEVHTA QTQTHREDYNSTLRVVSALPIQHQDWMSGKEFKCKVNNKD LPAPIERTISKPKGSVRAPQVYVLPPPEEEMTKKQVTLTCMV TDFMPEDIYVEWTNNGKTELNYKNTEPVLDSDGSYFMYSKL RVEKKNWVERNSYSCSVVHEGLHNHHTTKSFSRTPGK | 74 |
| | $V_L$ kappa | DIVMTQSQKFMSTSVGDRVSITCKANQNVGTAVAWYQQKP GQSPKLLIYSTSNRDTGVPDRFTGSGSGTDFTLTINYIQSEDL ADYFCQQYRNYPTFGGGTKLEIK | 47 |
| | $C_L$ | RADAAPTVSIFPPSSEQLTSGGASVVCFLNNFYPKDINVKWKI DGSERQNGVLNSWTDQDSKDSTYSMSSTLTLTKDEYERHNS YTCEATHKTSTSPIVKSFNRNEC | 75 |
| cAb4855 01F11A01 | $V_H$ IgG2a | QVTLKESGPGILQPSQTLSLTCSFSGFSLSTSGMGVGWIRQPS GKGLEWLAHIWWNDEKYYNAALKSRLTISKDTSKNQVFLKI ASVDAADTATYYCARITGAWFPYWGQGTLVTVSA | 48 |

TABLE 12-continued

| mAb/Fab name | Region | Sequence | SEQ ID NO: |
|---|---|---|---|
| | $C_H$ | AKTTAPSVYPLAPVCGDTTGSSVTLGCLVKGYFPEPVTLTW NSGSLSSGVHTFPAVLQSDLYTLSSSVTVTSSTWPSQSITCNV AHPASSTKVDKKIEPRGPTIKPCPPCKCPAPNLLGGPSVFIFPP KIKDVLMISLSPMVTCVVVDVSEDDPDVQISWFVNNVEVLT AQTQTHREDYNSTLRVVSALPIQHQDWMSGKEFKCKVNNK DLPAPIERTISKPKGSVRAPQVYVLPPPEEEMTKKQVTLTCM VTDFMPEDIYVEWTNNGKTELNYKNTEPVLDSDGSYFMYSK LRVEKKNWVERNSYSCSVVHEGLHNHHTTKSFSRTPGK | 76 |
| | $V_L$ kappa | DIVMTQSPATLSVTPGDRVSLSCRASQHISEYLHWYQQKSHE SPRLLIKYGSQSISGIPSRFSGSGSGSDFTLNINSVEPEDVGVY YCQNGHSFPYTFGGGTKLEIK | 49 |
| | $C_L$ | RADAAPTVSIFPPSSEQLTSGGASVVCFLNNFYPKDINVKWKI DGSERQNGVLNSWTDQDSKDSTYSMSSTLTLTKDEYERHNS YTCEATHKTSTSPIVKSFNRNEC | 77 |
| cAb5775 12D02 | $V_H$ IgG1 | EVQLQQSGPELVKPGASMKISCKASGYSFTAYTMNWVKQS HGENLEWIGLINPYNGGTTYNQKFKGKATLTVDKSSSTAYM ELLSLTSEDSAVYYCASYDYGYAMDYWGQGTSVTVSS | 50 |
| | $C_H$ | AKTTPPSVYPLAPGSAAQTNSMVTLGCLVKGYFPEPVTVTW NSGSLSSGVHTFPAVLQSDLYTLSSSVTVPSSTWPSETVTCNV AHPASSTKVDKKIVPRDCGCKPCICTVPEVSSVFIFPPKPKDV LTITLTPKVTCVVVDISKDDPEVQFSWFVDDVEVHTAQTQPR EEQFNSTFRSVSELPIMHQDWLNGKEFKCRVNSAAFPAPIEK TISKTKGRPKAPQVYTIPPPKEQMAKDKVSLTCMITDFFPEDI TVEWQWNGQPAENYKNTQPIMDTDGSYFVYSKLNVQKSN WEAGNTFTCSVLHEGLHNHHTEKSLSHSPGK | 78 |
| | $V_L$ kappa | DVLMTQTPLSLPVSLGDQASISCRSSQSIVHRNGNTYLEWYL QKPGQSPKLLIYKVSNRFSGVPDRFSGSGSGTDFTLKISRVEA EDLGVYYCFQGSHVPWTFGGGTKLEIK | 51 |
| | $C_L$ | RADAAPTVSIFPPSSEQLTSGGASVVCFLNNFYPKDINVKWKI DGSERQNGVLNSWTDQDSKDSTYSMSSTLTLTKDEYERHNS YTCEATHKTSTSPIVKSFNRNEC | 79 |
| cAb5776 12A12 | $V_H$ IgG1 | EVQLQQSGPELVKPGVSMKISCKASGYSFTAYTMNWVKQS HGENLEWIGLINPYNGGTTYNQKFKGKATLTVDKSSSTAYM ELLSLTSEDSAVYYCASYDYGYAMDYWGQGTSVTVSS | 52 |
| | $C_H$ | AKTTPPSVYPLAPGSAAQTNSMVTLGCLVKGYFPEPVTVTW NSGSLSSGVHTFPAVLQSDLYTLSSSVTVPSSTWPSETVTCNV AHPASSTKVDKKIVPRDCGCKPCICTVPEVSSVFIFPPKPKDV LTITLTPKVTCVVVDISKDDPEVQFSWFVDDVEVHTAQTQPR EEQFNSTFRSVSELPIMHQDWLNGKEFKCRVNSAAFPAPIEK TISKTKGRPKAPQVYTIPPPKEQMAKDKVSLTCMITDFFPEDI TVEWQWNGQPAENYKNTQPIMDTDGSYFVYSKLNVQKSN WEAGNTFTCSVLHEGLHNHHTEKSLSHSPGK | 80 |
| | $V_L$ kappa | DVLMTQTPLSLPVSLGDQASISCRSSQSIVHRSGNTYLEWYL QKPGQSPKLLIYKVSNRFSGVPDRFSGSGSGTDFTLKISRVEA EDLGVYYCFQGSHVPWTFGGGTKLEIK | 53 |
| | $C_L$ | RADAAPTVSIFPPSSEQLTSGGASVVCFLNNFYPKDINVKWKI DGSERQNGVLNSWTDQDSKDSTYSMSSTLTLTKDEYERHNS YTCEATHKTSTSPIVKSFNRNEC | 81 |
| cAb5777 12D08 | $V_H$ IgG2a | EVQLQQSGAELVKPGASVKLSCTASGFNIKDTYMHWVKQR PEQGLIWIGNIDPANGHTKYAPKFQGKATITADTSSNTAYLQ LSSSLTSEDTAVYYCARSNDYDVDFDYWGQGTTLTVSS | 54 |
| | $C_H$ | AKTTAPSVYPLAPVCGDTTGSSVTLGCLVKGYFPEPVTLTW NSGSLSSGVHTFPAVLQSDLYTLSSSVTVTSSTWPSQSITCNV AHPASSTKVDKKIEPRGPTIKPCPPCKCPAPNLLGGPSVFIFPP KIKDVLMISLSPIVTCVVVDVSEDDPDVQISWFVNNVEVHTA QTQTHREDYNSTLRVVSALPIQHQDWMSGKEFKCKVNNKD LPAPIERTISKPKGSVRAPQVYVLPPPEEEMTKKQVTLTCMV TDFMPEDIYVEWTNNGKTELNYKNTEPVLDSDGSYFMYSKL RVEKKNWVERNSYSCSVVHEGLHNHHTTKSFSRTPGK | 82 |
| | $V_L$ kappa | DIVMSQSPSSLAVSAGEKVTMSCKSSQSLLNSRTRKNYLAW YQQKPGQSPKLLIYWASTRESGVPDRFTGSGSGTDFSLTISSV QAEDLAVYYCKQSYNLYTFGGGTKLEIK | 55 |
| | $C_L$ | RADAAPTVSIFPPSSEQLTSGGASVVCFLNNFYPKDINVKWKI DGSERQNGVLNSWTDQDSKDSTYSMSSTLTLTKDEYERHNS YTCEATHKTSTSPIVKSFNRNEC | 83 |
| cAb5778 13G04 | $V_H$ IgG1 | EVHLQQSGPELVKPGASMKISCKASGYSFTAYTMNWVKQS HGKNLEWIGLINPYNGGTTYNQKFKGKATLTVDKSSSTAYM ELLSLTSEDSAVYYCASYYGGRGWYFDVWGAGTSVTVSS | 56 |
| | $C_H$ | AKTTPPSVYPLAPGSAAQTNSMVTLGCLVKGYFPEPVTVTW NSGSLSSGVHTFPAVLQSDLYTLSSSVTVPSSTWPSETVTCNV AHPASSTKVDKKIVPRDCGCKPCICTVPEVSSVFIFPPKPKDV | 84 |

TABLE 12-continued

| mAb/Fab name | Region | Sequence | SEQ ID NO: |
|---|---|---|---|
| | | LTITLTPKVTCVVVDISKDDPEVQFSWFVDDVEVHTAQTQPR EEQFNSTFRSVSELPIMHQDWLNGKEFKCRVNSAAFPAPIEK TISKTKGRPKAPQVYTIPPPKEQMAKDKVSLTCMITDFFPEDI TVEWQWNGQPAENYKNTQPIMDTDGSYFVYSKLNVQKSN WEAGNTFTCSVLHEGLHNHHTEKSLSHSPGK | |
| | V$_L$ kappa | DIVLTQSPASLAVSLGQRATISCRASKSVSTSGYSYVHWYQQ KPGQPPKLLIYLASNLESGVPARFSGSGSGTDFTLNIHPVEEE DAATYYCQNSRELPYTFGGGTKLEMK | 57 |
| | C$_L$ | RADAAPTVSIFPPSSEQLTSGGASVVCFLNNFYPKDINVKWKI DGSERQNGVLNSWTDQDSKDSTYSMSSTLTLTKDEYERHNS YTCEATHKTSTSPIVKSFNRNEC | 85 |

TABLE 13

| mAb/Fab name | Region | Sequence | SEQ ID NO: |
|---|---|---|---|
| cAb4853 07F11C02 | V$_H$ | GATGTGCAGCTGGTGGAGTCTGGGGGAGGCTTAGTGCAG CCTGGAGGGTCCCGGAAACTCTCCTGTGCAGCCTCTGGAT TCGCTTTCAGTAGCTTTGGAATGCACTGGGTTCGTCAGGC TCCAGAGAGGGGGCTGGAGTGGGTCGCATACATTAGTAG TGCCAGCAATACCATCTACTATGCAGACACAGTGAAGGGC CGATTCACCATCTCCAGAGACAATCCCAAGAGCACCCTGT TCCTGCAAATGACCAGTCTAAGGTCTGAGGACACGGCCAT TTATTACTGTGCAAAGCGAGACTGGGACCTCTATGCTATG GACTACTGGGGTCAAGGAACCTCAGTCACCGTCTCGTCA | 58 |
| | C$_H$ | GCCAAAACAACAGCCCCATCGGTCTATCCACTGGCCCCTG TGTGTGGAGATACAACTGGCTCCTCGGTGACTCTAGGATG CCTGGTCAAGGGTTATTTCCCTGAGCCAGTGACCTTGACC TGGAACTCTGGATCCCTGTCCAGTGGTGTGCACACCTTCC CAGCTGTCCTGCAGTCTGACCTCTACACCCTCAGCAGCTC AGTGACTGTAACCTCGAGCACCTGGCCCAGCCAGTCCATC ACCTGCAATGTGGCCCACCCGGCAAGCAGCACCAAGGTG GACAAGAAAATTGAGCCCAGAGGGCCCACAATCAAGCCC TGTCCTCCATGCAAATGCCCAGCACCTAACCTCTTGGGTG GACCATCCGTCTTCATCTTCCCTCCAAAGATCAAGGATGT ACTCATGATCTCCCTGAGCCCCATAGTCACATGTGTGGTG GTGGATGTGAGCGAGGATGACCCAGATGTCCAGATCAGC TGGTTTGTGAACAACGTGGAAGTACACACAGCTCAGACAC AAACCCATAGAGAGGATTACAACAGTACTCTCCGGGTGGT CAGTGCCCTCCCCATCCAGCACCAGGACTGGATGAGTGGC AAGGAGTTCAAATGCAAGGTCAACAACAAAGACCTCCCA GCGCCCATCGAGAGAACCATCTCAAAACCCAAAGGGTCA GTAAGAGCTCCACAGGTATATGTCTTGCCTCCACCAGAAG AAGAGATGACTAAGAAACAGGTCACTCTGACCTGCATGG TCACAGACTTCATGCCTGAAGACATTTACGTGGAGTGGAC CAACAACGGGAAAACAGAGCTAAACTACAAGAACACTGA ACCAGTCCTGGACTCTGATGGTTCTTACTTCATGTACAGC AAGCTGAGAGTGGAAAAGAAGAACTGGGTGGAAAGAAAT AGCTACTCCTGTTCAGTGGTCCACGAGGGTCTGCACAATC ACCACACGACTAAGAGCTTCTCCCGGACTCCGGGTAAA | 86 |
| | HC signal | ATGGACTCCAGGCTCAATTTAGTTTTCCTTGTCCTTATTTT AAAAGGTGTCCAATGT | 87 |
| | V$_L$ | GACATTGTGATGACCCAGTCTCAAAAATTCTTGTCCACAT CAGTGGGAGACAGGGTCACCATCACCTGCAAGGCCAGTC AGAATGTGGGAACTGCTGTTGCCTGGTATCAACAGAAACC AGGGCAATCTCCTGAACTTCTGATTTACTCGGCATCCAAT CGGCACACTGGAGTCCCTGCTCGCTTCACAGGCAGTGGAT CTGGGACAGATTTCACTCTCACCATCACCAATATGCAGTC TGAAGACCTGGCAGATTATTTCTGCCAGCAATATAGTAGC TCGCCGACATTCGGTGGAGGCACCAAGTTGGAATCCAAA | 59 |
| | C$_L$ | CGGGCTGATGCTGCACCAACTGTATCCATCTTCCCACCAT CCAGTGAGCAGTTAACATCTGGAGGTGCCTCAGTCGTGTG CTTCTTGAACAACTTCTACCCCAAAGACATCAATGTCAAG TGGAAGATTGATGGCAGTGAACGACAAAATGGCGTCCTG AACAGTTGGACTGATCAGGACAGCAAAGACAGCACCTAC | 88 |

TABLE 13-continued

| mAb/Fab name | Region | Sequence | SEQ ID NO: |
|---|---|---|---|
| | | AGCATGAGCAGCACCCTCACGTTGACCAAGGACGAGTAT GAACGACATAACAGCTATACCTGTGAGGCCACTCACAAG ACATCAACTTCACCCATTGTCAAGAGCTTCAACAGGAATG AGTGT | |
| | LC signal | ATGGAGTCTCATACTCAGGCCTTTGTATTCGCGTTTCTCTG GTTGTCTGGTGTTGATGGA | 89 |
| cAb4854 10F01B02 | V$_H$ | GATGTGCAGCTGGTGGAGTCTGGGGGAGGCTTAGTGCAG CCTGGAGGGTCCCGGAAACTCTCCTGTGCAGCCTCTGGAT TCCCTTTCAGTAGCTTTGGAATGCACTGGGTTCGTCAGGCT CCAGACAAGGGACTGGAGTGGGTCGCATACATTAGTAGT GCCAGTAATACCATCTACTATGCTGACACAGTGAAGGGCC GATTCACCGTCTCCAGAGACAATCCCAAGAACACCCTGTT CCTGCAAATGACCAGTCTAAGGTCTGAGGACACGGCCATT TATTACTGTACAAAGCGAAATTGGGACCTCTATGCTATGG ACTACTGGGGTCAAGGAACCTCAGTCACCGTCTCCTCA | 60 |
| | C$_H$ | GCCAAAACAACAGCCCCATCGGTCTATCCACTGGCCCCTG TGTGTGGAGATACAACTGGCTCCTCGGTGACTCTAGGATG CCTGGTCAAGGGTTATTTCCCTGAGCCAGTGACCTTGACC TGGAACTCTGGATCCCTGTCCAGTGGTGTGCACACCTTCC CAGCTGTCCTGCAGTCTGACCTCTACACCCTCAGCAGCTC AGTGACTGTAACCTCGAGCACCTGGCCCAGCCAGTCCATC ACCTGCAATGTGGCCCACCCGGCAAGCAGCACCAAGGTG GACAAGAAAATTGAGCCCAGAGGGCCCACAATCAAGCCC TGTCCTCCATGCAAATGCCCAGCACCTAACCTCTTGGGTG GACCATCCGTCTTCATCTTCCCTCCAAAGATCAAGGATGT ACTCATGATCTCCCTGAGCCCCATAGTCACATGTGTGGTG GTGGATGTGAGCGAGGATGACCCAGATGTCCAGATCAGC TGGTTTGTGAACAACGTGGAAGTACACACAGCTCAGACAC AAACCCATAGAGAGGATTACAACAGTACTCTCCGGGTGGT CAGTGCCCTCCCCATCCAGCACCAGGACTGGATGAGTGGC AAGGAGTTCAAATGCAAGGTCAACAACAAAGACCTCCCA GCGCCCATCGAGAGAACCATCTCAAAACCCAAAGGGTCA GTAAGAGCTCCACAGGTATATGTCTTGCCTCCACCAGAAG AAGAGATGACTAAGAAACAGGTCACTCTGACCTGCATGG TCACAGACTTCATGCCTGAAGACATTTACGTGGAGTGGAC CAACAACGGGAAAACAGAGCTAAACTACAAGAACACTGA ACCAGTCCTGGACTCTGATGGTTCTTACTTCATGTACAGC AAGCTGAGAGTGGAAAAGAAGAACTGGGTGGAAAGAAAT AGCTACTCCTGTTCAGTGGTCCACGAGGGTCTGCACAATC ACCACACGACTAAGAGCTTCTCCCGGACTCCGGGTAAA | 90 |
| | HC Signal | ATGGACTCCAGGCTCAATTTAGTTTTCCTTGTCCTTATTTT AAAAGGTGTCCAGTGT | 91 |
| | V$_L$ | GACATTGTGATGACCCAGTCTCAAAAATTCATGTCCACAT CAGTGGGAGACAGGGTCAGCATCACCTGCAAGGCCAATC AGAATGTGGGTACTGCTGTAGCCTGGTATCAACAGAAACC AGGACAATCTCCTAAACTACTGATTTATTCGACATCCAAT CGGGACACTGGAGTCCCTGACCGCTTCACAGGCAGTGGAT CTGGGACAGATTTCACTCTCACCATCAACTATATTCAATCT GAAGACCTGGCAGATTATTTCTGCCAGCAATATAGAAATT ATCCGACGTTCGGTGGAGGCACCAAGCTGGAAATCAAA | 61 |
| | C$_L$ | CGGGCTGATGCTGCACCAACTGTATCCATCTTCCCACCAT CCAGTGAGCAGTTAACATCTGGAGGTGCCTCAGTCGTGTG CTTCTTGAACAACTTCTACCCCAAAGACATCAATGTCAAG TGGAAGATTGATGGCAGTGAACGACAAAATGGCGTCCTG AACAGTTGGACTGATCAGGACAGCAAAGACAGCACCTAC AGCATGAGCAGCACCCTCACGTTGACCAAGGACGAGTAT GAACGACATAACAGCTATACCTGTGAGGCCACTCACAAG ACATCAACTTCACCCATTGTCAAGAGCTTCAACAGGAATG AGTGT | 92 |
| | LC signal | ATGGAGTCTCGTACTCAGGCCTTTGTAATCGCGTTTCTCTG GATGTCTGGTATTGATGGA | 93 |
| cAb4855 01F11A01 | V$_H$ | CAGGTTACTCTGAAAGAGTCTGGCCCTGGGATATTGCAGC CCTCCCAGACCCTCAGTCTGACTTGTTCTTTCTCTGGGTTT TCACTGAGCACTTCTGGTATGGGTGTAGGCTGGATTCGTC AGCCTTCAGGGAAGGGTCTGGAGTGGCTGGCACACATTTG GTGGAATGATGAGAAATACTATAACGCAGCCCTGAAGAG CCGGCTCACAATCTCCAAGGATACCTCCAAAAACCAGGTT TTCCTCAAGATCGCCAGTGTGGACGCTGCAGATACTGCCA CATACTACTGTGCTCGCATCACTGGTGCCTGGTTTCCTTAT TGGGGCCAAGGGACTCTGGTCACTGTCTCTGCA | 62 |
| | C$_H$ | GCCAAAACAACAGCCCCATCGGTCTATCCACTGGCCCCTG TGTGTGGAGATACAACTGGCTCCTCGGTGACTCTAGGATG CCTGGTCAAGGGTTATTTCCCTGAGCCAGTGACCTTGACC | 94 |

TABLE 13-continued

Nucleotide Sequences of Exemplary Antibodies of the Disclosure

| mAb/Fab name | Region | Sequence | SEQ ID NO: |
|---|---|---|---|
| | | TGGAACTCTGGATCCCTGTCCAGTGGTGTGCACACCTTCC CAGCTGTCCTGCAGTCTGACCTCTACACCCTCAGCAGCTC AGTGACTGTAACCTCGAGCACCTGGCCCAGCCAGTCCATC ACCTGCAATGTGGCCCACCCGGCAAGCAGCACCAAGGTG GACAAGAAAATTGAGCCCAGAGGGCCCACAATCAAGCCC TGTCCTCCATGCAAATGCCCAGCACCTAACCTCTTGGGTG GACCATCCGTCTTCATCTTCCCTCCAAAGATCAAGGATGT ACTCATGATCTCCCTGAGTCCCATGGTCACATGTGTGGTG GTGGATGTGAGCGAGGATGACCCAGATGTCCAGATCAGC TGGTTCGTGAACAACGTGGAAGTACTCACAGCTCAGACAC AAACCCATAGAGAGGATTACAACAGTACTCTCCGGGTGGT CAGTGCCCTCCCCATCCAGCACCAGGACTGGATGAGTGGC AAGGAGTTCAAATGCAAGGTCAACAACAAAGACCTCCCA GCACCCATCGAGAGAACCATCTCAAAACCCAAAGGGTCA GTAAGAGCTCCACAGGTATATGTCTTGCCTCCACCAGAAG AAGAGATGACTAAGAAACAGGTCACTCTGACCTGCATGG TCACAGACTTCATGCCTGAAGACATTTACGTGGAGTGGAC CAACAACGGGAAACAGAGCTAAACTACAAGAACACTGA ACCAGTCCTGGACTCTGATGGTTCTTACTTCATGTACAGC AAGCTGAGAGTGGAAAAGAAGAACTGGGTGGAAAGAAAT AGCTACTCCTGTTCAGTGGTCCACGAGGGTCTGCACAATC ACCACACGACTAAGAGCTTCTCCCGGACTCCGGGTAAA | |
| | HC Signal | ATGGGCAGACTTACTTCTTCATTCTTGCTACTGATTGTCCC TGCATATGTCCTGTCC | 95 |
| | V_L | GACATTGTGATGACTCAGTCTCCAGCCACCCTGTCTGTGA CTCCAGGAGATAGAGTCTCTCTTTCCTGCAGGGCCAGTCA GCATATTAGCGAATACTTACACTGGTATCAACAAAAATCA CACGAGTCTCCAAGGCTTCTCATCAAATATGGTTCCCAAT CCATCTCTGGGATCCCCTCCAGGTTCAGTGGCAGTGGATC AGGGTCAGATTTCACTCTCAATATCAACAGTGTGGAACCT GAAGATGTTGGAGTGTATTACTGTCAAAATGGTCACAGCT TTCCGTACACGTTCGGAGGGGGGACCAAGCTGGAAATAA AA | 63 |
| | C_L | CGGGCTGATGCTGCACCAACTGTATCCATCTTCCCACCAT CCAGTGAGCAGTTAACATCTGGAGGTGCCTCAGTCGTGTG CTTCTTGAACAACTTCTACCCCAAAGACATCAATGTCAAG TGGAAGATTGATGGCAGTGAACGACAAAATGGCGTCCTG AACAGTTGGACTGATCAGGACAGCAAAGACAGCACCTAC AGCATGAGCAGCACCCTCACGTTGACCAAGGACGAGTAT GAACGACATAACAGCTATACCTGTGAGGCCACTCACAAG ACATCAACTTCACCCATTGTCAAGAGCTTCAACAGGAATG AGTGT | 96 |
| | LC signal | ATGGGTGTCCACTTCTCAGCTCCTTGGACTTTTGCTTTTCTG GACTTCAGCCTCCAGATGT | 97 |
| cAb5775 12D02 | V_H | GAGGTCCAGCTGCAACAGTCTGGACCTGAGCTGGTGAAG CCTGGAGCCTCAATGAAGATATCTTGCAAGGCTTCTGGTT ACTCATTCACTGCCTACACCATGAACTGGGTGAAGCAGAG CCATGGAGAGAACCTTGAGTGGATTGGACTTATTAATCCT TATAATGGTGGTACTACCTACAACCAGAAGTTCAAGGGCA AGGCCACATTAACTGTAGACAAGTCATCCAGCACAGCCTA CATGGAGCTCCTCAGTCTGACATCTGAGGACTCTGCAGTC TATTACTGTGCATCATATGATTACGGCTATGCTATGGACT ACTGGGGTCAAGGAACCTCAGTCACCGTCTCCTCA | 64 |
| | C_H | GCCAAAACGACACCCCCATCTGTCTATCCACTGGCCCCTG GATCTGCTGCCCAAACTAACTCCATGGTGACCCTGGGATG CCTGGTCAAGGGCTATTTCCCTGAGCCAGTGACAGTGACC TGGAACTCTGGATCCCTGTCCAGCGGTGTGCACACCTTCC CAGCTGTCCTGCAGTCTGACCTCTACACTCTGAGCAGCTC AGTGACTGTCCCCTCCAGCACCTGGCCCAGCGAGACCGTC ACCTGCAACGTTGCCCACCCGGCCAGCAGCACCAAGGTG GACAAGAAAATTGTGCCCAGGGATTGTGGTTGTAAGCCTT GCATATGTACAGTCCCAGAAGTATCATCTGTCTTCATCTTC CCCCCAAAGCCCAAGGATGTGCTCACCATTACTCTGACTC CTAAGGTCACGTGTGTTGTGGTAGACATCAGCAAGGATGA TCCCGAGGTCCAGTTCAGCTGGTTTGTAGATGATGTGGAG GTGCACACAGCTCAGACGCAACCCCGGGAGGAGCAGTTC AACAGCACTTTCCGCTCAGTCAGTGAACTTCCCATCATGC ACCAGGACTGGCTCAATGGCAAGGAGTTCAAATGCAGGG TCAACAGTGCAGCTTTCCCTGCCCCCATCGAGAAAACCAT CTCCAAAACCAAAGGCAGACCGAAGGCTCCACAGGTGTA CACCATTCCACCTCCCAAGGAGCAGATGGCCAAGGATAA AGTCAGTCTGACCTGCATGATAACAGACTTCTTCCCTGAA GACATTACTGTGGAGTGGCAGTGGAATGGGCAGCCAGCG GAGAACTACAAGAACACTCAGCCCATCATGGACACAGAT | 98 |

TABLE 13-continued

| mAb/Fab name | Region | Sequence | SEQ ID NO: |
|---|---|---|---|
| | | GGCTCTTACTTCGTCTACAGCAAGCTCAATGTGCAGAAGA GCAACTGGGAGGCAGGAAATACTTTCACCTGCTCTGTGTT ACATGAGGGCCTGCACAACCACCATACTGAGAAGAGCCT CTCCCACTCTCCTGGTAAA | |
| | HC Signal | ATGGGATGGAGCTGGATCTTTCTCTTCCTCCTGTCAGGAA CTGCAGGTGTCCACTCT | 99 |
| | V_L | GATGTTTTGATGACCCAAACTCCACTCTCCCTGCCTGTCAG TCTTGGAGATCAAGCCTCCATCTCTTGCAGATCTAGTCAG AGCATTGTACATAGAAATGGAAACACCTATCTAGAATGGT ACCTGCAGAAACCAGGCCAGTCTCCAAAGCTCCTGATCTA CAAAGTTTCCAACCGATTTTCTGGGGTCCCAGACAGGTTC AGTGGCAGTGGATCAGGGACAGATTTCACACTCAAGATC AGCAGAGTGGAGGCTGAGGATCTGGGAGTTTATTACTGCT TTCAAGGTTCACATGTTCCGTGGACGTTCGGTGGAGGCAC CAAGCTGGAAATCAAA | 65 |
| | C_L | CGGGCTGATGCTGCACCAACTGTATCCATCTTCCCACCAT CCAGTGAGCAGTTAACATCTGGAGGTGCCTCAGTCGTGTG CTTCTTGAACAACTTCTACCCCAAAGACATCAATGTCAAG TGGAAGATTGATGGCAGTGAACGACAAAATGGCGTCCTG AACAGTTGGACTGATCAGGACAGCAAAGACAGCACCTAC AGCATGAGCAGCACCCTCACGTTGACCAAGGACGAGTAT GAACGACATAACAGCTATACCTGTGAGGCCACTCACAAG ACATCAACTTCACCCATTGTCAAGAGCTTCAACAGGAATG AGTGT | 100 |
| | LC signal | ATGAAGTTGCCTGTTAGGCTGTTGGTGCTGATGTTCTGGA TTCCTGCTTCCAGTAGT | 101 |
| cAb5776 12A12 | V_H | GAGGTCCAGCTGCAACAGTCTGGACCTGAGCTGGTGAAG CCTGGAGTTTCAATGAAGATATCCTGCAAGGCTTCTGGTT ACTCATTCACTGCCTACACTATGAATTGGGTGAAGCAGAG TCATGGAGAGAACCTTGAGTGGATTGGACTTATTAATCCT TATAATGGTGGTACTACCTACAACCAGAAGTTCAAGGGCA AGGCCACATTAACTGTAGACAAGTCATCCAGCACAGCCTA CATGGAGCTCCTCAGTCTGACATCTGAGGACTCTGCAGTC TATTACTGTGCATCATATGATTACGGCTATGCTATGGACT ACTGGGGTCAAGGAACCTCAGTCACCGTCTCCTCA | 66 |
| | C_H | GCCAAAACGACACCCCCATCTGTCTATCCACTGGCCCCTG GATCTGCTGCCCAAACTAACTCCATGGTGACCCTGGGATG CCTGGTCAAGGGCTATTTCCCTGAGCCAGTGACAGTGACC TGGAACTCTGGATCCCTGTCCAGCGGTGTGCACACCTTCC CAGCTGTCCTGCAGTCTGACCTCTACACTCTGAGCAGCTC AGTGACTGTCCCCTCCAGCACCTGGCCCAGCGAGACCGTC ACCTGCAACGTTGCCCACCCGGCCAGCAGCACCAAGGTG GACAAGAAAATTGTGCCCAGGGATTGTGGTTGTAAGCCTT GCATATGTACAGTCCCAGAAGTATCATCTGTCTTCATCTTC CCCCCAAAGCCCAAGGATGTGCTCACCATTACTCTGACTC CTAAGGTCACGTGTGTTGTGGTAGACATCAGCAAGGATGA TCCCGAGGTCCAGTTCAGCTGGTTTGTAGATGATGTGGAG GTGCACACAGCTCAGACGCAACCCCGGGAGGAGCAGTTC AACAGCACTTTCCGCTCAGTCAGTGAACTTCCCATCATGC ACCAGGACTGGCTCAATGGCAAGGAGTTCAAATGCAGGG TCAACAGTGCAGCTTTCCCTGCCCCCATCGAGAAAACCAT CTCCAAAACCAAAGGCAGACCGAAGGCTCCACAGGTGTA CACCATTCCACCTCCCAAGGAGCAGATGGCCAAGGATAA AGTCAGTCTGACCTGCATGATAACAGACTTCTTCCCTGAA GACATTACTGTGGAGTGGCAGTGGAATGGGCAGCCAGCG GAGAACTACAAGAACACTCAGCCCATCATGGACACAGAT GGCTCTTACTTCGTCTACAGCAAGCTCAATGTGCAGAAGA GCAACTGGGAGGCAGGAAATACTTTCACCTGCTCTGTGTT ACATGAGGGCCTGCACAACCACCATACTGAGAAGAGCCT CTCCCACTCTCCTGGTAAA | 102 |
| | HC Signal | ATGGGATGGAGCTGGATCTTTCTCTTCCTCCTGTCAGGAA CTGCAGGTGTCCACTCT | 103 |
| | V_L | GATGTTTTGATGACCCAAACTCCACTCTCCCTGCCTGTCAG TCTTGGAGATCAAGCCTCCATCTCTTGCAGATCTAGTCAG AGCATTGTACATCGTAGTGGAAACACCTATTTAGAATGGT ACCTGCAGAAACCAGGCCAGTCTCCAAAGCTCCTGATCTA CAAAGTTTCCAACCGATTTTCTGGGGTCCCAGACAGGTTC AGTGGCAGTGGATCAGGGACAGATTTCACACTCAAGATC AGCAGAGTGGAGGCTGAGGATCTGGGAGTTTATTACTGCT TTCAAGGTTCACATGTTCCGTGGACGTTCGGTGGAGGCAC CAAGTTGGAAATCAAA | 67 |
| | C_L | CGGGCTGATGCTGCACCAACTGTATCCATCTTCCCACCAT CCAGTGAGCAGTTAACATCTGGAGGTGCCTCAGTCGTGTG CTTCTTGAACAACTTCTACCCCAAAGACATCAATGTCAAG | 104 |

TABLE 13-continued

| mAb/Fab name | Region | Sequence | SEQ ID NO: |
|---|---|---|---|
| | | TGGAAGATTGATGGCAGTGAACGACAAAATGGCGTCCTG<br>AACAGTTGGACTGATCAGGACAGCAAAGACAGCACCTAC<br>AGCATGAGCAGCACCCTCACGTTGACCAAGGACGAGTAT<br>GAACGACATAACAGCTATACCTGTGAGGCCACTCACAAG<br>ACATCAACTTCACCCATTGTCAAGAGCTTCAACAGGAATG<br>AGTGT | |
| | LC signal | ATGAAGTTGCCTGTTAGGCTGTTGGTGCTGATGTTCTGGA<br>TTCCTGCTTCCAGCAGT | 105 |
| cAb5777 12D08 | V_H | GAGGTTCAACTGCAGCAGTCTGGGGCAGAGCTTGTGAAG<br>CCAGGGGCCTCAGTCAAGTTGTCCTGCACAGCTTCTGGCT<br>TCAACATTAAAGACACCTATATGCACTGGGTGAAACAGA<br>GGCCTGAGCAGGGCCTGATTTGGATTGGAAACATTGATCC<br>TGCGAATGGTCATACTAAATATGCCCCGAAGTTCCAGGGC<br>AAGGCCACTATCACAGCAGACACATCCTCCAACACAGCCT<br>ACCTGCAGCTCAGCAGCCTGACATCTGAGGACACTGCCGT<br>CTATTACTGTGCTAGATCTAATGATTACGACGTCGACTTTG<br>ACTACTGGGGCCAAGGCACCACTCTCACAGTCTCCTCA | 68 |
| | C_H | GCCAAAACAACAGCCCCATCGGTCTATCCACTGGCCCCTG<br>TGTGTGGAGATACAACTGGCTCCTCGGTGACTCTAGGATG<br>CCTGGTCAAGGGTTATTTCCCTGAGCCAGTGACCTTGACC<br>TGGAACTCTGGATCCCTGTCCAGTGGTGTGCACACCTTCC<br>CAGCTGTCCTGCAGTCTGACCTCTACACCCTCAGCAGCTC<br>AGTGACTGTAACCTCGAGCACCTGGCCCAGCCAGTCCATC<br>ACCTGCAATGTGGCCCACCCGGCAAGCAGCACCAAGGTG<br>GACAAGAAAATTGAGCCCAGAGGGCCCACAATCAAGCCC<br>TGTCCTCCATGCAAATGCCCAGCACCTAACCTCTTGGGTG<br>GACCATCCGTCTTCATCTTCCCTCCAAAGATCAAGGATGT<br>ACTCATGATCTCCCTGAGCCCCATAGTCACATGTGTGGTG<br>GTGGATGTGAGCGAGGATGACCCAGATGTCCAGATCAGC<br>TGGTTTGTGAACAACGTGGAAGTACACACAGCTCAGACAC<br>AAACCCATAGAGAGGATTACAACAGTACTCTCCGGGTGGT<br>CAGTGCCCTCCCCATCCAGCACCAGGACTGGATGAGTGGC<br>AAGGAGTTCAAATGCAAGGTCAACAACAAAGACCTCCCA<br>GCGCCCATCGAGAGAACCATCTCAAAACCCAAAGGGTCA<br>GTAAGAGCTCCACAGGTATATGTCTTGCCTCCACCAGAAG<br>AAGAGATGACTAAGAAACAGGTCACTCTGACCTGCATGG<br>TCACAGACTTCATGCCTGAAGACATTTACGTGGAGTGGAC<br>CAACAACGGGAAAACAGAGCTAAACTACAAGAACACTGA<br>ACCAGTCCTGGACTCTGATGGTTCTTACTTCATGTACAGC<br>AAGCTGAGAGTGGAAAAGAAGAACTGGGTGGAAAGAAAT<br>AGCTACTCCTGTTCAGTGGTCCACGAGGGTCTGCACAATC<br>ACCACACGACTAAGAGCTTCTCCCGGACTCCGGGTAAA | 106 |
| | HC Signal | ATGAAATGCAGCTGGGTTATCTTCTTCCTGATGGCAGTGG<br>TTACAGGGGTCAATTCA | 107 |
| | V_L | GACATTGTGATGTCACAGTCTCCATCCTCCCTGGCTGTGTC<br>AGCAGGAGAGAAGGTCACTATGAGCTGCAAATCCAGTCA<br>GAGTCTGCTCAACAGTAGAACCCGAAAGAACTACTTGGCT<br>TGGTACCAGCAGAAACCAGGGCAGTCTCCTAAACTGCTGA<br>TCTACTGGGCATCCACTAGGGAATCTGGGGTCCCTGATCG<br>CTTCACAGGCAGTGGATCTGGGACAGATTTCAGTCTCACC<br>ATCAGCAGTGTGCAGGCTGAAGACCTGGCAGTTTATTACT<br>GCAAGCAATCTTATAATCTATACACGTTCGGAGGGGGGAC<br>CAAGCTGGAAATAAAA | 69 |
| | C_L | CGGGCTGATGCTGCACCAACTGTATCCATCTTCCCACCAT<br>CCAGTGAGCAGTTAACATCTGGAGGTGCCTCAGTCGTGTG<br>CTTCTTGAACAACTTCTACCCCAAAGACATCAATGTCAAG<br>TGGAAGATTGATGGCAGTGAACGACAAAATGGCGTCCTG<br>AACAGTTGGACTGATCAGGACAGCAAAGACAGCACCTAC<br>AGCATGAGCAGCACCCTCACGTTGACCAAGGACGAGTAT<br>GAACGACATAACAGCTATACCTGTGAGGCCACTCACAAG<br>ACATCAACTTCACCCATTGTCAAGAGCTTCAACAGGAATG<br>AGTGT | 108 |
| | LC signal | ATGGATTCACGGGCCCAGGTTCTTATATTGCTGCTGCAAT<br>GGGTATCTGGTACCTGTGGG | 109 |
| cAb5778 13G04 | V_H | GAGGTCCACCTGCAACAGTCTGGACCTGAGCTGGTGAAGC<br>CTGGAGCTTCAATGAAGATATCCTGCAAGGCTTCTGGTTA<br>CTCCTTCACTGCCTACACCATGAACTGGGTGAAACAGAGC<br>CATGGAAAGAACCTTGAGTGGATTGGACTTATTAATCCTT<br>ACAATGGTGGTACTACCTACAACCAGAAATTCAAGGGCA<br>AGGCCACATTAACTGTAGACAAGTCATCCAGCACAGCCTA<br>CATGGAGCTCCTCAGTCTGACATCTGAGGACTCTGCAGTC<br>TATTACTGTGCTTCTTACTACGGTGGTAGGGGCTGGTACTT<br>CGATGTCTGGGGCGCAGGGACCTCGGTCACCGTCTCCTCA | 70 |

TABLE 13-continued

Nucleotide Sequences of Exemplary Antibodies of the Disclosure

| mAb/Fab name | Region | Sequence | SEQ ID NO: |
|---|---|---|---|
| | C$_H$ | GCCAAAACGACACCCCCATCTGTCTATCCACTGGCCCCTG GATCTGCTGCCCAAACTAACTCCATGGTGACCCTGGGATG CCTGGTCAAGGGCTATTTCCCTGAGCCAGTGACAGTGACC TGGAACTCTGGATCCCTGTCCAGCGGTGTGCACACCTTCC CAGCTGTCCTGCAGTCTGACCTCTACACTCTGAGCAGCTC AGTGACTGTCCCCTCCAGCACCTGGCCCAGCGAGACCGTC ACCTGCAACGTTGCCCACCCGGCCAGCAGCACCAAGGTG GACAAGAAAATTGTGCCCAGGGATTGTGGTTGTAAGCCTT GCATATGTACAGTCCCAGAAGTATCATCTGTCTTCATCTTC CCCCCAAAGCCCAAGGATGTGCTCACCATTACTCTGACTC CTAAGGTCACGTGTGTTGTGGTAGACATCAGCAAGGATGA TCCCGAGGTCCAGTTCAGCTGGTTTGTAGATGATGTGGAG GTGCACACAGCTCAGACGCAACCCCGGGAGGAGCAGTTC AACAGCACTTTCCGCTCAGTCAGTGAACTTCCCATCATGC ACCAGGACTGGCTCAATGGCAAGGAGTTCAAATGCAGGG TCAACAGTGCAGCTTTCCCTGCCCCCATCGAGAAAACCAT CTCCAAAACCAAAGGCAGACCGAAGGCTCCACAGGTGTA CACCATTCCACCTCCCAAGGAGCAGATGGCCAAGGATAA AGTCAGTCTGACCTGCATGATAACAGACTTCTTCCCTGAA GACATTACTGTGGAGTGGCAGTGGAATGGGCAGCCAGCG GAGAACTACAAGAACACTCAGCCCATCATGGACACAGAT GGCTCTTACTTCGTCTACAGCAAGCTCAATGTGCAGAAGA GCAACTGGGAGGCAGGAAATACTTTCACCTGCTCTGTGTT ACATGAGGGCCTGCACAACCACCATACTGAGAAGAGCCT CTCCCACTCTCCTGGTAAA | 110 |
| | HC Signal | ATGGGATGGAGCTGGATCTTTCTCTTCCTCCTGTCAGGAA CTGCAGGTGTCCACTCT | 111 |
| | V$_L$ | GACATTGTGCTGACACAGTCTCCTGCTTCCTTAGCTGTATC TCTGGGGCAGAGGGCCACCATCTCATGCAGGGCCAGCAA AAGTGTCAGTACATCTGGCTATAGTTATGTTCACTGGTAC CAACAGAAACCAGGACAGCCACCCAAACTCCTCATCTATC TTGCATCCAACCTAGAATCTGGGGTCCCTGCCAGGTTCAG TGGCAGTGGGTCTGGGACAGACTTCACCCTCAACATCCAT CCTGTGGAGGAGGAAGATGCTGCAACCTATTACTGTCAGA ATAGTAGGGAACTTCCGTACACGTTCGGAGGGGGGACCA AGCTGGAAATGAAA | 71 |
| | C$_L$ | CGGGCTGATGCTGCACCAACTGTATCCATCTTCCCACCAT CCAGTGAGCAGTTAACATCTGGAGGTGCCTCAGTCGTGTG CTTCTTGAACAACTTCTACCCCAAAGACATCAATGTCAAG TGGAAGATTGATGGCAGTGAACGACAAAATGGCGTCCTG AACAGTTGGACTGATCAGGACAGCAAAGACAGCACCTAC AGCATGAGCAGCACCCTCACGTTGACCAAGGACGAGTAT GAACGACATAACAGCTATACCTGTGAGGCCACTCACAAG ACATCAACTTCACCCATTGTCAAGAGCTTCAACAGGAATG AGTGT | 112 |
| | LC signal | ATGGAGACAGACACACTCCTGTTATGGGTACTGCTGCTCT GGGTTCCAGGTTCCACTGGT | 113 |

Example 8-Development of Reagents for Anti-CEMIP/KIAA1199 Validation and Pre-Clinical In Vivo Models for Testing KIAA1199 Neutralization for Treating or Preventing Brain Metastasis Numerous KIAA1199 (CEMIP) CRISPR KO clones in MKN45 cells have been generated, which were screened first at the genomic level. Of 6 potential KO clones, 4 clones, KO6, KO11, KO13 and KO18 were confirmed as lacking cell surface CEMIP expression based on flow cytometry, which can be used to validate the specificity of anti-human CEMIP/KIAA1199 antibodies (FIG. 16). Interestingly, clone KO7 has a 50% reduction in the surface levels of CEMIP/KIAA1199 compared with the parental wild-type cell line, which may be useful in performing studies on neutralization efficiency of our antibodies at various levels (high, medium, low) of antigen expression. Thus, these clones and their exosomes can be used as negative controls on platforms testing the binding and neutralizing ability of anti-KIAA1199/CEMIP antibodies.

Discussion of Examples

Gaining insight into the mechanisms of BrM and the specific contribution of tumour-derived exosomes to this process provides opportunities for early diagnosis and therapeutic targeting of BrM. It is now shown that pre-conditioning the brain microenvironment with exosomes derived from brain metastatic cells generates a metastatic niche that supports colonization. CEMIP, a protein expressed in the brain and involved in memory and synaptic formation (Abe et al., "Mutations in the Gene Encoding KIAA1199 Protein, an Inner-ear Protein Expressed in Deiters' Cells and the Fibrocytes, as the Cause of Nonsyndromic Hearing Loss," *J Hum Genet* 48:564-570 (2003); Yoshino et al., "Distribution and Function of Hyaluronan Binding Protein Involved in Hyaluronan Depolymerization (HYBID, KIAA1199) in the Mouse Central Nervous System," *Neuroscience* 347:1-10 (2017), which are hereby incorporated by reference in their entirety) was identified as specifically enriched in brain metastatic exosomes. While cellular expression of CEMIP has been previously associated with cancer progression (Zhang et al., "KIAA1199 and its Biological Role in Human Cancer and Cancer Cells (review)," *Oncol Rep* 31:1503-1508 (2014), which is hereby incorporated by reference in its entirety) and inflammatory diseases (Yang et al., "KIAA1199 as a Potential Diagnostic Biomarker of Rheumatoid Arthritis Related to Angiogenesis," *Arthritis Res Ther* 17:140 (2015); Shimizu et al., "Hyaluronan-Binding Protein Involved in Hyaluronan Depolymerization Is Up-Regulated and Involved in Hyaluronan Degradation in Human Osteoarthritic Cartilage," *Am J Pathol* 188:2109-2119 (2018), which are hereby incorporated by reference in their entirety) this study reveals a role for exosomal CEMIP in brain metastasis.

It is demonstrated that CEMIP targeting impairs brain metastatic ability but not primary tumor growth, underscoring that CEMIP functions are exerted upon the brain microenvironment. CEMIP loss reduced the number of brain metastatic colonies formed in an experimental brain metastatic setting, but not in situ brain outgrowth, suggesting CEMIP is critical in the early phases of brain colonization. Remarkably, exosomal CEMIP pre-conditioning enhanced brain metastatic colonization, restoring the ability of CEMIP-depleted cells to associate with brain vasculature.

Brain metastatic cancer cells often display angiocentric growth in the brain (Winkler, "Hostile Takeover: How Tumours Hijack Pre-existing Vascular Environments to Thrive," *J Pathol* 242:267-272 (2017), which is hereby incorporated by reference in its entirety) hijacking existing vasculature and generating tortuous and enlarged vessels (Fidler, "The Role of the Organ Microenvironment in Brain Metastasis," *Semin Cancer Biol* 21:107-112 (2011), which is hereby incorporated by reference in its entirety) typically through an angiogenic strategy known as non-sprouting or intussusceptive angiogenesis (IA). This is distinct from tumour neo-angiogenesis observed outside of the brain. Thus, IA allows incorporation and growth of host vasculature into developing metastases likely through the combined action of diverse tumour cell-surface receptors and tumour-secreted factors, however, its regulation remains mostly unexplored (Burri et al., "Intussusceptive Angiogenesis: its Emergence, its Characteristics, and its Significance," *Dev Dyn* 231:474-488 (2004), which is hereby incorporated by reference in its entirety). The work showing exosomal CEMIP promotes vascular network formation and triggers a pro-inflammatory gene signature in the brain provides mechanistic insight into IA-dependent BrM. Vessel morphogenesis was among the top biological processes reprogrammed by exosomal CEMIP in BrECs and may underlie the changes in BrEC branching and metastatic vascular remodeling observed. Exosomal CEMIP-dependent BrEC gene expression changes associated with inositol signaling, cell junction and adhesion (FIG. 11D) are consistent with previous studies demonstrating CEMIP interacts with inositol pathway-related proteins, promoting migration via calcium-mediated cytoskeletal re-arrangements, and stimulating vessel growth and enlargement in vivo. Exosomal CEMIP also led to Notch signaling inhibition and ephrin B2 downregulation in BrECs, both processes that stimulate IA (Dimova et al., "Inhibition of Notch Signaling Induces Extensive Intussusceptive Neo-angiogenesis by Recruitment of Mononuclear Cells," *Angiogenesis* 16:921-937 (2013), which is hereby incorporated by reference in its entirety) while in microglia it induced a pro-inflammatory signature consistent with neuro-inflammation mediated-IA (Giacomini et al., "Brain Angioarchitecture and Intussusceptive Microvascular Growth in a Murine Model of Krabbe Disease," *Angiogenesis* 18:499-510 (2015), which is hereby incorporated by reference in its entirety).

Microglia, known players in brain microenvironment reshaping and BrM, exhibited gene expression alterations in additional inflammatory pathways involved in rheumatoid arthritis, neuroinflammation, immune cell adhesion and vascular transmigration. Exosomal CEMIP upregulated pro-inflammatory cytokines Tnf, Ptgs2, and Ccl/Cxcl in microglia, that promote BrM and blood-brain barrier dysfunction (Doron et al., "A Blazing Landscape: Neuroinflammation Shapes Brain Metastasis," *Cancer Res* 79:423-436 (2019), which is hereby incorporated by reference in its entirety) consistent with the vascular leakiness induced by brain metastatic exosomes that has been observed (Tominaga et al., "Brain Metastatic Cancer Cells Release MicroRNA-181c-containing Extracellular Vesicles Capable of Destructing Blood-brain Barrier," *Nat Commun* 6:6716 (2015), which is hereby incorporated by reference in its entirety). The results described herein results also agree with recent findings that extracellular vesicles interact with blood vessel-associated microglia associated within primary brain tumours (van der Vos K E et al., "Directly Visualized Glioblastoma-derived Extracellular Vesicles Transfer RNA to Microglia/Macrophages in the Brain," *Neuro Oncol* 18:58-69 (2016), which is hereby incorporated by reference in its entirety).

Taken together, the findings described herein suggest that exosomal CEMIP induces a pro-inflammatory state in the brain vascular niche that supports brain metastatic colonization. A more detailed characterization of the pathways downstream of exosomal CEMIP should shed light on the contribution of Wnt signaling and intracellular calcium release for pre-metastatic niche formation in the brain.

The clinical relevance of CEMIP in BrM is underscored by significantly increased expression in human brain metastases, compared to adjacent brain stroma and non-brain metastatic lesions, and association with poor patient survival. Moreover, CEMIP expression at the PT level correlated with metastasis to brain but not other organs. Further, high levels of CEMIP expression were associated with rapid metastatic progression to the brain, suggesting that CEMIP may be a reliable biomarker of brain metastatic risk.

Overall, these findings identify role for CEMIP in BrM, demonstrating it is a prognostic biomarker and therapeutic target for BrM.

---

What is claimed:

1. A method comprising:

selecting a subject having a primary tumor;

obtaining, from the selected subject, a sample containing tumor-derived exosomes from primary tumor cells, wherein the tumor-derived exosomes carry tumor-associated surface molecules or lack CD45, CD80, and CD86 expression;

isolating and/or enriching the tumor-derived exosomes from said sample based on said surface molecules or lack thereof; and detecting, in said isolated tumor-derived exosomes, expression levels of cell migration-inducing and hyaluronan-binding protein (CEMIP).

2. The method of claim 1, wherein the primary tumor is a breast tumor, lung tumor, melanoma, renal tumor, colorectal tumor, esophageal tumor, small intestine tumor, stomach tumor, bladder tumor, liver tumor, pancreatic tumor, brain tumor, or prostate tumor.

3. The method of claim 1, wherein detecting comprises:

contacting the isolated and/or enriched exosomes with one or more reagents suitable to detect exosomal protein levels of CEMIP in an immunoassay, whereby CEMIP expression is detected as a result of said contacting.

4. The method of claim 3, wherein the immunoassay is selected from the group consisting of immunohistochemical assay, radioimmunoassay, enzyme-linked immunosorbent assay (ELISA), immunoradiometric assay, gel diffusion precipitation reaction, immunodiffusion assay, in situ immunoassay, Western blot, precipitation reaction, complement fixation assay, immunofluorescence assay, and immunoelectrophoresis assay.

5. The method of claim 1 further comprising:
quantifying the expression level of CEMIP in said isolated and/or enriched exosomes based on said detecting.

6. A method of identifying a subject's risk of developing metastatic brain disease, said method comprising:
selecting a subject having a primary tumor;
isolating and/or enriching, from said subject, a sample comprising tumor-derived exosomes derived from primary tumor cells, wherein the tumor-derived exosomes carry tumor-associated surface molecules or lack CD45, CD80, and CD86 expression;
detecting an increase in cell migration-inducing and hyaluronan-binding protein (CEMIP) expression in said tumor-derived exosomes relative to average CEMIP expression in a subject with metastasis to organ sites other than the brain, or without metastasis;
prognosing that the subject has an increased risk of developing metastatic brain disease based on said detecting increased expression of CEMIP; and
administering, to the subject prognosed to have an increased risk of developing metastatic brain disease, a brain metastasis prophylactic treatment suitable for inhibiting metastatic brain disease.

7. The method of claim 6, wherein the sample is a liquid biopsy sample.

8. The method of claim 6, wherein the primary tumor is a breast tumor, lung tumor, melanoma, renal tumor, colorectal tumor, esophageal tumor, small intestine tumor, stomach tumor, bladder tumor, liver tumor, pancreatic tumor, brain tumor, or prostate tumor.

9. The method of claim 6, wherein said detecting comprises:
contacting the isolated and/or enriched sample with one or more reagents suitable to detect protein levels of CEMIP in an immunoassay, whereby CEMIP expression is detected as a result of said contacting.

10. The method of claim 9, wherein the immunoassay is selected from the group consisting of immunohistochemical assay, radioimmunoassay, enzyme-linked immunosorbent assay (ELISA), immunoradiometric assay, gel diffusion precipitation reaction, immunodiffusion assay, in situ immunoassay, Western blot, precipitation reaction, complement fixation assay, immunofluorescence assay, and immunoelectrophoresis assay.

11. The method of claim 6, wherein said detecting comprises:
contacting the isolated sample with one or more reagents suitable to detect nucleic acid levels of CEMIP in a nucleic acid detection assay, whereby CEMIP expression is detected as a result of said contacting.

12. The method of claim 11, wherein the nucleic acid detection assay is selected from the group consisting of a quantitative polymerase chain reaction (qPCR) assay, a quantitative reverse-transcription PCR assay, a solid-phase nucleic acid detection assay, and a next-generation sequencing assay.

13. The method of claim 11, wherein the nucleic acid levels comprise mRNA levels.

14. The method of claim 8 further comprising:
quantifying the expression level of CEMIP in said isolated sample based on said detecting.

15. The method of claim 14, wherein an increase in primary tumor cell derived exosomal expression level of CEMIP relative to CEMIP expression level in non-tumor cell derived exosomes identifies an increased risk of developing brain metastatic disease for said subject.

16. A method of inhibiting metastatic brain disease in a subject, said method comprising:
selecting a subject having a primary tumor,
isolating and/or enriching, from said subject, a sample comprising tumor-derived exosomes derived from primary tumor cells, wherein the tumor-derived exosomes carry tumor-associated surface molecules or lack CD45, CD80, and CD86 expression, and wherein expression level of cell migration-inducing and hyaluronan-binding protein (CEMIP) from said exosomes derived from primary tumor cells is increased relative to average CEMIP expression levels in exosomes derived from non-tumor cells, and
administering, to the selected subject, a brain metastasis prophylactic treatment suitable for inhibiting metastatic brain disease.

17. The method of claim 16, wherein the primary tumor is a breast tumor, lung tumor, melanoma, renal tumor, colorectal tumor, esophageal tumor, small intestine tumor, stomach tumor, bladder tumor, liver tumor, pancreatic tumor, brain tumor, or prostate tumor.

18. The method of claim 16, wherein the prophylactic treatment includes whole brain radiation therapy.

19. The method of claim 16, wherein the prophylactic treatment comprises one more inhibitors of human epidermal growth factor receptor 2 (HER2), vascular endothelial growth factor receptor (VEGFR), histone deacetylase (HDAC), integrin $\alpha v\beta 3$, phosphodiesterase 5 (PDE5), proto-oncogene B-Raf, polo-like kinase 1 (Plk1), microtubule function, phosphatidylinositide 3-kinase (PI3K), epidermal growth factor receptor (EGFR), angiopoietin-2 (Ang-2), PTGS2 (COX-2), and cathepsin S.

* * * * *

SEQUENCE LISTING

<160> NUMBER OF SEQ ID NOS: 117

<210> SEQ ID NO 1
<211> LENGTH: 1361
<212> TYPE: PRT
<213> ORGANISM: Homo sapiens

<400> SEQUENCE: 1

```
Met Gly Ala Ala Gly Arg Gln Asp Phe Leu Phe Lys Ala Met Leu Thr
1               5                   10                  15

Ile Ser Trp Leu Thr Leu Thr Cys Phe Pro Gly Ala Thr Ser Thr Val
            20                  25                  30

Ala Ala Gly Cys Pro Asp Gln Ser Pro Glu Leu Gln Pro Trp Asn Pro
        35                  40                  45

Gly His Asp Gln Asp His His Val His Ile Gly Gln Gly Lys Thr Leu
    50                  55                  60

Leu Leu Thr Ser Ser Ala Thr Val Tyr Ser Ile His Ile Ser Glu Gly
65                  70                  75                  80

Gly Lys Leu Val Ile Lys Asp His Asp Glu Pro Ile Val Leu Arg Thr
                85                  90                  95

Arg His Ile Leu Ile Asp Asn Gly Gly Glu Leu His Ala Gly Ser Ala
            100                 105                 110

Leu Cys Pro Phe Gln Gly Asn Phe Thr Ile Ile Leu Tyr Gly Arg Ala
            115                 120                 125

Asp Glu Gly Ile Gln Pro Asp Pro Tyr Tyr Gly Leu Lys Tyr Ile Gly
    130                 135                 140

Val Gly Lys Gly Gly Ala Leu Glu Leu His Gly Gln Lys Lys Leu Ser
145                 150                 155                 160

Trp Thr Phe Leu Asn Lys Thr Leu His Pro Gly Gly Met Ala Glu Gly
            165                 170                 175

Gly Tyr Phe Phe Glu Arg Ser Trp Gly His Arg Gly Val Ile Val His
            180                 185                 190

Val Ile Asp Pro Lys Ser Gly Thr Val Ile His Ser Asp Arg Phe Asp
            195                 200                 205

Thr Tyr Arg Ser Lys Lys Glu Ser Glu Arg Leu Val Gln Tyr Leu Asn
    210                 215                 220

Ala Val Pro Asp Gly Arg Ile Leu Ser Val Ala Val Asn Asp Glu Gly
225                 230                 235                 240

Ser Arg Asn Leu Asp Asp Met Ala Arg Lys Ala Met Thr Lys Leu Gly
            245                 250                 255

Ser Lys His Phe Leu His Leu Gly Phe Arg His Pro Trp Ser Phe Leu
            260                 265                 270

Thr Val Lys Gly Asn Pro Ser Ser Ser Val Glu Asp His Ile Glu Tyr
            275                 280                 285

His Gly His Arg Gly Ser Ala Ala Ala Arg Val Phe Lys Leu Phe Gln
    290                 295                 300

Thr Glu His Gly Glu Tyr Phe Asn Val Ser Leu Ser Ser Glu Trp Val
305                 310                 315                 320

Gln Asp Val Glu Trp Thr Glu Trp Phe Asp His Asp Lys Val Ser Gln
            325                 330                 335

Thr Lys Gly Gly Glu Lys Ile Ser Asp Leu Trp Lys Ala His Pro Gly
            340                 345                 350

Lys Ile Cys Asn Arg Pro Ile Asp Ile Gln Ala Thr Thr Met Asp Gly
            355                 360                 365

Val Asn Leu Ser Thr Glu Val Val Tyr Lys Lys Gly Gln Asp Tyr Arg
    370                 375                 380

Phe Ala Cys Tyr Asp Arg Gly Arg Ala Cys Arg Ser Tyr Arg Val Arg
385                 390                 395                 400

Phe Leu Cys Gly Lys Pro Val Arg Pro Lys Leu Thr Val Thr Ile Asp
            405                 410                 415
```

-continued

```
Thr Asn Val Asn Ser Thr Ile Leu Asn Leu Glu Asp Asn Val Gln Ser
            420                 425                 430

Trp Lys Pro Gly Asp Thr Leu Val Ile Ala Ser Thr Asp Tyr Ser Met
            435                 440                 445

Tyr Gln Ala Glu Glu Phe Gln Val Leu Pro Cys Arg Ser Cys Ala Pro
        450                 455                 460

Asn Gln Val Lys Val Ala Gly Lys Pro Met Tyr Leu His Ile Gly Glu
465                 470                 475                 480

Glu Ile Asp Gly Val Asp Met Arg Ala Glu Val Gly Leu Leu Ser Arg
                485                 490                 495

Asn Ile Ile Val Met Gly Glu Met Glu Asp Lys Cys Tyr Pro Tyr Arg
                500                 505                 510

Asn His Ile Cys Asn Phe Phe Asp Phe Asp Thr Phe Gly Gly His Ile
            515                 520                 525

Lys Phe Ala Leu Gly Phe Lys Ala Ala His Leu Glu Gly Thr Glu Leu
            530                 535                 540

Lys His Met Gly Gln Gln Leu Val Gly Gln Tyr Pro Ile His Phe His
545                 550                 555                 560

Leu Ala Gly Asp Val Asp Glu Arg Gly Gly Tyr Asp Pro Pro Thr Tyr
                565                 570                 575

Ile Arg Asp Leu Ser Ile His His Thr Phe Ser Arg Cys Val Thr Val
            580                 585                 590

His Gly Ser Asn Gly Leu Leu Ile Lys Asp Val Val Gly Tyr Asn Ser
        595                 600                 605

Leu Gly His Cys Phe Phe Thr Glu Asp Gly Pro Glu Glu Arg Asn Thr
        610                 615                 620

Phe Asp His Cys Leu Gly Leu Leu Val Lys Ser Gly Thr Leu Leu Pro
625                 630                 635                 640

Ser Asp Arg Asp Ser Lys Met Cys Lys Met Ile Thr Glu Asp Ser Tyr
                645                 650                 655

Pro Gly Tyr Ile Pro Lys Pro Arg Gln Asp Cys Asn Ala Val Ser Thr
            660                 665                 670

Phe Trp Met Ala Asn Pro Asn Asn Asn Leu Ile Asn Cys Ala Ala Ala
            675                 680                 685

Gly Ser Glu Glu Thr Gly Phe Trp Phe Ile Phe His His Val Pro Thr
        690                 695                 700

Gly Pro Ser Val Gly Met Tyr Ser Pro Gly Tyr Ser Glu His Ile Pro
705                 710                 715                 720

Leu Gly Lys Phe Tyr Asn Asn Arg Ala His Ser Asn Tyr Arg Ala Gly
                725                 730                 735

Met Ile Ile Asp Asn Gly Val Lys Thr Thr Glu Ala Ser Ala Lys Asp
            740                 745                 750

Lys Arg Pro Phe Leu Ser Ile Ile Ser Ala Arg Tyr Ser Pro His Gln
            755                 760                 765

Asp Ala Asp Pro Leu Lys Pro Arg Glu Pro Ala Ile Ile Arg His Phe
        770                 775                 780

Ile Ala Tyr Lys Asn Gln Asp His Gly Ala Trp Leu Arg Gly Gly Asp
785                 790                 795                 800

Val Trp Leu Asp Ser Cys Arg Phe Ala Asp Asn Gly Ile Gly Leu Thr
                805                 810                 815

Leu Ala Ser Gly Gly Thr Phe Pro Tyr Asp Asp Gly Ser Lys Gln Glu
            820                 825                 830

Ile Lys Asn Ser Leu Phe Val Gly Glu Ser Gly Asn Val Gly Thr Glu
```

-continued

```
                    835                 840                 845

Met Met Asp Asn Arg Ile Trp Gly Pro Gly Gly Leu Asp His Ser Gly
    850                 855                 860

Arg Thr Leu Pro Ile Gly Gln Asn Phe Pro Ile Arg Gly Ile Gln Leu
865                 870                 875                 880

Tyr Asp Gly Pro Ile Asn Ile Gln Asn Cys Thr Phe Arg Lys Phe Val
                885                 890                 895

Ala Leu Glu Gly Arg His Thr Ser Ala Leu Ala Phe Arg Leu Asn Asn
            900                 905                 910

Ala Trp Gln Ser Cys Pro His Asn Asn Val Thr Gly Ile Ala Phe Glu
            915                 920                 925

Asp Val Pro Ile Thr Ser Arg Val Phe Phe Gly Glu Pro Gly Pro Trp
        930                 935                 940

Phe Asn Gln Leu Asp Met Asp Gly Asp Lys Thr Ser Val Phe His Asp
945                 950                 955                 960

Val Asp Gly Ser Val Ser Glu Tyr Pro Gly Ser Tyr Leu Thr Lys Asn
                965                 970                 975

Asp Asn Trp Leu Val Arg His Pro Asp Cys Ile Asn Val Pro Asp Trp
            980                 985                 990

Arg Gly Ala Ile Cys Ser Gly Cys  Tyr Ala Gln Met Tyr  Ile Gln Ala
            995                 1000                1005

Tyr Lys  Thr Ser Asn Leu Arg  Met Lys Ile Ile Lys  Asn Asp Phe
    1010                1015                1020

Pro Ser  His Pro Leu Tyr Leu  Glu Gly Ala Leu Thr  Arg Ser Thr
    1025                1030                1035

His Tyr  Gln Gln Tyr Gln Pro  Val Val Thr Leu Gln  Lys Gly Tyr
    1040                1045                1050

Thr Ile  His Trp Asp Gln Thr  Ala Pro Ala Glu Leu  Ala Ile Trp
    1055                1060                1065

Leu Ile  Asn Phe Asn Lys Gly  Asp Trp Ile Arg Val  Gly Leu Cys
    1070                1075                1080

Tyr Pro  Arg Gly Thr Thr Phe  Ser Ile Leu Ser Asp  Val His Asn
    1085                1090                1095

Arg Leu  Leu Lys Gln Thr Ser  Lys Thr Gly Val Phe  Val Arg Thr
    1100                1105                1110

Leu Gln  Met Asp Lys Val Glu  Gln Ser Tyr Pro Gly  Arg Ser His
    1115                1120                1125

Tyr Tyr  Trp Asp Glu Asp Ser  Gly Leu Leu Phe Leu  Lys Leu Lys
    1130                1135                1140

Ala Gln  Asn Glu Arg Glu Lys  Phe Ala Phe Cys Ser  Met Lys Gly
    1145                1150                1155

Cys Glu  Arg Ile Lys Ile Lys  Ala Leu Ile Pro Lys  Asn Ala Gly
    1160                1165                1170

Val Ser  Asp Cys Thr Ala Thr  Ala Tyr Pro Lys Phe  Thr Glu Arg
    1175                1180                1185

Ala Val  Val Asp Val Pro Met  Pro Lys Lys Leu Phe  Gly Ser Gln
    1190                1195                1200

Leu Lys  Thr Lys Asp His Phe  Leu Glu Val Lys Met  Glu Ser Ser
    1205                1210                1215

Lys Gln  His Phe Phe His Leu  Trp Asn Asp Phe Ala  Tyr Ile Glu
    1220                1225                1230

Val Asp  Gly Lys Lys Tyr Pro  Ser Ser Glu Asp Gly  Ile Gln Val
    1235                1240                1245
```

-continued

```
Val Val  Ile Asp Gly Asn Gln  Gly Arg Val Val Ser  His Thr Ser
    1250              1255              1260

Phe Arg  Asn Ser Ile Leu Gln  Gly Ile Pro Trp Gln  Leu Phe Asn
    1265              1270              1275

Tyr Val  Ala Thr Ile Pro Asp  Asn Ser Ile Val Leu  Met Ala Ser
    1280              1285              1290

Lys Gly  Arg Tyr Val Ser Arg  Gly Pro Trp Thr Arg  Val Leu Glu
    1295              1300              1305

Lys Leu  Gly Ala Asp Arg Gly  Leu Lys Leu Lys Glu  Gln Met Ala
    1310              1315              1320

Phe Val  Gly Phe Lys Gly Ser  Phe Arg Pro Ile Trp  Val Thr Leu
    1325              1330              1335

Asp Thr  Glu Asp His Lys Ala  Lys Ile Phe Gln Val  Val Pro Ile
    1340              1345              1350

Pro Val  Val Lys Lys Lys Lys  Leu
    1355              1360

<210> SEQ ID NO 2
<211> LENGTH: 5
<212> TYPE: PRT
<213> ORGANISM: Artificial
<220> FEATURE:
<223> OTHER INFORMATION: cAb4853 07F11C02 HCDR1

<400> SEQUENCE: 2

Ser Phe Gly Met His
1           5

<210> SEQ ID NO 3
<211> LENGTH: 5
<212> TYPE: PRT
<213> ORGANISM: Artificial
<220> FEATURE:
<223> OTHER INFORMATION: cAb4854 10F01B02 HCDR1

<400> SEQUENCE: 3

Ser Phe Gly Met His
1           5

<210> SEQ ID NO 4
<211> LENGTH: 7
<212> TYPE: PRT
<213> ORGANISM: Artificial
<220> FEATURE:
<223> OTHER INFORMATION: cAb4855 01F11A01 HCDR1

<400> SEQUENCE: 4

Thr Ser Gly Met Gly Val Gly
1           5

<210> SEQ ID NO 5
<211> LENGTH: 5
<212> TYPE: PRT
<213> ORGANISM: Artificial
<220> FEATURE:
<223> OTHER INFORMATION: cAb5775 12D02 HCDR1

<400> SEQUENCE: 5

Ala Tyr Thr Met Asn
1           5

<210> SEQ ID NO 6
```

```
<211> LENGTH: 5
<212> TYPE: PRT
<213> ORGANISM: Artificial
<220> FEATURE:
<223> OTHER INFORMATION: cAb5776 12A12 HCDR1

<400> SEQUENCE: 6

Ala Tyr Thr Met Asn
1               5

<210> SEQ ID NO 7
<211> LENGTH: 5
<212> TYPE: PRT
<213> ORGANISM: Artificial
<220> FEATURE:
<223> OTHER INFORMATION: cAb5777 12D08 HCDR1

<400> SEQUENCE: 7

Asp Thr Tyr Met His
1               5

<210> SEQ ID NO 8
<211> LENGTH: 5
<212> TYPE: PRT
<213> ORGANISM: Artificial
<220> FEATURE:
<223> OTHER INFORMATION: cAb5778 13G04 HCDR1

<400> SEQUENCE: 8

Ala Tyr Thr Met Asn
1               5

<210> SEQ ID NO 9
<211> LENGTH: 17
<212> TYPE: PRT
<213> ORGANISM: Artificial
<220> FEATURE:
<223> OTHER INFORMATION: cAb4853 07F11C02 HCDR2

<400> SEQUENCE: 9

Tyr Ile Ser Ser Ala Ser Asn Thr Ile Tyr Tyr Ala Asp Thr Val Lys
1               5                   10                  15

Gly

<210> SEQ ID NO 10
<211> LENGTH: 17
<212> TYPE: PRT
<213> ORGANISM: Artificial
<220> FEATURE:
<223> OTHER INFORMATION: cAb4854 10F01B02 HCDR2

<400> SEQUENCE: 10

Tyr Ile Ser Ser Ala Ser Asn Thr Ile Tyr Tyr Ala Asp Thr Val Lys
1               5                   10                  15

Gly

<210> SEQ ID NO 11
<211> LENGTH: 16
<212> TYPE: PRT
<213> ORGANISM: Artificial
<220> FEATURE:
<223> OTHER INFORMATION: cAb4855 01F11A01 HCDR2

<400> SEQUENCE: 11

His Ile Trp Trp Asn Asp Glu Lys Tyr Tyr Asn Ala Ala Leu Lys Ser
1               5                   10                  15
```

-continued

```
<210> SEQ ID NO 12
<211> LENGTH: 17
<212> TYPE: PRT
<213> ORGANISM: Artificial
<220> FEATURE:
<223> OTHER INFORMATION: cAb5775 12D02 HCDR2

<400> SEQUENCE: 12

Leu Ile Asn Pro Tyr Asn Gly Gly Thr Thr Tyr Asn Gln Lys Phe Lys
1               5                   10                  15

Gly

<210> SEQ ID NO 13
<211> LENGTH: 17
<212> TYPE: PRT
<213> ORGANISM: Artificial
<220> FEATURE:
<223> OTHER INFORMATION: cAb5776 12A12 HCDR2

<400> SEQUENCE: 13

Leu Ile Asn Pro Tyr Asn Gly Gly Thr Thr Tyr Asn Gln Lys Phe Lys
1               5                   10                  15

Gly

<210> SEQ ID NO 14
<211> LENGTH: 17
<212> TYPE: PRT
<213> ORGANISM: Artificial
<220> FEATURE:
<223> OTHER INFORMATION: cAb5777 12D08 HCDR2

<400> SEQUENCE: 14

Asn Ile Asp Pro Ala Asn Gly His Thr Lys Tyr Ala Pro Lys Phe Gln
1               5                   10                  15

Gly

<210> SEQ ID NO 15
<211> LENGTH: 17
<212> TYPE: PRT
<213> ORGANISM: Artificial
<220> FEATURE:
<223> OTHER INFORMATION: cAb5778 13G04 HCDR2

<400> SEQUENCE: 15

Leu Ile Asn Pro Tyr Asn Gly Gly Thr Thr Tyr Asn Gln Lys Phe Lys
1               5                   10                  15

Gly

<210> SEQ ID NO 16
<211> LENGTH: 10
<212> TYPE: PRT
<213> ORGANISM: Artificial
<220> FEATURE:
<223> OTHER INFORMATION: cAb4853 07F11C02  HCDR3

<400> SEQUENCE: 16

Arg Asp Trp Asp Leu Tyr Ala Met Asp Tyr
1               5                   10

<210> SEQ ID NO 17
<211> LENGTH: 10
<212> TYPE: PRT
<213> ORGANISM: Artificial
```

-continued

```
<220> FEATURE:
<223> OTHER INFORMATION: cAb4854 10F01B02 HCDR3

<400> SEQUENCE: 17

Arg Asn Trp Asp Leu Tyr Ala Met Asp Tyr
1               5                   10

<210> SEQ ID NO 18
<211> LENGTH: 8
<212> TYPE: PRT
<213> ORGANISM: Artificial
<220> FEATURE:
<223> OTHER INFORMATION: cAb4855 01F11A01 HCDR3

<400> SEQUENCE: 18

Ile Thr Gly Ala Trp Phe Pro Tyr
1               5

<210> SEQ ID NO 19
<211> LENGTH: 9
<212> TYPE: PRT
<213> ORGANISM: Artificial
<220> FEATURE:
<223> OTHER INFORMATION: cAb5775 12D02 HCDR3

<400> SEQUENCE: 19

Tyr Asp Tyr Gly Tyr Ala Met Asp Tyr
1               5

<210> SEQ ID NO 20
<211> LENGTH: 9
<212> TYPE: PRT
<213> ORGANISM: Artificial
<220> FEATURE:
<223> OTHER INFORMATION: cAb5776 12A12 HCDR3

<400> SEQUENCE: 20

Tyr Asp Tyr Gly Tyr Ala Met Asp Tyr
1               5

<210> SEQ ID NO 21
<211> LENGTH: 10
<212> TYPE: PRT
<213> ORGANISM: Artificial
<220> FEATURE:
<223> OTHER INFORMATION: cAb5777 12D08 HCDR3

<400> SEQUENCE: 21

Ser Asn Asp Tyr Asp Val Asp Phe Asp Tyr
1               5                   10

<210> SEQ ID NO 22
<211> LENGTH: 11
<212> TYPE: PRT
<213> ORGANISM: Artificial
<220> FEATURE:
<223> OTHER INFORMATION: cAb5778 13G04 HCDR3

<400> SEQUENCE: 22

Tyr Tyr Gly Gly Arg Gly Trp Tyr Phe Asp Val
1               5                   10

<210> SEQ ID NO 23
<211> LENGTH: 11
<212> TYPE: PRT
<213> ORGANISM: Artificial
<220> FEATURE:
```

-continued

<223> OTHER INFORMATION: cAb4853 07F11C02 LCDR1

<400> SEQUENCE: 23

Lys Ala Ser Gln Asn Val Gly Thr Ala Val Ala
1               5                   10

<210> SEQ ID NO 24
<211> LENGTH: 11
<212> TYPE: PRT
<213> ORGANISM: Artificial
<220> FEATURE:
<223> OTHER INFORMATION: cAb4854 10F01B02 LCDR1

<400> SEQUENCE: 24

Lys Ala Asn Gln Asn Val Gly Thr Ala Val Ala
1               5                   10

<210> SEQ ID NO 25
<211> LENGTH: 11
<212> TYPE: PRT
<213> ORGANISM: Artificial
<220> FEATURE:
<223> OTHER INFORMATION: cAb4855 01F11A01 LCDR1

<400> SEQUENCE: 25

Arg Ala Ser Gln His Ile Ser Glu Tyr Leu His
1               5                   10

<210> SEQ ID NO 26
<211> LENGTH: 16
<212> TYPE: PRT
<213> ORGANISM: Artificial
<220> FEATURE:
<223> OTHER INFORMATION: cAb5775 12D02 LCDR1

<400> SEQUENCE: 26

Arg Ser Ser Gln Ser Ile Val His Arg Asn Gly Asn Thr Tyr Leu Glu
1               5                   10                  15

<210> SEQ ID NO 27
<211> LENGTH: 16
<212> TYPE: PRT
<213> ORGANISM: Artificial
<220> FEATURE:
<223> OTHER INFORMATION: cAb5776 12A12 LCDR1

<400> SEQUENCE: 27

Arg Ser Ser Gln Ser Ile Val His Arg Ser Gly Asn Thr Tyr Leu Glu
1               5                   10                  15

<210> SEQ ID NO 28
<211> LENGTH: 17
<212> TYPE: PRT
<213> ORGANISM: Artificial
<220> FEATURE:
<223> OTHER INFORMATION: cAb5777 12D08  LCDR1

<400> SEQUENCE: 28

Lys Ser Ser Gln Ser Leu Leu Asn Ser Arg Thr Arg Lys Asn Tyr Leu
1               5                   10                  15

Ala

<210> SEQ ID NO 29
<211> LENGTH: 15
<212> TYPE: PRT
<213> ORGANISM: Artificial

-continued

```
<220> FEATURE:
<223> OTHER INFORMATION: cAb5778 13G04 LCDR1

<400> SEQUENCE: 29

Arg Ala Ser Lys Ser Val Ser Thr Ser Gly Tyr Ser Tyr Val His
1               5                   10                  15

<210> SEQ ID NO 30
<211> LENGTH: 7
<212> TYPE: PRT
<213> ORGANISM: Artificial
<220> FEATURE:
<223> OTHER INFORMATION: cAb4853 07F11C02 LCDR2

<400> SEQUENCE: 30

Ser Ala Ser Asn Arg His Thr
1               5

<210> SEQ ID NO 31
<211> LENGTH: 7
<212> TYPE: PRT
<213> ORGANISM: Artificial
<220> FEATURE:
<223> OTHER INFORMATION: cAb4854 10F01B02 LCDR2

<400> SEQUENCE: 31

Ser Thr Ser Asn Arg Asp Thr
1               5

<210> SEQ ID NO 32
<211> LENGTH: 7
<212> TYPE: PRT
<213> ORGANISM: Artificial
<220> FEATURE:
<223> OTHER INFORMATION: cAb4855 01F11A01 LCDR2

<400> SEQUENCE: 32

Tyr Gly Ser Gln Ser Ile Ser
1               5

<210> SEQ ID NO 33
<211> LENGTH: 7
<212> TYPE: PRT
<213> ORGANISM: Artificial
<220> FEATURE:
<223> OTHER INFORMATION: cAb5775 12D02 LCDR2

<400> SEQUENCE: 33

Lys Val Ser Asn Arg Phe Ser
1               5

<210> SEQ ID NO 34
<211> LENGTH: 7
<212> TYPE: PRT
<213> ORGANISM: Artificial
<220> FEATURE:
<223> OTHER INFORMATION: cAb5776 12A12  LCDR2

<400> SEQUENCE: 34

Lys Val Ser Asn Arg Phe Ser
1               5

<210> SEQ ID NO 35
<211> LENGTH: 7
<212> TYPE: PRT
<213> ORGANISM: Artificial
<220> FEATURE:
```

<223> OTHER INFORMATION: cAb5777 12D08 LCDR2

<400> SEQUENCE: 35

Trp Ala Ser Thr Arg Glu Ser
1               5

<210> SEQ ID NO 36
<211> LENGTH: 7
<212> TYPE: PRT
<213> ORGANISM: Artificial
<220> FEATURE:
<223> OTHER INFORMATION: cAb5778 13G04 LCDR2

<400> SEQUENCE: 36

Leu Ala Ser Asn Leu Glu Ser
1               5

<210> SEQ ID NO 37
<211> LENGTH: 8
<212> TYPE: PRT
<213> ORGANISM: Artificial
<220> FEATURE:
<223> OTHER INFORMATION: cAb4853 07F11C02 LCDR3

<400> SEQUENCE: 37

Gln Gln Tyr Ser Ser Ser Pro Thr
1               5

<210> SEQ ID NO 38
<211> LENGTH: 8
<212> TYPE: PRT
<213> ORGANISM: Artificial
<220> FEATURE:
<223> OTHER INFORMATION: cAb4854 10F01B02 LCDR3

<400> SEQUENCE: 38

Gln Gln Tyr Arg Asn Tyr Pro Thr
1               5

<210> SEQ ID NO 39
<211> LENGTH: 9
<212> TYPE: PRT
<213> ORGANISM: Artificial
<220> FEATURE:
<223> OTHER INFORMATION: cAb4855 01F11A01  LCDR3

<400> SEQUENCE: 39

Gln Asn Gly His Ser Phe Pro Tyr Thr
1               5

<210> SEQ ID NO 40
<211> LENGTH: 9
<212> TYPE: PRT
<213> ORGANISM: Artificial
<220> FEATURE:
<223> OTHER INFORMATION: cAb5775 12D02 LCDR3

<400> SEQUENCE: 40

Phe Gln Gly Ser His Val Pro Trp Thr
1               5

<210> SEQ ID NO 41
<211> LENGTH: 9
<212> TYPE: PRT
<213> ORGANISM: Artificial
<220> FEATURE:
<223> OTHER INFORMATION: cAb5776 12A12 LCDR3

```
<400> SEQUENCE: 41

Phe Gln Gly Ser His Val Pro Trp Thr
1               5

<210> SEQ ID NO 42
<211> LENGTH: 8
<212> TYPE: PRT
<213> ORGANISM: Artificial
<220> FEATURE:
<223> OTHER INFORMATION: cAb5777 12D08 LCDR3

<400> SEQUENCE: 42

Lys Gln Ser Tyr Asn Leu Tyr Thr
1               5

<210> SEQ ID NO 43
<211> LENGTH: 9
<212> TYPE: PRT
<213> ORGANISM: Artificial
<220> FEATURE:
<223> OTHER INFORMATION: cAb5778 13G04 LCDR3

<400> SEQUENCE: 43

Gln Asn Ser Arg Glu Leu Pro Tyr Thr
1               5

<210> SEQ ID NO 44
<211> LENGTH: 119
<212> TYPE: PRT
<213> ORGANISM: Artificial
<220> FEATURE:
<223> OTHER INFORMATION: cAb4853 VH IgG2a

<400> SEQUENCE: 44

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Ala Phe Ser Ser Phe
            20                  25                  30

Gly Met His Trp Val Arg Gln Ala Pro Glu Arg Gly Leu Glu Trp Val
        35                  40                  45

Ala Tyr Ile Ser Ser Ala Ser Asn Thr Ile Tyr Tyr Ala Asp Thr Val
    50                  55                  60

Lys Gly Arg Phe Thr Ile Ser Arg Asp Asn Pro Lys Ser Thr Leu Phe
65                  70                  75                  80

Leu Gln Met Thr Ser Leu Arg Ser Glu Asp Thr Ala Ile Tyr Tyr Cys
                85                  90                  95

Ala Lys Arg Asp Trp Asp Leu Tyr Ala Met Asp Tyr Trp Gly Gln Gly
            100                 105                 110

Thr Ser Val Thr Val Ser Ser
        115

<210> SEQ ID NO 45
<211> LENGTH: 106
<212> TYPE: PRT
<213> ORGANISM: Artificial
<220> FEATURE:
<223> OTHER INFORMATION: cAb4853 VL kappa

<400> SEQUENCE: 45

Asp Ile Val Met Thr Gln Ser Gln Lys Phe Leu Ser Thr Ser Val Gly
1               5                   10                  15
```

```
Asp Arg Val Thr Ile Thr Cys Lys Ala Ser Gln Asn Val Gly Thr Ala
            20              25              30

Val Ala Trp Tyr Gln Gln Lys Pro Gly Gln Ser Pro Glu Leu Leu Ile
        35              40              45

Tyr Ser Ala Ser Asn Arg His Thr Gly Val Pro Ala Arg Phe Thr Gly
    50              55              60

Ser Gly Ser Gly Thr Asp Phe Thr Leu Thr Ile Thr Asn Met Gln Ser
65              70              75              80

Glu Asp Leu Ala Asp Tyr Phe Cys Gln Gln Tyr Ser Ser Ser Pro Thr
                85              90              95

Phe Gly Gly Gly Thr Lys Leu Glu Ser Lys
            100             105
```

<210> SEQ ID NO 46
<211> LENGTH: 119
<212> TYPE: PRT
<213> ORGANISM: Artificial
<220> FEATURE:
<223> OTHER INFORMATION: cAb4854 VH IgG2a

<400> SEQUENCE: 46

```
Asp Val Gln Leu Val Glu Ser Gly Gly Gly Leu Val Gln Pro Gly Gly
1               5               10              15

Ser Arg Lys Leu Ser Cys Ala Ala Ser Gly Phe Pro Phe Ser Ser Phe
            20              25              30

Gly Met His Trp Val Arg Gln Ala Pro Asp Lys Gly Leu Glu Trp Val
        35              40              45

Ala Tyr Ile Ser Ser Ala Ser Asn Thr Ile Tyr Tyr Ala Asp Thr Val
    50              55              60

Lys Gly Arg Phe Thr Val Ser Arg Asp Asn Pro Lys Asn Thr Leu Phe
65              70              75              80

Leu Gln Met Thr Ser Leu Arg Ser Glu Asp Thr Ala Ile Tyr Tyr Cys
                85              90              95

Thr Lys Arg Asn Trp Asp Leu Tyr Ala Met Asp Tyr Trp Gly Gln Gly
            100             105             110

Thr Ser Val Thr Val Ser Ser
        115
```

<210> SEQ ID NO 47
<211> LENGTH: 106
<212> TYPE: PRT
<213> ORGANISM: Artificial
<220> FEATURE:
<223> OTHER INFORMATION: cAb4854 VL kappa

<400> SEQUENCE: 47

```
Asp Ile Val Met Thr Gln Ser Gln Lys Phe Met Ser Thr Ser Val Gly
1               5               10              15

Asp Arg Val Ser Ile Thr Cys Lys Ala Asn Gln Asn Val Gly Thr Ala
            20              25              30

Val Ala Trp Tyr Gln Gln Lys Pro Gly Gln Ser Pro Lys Leu Leu Ile
        35              40              45

Tyr Ser Thr Ser Asn Arg Asp Thr Gly Val Pro Asp Arg Phe Thr Gly
    50              55              60

Ser Gly Ser Gly Thr Asp Phe Thr Leu Thr Ile Asn Tyr Ile Gln Ser
65              70              75              80

Glu Asp Leu Ala Asp Tyr Phe Cys Gln Gln Tyr Arg Asn Tyr Pro Thr
                85              90              95
```

```
Phe Gly Gly Gly Thr Lys Leu Glu Ile Lys
          100                 105

<210> SEQ ID NO 48
<211> LENGTH: 118
<212> TYPE: PRT
<213> ORGANISM: Artificial
<220> FEATURE:
<223> OTHER INFORMATION: cAb4855 VH IgG2a

<400> SEQUENCE: 48

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
          20                  25                  30

Gly Met Gly Val Gly Trp Ile Arg Gln Pro Ser Gly Lys Gly Leu Glu
          35                  40                  45

Trp Leu Ala His Ile Trp Trp Asn Asp Glu Lys Tyr Tyr Asn Ala Ala
     50                  55                  60

Leu Lys Ser Arg Leu Thr Ile Ser Lys Asp Thr Ser Lys Asn Gln Val
65                  70                  75                  80

Phe Leu Lys Ile Ala Ser Val Asp Ala Ala Asp Thr Ala Thr Tyr Tyr
                85                  90                  95

Cys Ala Arg Ile Thr Gly Ala Trp Phe Pro Tyr Trp Gly Gln Gly Thr
          100                 105                 110

Leu Val Thr Val Ser Ala
          115

<210> SEQ ID NO 49
<211> LENGTH: 107
<212> TYPE: PRT
<213> ORGANISM: Artificial
<220> FEATURE:
<223> OTHER INFORMATION: cAb4855 VL kappa

<400> SEQUENCE: 49

Asp Ile Val Met Thr Gln Ser Pro Ala Thr Leu Ser Val Thr Pro Gly
1               5                   10                  15

Asp Arg Val Ser Leu Ser Cys Arg Ala Ser Gln His Ile Ser Glu Tyr
          20                  25                  30

Leu His Trp Tyr Gln Gln Lys Ser His Glu Ser Pro Arg Leu Leu Ile
          35                  40                  45

Lys Tyr Gly Ser Gln Ser Ile Ser Gly Ile Pro Ser Arg Phe Ser Gly
     50                  55                  60

Ser Gly Ser Gly Ser Asp Phe Thr Leu Asn Ile Asn Ser Val Glu Pro
65                  70                  75                  80

Glu Asp Val Gly Val Tyr Tyr Cys Gln Asn Gly His Ser Phe Pro Tyr
                85                  90                  95

Thr Phe Gly Gly Gly Thr Lys Leu Glu Ile Lys
          100                 105

<210> SEQ ID NO 50
<211> LENGTH: 118
<212> TYPE: PRT
<213> ORGANISM: Artificial
<220> FEATURE:
<223> OTHER INFORMATION: cAb5775 VH IgG1

<400> SEQUENCE: 50
```

```
Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Ala Tyr
                20                  25                  30

Thr Met Asn Trp Val Lys Gln Ser His Gly Glu Asn Leu Glu Trp Ile
            35                  40                  45

Gly Leu Ile Asn Pro Tyr Asn Gly Gly Thr Thr Tyr Asn Gln Lys Phe
        50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Ser Tyr Asp Tyr Gly Tyr Ala Met Asp Tyr Trp Gly Gln Gly Thr
            100                 105                 110

Ser Val Thr Val Ser Ser
        115
```

```
<210> SEQ ID NO 51
<211> LENGTH: 112
<212> TYPE: PRT
<213> ORGANISM: Artificial
<220> FEATURE:
<223> OTHER INFORMATION: cAb5775 VL kappa

<400> SEQUENCE: 51
```

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Arg
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110
```

```
<210> SEQ ID NO 52
<211> LENGTH: 118
<212> TYPE: PRT
<213> ORGANISM: Artificial
<220> FEATURE:
<223> OTHER INFORMATION: cAb5776 VH IgG1

<400> SEQUENCE: 52
```

```
Glu Val Gln Leu Gln Gln Ser Gly Pro Glu Leu Val Lys Pro Gly Val
1               5                   10                  15

Ser Met Lys Ile Ser Cys Lys Ala Ser Gly Tyr Ser Phe Thr Ala Tyr
                20                  25                  30

Thr Met Asn Trp Val Lys Gln Ser His Gly Glu Asn Leu Glu Trp Ile
            35                  40                  45

Gly Leu Ile Asn Pro Tyr Asn Gly Gly Thr Thr Tyr Asn Gln Lys Phe
        50                  55                  60

Lys Gly Lys Ala Thr Leu Thr Val Asp Lys Ser Ser Ser Thr Ala Tyr
65                  70                  75                  80
```

```
Met Glu Leu Leu Ser Leu Thr Ser Glu Asp Ser Ala Val Tyr Tyr Cys
                85                  90                  95

Ala Ser Tyr Asp Tyr Gly Tyr Ala Met Asp Tyr Trp Gly Gln Gly Thr
            100                 105                 110

Ser Val Thr Val Ser Ser
        115
```

<210> SEQ ID NO 53
<211> LENGTH: 112
<212> TYPE: PRT
<213> ORGANISM: Artificial
<220> FEATURE:
<223> OTHER INFORMATION: cAb5776 VL kappa

<400> SEQUENCE: 53

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Arg
            20                  25                  30

Ser Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110
```

<210> SEQ ID NO 54
<211> LENGTH: 119
<212> TYPE: PRT
<213> ORGANISM: Artificial
<220> FEATURE:
<223> OTHER INFORMATION: cAb5777 VH IgG2a

<400> SEQUENCE: 54

```
Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Ile Trp Ile
        35                  40                  45

Gly Asn Ile Asp Pro Ala Asn Gly His Thr Lys Tyr Ala Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Ser Asn Asp Tyr Asp Val Asp Phe Asp Tyr Trp Gly Gln Gly
            100                 105                 110

Thr Thr Leu Thr Val Ser Ser
        115
```

<210> SEQ ID NO 55
<211> LENGTH: 112
<212> TYPE: PRT

<213> ORGANISM: Artificial
<220> FEATURE:
<223> OTHER INFORMATION: cAb5777 VL kappa

<400> SEQUENCE: 55

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Ser Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Tyr Thr Phe Gly Gly Gly Thr Lys Leu Glu Ile Lys
            100                 105                 110

<210> SEQ ID NO 56
<211> LENGTH: 120
<212> TYPE: PRT
<213> ORGANISM: Artificial
<220> FEATURE:
<223> OTHER INFORMATION: cAb5778 VH IgG1

<400> SEQUENCE: 56

Glu Val His Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Ala Tyr
            20                  25                  30

Thr Met Asn Trp Val Lys Gln Ser His Gly Lys Asn Leu Glu Trp Ile
        35                  40                  45

Gly Leu Ile Asn Pro Tyr Asn Gly Gly Thr Thr Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Ser Tyr Tyr Gly Gly Arg Gly Trp Tyr Phe Asp Val Trp Gly Ala
            100                 105                 110

Gly Thr Ser Val Thr Val Ser Ser
        115                 120

<210> SEQ ID NO 57
<211> LENGTH: 111
<212> TYPE: PRT
<213> ORGANISM: Artificial
<220> FEATURE:
<223> OTHER INFORMATION: cAb5778 VL kappa

<400> SEQUENCE: 57

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Val His Trp Tyr Gln Gln Lys Pro Gly Gln Pro Pro
        35                  40                  45

```
Lys Leu Leu Ile Tyr Leu Ala Ser Asn Leu Glu Ser Gly Val Pro Ala
    50              55              60

Arg Phe Ser Gly Ser Gly Ser Gly Thr Asp Phe Thr Leu Asn Ile His
65              70              75              80

Pro Val Glu Glu Glu Asp Ala Ala Thr Tyr Tyr Cys Gln Asn Ser Arg
                85              90              95

Glu Leu Pro Tyr Thr Phe Gly Gly Gly Thr Lys Leu Glu Met Lys
            100             105             110
```

```
<210> SEQ ID NO 58
<211> LENGTH: 357
<212> TYPE: DNA
<213> ORGANISM: Artificial
<220> FEATURE:
<223> OTHER INFORMATION: cAb4853 VH

<400> SEQUENCE: 58
gatgtgcagc tggtggagtc tgggggaggc ttagtgcagc ctggagggtc ccggaaactc      60
tcctgtgcag cctctggatt cgctttcagt agctttggaa tgcactgggt tcgtcaggct     120
ccagagaggg ggctggagtg ggtcgcatac attagtagtg ccagcaatac catctactat     180
gcagacacag tgaagggccg attcaccatc tccagagaca tcccaagag caccctgttc      240 ctgcaaatga ccagtctaag gtctgaggac acggccattt attactgtgc aaagcgagac     300
tgggacctct atgctatgga ctactggggt caaggaacct cagtcaccgt ctcgtca        357
```

```
<210> SEQ ID NO 59
<211> LENGTH: 318
<212> TYPE: DNA
<213> ORGANISM: Artificial
<220> FEATURE:
<223> OTHER INFORMATION: cAb4853 VL

<400> SEQUENCE: 59
gacattgtga tgacccagtc tcaaaaattc ttgtccacat cagtgggaga cagggtcacc      60
atcacctgca aggccagtca gaatgtggga actgctgttg cctggtatca acagaaacca     120
gggcaatctc ctgaacttct gatttactcg gcatccaatc ggcacactgg agtccctgct     180
cgcttcacag gcagtggatc tgggacagat ttcactctca ccatcaccaa tatgcagtct     240
gaagacctgg cagattattt ctgccagcaa tatagtagct cgccgacatt cggtggaggc     300
accaagttgg aatccaaa                                                    318
```

```
<210> SEQ ID NO 60
<211> LENGTH: 357
<212> TYPE: DNA
<213> ORGANISM: Artificial
<220> FEATURE:
<223> OTHER INFORMATION: cAb4854  VH

<400> SEQUENCE: 60
gatgtgcagc tggtggagtc tgggggaggc ttagtgcagc ctggagggtc ccggaaactc      60
tcctgtgcag cctctggatt cccttttcagt agctttggaa tgcactgggt tcgtcaggct    120
ccagacaagg gactggagtg ggtcgcatac attagtagtg ccagtaatac catctactat     180
gctgacacag tgaagggccg attcaccgtc tccagagaca tcccaagaa cacctgttc       240 ctgcaaatga ccagtctaag gtctgaggac acggccattt attactgtac aaagcgaaat     300
tgggacctct atgctatgga ctactggggt caaggaacct cagtcaccgt ctcctca        357
```

```
<210> SEQ ID NO 61
<211> LENGTH: 318
<212> TYPE: DNA
<213> ORGANISM: Artificial
<220> FEATURE:
<223> OTHER INFORMATION: cAb4854  VL

<400> SEQUENCE: 61
gacattgtga tgacccagtc tcaaaaattc atgtccacat cagtgggaga cagggtcagc    60
atcacctgca aggccaatca gaatgtgggt actgctgtag cctggtatca acagaaacca   120
ggacaatctc ctaaactact gatttattcg acatccaatc gggacactgg agtccctgac   180
cgcttcacag gcagtggatc tgggacagat ttcactctca ccatcaacta tattcaatct   240
gaagacctgg cagattattt ctgccagcaa tatagaaatt atccgacgtt cggtggaggc   300
accaagctgg aaatcaaa                                                 318

<210> SEQ ID NO 62
<211> LENGTH: 354
<212> TYPE: DNA
<213> ORGANISM: Artificial
<220> FEATURE:
<223> OTHER INFORMATION: cAb4855 VH

<400> SEQUENCE: 62
caggttactc tgaaagagtc tggccctggg atattgcagc cctcccagac cctcagtctg    60
acttgttctt tctctgggtt ttcactgagc acttctggta tgggtgtagg ctggattcgt   120
cagccttcag ggaagggtct ggagtggctg gcacacattt ggtggaatga tgagaaatac   180
tataacgcag ccctgaagag ccggctcaca atctccaagg ataacctccaa aaaccaggtt   240 ttcctcaaga tcgccagtgt ggacgctgca gatactgcca catactactg tgctcgcatc   300
actggtgcct ggtttcctta ttggggccaa gggactctgg tcactgtctc tgca         354

<210> SEQ ID NO 63
<211> LENGTH: 321
<212> TYPE: DNA
<213> ORGANISM: Artificial
<220> FEATURE:
<223> OTHER INFORMATION: cAb4855 VL

<400> SEQUENCE: 63
gacattgtga tgactcagtc tccagccacc ctgtctgtga ctccaggaga tagagtctct    60
ctttcctgca gggccagtca gcatattagc gaatacttac actggtatca acaaaaatca   120
cacgagtctc caaggcttct catcaaatat ggttcccaat ccatctctgg gatcccctcc   180
aggttcagtg gcagtggatc agggtcagat ttcactctca atatcaacag tgtggaacct   240
gaagatgttg gagtgtatta ctgtcaaaat ggtcacagct ttccgtacac gttcggaggg   300
gggaccaagc tggaaataaa a                                             321

<210> SEQ ID NO 64
<211> LENGTH: 354
<212> TYPE: DNA
<213> ORGANISM: Artificial
<220> FEATURE:
<223> OTHER INFORMATION: cAb5775 VH

<400> SEQUENCE: 64
gaggtccagc tgcaacagtc tggacctgag ctggtgaagc ctggagcctc aatgaagata    60
tcttgcaagg cttctggtta ctcattcact gcctacacca tgaactgggt gaagcagagc   120
```

-continued

```
catggagaga accttgagtg gattggactt attaatcctt ataatggtgg tactacctac      180
aaccagaagt tcaagggcaa ggccacatta actgtagaca agtcatccag cacagcctac      240
atggagctcc tcagtctgac atctgaggac tctgcagtct attactgtgc atcatatgat      300
tacggctatg ctatggacta ctggggtcaa ggaacctcag tcaccgtctc ctca           354

<210> SEQ ID NO 65
<211> LENGTH: 336
<212> TYPE: DNA
<213> ORGANISM: Artificial
<220> FEATURE:
<223> OTHER INFORMATION: cAb5775 VL

<400> SEQUENCE: 65
gatgttttga tgacccaaac tccactctcc ctgcctgtca gtcttggaga tcaagcctcc       60
atctcttgca gatctagtca gagcattgta catagaaatg gaaacaccta tctagaatgg      120
tacctgcaga aaccaggcca gtctccaaag ctcctgatct acaaagtttc caaccgattt      180
tctggggtcc cagacaggtt cagtggcagt ggatcaggga cagatttcac actcaagatc      240
agcagagtgg aggctgagga tctgggagtt tattactgct ttcaaggttc acatgttccg      300
tggacgttcg gtggaggcac caagctggaa atcaaa                                336

<210> SEQ ID NO 66
<211> LENGTH: 354
<212> TYPE: DNA
<213> ORGANISM: Artificial
<220> FEATURE:
<223> OTHER INFORMATION: cAb5776 VH

<400> SEQUENCE: 66
gaggtccagc tgcaacagtc tggacctgag ctggtgaagc ctggagtttc aatgaagata       60
tcctgcaagg cttctggtta ctcattcact gcctacacta tgaattgggt gaagcagagt      120
catggagaga accttgagtg gattggactt attaatcctt ataatggtgg tactacctac      180
aaccagaagt tcaagggcaa ggccacatta actgtagaca agtcatccag cacagcctac      240
atggagctcc tcagtctgac atctgaggac tctgcagtct attactgtgc atcatatgat      300
tacggctatg ctatggacta ctggggtcaa ggaacctcag tcaccgtctc ctca           354

<210> SEQ ID NO 67
<211> LENGTH: 336
<212> TYPE: DNA
<213> ORGANISM: Artificial
<220> FEATURE:
<223> OTHER INFORMATION: cAb5776 VL

<400> SEQUENCE: 67
gatgttttga tgacccaaac tccactctcc ctgcctgtca gtcttggaga tcaagcctcc       60
atctcttgca gatctagtca gagcattgta catcgtagtg aaacaccta tttagaatgg       120 tacctgcaga aaccaggcca gtctccaaag ctcctgatct acaaagtttc caaccgattt      180
tctggggtcc cagacaggtt cagtggcagt ggatcaggga cagatttcac actcaagatc      240
agcagagtgg aggctgagga tctgggagtt tattactgct ttcaaggttc acatgttccg      300
tggacgttcg gtggaggcac caagttggaa atcaaa                                336

<210> SEQ ID NO 68
<211> LENGTH: 357
<212> TYPE: DNA
```

-continued

<213> ORGANISM: Artificial
<220> FEATURE:
<223> OTHER INFORMATION: cAb5777 VH

<400> SEQUENCE: 68

```
gaggttcaac tgcagcagtc tggggcagag cttgtgaagc caggggcctc agtcaagttg      60
tcctgcacag cttctggctt caacattaaa gacacctata tgcactgggt gaaacagagg     120
cctgagcagg gcctgatttg gattggaaac attgatcctg cgaatggtca tactaaatat     180
gccccgaagt tccagggcaa ggccactatc acagcagaca tcctccaa cacagcctac       240 ctgcagctca gcagcctgac atctgaggac actgccgtct attactgtgc tagatctaat     300
gattacgacg tcgactttga ctactggggc caaggcacca ctctcacagt ctcctca       357
```

<210> SEQ ID NO 69
<211> LENGTH: 336
<212> TYPE: DNA
<213> ORGANISM: Artificial
<220> FEATURE:
<223> OTHER INFORMATION: cAb5777 VL

<400> SEQUENCE: 69

```
gacattgtga tgtcacagtc tccatcctcc ctggctgtgt cagcaggaga gaaggtcact      60
atgagctgca aatccagtca gagtctgctc aacagtagaa cccgaaagaa ctacttggct     120
tggtaccagc agaaaccagg gcagtctcct aaactgctga tctactgggc atccactagg     180
gaatctgggg tccctgatcg cttcacaggc agtggatctg ggacagattt cagtctcacc     240
atcagcagtg tgcaggctga agacctggca gtttattact gcaagcaatc ttataatcta     300
tacacgttcg gaggggggac caagctggaa ataaaa                               336
```

<210> SEQ ID NO 70
<211> LENGTH: 360
<212> TYPE: DNA
<213> ORGANISM: Artificial
<220> FEATURE:
<223> OTHER INFORMATION: cAb5778 VH

<400> SEQUENCE: 70

```
gaggtccacc tgcaacagtc tggacctgag ctggtgaagc ctggagcttc aatgaagata      60
tcctgcaagg cttctggtta ctccttcact gcctacacca tgaactgggt gaaacagagc     120
catggaaaga accttgagtg gattggactt attaatcctt acaatggtgg tactacctac     180
aaccagaaat tcaagggcaa ggccacatta actgtagaca agtcatccag cacagcctac     240
atggagctcc tcagtctgac atctgaggac tctgcagtct attactgtgc ttcttactac     300
ggtggtaggg gctggtactt cgatgtctgg ggcgcaggga cctcggtcac cgtctcctca     360
```

<210> SEQ ID NO 71
<211> LENGTH: 333
<212> TYPE: DNA
<213> ORGANISM: Artificial
<220> FEATURE:
<223> OTHER INFORMATION: cAb5778 VL

<400> SEQUENCE: 71

```
gacattgtgc tgacacagtc tcctgcttcc ttagctgtat ctctggggca gagggccacc      60
atctcatgca gggccagcaa aagtgtcagt acatctggct atagttatgt tcactggtac     120
caacagaaac caggacagcc acccaaactc ctcatctatc ttgcatccaa cctagaatct     180
ggggtccctg ccaggttcag tggcagtggg tctgggacag acttcaccct caacatccat     240
```

```
cctgtggagg aggaagatgc tgcaacctat tactgtcaga atagtaggga acttccgtac      300
acgttcggag gggggaccaa gctggaaatg aaa                                   333

<210> SEQ ID NO 72
<211> LENGTH: 330
<212> TYPE: PRT
<213> ORGANISM: Artificial
<220> FEATURE:
<223> OTHER INFORMATION: cAb4853  CH

<400> SEQUENCE: 72

Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
                20                  25                  30

Phe Pro Glu Pro Val Thr Leu Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
                100                 105                 110

Pro Ala Pro Asn Leu Leu Gly Gly Pro Ser Val Phe Ile Phe Pro Pro
        115                 120                 125

Lys Ile Lys Asp Val Leu Met Ile Ser Leu Ser Pro Ile Val Thr Cys
    130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
                180                 185                 190

His Gln Asp Trp Met Ser Gly Lys Glu Phe Lys Cys Lys Val Asn Asn
        195                 200                 205

Lys Asp Leu Pro Ala Pro Ile Glu Arg Thr Ile Ser Lys Pro Lys Gly
    210                 215                 220

Ser Val Arg Ala Pro Gln Val Tyr Val Leu Pro Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
                260                 265                 270

Asn Tyr Lys Asn Thr Glu Pro Val Leu Asp Ser Asp Gly Ser Tyr Phe
        275                 280                 285

Met Tyr Ser Lys Leu Arg Val Glu Lys Lys Asn Trp Val Glu Arg Asn
    290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
                325                 330
```

<210> SEQ ID NO 73
<211> LENGTH: 107
<212> TYPE: PRT
<213> ORGANISM: Artificial
<220> FEATURE:
<223> OTHER INFORMATION: cAb4853  CL

<400> SEQUENCE: 73

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105

<210> SEQ ID NO 74
<211> LENGTH: 330
<212> TYPE: PRT
<213> ORGANISM: Artificial
<220> FEATURE:
<223> OTHER INFORMATION: cAb4854 CH

<400> SEQUENCE: 74

Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
                100                 105                 110

Pro Ala Pro Asn Leu Leu Gly Gly Pro Ser Val Phe Ile Phe Pro Pro
            115                 120                 125

Lys Ile Lys Asp Val Leu Met Ile Ser Leu Ser Pro Ile Val Thr Cys
        130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
            195                 200                 205

```
Lys Asp Leu Pro Ala Pro Ile Glu Arg Thr Ile Ser Lys Pro Lys Gly
    210             215             220

Ser Val Arg Ala Pro Gln Val Tyr Val Leu Pro Pro Glu Glu Glu
225             230             235             240

Met Thr Lys Lys Gln Val Thr Leu Thr Cys Met Val Thr Asp Phe Met
            245             250             255

Pro Glu Asp Ile Tyr Val Glu Trp Thr Asn Asn Gly Lys Thr Glu Leu
            260             265             270

Asn Tyr Lys Asn Thr Glu Pro Val Leu Asp Ser Asp Gly Ser Tyr Phe
        275             280             285

Met Tyr Ser Lys Leu Arg Val Glu Lys Lys Asn Trp Val Glu Arg Asn
    290             295             300

Ser Tyr Ser Cys Ser Val Val His Glu Gly Leu His Asn His His Thr
305             310             315             320

Thr Lys Ser Phe Ser Arg Thr Pro Gly Lys
            325             330
```

<210> SEQ ID NO 75
<211> LENGTH: 107
<212> TYPE: PRT
<213> ORGANISM: Artificial
<220> FEATURE:
<223> OTHER INFORMATION: cAb4854 CL

<400> SEQUENCE: 75

```
Arg Ala Asp Ala Ala Pro Thr Val Ser Ile Phe Pro Pro Ser Ser Glu
1               5               10              15

Gln Leu Thr Ser Gly Gly Ala Ser Val Val Cys Phe Leu Asn Asn Phe
            20              25              30

Tyr Pro Lys Asp Ile Asn Val Lys Trp Lys Ile Asp Gly Ser Glu Arg
        35              40              45

Gln Asn Gly Val Leu Asn Ser Trp Thr Asp Gln Asp Ser Lys Asp Ser
    50              55              60

Thr Tyr Ser Met Ser Ser Thr Leu Thr Leu Thr Lys Asp Glu Tyr Glu
65              70              75              80

Arg His Asn Ser Tyr Thr Cys Glu Ala Thr His Lys Thr Ser Thr Ser
            85              90              95

Pro Ile Val Lys Ser Phe Asn Arg Asn Glu Cys
            100             105
```

<210> SEQ ID NO 76
<211> LENGTH: 330
<212> TYPE: PRT
<213> ORGANISM: Artificial
<220> FEATURE:
<223> OTHER INFORMATION: cAb4855 CH

<400> SEQUENCE: 76

```
Ala Lys Thr Thr Ala Pro Ser Val Tyr Pro Leu Ala Pro Val Cys Gly
1               5               10              15

Asp Thr Thr Gly Ser Ser Val Thr Leu Gly Cys Leu Val Lys Gly Tyr
            20              25              30

Phe Pro Glu Pro Val Thr Leu Thr Trp Asn Ser Gly Ser Leu Ser Ser
        35              40              45

Gly Val His Thr Phe Pro Ala Val Leu Gln Ser Asp Leu Tyr Thr Leu
    50              55              60

Ser Ser Ser Val Thr Val Thr Ser Ser Thr Trp Pro Ser Gln Ser Ile
65              70              75              80
```

-continued

```
Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
               100                 105                 110

Pro Ala Pro Asn Leu Leu Gly Gly Pro Ser Val Phe Ile Phe Pro Pro
               115                 120                 125

Lys Ile Lys Asp Val Leu Met Ile Ser Leu Ser Pro Met Val Thr Cys
           130                 135                 140

Val Val Val Asp Val Ser Glu Asp Asp Pro Asp Val Gln Ile Ser Trp
145                 150                 155                 160

Phe Val Asn Asn Val Glu Val Leu Thr Ala Gln Thr Gln Thr His Arg
               165                 170                 175

Glu Asp Tyr Asn Ser Thr Leu Arg Val Val Ser Ala Leu Pro Ile Gln
               180                 185                 190

His Gln Asp Trp Met Ser Gly Lys Glu Phe Lys Cys Lys Val Asn Asn
           195                 200                 205

Lys Asp Leu Pro Ala Pro Ile Glu Arg Thr Ile Ser Lys Pro Lys Gly
       210                 215                 220

Ser Val Arg Ala Pro Gln Val Tyr Val Leu Pro Pro Pro Glu Glu Glu
225                 230                 235                 240

Met Thr Lys Lys Gln Val Thr Leu Thr Cys Met Val Thr Asp Phe Met
               245                 250                 255

Pro Glu Asp Ile Tyr Val Glu Trp Thr Asn Asn Gly Lys Thr Glu Leu
               260                 265                 270

Asn Tyr Lys Asn Thr Glu Pro Val Leu Asp Ser Asp Gly Ser Tyr Phe
           275                 280                 285

Met Tyr Ser Lys Leu Arg Val Glu Lys Lys Asn Trp Val Glu Arg Asn
       290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
               325                 330
```

<210> SEQ ID NO 77
<211> LENGTH: 107
<212> TYPE: PRT
<213> ORGANISM: Artificial
<220> FEATURE:
<223> OTHER INFORMATION: cAb4855 CL

<400> SEQUENCE: 77

```
Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
               20                  25                  30

Tyr Pro Lys Asp Ile Asn Val Lys Trp Lys Ile Asp Gly Ser Glu Arg
           35                  40                  45

Gln Asn Gly Val Leu Asn Ser Trp Thr Asp Gln Asp Ser Lys Asp Ser
       50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
               85                  90                  95

Pro Ile Val Lys Ser Phe Asn Arg Asn Glu Cys
               100                 105
```

```
<210> SEQ ID NO 78
<211> LENGTH: 324
<212> TYPE: PRT
<213> ORGANISM: Artificial
<220> FEATURE:
<223> OTHER INFORMATION: cAb5775 CH

<400> SEQUENCE: 78

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
                100                 105                 110

Glu Val Ser Ser Val Phe Ile Phe Pro Pro Lys Pro Lys Asp Val Leu
            115                 120                 125

Thr Ile Thr Leu Thr Pro Lys Val Thr Cys Val Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
            195                 200                 205

Ile Glu Lys Thr Ile Ser Lys Thr Lys Gly Arg Pro Lys Ala Pro Gln
    210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
            275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys

<210> SEQ ID NO 79
<211> LENGTH: 107
<212> TYPE: PRT
<213> ORGANISM: Artificial
<220> FEATURE:
```

<223> OTHER INFORMATION: cAb5775 CL

<400> SEQUENCE: 79

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
                100                 105

<210> SEQ ID NO 80
<211> LENGTH: 324
<212> TYPE: PRT
<213> ORGANISM: Artificial
<220> FEATURE:
<223> OTHER INFORMATION: cAb5776 CH

<400> SEQUENCE: 80

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
            35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
                100                 105                 110

Glu Val Ser Ser Val Phe Ile Phe Pro Pro Lys Pro Lys Asp Val Leu
            115                 120                 125

Thr Ile Thr Leu Thr Pro Lys Val Thr Cys Val Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
                180                 185                 190

Gly Lys Glu Phe Lys Cys Arg Val Asn Ser Ala Ala Phe Pro Ala Pro
            195                 200                 205

Ile Glu Lys Thr Ile Ser Lys Thr Lys Gly Arg Pro Lys Ala Pro Gln
    210                 215                 220

Val Tyr Thr Ile Pro Pro Pro Lys Glu Gln Met Ala Lys Asp Lys Val
225                 230                 235                 240

-continued

```
Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
                260                 265                 270

Pro Ile Met Asp Thr Asp Gly Ser Tyr Phe Val Tyr Ser Lys Leu Asn
                275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys

<210> SEQ ID NO 81
<211> LENGTH: 107
<212> TYPE: PRT
<213> ORGANISM: Artificial
<220> FEATURE:
<223> OTHER INFORMATION: cAb5776 CL

<400> SEQUENCE: 81

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
                20                  25                  30

Tyr Pro Lys Asp Ile Asn Val Lys Trp Lys Ile Asp Gly Ser Glu Arg
            35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
                100                 105

<210> SEQ ID NO 82
<211> LENGTH: 330
<212> TYPE: PRT
<213> ORGANISM: Artificial
<220> FEATURE:
<223> OTHER INFORMATION: cAb5777  CH

<400> SEQUENCE: 82

Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
                20                  25                  30

Phe Pro Glu Pro Val Thr Leu Thr Trp Asn Ser Gly Ser Leu Ser Ser
            35                  40                  45

Gly Val His Thr Phe Pro Ala Val Leu Gln Ser Asp Leu Tyr Thr Leu
    50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
                100                 105                 110
```

```
Pro Ala Pro Asn Leu Leu Gly Gly Pro Ser Val Phe Ile Phe Pro Pro
        115              120              125

Lys Ile Lys Asp Val Leu Met Ile Ser Leu Ser Pro Ile Val Thr Cys
    130              135              140

Val Val Val Asp Val Ser Glu Asp Asp Pro Asp Val Gln Ile Ser Trp
145              150              155              160

Phe Val Asn Asn Val Glu Val His Thr Ala Gln Thr Gln Thr His Arg
            165              170              175

Glu Asp Tyr Asn Ser Thr Leu Arg Val Val Ser Ala Leu Pro Ile Gln
            180              185              190

His Gln Asp Trp Met Ser Gly Lys Glu Phe Lys Cys Lys Val Asn Asn
            195              200              205

Lys Asp Leu Pro Ala Pro Ile Glu Arg Thr Ile Ser Lys Pro Lys Gly
    210              215              220

Ser Val Arg Ala Pro Gln Val Tyr Val Leu Pro Pro Pro Glu Glu Glu
225              230              235              240

Met Thr Lys Lys Gln Val Thr Leu Thr Cys Met Val Thr Asp Phe Met
            245              250              255

Pro Glu Asp Ile Tyr Val Glu Trp Thr Asn Asn Gly Lys Thr Glu Leu
            260              265              270

Asn Tyr Lys Asn Thr Glu Pro Val Leu Asp Ser Asp Gly Ser Tyr Phe
            275              280              285

Met Tyr Ser Lys Leu Arg Val Glu Lys Lys Asn Trp Val Glu Arg Asn
    290              295              300

Ser Tyr Ser Cys Ser Val Val His Glu Gly Leu His Asn His His Thr
305              310              315              320

Thr Lys Ser Phe Ser Arg Thr Pro Gly Lys
            325              330
```

```
<210> SEQ ID NO 83
<211> LENGTH: 107
<212> TYPE: PRT
<213> ORGANISM: Artificial
<220> FEATURE:
<223> OTHER INFORMATION: cAb5777  CL

<400> SEQUENCE: 83
```

```
Arg Ala Asp Ala Ala Pro Thr Val Ser Ile Phe Pro Pro Ser Ser Glu
1                5              10              15

Gln Leu Thr Ser Gly Gly Ala Ser Val Val Cys Phe Leu Asn Asn Phe
            20              25              30

Tyr Pro Lys Asp Ile Asn Val Lys Trp Lys Ile Asp Gly Ser Glu Arg
        35              40              45

Gln Asn Gly Val Leu Asn Ser Trp Thr Asp Gln Asp Ser Lys Asp Ser
    50              55              60

Thr Tyr Ser Met Ser Ser Thr Leu Thr Leu Thr Lys Asp Glu Tyr Glu
65              70              75              80

Arg His Asn Ser Tyr Thr Cys Glu Ala Thr His Lys Thr Ser Thr Ser
            85              90              95

Pro Ile Val Lys Ser Phe Asn Arg Asn Glu Cys
            100              105
```

```
<210> SEQ ID NO 84
<211> LENGTH: 324
<212> TYPE: PRT
<213> ORGANISM: Artificial
```

-continued

```
<220> FEATURE:
<223> OTHER INFORMATION: cAb5778 CH

<400> SEQUENCE: 84

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Asp Ile Ser
        130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
            195                 200                 205

Ile Glu Lys Thr Ile Ser Lys Thr Lys Gly Arg Pro Lys Ala Pro Gln
        210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys

<210> SEQ ID NO 85
<211> LENGTH: 107
<212> TYPE: PRT
<213> ORGANISM: Artificial
<220> FEATURE:
<223> OTHER INFORMATION: cAb5778 CL

<400> SEQUENCE: 85

Arg Ala Asp Ala Ala Pro Thr Val Ser Ile Phe Pro Pro Ser Ser Glu
1               5                   10                  15
```

-continued

```
Gln Leu Thr Ser Gly Gly Ala Ser Val Val Cys Phe Leu Asn Asn Phe
        20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
        100                 105
```

<210> SEQ ID NO 86
<211> LENGTH: 990
<212> TYPE: DNA
<213> ORGANISM: Artificial
<220> FEATURE:
<223> OTHER INFORMATION: cAb4853   CH

<400> SEQUENCE: 86

```
gccaaaacaa cagccccatc ggtctatcca ctggcccctg tgtgtggaga tacaactggc       60
tcctcggtga ctctaggatg cctggtcaag ggttatttcc ctgagccagt gaccttgacc      120
tggaactctg atccctgtc cagtggtgtg cacaccttcc cagctgtcct gcagtctgac      180
ctctacaccc tcagcagctc agtgactgta acctcgagca cctggcccag ccagtccatc      240
acctgcaatg tggcccaccc ggcaagcagc accaaggtgg acaagaaaat tgagcccaga      300
gggcccacaa tcaagccctg tcctccatgc aaatgcccag cacctaacct cttgggtgga      360
ccatccgtct tcatcttccc tccaaagatc aaggatgtac tcatgatctc cctgagcccc      420
atagtcacat gtgtggtggt ggatgtgagc gaggatgacc cagatgtcca gatcagctgg      480
tttgtgaaca acgtggaagt acacacagct cagacacaaa cccatagaga ggattacaac      540
agtactctcc gggtggtcag tgccctcccc atccagcacc aggactggat gagtggcaag      600
gagttcaaat gcaaggtcaa caacaaagac ctcccagcgc ccatcgagag aaccatctca      660
aaacccaaag ggtcagtaag agctccacag gtatatgtct tgcctccacc agaagaagag      720
atgactaaga aacaggtcac tctgacctgc atggtcacag acttcatgcc tgaagacatt      780
tacgtggagt ggaccaacaa cgggaaaaca gagctaaact acaagaacac tgaaccagtc      840
ctggactctg atggttctta cttcatgtac agcaagctga gagtggaaaa gaagaactgg      900
gtggaaagaa atagctactc ctgttcagtg gtccacgagg gtctgcacaa tcaccacacg      960
actaagagct ctcccggac tccgggtaaa                                       990
```

<210> SEQ ID NO 87
<211> LENGTH: 57
<212> TYPE: DNA
<213> ORGANISM: Artificial
<220> FEATURE:
<223> OTHER INFORMATION: cAb4853   HC signal

<400> SEQUENCE: 87

```
atggactcca ggctcaattt agttttcctt gtccttattt taaaaggtgt ccaatgt         57
```

<210> SEQ ID NO 88
<211> LENGTH: 321
<212> TYPE: DNA

<213> ORGANISM: Artificial
<220> FEATURE:
<223> OTHER INFORMATION: cAb4853  CL

<400> SEQUENCE: 88
cgggctgatg ctgcaccaac tgtatccatc ttcccaccat ccagtgagca gttaacatct      60
ggaggtgcct cagtcgtgtg cttcttgaac aacttctacc ccaaagacat caatgtcaag     120
tggaagattg atggcagtga acgacaaaat ggcgtcctga acagttggac tgatcaggac     180
agcaaagaca gcacctacag catgagcagc accctcacgt tgaccaagga cgagtatgaa     240
cgacataaca gctatacctg tgaggccact cacaagacat caacttcacc cattgtcaag     300
agcttcaaca ggaatgagtg t                                               321

<210> SEQ ID NO 89
<211> LENGTH: 60
<212> TYPE: DNA
<213> ORGANISM: Artificial
<220> FEATURE:
<223> OTHER INFORMATION: cAb4853  LC signal

<400> SEQUENCE: 89
atggagtctc atactcaggc ctttgtattc gcgtttctct ggttgtctgg tgttgatgga      60

<210> SEQ ID NO 90
<211> LENGTH: 990
<212> TYPE: DNA
<213> ORGANISM: Artificial
<220> FEATURE:
<223> OTHER INFORMATION: cAb4854  CH

<400> SEQUENCE: 90
gccaaaacaa cagccccatc ggtctatcca ctggcccctg tgtgtggaga tacaactggc      60
tcctcggtga ctctaggatg cctggtcaag ggttatttcc ctgagccagt gaccttgacc     120
tggaactctg gatccctgtc cagtggtgtg cacaccttcc cagctgtcct gcagtctgac     180
ctctacaccc tcagcagctc agtgactgta acctcgagca cctggcccag ccagtccatc     240
acctgcaatg tggcccaccc ggcaagcagc accaaggtgg acaagaaaat tgagcccaga     300
gggcccacaa tcaagccctg tcctccatgc aaatgcccag cacctaacct cttgggtgga     360
ccatccgtct tcatcttccc tccaaagatc aaggatgtac tcatgatctc cctgagcccc     420
atagtcacat gtgtggtggt ggatgtgagc gaggatgacc cagatgtcca gatcagctgg     480
tttgtgaaca cgtggaagt acacacagct cagacacaaa cccatagaga ggattacaac     540
agtactctcc gggtggtcag tgccctcccc atccagcacc aggactggat gagtggcaag     600
gagttcaaat gcaaggtcaa caacaaagac ctcccagcgc ccatcgagag aaccatctca     660
aaacccaaag ggtcagtaag agctccacag gtatatgtct tgcctccacc agaagaagag     720
atgactaaga aacaggtcac tctgacctgc atggtcacag acttcatgcc tgaagacatt     780
tacgtggagt ggaccaacaa cgggaaaaca gagctaaact acaagaacac tgaaccagtc     840
ctggactctg atggttctta cttcatgtac agcaagctga gagtggaaaa gaagaactgg     900
gtggaaagaa atagcactc ctgttcagtg gtccacgagg gtctgcacaa tcaccacacg     960
actaagagct ctccccggac tccgggtaaa                                      990

<210> SEQ ID NO 91
<211> LENGTH: 57
<212> TYPE: DNA
<213> ORGANISM: Artificial

```
<220> FEATURE:
<223> OTHER INFORMATION: cAb4854  HC signal

<400> SEQUENCE: 91
atggactcca ggctcaattt agttttcctt gtccttattt taaaaggtgt ccagtgt         57

<210> SEQ ID NO 92
<211> LENGTH: 321
<212> TYPE: DNA
<213> ORGANISM: Artificial
<220> FEATURE:
<223> OTHER INFORMATION: cAb4854  CL

<400> SEQUENCE: 92
cgggctgatg ctgcaccaac tgtatccatc ttcccaccat ccagtgagca gttaacatct         60
ggaggtgcct cagtcgtgtg cttcttgaac aacttctacc ccaaagacat caatgtcaag        120
tggaagattg atggcagtga acgacaaaat ggcgtcctga acagttggac tgatcaggac        180
agcaaagaca gcacctacag catgagcagc accctcacgt tgaccaagga cgagtatgaa        240
cgacataaca gctatacctg tgaggccact cacaagacat caacttcacc cattgtcaag        300
agcttcaaca ggaatgagtg t                                                  321

<210> SEQ ID NO 93
<211> LENGTH: 60
<212> TYPE: DNA
<213> ORGANISM: Artificial
<220> FEATURE:
<223> OTHER INFORMATION: cAb4854  LC signal

<400> SEQUENCE: 93
atggagtctc gtactcaggc ctttgtaatc gcgtttctct ggatgtctgg tattgatgga         60

<210> SEQ ID NO 94
<211> LENGTH: 990
<212> TYPE: DNA
<213> ORGANISM: Artificial
<220> FEATURE:
<223> OTHER INFORMATION: cAb4855 CH

<400> SEQUENCE: 94
gccaaaacaa cagccccatc ggtctatcca ctggcccctg tgtgtggaga tacaactggc         60
tcctcggtga ctctaggatg cctggtcaag ggttatttcc ctgagccagt gaccttgacc        120
tggaactctg atccctgtc agtggtgtg cacaccttcc agctgtcct gcagtctgac        180 ctctacaccc tcagcagctc agtgactgta acctcgagca cctggcccag ccagtccatc        240
acctgcaatg tggcccaccc ggcaagcagc accaaggtgg acaagaaaat tgagcccaga        300
gggcccacaa tcaagccctg tcctccatgc aaatgcccag cacctaacct cttgggtgga        360
ccatccgtct tcatcttccc tccaaagatc aaggatgtac tcatgatctc cctgagtccc        420
atggtcacat gtgtggtggt ggatgtgagc gaggatgacc cagatgtcca gatcagctgg        480
ttcgtgaaca cgtggaagt actcacagct cagacacaaa cccatagaga ggattacaac        540
agtactctcc gggtggtcag tgccctcccc atccagcacc aggactggat gagtggcaag        600
gagttcaaat gcaaggtcaa caacaaagac ctcccagcac ccatcgagag aaccatctca        660
aaacccaaag ggtcagtaag agctccacag gtatatgtct tgcctccacc agaagaagag        720
atgactaaga aacaggtcac tctgacctgc atggtcacag acttcatgcc tgaagacatt        780
tacgtggagt ggaccaacaa cgggaaaaca gagctaaact acaagaacac tgaaccagtc        840
```

-continued

___ ctggactctg atggttctta cttcatgtac agcaagctga gagtggaaaa gaagaactgg     900
gtggaaagaa atagctactc ctgttcagtg gtccacgagg gtctgcacaa tcaccacacg     960
actaagagct tctcccggac tccgggtaaa     990

<210> SEQ ID NO 95
<211> LENGTH: 57
<212> TYPE: DNA
<213> ORGANISM: Artificial
<220> FEATURE:
<223> OTHER INFORMATION: cAb4855 HC signal

<400> SEQUENCE: 95
atgggcagac ttacttcttc attcttgcta ctgattgtcc ctgcatatgt cctgtcc     57

<210> SEQ ID NO 96
<211> LENGTH: 321
<212> TYPE: DNA
<213> ORGANISM: Artificial
<220> FEATURE:
<223> OTHER INFORMATION: cAb4855 CL

<400> SEQUENCE: 96
cgggctgatg ctgcaccaac tgtatccatc ttcccaccat ccagtgagca gttaacatct     60
ggaggtgcct cagtcgtgtg cttcttgaac aacttctacc ccaaagacat caatgtcaag     120
tggaagattg atggcagtga acgacaaaat ggcgtcctga acagttggac tgatcaggac     180
agcaaagaca gcacctacag catgagcagc accctcacgt tgaccaagga cgagtatgaa     240
cgacataaca gctatacctg tgaggccact cacaagacat caacttcacc cattgtcaag     300
agcttcaaca ggaatgagtg t     321

<210> SEQ ID NO 97
<211> LENGTH: 60
<212> TYPE: DNA
<213> ORGANISM: Artificial
<220> FEATURE:
<223> OTHER INFORMATION: cAb4855 LC signal

<400> SEQUENCE: 97
atggtgtcca cttctcagct ccttggactt ttgcttttct ggacttcagc ctccagatgt     60

<210> SEQ ID NO 98
<211> LENGTH: 972
<212> TYPE: DNA
<213> ORGANISM: Artificial
<220> FEATURE:
<223> OTHER INFORMATION: cAb5775 CH

<400> SEQUENCE: 98
gccaaaacga cacccccatc tgtctatcca ctggcccctg gatctgctgc ccaaactaac     60
tccatggtga ccctgggatg cctggtcaag ggctatttcc ctgagccagt gacagtgacc     120
tggaactctg atccctgtc cagcggtgtg cacaccttcc cagctgtcct gcagtctgac     180
ctctacactc tgagcagctc agtgactgtc ccctccagca cctggcccag cgagaccgtc     240
acctgcaacg ttgcccaccc ggccagcagc accaaggtgg acaagaaaat tgtgcccagg     300
gattgtggtt gtaagccttg catatgtaca gtcccagaag tatcatctgt cttcatcttc     360
cccccaaagc ccaaggatgt gctcaccatt actctgactc ctaaggtcac gtgtgttgtg     420
gtagacatca gcaaggatga tcccgaggtc cagttcagct ggtttgtaga tgatgtggag     480
gtgcacacag ctcagacgca accccgggag gagcagttca acagcacttt ccgctcagtc     540
agtgaacttc ccatcatgca ccaggactgg ctcaatggca aggagttcaa atgcagggtc          600
aacagtgcag ctttccctgc ccccatcgag aaaaccatct ccaaaaccaa aggcagaccg          660
aaggctccac aggtgtacac cattccacct cccaaggagc agatggccaa ggataaagtc          720
agtctgacct gcatgataac agacttcttc cctgaagaca ttactgtgga gtggcagtgg          780
aatgggcagc cagcggagaa ctacaagaac actcagccca tcatggacac agatggctct          840
tacttcgtct acagcaagct caatgtgcag aagagcaact gggaggcagg aaatactttc          900
acctgctctg tgttacatga gggcctgcac aaccaccata ctgagaagag cctctcccac          960
tctcctggta aa                                                             972

<210> SEQ ID NO 99
<211> LENGTH: 57
<212> TYPE: DNA
<213> ORGANISM: Artificial
<220> FEATURE:
<223> OTHER INFORMATION: cAb5775 HC signal

<400> SEQUENCE: 99
atgggatgga gctggatctt tctcttcctc ctgtcaggaa ctgcaggtgt ccactct          57

<210> SEQ ID NO 100
<211> LENGTH: 321
<212> TYPE: DNA
<213> ORGANISM: Artificial
<220> FEATURE:
<223> OTHER INFORMATION: cAb5775 CL

<400> SEQUENCE: 100
cgggctgatg ctgcaccaac tgtatccatc ttcccaccat ccagtgagca gttaacatct          60
ggaggtgcct cagtcgtgtg cttcttgaac aacttctacc ccaaagacat caatgtcaag          120
tggaagattg atggcagtga acgacaaaat ggcgtcctga acagttggac tgatcaggac          180
agcaaagaca gcacctacag catgagcagc accctcacgt tgaccaagga cgagtatgaa          240
cgacataaca gctatacctg tgaggccact cacaagacat caacttcacc cattgtcaag          300
agcttcaaca ggaatgagtg t                                                  321

<210> SEQ ID NO 101
<211> LENGTH: 57
<212> TYPE: DNA
<213> ORGANISM: Artificial
<220> FEATURE:
<223> OTHER INFORMATION: cAb5775 LC signal

<400> SEQUENCE: 101
atgaagttgc ctgttaggct gttggtgctg atgttctgga ttcctgcttc cagtagt          57

<210> SEQ ID NO 102
<211> LENGTH: 972
<212> TYPE: DNA
<213> ORGANISM: Artificial
<220> FEATURE:
<223> OTHER INFORMATION: cAb5776 CH

<400> SEQUENCE: 102
gccaaaacga caccccatc tgtctatcca ctggcccctg gatctgctgc ccaaactaac          60
tccatggtga ccctgggatg cctggtcaag ggctatttcc ctgagccagt gacagtgacc          120
tggaactctg gatccctgtc cagcggtgtg cacaccttcc cagctgtcct gcagtctgac          180

```
ctctacactc tgagcagctc agtgactgtc ccctccagca cctggcccag cgagaccgtc       240
acctgcaacg ttgcccaccc ggccagcagc accaaggtgg acaagaaaat tgtgcccagg       300
gattgtggtt gtaagccttg catatgtaca gtcccagaag tatcatctgt cttcatcttc       360
cccccaaagc ccaaggatgt gctcaccatt actctgactc ctaaggtcac gtgtgttgtg       420
gtagacatca gcaaggatga tcccgaggtc cagttcagct ggtttgtaga tgatgtggag       480
gtgcacacag ctcagacgca accccgggag gagcagttca acagcacttt ccgctcagtc       540
agtgaacttc ccatcatgca ccaggactgg ctcaatggca aggagttcaa atgcagggtc       600
aacagtgcag ctttccctgc ccccatcgag aaaaccatct ccaaaaccaa aggcagaccg       660
aaggctccac aggtgtacac cattccacct cccaaggagc agatggccaa ggataaagtc       720
agtctgacct gcatgataac agacttcttc cctgaagaca ttactgtgga gtggcagtgg       780
aatgggcagc cagcggagaa ctacaagaac actcagccca tcatggacac agatggctct       840
tacttcgtct acagcaagct caatgtgcag aagagcaact gggaggcagg aaatactttc       900
acctgctctg tgttacatga gggcctgcac aaccaccata ctgagaagag cctctcccac       960
tctcctggta aa                                                          972

<210> SEQ ID NO 103
<211> LENGTH: 57
<212> TYPE: DNA
<213> ORGANISM: Artificial
<220> FEATURE:
<223> OTHER INFORMATION: cAb5776 HC signal

<400> SEQUENCE: 103
atgggatgga ctggatctt tctcttcctc ctgtcaggaa ctgcaggtgt ccactct           57

<210> SEQ ID NO 104
<211> LENGTH: 321
<212> TYPE: DNA
<213> ORGANISM: Artificial
<220> FEATURE:
<223> OTHER INFORMATION: cAb5776 CL

<400> SEQUENCE: 104
cgggctgatg ctgcaccaac tgtatccatc ttcccaccat ccagtgagca gttaacatct        60
ggaggtgcct cagtcgtgtg cttcttgaac aacttctacc ccaaagacat caatgtcaag       120
tggaagattg atggcagtga acgacaaaat ggcgtcctga cagttggac tgatcaggac        180 agcaaagaca gcacctacag catgagcagc accctcacgt tgaccaagga cgagtatgaa       240
cgacataaca gctatacctg tgaggccact cacaagacat caacttcacc cattgtcaag       300
agcttcaaca ggaatgagtg t                                                 321

<210> SEQ ID NO 105
<211> LENGTH: 57
<212> TYPE: DNA
<213> ORGANISM: Artificial
<220> FEATURE:
<223> OTHER INFORMATION: cAb5776 LC signal

<400> SEQUENCE: 105
atgaagttgc ctgttaggct gttggtgctg atgttctgga ttcctgcttc cagcagt           57

<210> SEQ ID NO 106
<211> LENGTH: 990
<212> TYPE: DNA
<213> ORGANISM: Artificial
```

<220> FEATURE:
<223> OTHER INFORMATION: cAb5777 CH

<400> SEQUENCE: 106
gccaaaacaa cagccccatc ggtctatcca ctggcccctg tgtgtggaga tacaactggc          60
tcctcggtga ctctaggatg cctggtcaag ggttatttcc ctgagccagt gaccttgacc         120
tggaactctg datccctgtc cagtggtgtg cacaccttcc cagctgtcct gcagtctgac         180
ctctacaccc tcagcagctc agtgactgta acctcgagca cctggcccag ccagtccatc         240
acctgcaatg tggcccaccc ggcaagcagc accaaggtgg acaagaaaat tgagcccaga         300
gggcccacaa tcaagccctg tcctccatgc aaatgcccag cacctaacct cttgggtgga         360
ccatccgtct tcatcttccc tccaaagatc aaggatgtac tcatgatctc cctgagcccc         420
atagtcacat gtgtggtggt ggatgtgagc gaggatgacc cagatgtcca gatcagctgg         480
tttgtgaaca cgtggaagt acacacagct cagacacaaa cccatagaga ggattacaac         540
agtactctcc gggtggtcag tgccctcccc atccagcacc aggactggat gagtggcaag         600
gagttcaaat gcaaggtcaa caacaaagac ctcccagcgc ccatcgagag aaccatctca         660
aaacccaaag ggtcagtaag agctccacag gtatatgtct tgcctccacc agaagaagag         720
atgactaaga aacaggtcac tctgacctgc atggtcacag acttcatgcc tgaagacatt         780
tacgtggagt ggaccaacaa cgggaaaaca gagctaaact acaagaacac tgaaccagtc         840
ctggactctg atggttctta cttcatgtac agcaagctga gagtggaaaa gaagaactgg         900
gtggaaagaa atagctactc ctgttcagtg gtccacgagg gtctgcacaa tcaccacacg         960
actaagagct ctcccggac tccgggtaaa                                          990

<210> SEQ ID NO 107
<211> LENGTH: 57
<212> TYPE: DNA
<213> ORGANISM: Artificial
<220> FEATURE:
<223> OTHER INFORMATION: cAb5777 HC signal

<400> SEQUENCE: 107
atgaaatgca gctgggttat cttcttcctg atggcagtgg ttacaggggt caattca          57

<210> SEQ ID NO 108
<211> LENGTH: 321
<212> TYPE: DNA
<213> ORGANISM: Artificial
<220> FEATURE:
<223> OTHER INFORMATION: cAb5777 CL

<400> SEQUENCE: 108
cgggctgatg ctgcaccaac tgtatccatc ttcccaccat ccagtgagca gttaacatct          60
ggaggtgcct cagtcgtgtg cttcttgaac aacttctacc ccaaagacat caatgtcaag         120
tggaagattg atggcagtga acgacaaaat ggcgtcctga cagttggac tgatcaggac         180 agcaaagaca gcacctacag catgagcagc accctcacgt tgaccaagga cgagtatgaa         240
cgacataaca gctatacctg tgaggccact cacaagacat caacttcacc cattgtcaag         300
agcttcaaca ggaatgagtg t                                                 321

<210> SEQ ID NO 109
<211> LENGTH: 60
<212> TYPE: DNA
<213> ORGANISM: Artificial
<220> FEATURE:

-continued

<223> OTHER INFORMATION: cAb5777 LC signal

<400> SEQUENCE: 109

```
atggattcac gggcccaggt tcttatattg ctgctgcaat gggtatctgg tacctgtggg      60
```

```
<210> SEQ ID NO 110
<211> LENGTH: 972
<212> TYPE: DNA
<213> ORGANISM: Artificial
<220> FEATURE:
<223> OTHER INFORMATION: cAb5778 CH
```

<400> SEQUENCE: 110

```
gccaaaacga caccccatc tgtctatcca ctggcccctg gatctgctgc ccaaactaac      60
tccatggtga ccctgggatg cctggtcaag ggctatttcc ctgagccagt gacagtgacc     120
tggaactctg gatccctgtc cagcggtgtg cacaccttcc cagctgtcct gcagtctgac     180
ctctacactc tgagcagctc agtgactgtc ccctccagca cctggcccag cgagaccgtc     240
acctgcaacg ttgcccaccc ggccagcagc accaaggtgg acaagaaaat tgtgcccagg     300
gattgtggtt gtaagccttg catatgtaca gtcccagaag tatcatctgt cttcatcttc     360
cccccaaagc ccaaggatgt gctcaccatt actctgactc ctaaggtcac gtgtgttgtg     420
gtagacatca gcaaggatga tcccgaggtc cagttcagct ggtttgtaga tgatgtggag     480
gtgcacacag ctcagacgca accccgggag gagcagttca acagcacttt ccgctcagtc     540
agtgaacttc ccatcatgca ccaggactgg ctcaatggca aggagttcaa atgcagggtc     600
aacagtgcag ctttccctgc ccccatcgag aaaaccatct ccaaaaccaa aggcagaccg     660
aaggctccac aggtgtacac cattccacct cccaaggagc agatggccaa ggataaagtc     720
agtctgacct gcatgataac agacttcttc cctgaagaca ttactgtgga gtggcagtgg     780
aatgggcagc cagcggagaa ctacaagaac actcagccca tcatggacac agatggctct     840
tacttcgtct acagcaagct caatgtgcag aagagcaact gggaggcagg aaatactttc     900
acctgctctg tgttacatga gggcctgcac aaccaccata ctgagaagag cctctcccac     960
tctcctggta aa                                                        972
```

```
<210> SEQ ID NO 111
<211> LENGTH: 57
<212> TYPE: DNA
<213> ORGANISM: Artificial
<220> FEATURE:
<223> OTHER INFORMATION: cAb5778 HC signal
```

<400> SEQUENCE: 111

```
atgggatgga ctggatctt tctcttcctc ctgtcaggaa ctgcaggtgt ccactct        57
```

```
<210> SEQ ID NO 112
<211> LENGTH: 321
<212> TYPE: DNA
<213> ORGANISM: Artificial
<220> FEATURE:
<223> OTHER INFORMATION: cAb5778 CL
```

<400> SEQUENCE: 112

```
cgggctgatg ctgcaccaac tgtatccatc ttcccaccat ccagtgagca gttaacatct      60
ggaggtgcct cagtcgtgtg cttcttgaac aacttctacc ccaaagacat caatgtcaag     120
tggaagattg atggcagtga acgacaaaat ggcgtcctga cagttggac tgatcaggac      180 agcaaagaca gcacctacag catgagcagc accctcacgt tgaccaagga cgagtatgaa     240
```

-continued

```
cgacataaca gctatacctg tgaggccact cacaagacat caacttcacc cattgtcaag      300
agcttcaaca ggaatgagtg t                                               321

<210> SEQ ID NO 113
<211> LENGTH: 60
<212> TYPE: DNA
<213> ORGANISM: Artificial
<220> FEATURE:
<223> OTHER INFORMATION: cAb5778 LC signal

<400> SEQUENCE: 113
atggagacag acacactcct gttatgggta ctgctgctct gggttccagg ttccactggt       60

<210> SEQ ID NO 114
<211> LENGTH: 20
<212> TYPE: DNA
<213> ORGANISM: Artificial
<220> FEATURE:
<223> OTHER INFORMATION: Primer

<400> SEQUENCE: 114
cgtaccaacg ggcccctccg                                                   20

<210> SEQ ID NO 115
<211> LENGTH: 20
<212> TYPE: DNA
<213> ORGANISM: Artificial
<220> FEATURE:
<223> OTHER INFORMATION: Primer

<400> SEQUENCE: 115
gcggcttgga ccatagcgga                                                   20

<210> SEQ ID NO 116
<211> LENGTH: 35
<212> TYPE: DNA
<213> ORGANISM: Artificial
<220> FEATURE:
<223> OTHER INFORMATION: Primer

<400> SEQUENCE: 116
acgtactcga gcaccatggg agctgctggg aggca                                  35

<210> SEQ ID NO 117
<211> LENGTH: 31
<212> TYPE: DNA
<213> ORGANISM: Artificial
<220> FEATURE:
<223> OTHER INFORMATION: Primer

<400> SEQUENCE: 117
acgtgctagc ctacaacttc ttcttcttca c                                      31
```